United States Patent
Connor

(10) Patent No.: US 10,314,492 B2
(45) Date of Patent: Jun. 11, 2019

(54) WEARABLE SPECTROSCOPIC SENSOR TO MEASURE FOOD CONSUMPTION BASED ON INTERACTION BETWEEN LIGHT AND THE HUMAN BODY

(71) Applicant: Robert A. Connor, Forest Lake, MN (US)

(72) Inventor: Robert A. Connor, Forest Lake, MN (US)

(73) Assignee: Medibotics LLC, St. Paul, MN (US)

( * ) Notice: Subject to any disclaimer, the term of this patent is extended or adjusted under 35 U.S.C. 154(b) by 289 days.

(21) Appl. No.: 14/951,475

(22) Filed: Nov. 24, 2015

(65) Prior Publication Data

US 2016/0073886 A1 Mar. 17, 2016

Related U.S. Application Data

(63) Continuation-in-part of application No. 13/901,131, filed on May 23, 2013, now Pat. No. 9,536,449, and a continuation-in-part of application No. 14/071,112, filed on Nov. 4, 2013, now abandoned, and a continuation-in-part of application No. 14/623,337, filed on Feb. 16, 2015, now Pat. No. 9,582,035.

(Continued)

(51) Int. Cl.
*A61B 5/00* (2006.01)
*G09B 19/00* (2006.01)

(52) U.S. Cl.
CPC .......... *A61B 5/0075* (2013.01); *A61B 5/4866* (2013.01); *A61B 5/681* (2013.01); *A61B 5/6887* (2013.01); *G09B 19/0092* (2013.01); *A61B 2560/0214* (2013.01); *A61B 2576/00* (2013.01)

(58) Field of Classification Search
CPC . G09B 19/0092; A61B 5/0075; A61B 5/4866; A61B 5/6887; A61B 5/681; A61B 2560/0214; A61B 2576/00

See application file for complete search history.

(56) References Cited

U.S. PATENT DOCUMENTS 3,885,576 A 5/1975 Symmes
4,100,401 A 7/1978 Tutt et al.
(Continued)

FOREIGN PATENT DOCUMENTS

WO WO1997028738 8/1997
WO WO2003032629 4/2003
(Continued)

OTHER PUBLICATIONS

U.S. Appl. No. 13/523,739, filed Jun. 14, 2012, Connor.
U.S. Appl. No. 13/616,238, filed Sep. 14, 2012, Connor.

*Primary Examiner* — Nathan Hillery

(57) ABSTRACT

This is a wearable device to measure a person's food consumption based on the interaction between light energy and body tissue comprising: a wearable spectroscopic sensor that collects data concerning the spectrum of light energy reflected from body tissue or having passed through body tissue; a data processing unit; and a power source. Spectroscopic sensor data is analyzed to measure consumption of selected types of food, ingredients, and/or nutrients. This device can be embodied in a finger ring, smart watch, wrist band, wrist bracelet, armlet, cuff, or sleeve with close-fitting spectroscopic sensors.

1 Claim, 27 Drawing Sheets

Related U.S. Application Data

(60) Provisional application No. 62/245,311, filed on Oct. 23, 2015.

(56) References Cited

U.S. PATENT DOCUMENTS

| | | |
|---|---|---|
| 4,192,000 A | 3/1980 | Lipsey |
| 4,207,673 A | 6/1980 | DiGirolamo et al. |
| 4,212,079 A | 7/1980 | Segar et al. |
| 4,218,611 A | 8/1980 | Cannon |
| 4,221,959 A | 9/1980 | Sessler |
| 4,310,316 A | 1/1982 | Thomann |
| 4,321,674 A | 3/1982 | Krames et al. |
| 4,355,645 A | 10/1982 | Mitani et al. |
| 4,509,531 A | 4/1985 | Ward |
| 4,650,218 A | 3/1987 | Hawke |
| 4,686,624 A | 8/1987 | Blum et al. |
| 4,757,453 A | 7/1988 | Nasiff |
| 4,796,182 A | 1/1989 | Duboff |
| 4,819,860 A | 4/1989 | Hargrove et al. |
| 4,823,808 A | 4/1989 | Clegg et al. |
| 4,875,533 A | 10/1989 | Mihara et al. |
| 4,891,756 A | 1/1990 | Williams |
| 4,911,256 A | 3/1990 | Attikiouzel |
| 4,914,819 A | 4/1990 | Ash |
| 4,917,108 A | 4/1990 | Mault |
| 4,951,197 A | 8/1990 | Mellinger |
| 4,965,553 A | 10/1990 | DelBiondo et al. |
| 4,975,682 A | 12/1990 | Kerr et al. |
| 5,033,561 A | 7/1991 | Hettinger |
| 5,038,792 A | 8/1991 | Mault |
| 5,050,612 A | 9/1991 | Matsumura |
| 5,067,488 A | 11/1991 | Fukada et al. |
| 5,148,002 A | 9/1992 | Kuo et al. |
| 5,173,588 A | 12/1992 | Harrah |
| 5,233,520 A | 8/1993 | Kretsch et al. |
| 5,263,491 A | 11/1993 | Thornton |
| 5,285,398 A | 2/1994 | Janik |
| 5,299,356 A | 4/1994 | Maxwell |
| 5,301,679 A | 4/1994 | Taylor |
| 5,388,043 A | 2/1995 | Hettinger |
| 5,398,688 A | 3/1995 | Laniado |
| 5,412,564 A | 5/1995 | Ecer |
| 5,421,089 A | 6/1995 | Dubus et al. |
| 5,424,719 A | 6/1995 | Ravid |
| 5,478,989 A | 12/1995 | Shepley |
| 5,491,651 A | 2/1996 | Janik |
| 5,497,772 A | 3/1996 | Schulman et al. |
| 5,514,861 A | 5/1996 | Swartz et al. |
| 5,515,858 A | 5/1996 | Myllymaki |
| 5,542,420 A | 8/1996 | Goldman et al. |
| 5,555,490 A | 9/1996 | Carroll |
| 5,563,850 A | 10/1996 | Hanapole |
| 5,581,492 A | 12/1996 | Janik |
| 5,610,528 A | 3/1997 | Neely et al. |
| 5,636,146 A | 6/1997 | Flentov et al. |
| 5,673,691 A | 10/1997 | Abrams et al. |
| 5,691,927 A | 11/1997 | Gump |
| 5,704,350 A | 1/1998 | Williams |
| 5,729,479 A | 3/1998 | Golan |
| 5,817,006 A | 10/1998 | Bergh et al. |
| 5,819,735 A | 10/1998 | Mansfield et al. |
| 5,836,312 A | 11/1998 | Moore |
| 5,839,901 A | 11/1998 | Karkanen |
| 5,841,115 A | 11/1998 | Shepley |
| 5,890,128 A | 3/1999 | Diaz et al. |
| 5,908,301 A | 6/1999 | Lutz |
| 5,989,188 A | 11/1999 | Birkhoelzer |
| 6,024,281 A | 2/2000 | Shepley |
| 6,032,676 A | 3/2000 | Moore |
| 6,040,531 A | 3/2000 | Miller-Kovach |
| 6,050,962 A | 4/2000 | Kramer et al. |
| 6,083,006 A | 7/2000 | Coffman |
| 6,095,949 A | 8/2000 | Arai |
| 6,095,985 A | 8/2000 | Raymond et al. |
| 6,135,950 A | 10/2000 | Adams |
| 6,135,951 A | 10/2000 | Richardson et al. |
| 6,218,358 B1 | 4/2001 | Firestein et al. |
| 6,249,697 B1 | 6/2001 | Asano |
| 6,266,623 B1 | 7/2001 | Vock et al. |
| 6,283,914 B1 | 9/2001 | Mansfield et al. |
| 6,290,646 B1 | 9/2001 | Cosentino et al. |
| 6,336,136 B1 | 1/2002 | Harris |
| 6,341,295 B1 | 1/2002 | Stotler |
| 6,387,329 B1 | 5/2002 | Lewis et al. |
| 6,425,862 B1 | 7/2002 | Brown |
| 6,428,490 B1 | 8/2002 | Kramer et al. |
| 6,454,705 B1 | 9/2002 | Cosentino et al. |
| 6,473,368 B1 | 10/2002 | Stanfield |
| 6,478,736 B1 | 11/2002 | Mault |
| 6,487,906 B1 | 12/2002 | Hock |
| 6,498,994 B2 | 12/2002 | Vock et al. |
| 6,506,152 B1 | 1/2003 | Lackey et al. |
| 6,508,762 B2 | 1/2003 | Karnieli |
| 6,513,532 B2 | 2/2003 | Mault et al. |
| 6,525,997 B1 | 2/2003 | Narayanaswami |
| 6,527,711 B1 | 3/2003 | Stivoric et al. |
| 6,553,386 B1 | 4/2003 | Alabaster |
| 6,556,222 B1 | 4/2003 | Narayanaswami |
| 6,571,200 B1 | 5/2003 | Mault |
| 6,572,542 B1 | 6/2003 | Houben et al. |
| 6,595,929 B2 | 7/2003 | Stivoric et al. |
| 6,605,038 B1 | 8/2003 | Teller et al. |
| 6,610,367 B2 | 8/2003 | Lewis et al. |
| 6,635,015 B2 | 10/2003 | Sagel |
| 6,675,041 B2 | 1/2004 | Dickinson |
| 6,694,182 B1 | 2/2004 | Yamazaki et al. |
| 6,697,048 B2 | 2/2004 | Rosenberg et al. |
| 6,723,045 B2 | 4/2004 | Cosentino et al. |
| 6,745,214 B2 | 6/2004 | Inoue et al. |
| 6,755,783 B2 | 6/2004 | Cosentino et al. |
| 6,765,488 B2 | 7/2004 | Stanfield |
| 6,790,178 B1 | 9/2004 | Mault et al. |
| 6,850,861 B1 | 2/2005 | Faiola et al. |
| 6,856,934 B2 | 2/2005 | Vock et al. |
| 6,856,938 B2 | 2/2005 | Kurtz |
| 6,878,885 B2 | 4/2005 | Miller-Kovach |
| 6,893,406 B2 | 5/2005 | Takeuchi et al. |
| 6,917,897 B2 | 7/2005 | Mork |
| 6,930,608 B2 | 8/2005 | Grajales et al. |
| 6,978,221 B1 | 12/2005 | Rudy |
| 6,984,208 B2 | 1/2006 | Zheng |
| 7,020,508 B2 | 3/2006 | Stivoric et al. |
| 7,044,739 B2 | 5/2006 | Matson |
| 7,054,784 B2 | 5/2006 | Flentov et al. |
| 7,057,551 B1 | 6/2006 | Vogt |
| 7,070,571 B2 | 7/2006 | Kramer et al. |
| 7,073,129 B1 | 7/2006 | Robarts et al. |
| 7,096,221 B2 | 8/2006 | Nakano |
| 7,122,152 B2 | 10/2006 | Lewis et al. |
| 7,153,262 B2 | 12/2006 | Stivoric et al. |
| 7,192,136 B2 | 3/2007 | Howell et al. |
| 7,241,880 B2 | 7/2007 | Adler et al. |
| 7,247,023 B2 | 7/2007 | Peplinski et al. |
| 7,255,437 B2 | 8/2007 | Howell et al. |
| 7,261,690 B2 | 8/2007 | Teller et al. |
| 7,285,090 B2 | 10/2007 | Stivoric et al. |
| 7,361,141 B2 | 4/2008 | Nissila et al. |
| 7,373,820 B1 | 5/2008 | James |
| 7,395,507 B2 | 7/2008 | Robarts et al. |
| 7,398,151 B1 | 7/2008 | Burrell et al. |
| 7,401,918 B2 | 7/2008 | Howell et al. |
| 7,438,410 B1 | 10/2008 | Howell et al. |
| 7,451,056 B2 | 11/2008 | Flentov et al. |
| 7,454,002 B1 | 11/2008 | Gardner et al. |
| 7,481,531 B2 | 1/2009 | Howell et al. |
| 7,500,937 B2 | 3/2009 | Hercules |
| 7,502,643 B2 | 3/2009 | Farringdon et al. |
| 7,506,269 B2 | 3/2009 | Lang |
| 7,512,515 B2 | 3/2009 | Vock et al. |
| 7,550,683 B2 | 6/2009 | Daughtry |
| 7,558,057 B1 | 7/2009 | Naksen et al. |
| 7,577,475 B2 | 8/2009 | Cosentino et al. |
| 7,595,023 B2 | 9/2009 | Lewis et al. |
| 7,640,804 B2 | 1/2010 | Daumer et al. |

(56) References Cited

U.S. PATENT DOCUMENTS

| | | |
|---|---|---|
| 7,651,868 B2 | 1/2010 | Mcdevitt et al. |
| 7,658,612 B2 | 2/2010 | Lee et al. |
| 7,689,437 B1 | 3/2010 | Teller et al. |
| 7,717,866 B2 | 5/2010 | Damen |
| 7,736,318 B2 | 6/2010 | Cosentino et al. |
| 7,769,635 B2 | 8/2010 | Simons-Nikolova |
| 7,785,001 B2 | 8/2010 | Tao et al. |
| 7,805,196 B2 | 9/2010 | Miesel et al. |
| 7,821,496 B2 | 10/2010 | Rosenberg et al. |
| 7,841,966 B2 | 11/2010 | Aaron et al. |
| 7,855,936 B2 | 12/2010 | Czarnek |
| 7,857,730 B2 | 12/2010 | Dugan |
| 7,878,975 B2 | 2/2011 | Liljeryd et al. |
| 7,882,150 B2 | 2/2011 | Badyal |
| 7,899,709 B2 | 3/2011 | Allard et al. |
| 7,905,815 B2 | 3/2011 | Ellis et al. |
| 7,905,832 B1 | 3/2011 | Lau et al. |
| 7,914,468 B2 | 3/2011 | Shalon et al. |
| 7,931,562 B2 | 4/2011 | Ellis et al. |
| 7,949,506 B1 | 5/2011 | Hill et al. |
| 7,956,997 B2 | 6/2011 | Wang et al. |
| 7,959,567 B2 | 6/2011 | Stivoric et al. |
| 7,980,997 B2 | 7/2011 | Thukral et al. |
| 7,999,674 B2 | 8/2011 | Kamen |
| 8,021,297 B2 | 9/2011 | Aerts |
| 8,033,959 B2 | 10/2011 | Oleson |
| 8,036,851 B2 | 10/2011 | Vock et al. |
| 8,067,185 B2 | 11/2011 | Zoller et al. |
| 8,068,858 B2 | 11/2011 | Werner et al. |
| 8,073,707 B2 | 12/2011 | Teller et al. |
| 8,075,451 B2 | 12/2011 | Dugan |
| 8,087,937 B2 | 1/2012 | Peplinski et al. |
| 8,111,165 B2 | 2/2012 | Ortega et al. |
| 8,112,281 B2 | 2/2012 | Yeung et al. |
| 8,116,841 B2 | 2/2012 | Bly et al. |
| 8,121,673 B2 | 2/2012 | Tran |
| 8,146,171 B2 | 4/2012 | Chung et al. |
| 8,149,212 B2 | 4/2012 | Radley-Smith |
| 8,157,731 B2 | 4/2012 | Teller et al. |
| 8,158,082 B2 | 4/2012 | Imran |
| 8,161,826 B1 | 4/2012 | Taylor |
| 8,162,804 B2 | 4/2012 | Tagliabue |
| 8,170,656 B2 | 5/2012 | Tan et al. |
| 8,180,440 B2 | 5/2012 | McCombie et al. |
| 8,180,591 B2 | 5/2012 | Yuen et al. |
| 8,180,592 B2 | 5/2012 | Yuen et al. |
| 8,184,070 B1 | 5/2012 | Taubman |
| 8,228,315 B1 | 7/2012 | Starner et al. |
| 8,229,676 B2 | 7/2012 | Hyde et al. |
| 8,236,242 B2 | 8/2012 | Drucker et al. |
| 8,244,278 B2 | 8/2012 | Werner et al. |
| 8,265,907 B2 | 9/2012 | Nanikashvili et al. |
| 8,275,438 B2 | 9/2012 | Simpson et al. |
| 8,275,635 B2 | 9/2012 | Stivoric et al. |
| 8,279,716 B1 | 10/2012 | Gossweiler et al. |
| 8,280,476 B2 | 10/2012 | Jina |
| 8,285,356 B2 | 10/2012 | Bly et al. |
| 8,285,488 B2 | 10/2012 | Hyde et al. |
| 8,287,453 B2 | 10/2012 | Li et al. |
| 8,290,712 B2 | 10/2012 | Hyde et al. |
| 8,294,581 B2 | 10/2012 | Kamen |
| 8,298,142 B2 | 10/2012 | Simpson et al. |
| 8,299,930 B2 | 10/2012 | Schmid-Schonbein et al. |
| 8,310,368 B2 | 11/2012 | Hoover et al. |
| 8,311,769 B2 | 11/2012 | Yuen et al. |
| 8,311,770 B2 | 11/2012 | Yuen et al. |
| 8,314,224 B2 | 11/2012 | Adler et al. |
| 8,321,141 B2 | 11/2012 | Hyde et al. |
| 8,323,188 B2 | 12/2012 | Tran |
| 8,323,189 B2 | 12/2012 | Tran et al. |
| 8,323,218 B2 | 12/2012 | Davis et al. |
| 8,328,718 B2 | 12/2012 | Tran |
| 8,330,057 B2 | 12/2012 | Sharawi et al. |
| 8,334,367 B2 | 12/2012 | Adler |
| 8,337,367 B2 | 12/2012 | Dugan |
| 8,340,754 B2 | 12/2012 | Chamney et al. |
| 8,344,325 B2 | 1/2013 | Merrell et al. |
| 8,344,998 B2 | 1/2013 | Fitzgerald et al. |
| 8,345,414 B2 | 1/2013 | Mooring et al. |
| 8,345,930 B2 | 1/2013 | Tamrakar et al. |
| 8,352,211 B2 | 1/2013 | Vock et al. |
| 8,355,875 B2 | 1/2013 | Hyde et al. |
| 8,362,882 B2 | 1/2013 | Heubel et al. |
| 8,363,913 B2 | 1/2013 | Boushey et al. |
| 8,364,250 B2 | 1/2013 | Moon et al. |
| 8,369,919 B2 | 2/2013 | Kamath et al. |
| 8,369,936 B2 | 2/2013 | Farringdon et al. |
| 8,370,176 B2 | 2/2013 | Vespasiani |
| 8,370,549 B2 | 2/2013 | Burton et al. |
| 8,378,811 B2 | 2/2013 | Crump et al. |
| 8,379,488 B1 | 2/2013 | Gossweiler et al. |
| 8,382,482 B2 | 2/2013 | Miller-Kovach et al. |
| 8,382,681 B2 | 2/2013 | Escutia et al. |
| 8,386,008 B2 | 2/2013 | Yuen et al. |
| 8,386,185 B2 | 2/2013 | Hyde et al. |
| 8,392,123 B2 | 3/2013 | Hyde et al. |
| 8,392,124 B2 | 3/2013 | Hyde et al. |
| 8,392,125 B2 | 3/2013 | Hyde et al. |
| 8,396,530 B1 | 3/2013 | Wilder-Smith et al. |
| 8,396,672 B2 | 3/2013 | Hyde et al. |
| 8,398,546 B2 | 3/2013 | Pacione et al. |
| 8,403,845 B2 | 3/2013 | Stivoric et al. |
| 8,408,436 B2 | 4/2013 | Berry et al. |
| 8,409,118 B2 | 4/2013 | Agrawal et al. |
| 8,412,317 B2 | 4/2013 | Mazar |
| 8,416,088 B2 | 4/2013 | Ortega et al. |
| 8,416,102 B2 | 4/2013 | Yin |
| 8,417,298 B2 | 4/2013 | Mittleman et al. |
| 8,417,312 B2 | 4/2013 | Kamath et al. |
| 8,419,268 B2 | 4/2013 | Yu |
| 8,421,620 B2 | 4/2013 | Boyd et al. |
| 8,421,634 B2 | 4/2013 | Tan et al. |
| 8,423,113 B2 | 4/2013 | Shariati et al. |
| 8,423,378 B1 | 4/2013 | Goldberg |
| 8,423,380 B1 | 4/2013 | Gelly |
| 8,425,415 B2 | 4/2013 | Tran |
| 8,437,823 B2 | 5/2013 | Ozawa et al. |
| 8,437,980 B2 | 5/2013 | Yuen et al. |
| 8,438,038 B2 | 5/2013 | Cosentino et al. |
| 8,438,163 B1 | 5/2013 | Li et al. |
| 8,446,275 B2 | 5/2013 | Utter |
| 8,457,719 B2 | 6/2013 | Moctezuma et al. |
| 8,464,036 B2 | 6/2013 | Rubin et al. |
| 8,475,370 B2 | 7/2013 | McCombie et al. |
| 8,527,217 B2 | 9/2013 | Moodie |
| 8,538,376 B2 | 9/2013 | Lee et al. |
| 8,576,199 B1 | 11/2013 | Pryor |
| 8,594,776 B2 | 11/2013 | McCombie et al. |
| 8,595,645 B2 | 11/2013 | Boettcher et al. |
| 8,624,836 B1 | 1/2014 | Miller et al. |
| 8,634,873 B2 | 1/2014 | Jones et al. |
| 8,648,799 B1 | 2/2014 | Lloyd |
| 8,659,553 B1 | 2/2014 | Chan et al. |
| D701,504 S | 3/2014 | Christopher et al. |
| 8,662,362 B1 | 3/2014 | Bastian et al. |
| 8,662,742 B2 | 3/2014 | Damasko |
| 8,665,223 B2 | 3/2014 | Harada et al. |
| 8,665,236 B2 | 3/2014 | Myers |
| 8,666,115 B2 | 3/2014 | Perski et al. |
| 8,666,447 B2 | 3/2014 | Cathey |
| 8,670,222 B2 | 3/2014 | Rothkopf |
| 8,676,238 B2 | 3/2014 | Marcellino et al. |
| 8,686,947 B2 | 4/2014 | Wine |
| 8,698,744 B2 | 4/2014 | Wehrenberg et al. |
| 8,717,852 B2 | 5/2014 | Cohen et al. |
| 8,744,418 B2 | 6/2014 | Novet |
| 8,754,831 B2 | 6/2014 | Kollin et al. |
| D709,874 S | 7/2014 | Aumiller et al. |
| D709,875 S | 7/2014 | Aumiller et al. |
| 8,764,653 B2 | 7/2014 | Kaminska et al. |
| 8,784,271 B2 | 7/2014 | Brumback et al. |
| 8,795,138 B1 | 8/2014 | Yeh et al. |
| 8,795,174 B2 | 8/2014 | Manicka et al. |
| 8,797,748 B2 | 8/2014 | Dabov |

(56) References Cited

U.S. PATENT DOCUMENTS

| | | | |
|---|---|---|---|
| 8,888,701 B2 | 11/2014 | LeBoeuf et al. | |
| 8,947,441 B2 | 2/2015 | Hodgins et al. | |
| 8,947,864 B2 | 2/2015 | Whitt et al. | |
| 8,956,293 B2 | 2/2015 | McCombie et al. | |
| 8,956,294 B2 | 2/2015 | McCombie et al. | |
| 8,957,858 B2 | 2/2015 | Osborn et al. | |
| 8,961,413 B2 | 2/2015 | Teller et al. | |
| 8,961,414 B2 | 2/2015 | Teller et al. | |
| 8,961,415 B2 | 2/2015 | LeBoeuf et al. | |
| 2001/0020937 A1 | 9/2001 | Rosenberg et al. | |
| 2001/0049470 A1 | 12/2001 | Mault et al. | |
| 2001/0056225 A1 | 12/2001 | DeVito | |
| 2002/0022774 A1 | 2/2002 | Karnieli | |
| 2002/0027164 A1 | 3/2002 | Mault et al. | |
| 2002/0047867 A1 | 4/2002 | Mault et al. | |
| 2002/0049482 A1 | 4/2002 | Fabian et al. | |
| 2002/0062069 A1 | 5/2002 | Mault | |
| 2002/0084415 A1* | 7/2002 | Kawano | G01N 21/03 250/339.09 |
| 2002/0109600 A1 | 8/2002 | Mault et al. | |
| 2002/0124017 A1 | 9/2002 | Mault | |
| 2002/0133378 A1 | 9/2002 | Mault et al. | |
| 2002/0156351 A1 | 10/2002 | Sagel | |
| 2002/0167863 A1 | 11/2002 | Davis et al. | |
| 2003/0060692 A1* | 3/2003 | Ruchti | A61B 5/0064 600/310 |
| 2003/0065257 A1 | 4/2003 | Mault et al. | |
| 2003/0076983 A1 | 4/2003 | Cox | |
| 2003/0083596 A1 | 5/2003 | Kramer et al. | |
| 2003/0152607 A1 | 8/2003 | Mault | |
| 2003/0163354 A1 | 8/2003 | Shamoun | |
| 2003/0165799 A1 | 9/2003 | Bisogno | |
| 2003/0208110 A1 | 11/2003 | Mault et al. | |
| 2003/0214408 A1 | 11/2003 | Grajales et al. | |
| 2003/0219513 A1 | 11/2003 | Gordon | |
| 2004/0034289 A1 | 2/2004 | Teller et al. | |
| 2004/0073142 A1 | 4/2004 | Takeuchi et al. | |
| 2004/0100376 A1 | 5/2004 | Lye et al. | |
| 2004/0133081 A1 | 7/2004 | Teller et al. | |
| 2004/0152957 A1 | 8/2004 | Stivoric et al. | |
| 2004/0164959 A1 | 8/2004 | Rosenberg et al. | |
| 2005/0004436 A1 | 1/2005 | Nissila et al. | |
| 2005/0008994 A1 | 1/2005 | Bisogno | |
| 2005/0011367 A1 | 1/2005 | Crow | |
| 2005/0014111 A1 | 1/2005 | Matson | |
| 2005/0113649 A1 | 5/2005 | Bergantino | |
| 2005/0113650 A1 | 5/2005 | Pacione et al. | |
| 2005/0131288 A1 | 6/2005 | Turner et al. | |
| 2005/0146419 A1 | 7/2005 | Porter | |
| 2005/0153052 A1 | 7/2005 | Williams et al. | |
| 2005/0184148 A1 | 8/2005 | Perlman | |
| 2005/0247213 A1 | 11/2005 | Slilaty | |
| 2005/0263160 A1 | 12/2005 | Utley et al. | |
| 2005/0266385 A1 | 12/2005 | Bisogno | |
| 2005/0283096 A1 | 12/2005 | Chau et al. | |
| 2006/0015016 A1 | 1/2006 | Thornton | |
| 2006/0031102 A1 | 2/2006 | Teller et al. | |
| 2006/0036395 A1 | 2/2006 | Shaya et al. | |
| 2006/0064037 A1 | 3/2006 | Shalon et al. | |
| 2006/0074716 A1 | 4/2006 | Tilles et al. | |
| 2006/0122468 A1 | 6/2006 | Tavor | |
| 2006/0122474 A1 | 6/2006 | Teller et al. | |
| 2006/0189853 A1 | 8/2006 | Brown | |
| 2006/0197670 A1 | 9/2006 | Breibart | |
| 2006/0229504 A1 | 10/2006 | Johnson | |
| 2006/0263750 A1 | 11/2006 | Gordon | |
| 2006/0264730 A1 | 11/2006 | Stivoric et al. | |
| 2006/0284979 A1 | 12/2006 | Clarkson | |
| 2007/0021979 A1 | 1/2007 | Cosentino et al. | |
| 2007/0027366 A1 | 2/2007 | Osburn | |
| 2007/0028453 A1 | 2/2007 | Crow | |
| 2007/0030339 A1 | 2/2007 | Findlay et al. | |
| 2007/0050058 A1 | 3/2007 | Zuziak et al. | |
| 2007/0059672 A1 | 3/2007 | Shaw | |
| 2007/0089335 A1 | 4/2007 | Smith et al. | |
| 2007/0098856 A1 | 5/2007 | LePine | |
| 2007/0100666 A1 | 5/2007 | Stivoric et al. | |
| 2007/0106129 A1 | 5/2007 | Srivathsa et al. | |
| 2007/0106145 A1 | 5/2007 | Kim et al. | |
| 2007/0173703 A1 | 7/2007 | Lee et al. | |
| 2007/0173705 A1 | 7/2007 | Teller et al. | |
| 2007/0179355 A1 | 8/2007 | Rosen | |
| 2007/0208593 A1 | 9/2007 | Hercules | |
| 2008/0019122 A1 | 1/2008 | Kramer | |
| 2008/0036737 A1 | 2/2008 | Hernandez-Rebollar | |
| 2008/0060853 A1 | 3/2008 | Davidson et al. | |
| 2008/0137486 A1 | 6/2008 | Czarnek et al. | |
| 2008/0140444 A1 | 6/2008 | Karkanias et al. | |
| 2008/0161654 A1 | 7/2008 | Teller et al. | |
| 2008/0161655 A1 | 7/2008 | Teller et al. | |
| 2008/0167535 A1 | 7/2008 | Andre et al. | |
| 2008/0167536 A1 | 7/2008 | Teller et al. | |
| 2008/0167537 A1 | 7/2008 | Teller et al. | |
| 2008/0167538 A1 | 7/2008 | Teller et al. | |
| 2008/0167539 A1 | 7/2008 | Teller et al. | |
| 2008/0171920 A1 | 7/2008 | Teller et al. | |
| 2008/0171921 A1 | 7/2008 | Teller et al. | |
| 2008/0171922 A1 | 7/2008 | Teller et al. | |
| 2008/0223890 A1 | 9/2008 | Tecchiolli et al. | |
| 2008/0255955 A1 | 10/2008 | Simons-Nikolova | |
| 2008/0262557 A1 | 10/2008 | Brown | |
| 2008/0267444 A1 | 10/2008 | Simons-Nikolova | |
| 2008/0270324 A1 | 10/2008 | Allard et al. | |
| 2008/0275309 A1 | 11/2008 | Stivoric et al. | |
| 2008/0276461 A1 | 11/2008 | Gold | |
| 2008/0287751 A1 | 11/2008 | Stivoric et al. | |
| 2008/0287817 A1 | 11/2008 | Stivoric et al. | |
| 2009/0012433 A1* | 1/2009 | Fernstrom | A61B 5/1112 600/593 |
| 2009/0112800 A1 | 4/2009 | Athsani | |
| 2009/0163241 A1 | 6/2009 | Vossoughi et al. | |
| 2009/0171180 A1 | 7/2009 | Pering et al. | |
| 2009/0176526 A1 | 7/2009 | Altman | |
| 2009/0177068 A1 | 7/2009 | Stivoric et al. | |
| 2009/0191514 A1 | 7/2009 | Barnow | |
| 2009/0219159 A1 | 9/2009 | Morgenstern | |
| 2009/0253105 A1 | 10/2009 | Lepine | |
| 2009/0261987 A1 | 10/2009 | Sun | |
| 2010/0000292 A1 | 1/2010 | Karabacak et al. | |
| 2010/0003647 A1 | 1/2010 | Brown et al. | |
| 2010/0010326 A1* | 1/2010 | Dalvi | A61B 5/14532 600/322 |
| 2010/0049004 A1 | 2/2010 | Edman et al. | |
| 2010/0049010 A1 | 2/2010 | Goldreich | |
| 2010/0055271 A1 | 3/2010 | Miller-Kovach et al. | |
| 2010/0055652 A1 | 3/2010 | Miller-Kovach et al. | |
| 2010/0055653 A1 | 3/2010 | Miller-Kovach et al. | |
| 2010/0057564 A1 | 3/2010 | Godsey et al. | |
| 2010/0062119 A1 | 3/2010 | Miller-Kovach et al. | |
| 2010/0062402 A1 | 3/2010 | Miller-Kovach et al. | |
| 2010/0069731 A1* | 3/2010 | Harra | A61B 5/05 600/365 |
| 2010/0079291 A1 | 4/2010 | Kroll et al. | |
| 2010/0080875 A1 | 4/2010 | Miller-Kovach et al. | |
| 2010/0109876 A1 | 5/2010 | Schmid-Schonbein et al. | |
| 2010/0111383 A1 | 5/2010 | Boushey et al. | |
| 2010/0125176 A1 | 5/2010 | Hyde et al. | |
| 2010/0125177 A1 | 5/2010 | Hyde et al. | |
| 2010/0125178 A1 | 5/2010 | Hyde et al. | |
| 2010/0125179 A1 | 5/2010 | Hyde et al. | |
| 2010/0125180 A1 | 5/2010 | Hyde et al. | |
| 2010/0125181 A1 | 5/2010 | Hyde et al. | |
| 2010/0125417 A1 | 5/2010 | Hyde et al. | |
| 2010/0125418 A1 | 5/2010 | Hyde et al. | |
| 2010/0125419 A1 | 5/2010 | Hyde et al. | |
| 2010/0125420 A1 | 5/2010 | Hyde et al. | |
| 2010/0173269 A1 | 7/2010 | Puri et al. | |
| 2010/0176166 A1 | 7/2010 | Siagri et al. | |
| 2010/0191155 A1 | 7/2010 | Kim et al. | |
| 2010/0194573 A1 | 8/2010 | Hoover et al. | |
| 2010/0205209 A1 | 8/2010 | Jokinen | |
| 2010/0209897 A1 | 8/2010 | Utley et al. | |
| 2010/0228160 A1 | 9/2010 | Schweizer | |
| 2010/0240962 A1 | 9/2010 | Contant | |

(56) References Cited

U.S. PATENT DOCUMENTS

| | | |
|---|---|---|
| 2010/0284135 A1 | 11/2010 | Tecchiolli et al. |
| 2010/0291515 A1 | 11/2010 | Pinnisi et al. |
| 2010/0332571 A1 | 12/2010 | Healey et al. |
| 2011/0053128 A1 | 3/2011 | Alman |
| 2011/0077471 A1 | 3/2011 | King |
| 2011/0087137 A1 | 4/2011 | Hanoun |
| 2011/0124978 A1 | 5/2011 | Williams |
| 2011/0125063 A1* | 5/2011 | Shalon ............... A61B 5/0006 600/590 |
| 2011/0182477 A1 | 7/2011 | Tamrakar et al. |
| 2011/0184247 A1 | 7/2011 | Contant et al. |
| 2011/0205851 A1 | 8/2011 | Harris |
| 2011/0218407 A1 | 9/2011 | Haberman et al. |
| 2011/0276312 A1* | 11/2011 | Shalon ............... A61B 5/11 702/187 |
| 2011/0281245 A1 | 11/2011 | Mansour |
| 2011/0288379 A1 | 11/2011 | Wu |
| 2011/0318717 A1 | 12/2011 | Adamowicz |
| 2012/0004883 A1 | 1/2012 | Vock et al. |
| 2012/0015432 A1 | 1/2012 | Adler |
| 2012/0016210 A1 | 1/2012 | Kim et al. |
| 2012/0021388 A1 | 1/2012 | Arbuckle et al. |
| 2012/0031805 A1 | 2/2012 | Stolarczyk |
| 2012/0053426 A1 | 3/2012 | Webster et al. |
| 2012/0055718 A1 | 3/2012 | Chen |
| 2012/0056509 A1 | 3/2012 | Anderson et al. |
| 2012/0071731 A1 | 3/2012 | Gottesman |
| 2012/0072233 A1 | 3/2012 | Hanlon et al. |
| 2012/0077154 A1 | 3/2012 | Highet et al. |
| 2012/0078071 A1 | 3/2012 | Bohm et al. |
| 2012/0082013 A1 | 4/2012 | Yeung et al. |
| 2012/0083669 A1 | 4/2012 | Abujbara |
| 2012/0083705 A1 | 4/2012 | Yuen et al. |
| 2012/0083714 A1 | 4/2012 | Yuen et al. |
| 2012/0083715 A1 | 4/2012 | Yuen et al. |
| 2012/0083716 A1 | 4/2012 | Yuen et al. |
| 2012/0084053 A1 | 4/2012 | Yuen et al. |
| 2012/0084054 A1 | 4/2012 | Yuen et al. |
| 2012/0096405 A1 | 4/2012 | Seo |
| 2012/0115111 A1 | 5/2012 | Lepine |
| 2012/0126983 A1 | 5/2012 | Breibart |
| 2012/0086366 A1 | 6/2012 | Anderson et al. |
| 2012/0144912 A1 | 6/2012 | Kates et al. |
| 2012/0149996 A1 | 6/2012 | Stivoric et al. |
| 2012/0150074 A1 | 6/2012 | Yanev et al. |
| 2012/0150327 A1 | 6/2012 | Altman et al. |
| 2012/0170801 A1 | 7/2012 | De Oliveira et al. |
| 2012/0178065 A1 | 7/2012 | Naghavi et al. |
| 2012/0179020 A1 | 7/2012 | Wekell |
| 2012/0179665 A1 | 7/2012 | Baarman et al. |
| 2012/0188158 A1 | 7/2012 | Tan et al. |
| 2012/0191052 A1 | 7/2012 | Rao |
| 2012/0194418 A1 | 8/2012 | Osterhout et al. |
| 2012/0194419 A1 | 8/2012 | Osterhout et al. |
| 2012/0194420 A1 | 8/2012 | Osterhout et al. |
| 2012/0194549 A1 | 8/2012 | Osterhout et al. |
| 2012/0194550 A1 | 8/2012 | Osterhout et al. |
| 2012/0194551 A1 | 8/2012 | Osterhout et al. |
| 2012/0194552 A1 | 8/2012 | Osterhout et al. |
| 2012/0194553 A1 | 8/2012 | Osterhout et al. |
| 2012/0200488 A1 | 8/2012 | Osterhout et al. |
| 2012/0200499 A1 | 8/2012 | Osterhout et al. |
| 2012/0200601 A1 | 8/2012 | Osterhout et al. |
| 2012/0201725 A1 | 8/2012 | Imran |
| 2012/0203081 A1 | 8/2012 | Leboeuf et al. |
| 2012/0206322 A1 | 8/2012 | Osterhout et al. |
| 2012/0206323 A1 | 8/2012 | Osterhout et al. |
| 2012/0206334 A1 | 8/2012 | Osterhout et al. |
| 2012/0206335 A1 | 8/2012 | Osterhout et al. |
| 2012/0206485 A1 | 8/2012 | Osterhout et al. |
| 2012/0212398 A1 | 8/2012 | Border et al. |
| 2012/0212399 A1 | 8/2012 | Border et al. |
| 2012/0212400 A1 | 8/2012 | Border et al. |
| 2012/0212406 A1 | 8/2012 | Osterhout et al. |
| 2012/0212414 A1 | 8/2012 | Osterhout et al. |
| 2012/0214594 A1 | 8/2012 | Kirovski et al. |
| 2012/0218172 A1 | 8/2012 | Border et al. |
| 2012/0218301 A1 | 8/2012 | Miller |
| 2012/0221495 A1 | 8/2012 | Landers |
| 2012/0226471 A1 | 9/2012 | Yuen et al. |
| 2012/0226472 A1 | 9/2012 | Yuen et al. |
| 2012/0231960 A1 | 9/2012 | Osterfeld et al. |
| 2012/0235647 A1 | 9/2012 | Chung et al. |
| 2012/0235883 A1 | 9/2012 | Border et al. |
| 2012/0235885 A1 | 9/2012 | Miller et al. |
| 2012/0235886 A1 | 9/2012 | Border et al. |
| 2012/0235887 A1 | 9/2012 | Border et al. |
| 2012/0235900 A1 | 9/2012 | Border et al. |
| 2012/0236030 A1 | 9/2012 | Border et al. |
| 2012/0236031 A1 | 9/2012 | Haddick et al. |
| 2012/0239304 A1 | 9/2012 | Hayter et al. |
| 2012/0242626 A1 | 9/2012 | Hu |
| 2012/0242678 A1 | 9/2012 | Border et al. |
| 2012/0242697 A1 | 9/2012 | Border et al. |
| 2012/0242698 A1 | 9/2012 | Haddick et al. |
| 2012/0245472 A1 | 9/2012 | Rulkov et al. |
| 2012/0245714 A1 | 9/2012 | Mueller et al. |
| 2012/0245716 A1 | 9/2012 | Srinivasan et al. |
| 2012/0249797 A1 | 10/2012 | Haddick et al. |
| 2012/0251079 A1 | 10/2012 | Meschter et al. |
| 2012/0253485 A1 | 10/2012 | Weast et al. |
| 2012/0254749 A1 | 10/2012 | Downs et al. |
| 2012/0258433 A1 | 10/2012 | Hope et al. |
| 2012/0258804 A1 | 10/2012 | Ahmed |
| 2012/0264446 A1 | 10/2012 | Xie et al. |
| 2012/0268592 A1 | 10/2012 | Aragones et al. |
| 2012/0271121 A1 | 10/2012 | Della Torre et al. |
| 2012/0274508 A1 | 11/2012 | Brown et al. |
| 2012/0274554 A1 | 11/2012 | Kinoshita et al. |
| 2012/0277638 A1 | 11/2012 | Skelton et al. |
| 2012/0283855 A1 | 11/2012 | Hoffman et al. |
| 2012/0289867 A1 | 11/2012 | Kasama |
| 2012/0290109 A1 | 11/2012 | Engelberg et al. |
| 2012/0295233 A1 | 11/2012 | Cooperman |
| 2012/0302855 A1 | 11/2012 | Kamath et al. |
| 2012/0303638 A1 | 11/2012 | Bousamra et al. |
| 2012/0310971 A1 | 12/2012 | Tran |
| 2012/0313746 A1 | 12/2012 | Rahman et al. |
| 2012/0313776 A1 | 12/2012 | Utter |
| 2012/0315609 A1 | 12/2012 | Miller-Kovach et al. |
| 2012/0315986 A1 | 12/2012 | Walling |
| 2012/0316406 A1 | 12/2012 | Rahman et al. |
| 2012/0316455 A1 | 12/2012 | Rahman et al. |
| 2012/0316456 A1 | 12/2012 | Rahman et al. |
| 2012/0316458 A1 | 12/2012 | Rahman et al. |
| 2012/0316471 A1 | 12/2012 | Rahman et al. |
| 2012/0316661 A1 | 12/2012 | Rahman et al. |
| 2012/0316793 A1 | 12/2012 | Jung et al. |
| 2012/0316896 A1 | 12/2012 | Rahman et al. |
| 2012/0316932 A1 | 12/2012 | Rahman et al. |
| 2012/0317167 A1 | 12/2012 | Rahman et al. |
| 2012/0317430 A1 | 12/2012 | Rahman et al. |
| 2012/0321759 A1 | 12/2012 | Marinkovich et al. |
| 2012/0323346 A1 | 12/2012 | Ashby et al. |
| 2012/0323496 A1 | 12/2012 | Burroughs et al. |
| 2012/0326863 A1 | 12/2012 | Johnson et al. |
| 2012/0326873 A1 | 12/2012 | Utter |
| 2012/0330109 A1 | 12/2012 | Tran |
| 2012/0330112 A1 | 12/2012 | Lamego et al. |
| 2012/0331201 A1 | 12/2012 | Rondel |
| 2013/0002435 A1 | 1/2013 | Utter |
| 2013/0002538 A1 | 1/2013 | Mooring et al. |
| 2013/0002545 A1 | 1/2013 | Heinrich et al. |
| 2013/0002724 A1 | 1/2013 | Heinrich et al. |
| 2013/0004923 A1 | 1/2013 | Utter |
| 2013/0005534 A1 | 1/2013 | Rosenbaum |
| 2013/0006063 A1 | 1/2013 | Wang |
| 2013/0006125 A1 | 1/2013 | Kroll et al. |
| 2013/0006583 A1 | 1/2013 | Weast et al. |
| 2013/0006802 A1 | 1/2013 | Dillahunt et al. |
| 2013/0006807 A1 | 1/2013 | Bai et al. |
| 2013/0009783 A1 | 1/2013 | Tran |
| 2013/0012788 A1 | 1/2013 | Horseman |
| 2013/0012789 A1 | 1/2013 | Horseman |

(56) References Cited

U.S. PATENT DOCUMENTS

| | | |
|---|---|---|
| 2013/0012790 A1 | 1/2013 | Horseman |
| 2013/0012802 A1 | 1/2013 | Horseman |
| 2013/0013331 A1 | 1/2013 | Horseman |
| 2013/0016070 A1 | 1/2013 | Starner et al. |
| 2013/0017789 A1 | 1/2013 | Chi et al. |
| 2013/0021226 A1 | 1/2013 | Bell |
| 2013/0021658 A1 | 1/2013 | Miao et al. |
| 2013/0027060 A1 | 1/2013 | Tralshawala et al. |
| 2013/0029807 A1 | 1/2013 | Amsel |
| 2013/0035563 A1 | 2/2013 | Angelides |
| 2013/0035575 A1 | 2/2013 | Mayou et al. |
| 2013/0035865 A1 | 2/2013 | Mayou et al. |
| 2013/0038056 A1 | 2/2013 | Donelan et al. |
| 2013/0041272 A1 | 2/2013 | Guillen et al. |
| 2013/0041617 A1 | 2/2013 | Pease et al. |
| 2013/0043997 A1 | 2/2013 | Cosentino et al. |
| 2013/0044042 A1 | 2/2013 | Olsson et al. |
| 2013/0044215 A1 | 2/2013 | Rothkopf |
| 2013/0045037 A1 | 2/2013 | Schaffer |
| 2013/0045467 A1 | 2/2013 | Kamen |
| 2013/0048737 A1 | 2/2013 | Baym et al. |
| 2013/0048738 A1 | 2/2013 | Baym et al. |
| 2013/0049931 A1 | 2/2013 | Baym et al. |
| 2013/0049932 A1 | 2/2013 | Baym et al. |
| 2013/0049933 A1 | 2/2013 | Baym et al. |
| 2013/0049934 A1 | 2/2013 | Baym et al. |
| 2013/0052623 A1 | 2/2013 | Thukral et al. |
| 2013/0053655 A1 | 2/2013 | Castellanos |
| 2013/0053661 A1 | 2/2013 | Alberth et al. |
| 2013/0053990 A1 | 2/2013 | Ackland |
| 2013/0063342 A1 | 3/2013 | Chen et al. |
| 2013/0065680 A1 | 3/2013 | Zavadsky et al. |
| 2013/0069780 A1 | 3/2013 | Tran et al. |
| 2013/0069931 A1 | 3/2013 | Wilson et al. |
| 2013/0069985 A1 | 3/2013 | Wong et al. |
| 2013/0070338 A1 | 3/2013 | Gupta et al. |
| 2013/0072765 A1 | 3/2013 | Kahn et al. |
| 2013/0072807 A1 | 3/2013 | Tran |
| 2013/0073254 A1 | 3/2013 | Yuen et al. |
| 2013/0073255 A1 | 3/2013 | Yuen et al. |
| 2013/0073368 A1 | 3/2013 | Squires |
| 2013/0080113 A1 | 3/2013 | Yuen et al. |
| 2013/0083003 A1 | 4/2013 | Perez et al. |
| 2013/0083009 A1 | 4/2013 | Geisner et al. |
| 2013/0083064 A1 | 4/2013 | Geisner et al. |
| 2013/0083496 A1 | 4/2013 | Franklin et al. |
| 2013/0090565 A1 | 4/2013 | Quy |
| 2013/0091454 A1 | 4/2013 | Papa et al. |
| 2013/0095459 A1 | 4/2013 | Tran |
| 2013/0096843 A1 | 4/2013 | Yuen et al. |
| 2013/0100027 A1 | 4/2013 | Wang et al. |
| 2013/0102387 A1 | 4/2013 | Barsoum et al. |
| 2013/0103416 A1 | 4/2013 | Amigo et al. |
| 2013/0105565 A1 | 5/2013 | Kamprath |
| 2013/0106603 A1 | 5/2013 | Weast et al. |
| 2013/0106684 A1 | 5/2013 | Weast et al. |
| 2013/0107674 A1 | 5/2013 | Gossweiler et al. |
| 2013/0108993 A1 | 5/2013 | Katz |
| 2013/0109947 A1 | 5/2013 | Wood |
| 2013/0110011 A1 | 5/2013 | McGregor et al. |
| 2013/0110264 A1 | 5/2013 | Weast et al. |
| 2013/0110549 A1 | 5/2013 | Laan et al. |
| 2013/0111611 A1 | 5/2013 | Barros Almedo et al. |
| 2013/0113933 A1 | 5/2013 | Boushey et al. |
| 2013/0115583 A1 | 5/2013 | Gordon et al. |
| 2013/0115584 A1 | 5/2013 | Gordon et al. |
| 2013/0115717 A1 | 5/2013 | Guo et al. |
| 2013/0116525 A1 | 5/2013 | Heller et al. |
| 2013/0117040 A1 | 5/2013 | James et al. |
| 2013/0117041 A1 | 5/2013 | Boyce et al. |
| 2013/0117135 A1 | 5/2013 | Riddiford et al. |
| 2013/0119255 A1 | 5/2013 | Dickinson et al. |
| 2013/0120106 A1 | 5/2013 | Cauwels et al. |
| 2013/0120459 A1 | 5/2013 | Dickinson et al. |
| 2013/0154838 A1 | 6/2013 | Alameh et al. |
| 2013/0169560 A1 | 7/2013 | Cederlund et al. |
| 2013/0173171 A1 | 7/2013 | Drysdale et al. |
| 2013/0190903 A1 | 7/2013 | Balakrishnan et al. |
| 2013/0191741 A1 | 7/2013 | Dickinson et al. |
| 2013/0198694 A1 | 8/2013 | Rahman et al. |
| 2013/0201098 A1 | 8/2013 | Schilit et al. |
| 2013/0217978 A1 | 8/2013 | Ma |
| 2013/0222137 A1 | 8/2013 | Alameh et al. |
| 2013/0222271 A1 | 8/2013 | Alberth et al. |
| 2013/0234924 A1 | 9/2013 | Janefalkar et al. |
| 2013/0241823 A1 | 9/2013 | Pryor |
| 2013/0275058 A1 | 10/2013 | Awed |
| 2013/0285577 A1 | 10/2013 | O'Brien et al. |
| 2013/0289886 A1* | 10/2013 | Ricks .................. G06F 19/3475 702/19 |
| 2013/0328842 A1 | 12/2013 | Barnhoefer et al. |
| 2013/0347102 A1 | 12/2013 | Shi |
| 2014/0002402 A1 | 1/2014 | Kang et al. |
| 2014/0006994 A1 | 1/2014 | Koch et al. |
| 2014/0007010 A1 | 1/2014 | Blom |
| 2014/0012154 A1 | 1/2014 | Mazar |
| 2014/0025973 A1 | 1/2014 | Schillings et al. |
| 2014/0028688 A1 | 1/2014 | Houjou et al. |
| 2014/0031081 A1 | 1/2014 | Vossoughi et al. |
| 2014/0031698 A1 | 1/2014 | Moon et al. |
| 2014/0035794 A1 | 2/2014 | Chen |
| 2014/0035875 A2 | 2/2014 | Theimer et al. |
| 2014/0036643 A1 | 2/2014 | Messenger et al. |
| 2014/0042406 A1 | 2/2014 | Degner et al. |
| 2014/0047864 A1 | 2/2014 | Lo et al. |
| 2014/0051948 A1 | 2/2014 | LeBoeuf et al. |
| 2014/0055338 A1 | 2/2014 | Ryan |
| 2014/0055483 A1 | 2/2014 | Pance et al. |
| 2014/0056452 A1 | 2/2014 | Moss et al. |
| 2014/0058220 A1 | 2/2014 | LeBoeuf et al. |
| 2014/0061486 A1 | 3/2014 | Bao et al. |
| 2014/0062469 A1 | 3/2014 | Yang et al. |
| 2014/0062510 A1 | 3/2014 | Cok et al. |
| 2014/0062511 A1 | 3/2014 | Cok et al. |
| 2014/0066124 A1 | 3/2014 | Novet |
| 2014/0087685 A1 | 3/2014 | Kellond et al. |
| 2014/0094675 A1 | 4/2014 | Luna et al. |
| 2014/0097765 A1 | 4/2014 | Hussain et al. |
| 2014/0098067 A1 | 4/2014 | Yang et al. |
| 2014/0104197 A1 | 4/2014 | Khosravy et al. |
| 2014/0104241 A1 | 4/2014 | Huppi et al. |
| 2014/0105086 A1 | 4/2014 | Chhabra et al. |
| 2014/0112371 A1 | 4/2014 | Yang et al. |
| 2014/0112510 A1 | 4/2014 | Yang et al. |
| 2014/0112556 A1 | 4/2014 | Kalinli-Akbacak |
| 2014/0113592 A1 | 4/2014 | Wu et al. |
| 2014/0116085 A1 | 5/2014 | Lam |
| 2014/0120839 A1 | 5/2014 | Lam |
| 2014/0120983 A1 | 5/2014 | Lam |
| 2014/0121982 A1 | 5/2014 | Rauhala |
| 2014/0122102 A1 | 5/2014 | Utter |
| 2014/0125480 A1 | 5/2014 | Utter |
| 2014/0125481 A1 | 5/2014 | Utter |
| 2014/0125493 A1 | 5/2014 | Utter |
| 2014/0127649 A1 | 5/2014 | Utter |
| 2014/0128754 A1 | 5/2014 | Luna et al. |
| 2014/0129007 A1 | 5/2014 | Utter |
| 2014/0129008 A1 | 5/2014 | Utter |
| 2014/0129239 A1 | 5/2014 | Utter |
| 2014/0129242 A1 | 5/2014 | Utter |
| 2014/0129243 A1 | 5/2014 | Utter |
| 2014/0132481 A1 | 5/2014 | Bell et al. |
| 2014/0138637 A1 | 5/2014 | Yang et al. |
| 2014/0139340 A1 | 5/2014 | Yang et al. |
| 2014/0139422 A1 | 5/2014 | Mistry et al. |
| 2014/0139454 A1 | 5/2014 | Mistry et al. |
| 2014/0139486 A1 | 5/2014 | Mistry et al. |
| 2014/0139637 A1 | 5/2014 | Mistry et al. |
| 2014/0143678 A1 | 5/2014 | Mistry et al. |
| 2014/0145150 A1 | 5/2014 | De Jong et al. |
| 2014/0146987 A1 | 5/2014 | Pontoppidan et al. |
| 2014/0156084 A1 | 6/2014 | Rahman et al. |
| 2014/0159903 A1 | 6/2014 | Tropper et al. |
| 2014/0160078 A1 | 6/2014 | Seo et al. |

(56) References Cited

U.S. PATENT DOCUMENTS

| | | |
|---|---|---|
| 2014/0164541 A1 | 6/2014 | Marcellino |
| 2014/0166850 A1 | 6/2014 | Zheng |
| 2014/0166867 A1 | 6/2014 | Shiu et al. |
| 2014/0167619 A1 | 6/2014 | Land et al. |
| 2014/0167973 A1 | 6/2014 | Letchner et al. |
| 2014/0171132 A1 | 6/2014 | Ziemianska et al. |
| 2014/0171146 A1 | 6/2014 | Ma et al. |
| 2014/0171759 A1 | 6/2014 | White et al. |
| 2014/0171809 A1 | 6/2014 | Bonutti et al. |
| 2014/0172313 A1* | 6/2014 | Rayner ............... G06F 19/3431 702/19 |
| 2014/0176335 A1 | 6/2014 | Brumback et al. |
| 2014/0176346 A1 | 6/2014 | Brumback et al. |
| 2014/0176422 A1 | 6/2014 | Brumback et al. |
| 2014/0176439 A1 | 6/2014 | Keller et al. |
| 2014/0176475 A1 | 6/2014 | Myers et al. |
| 2014/0180020 A1 | 6/2014 | Stivoric et al. |
| 2014/0180021 A1 | 6/2014 | Stivoric et al. |
| 2014/0180022 A1 | 6/2014 | Stivoric et al. |
| 2014/0180023 A1 | 6/2014 | Stivoric et al. |
| 2014/0180137 A1 | 6/2014 | Stivoric et al. |
| 2014/0180582 A1 | 6/2014 | Pontarelli et al. |
| 2014/0180595 A1 | 6/2014 | Brumback et al. |
| 2014/0181715 A1 | 6/2014 | Axelrod et al. |
| 2014/0181741 A1 | 6/2014 | Apacible et al. |
| 2014/0183342 A1 | 7/2014 | Shedletsky et al. |
| 2014/0191926 A1 | 7/2014 | Mathew et al. |
| 2014/0192002 A1 | 7/2014 | Herz et al. |
| 2014/0195166 A1 | 7/2014 | Rahman et al. |
| 2014/0197317 A1 | 7/2014 | Yang et al. |
| 2014/0206289 A1 | 7/2014 | Rahman et al. |
| 2014/0206323 A1 | 7/2014 | Scorcioni |
| 2014/0206327 A1 | 7/2014 | Ziemianska et al. |
| 2014/0206328 A1 | 7/2014 | Varoglu et al. |
| 2014/0206954 A1 | 7/2014 | Yuen et al. |
| 2014/0210640 A1 | 7/2014 | Rahman et al. |
| 2014/0210708 A1 | 7/2014 | Simmons et al. |
| 2014/0218856 A1 | 8/2014 | Raff et al. |
| 2014/0221020 A1 | 8/2014 | Xie et al. |
| 2014/0221789 A1* | 8/2014 | Pacione ............... A61B 5/0022 600/301 |
| 2014/0222734 A1 | 8/2014 | Stivoric et al. |
| 2014/0223165 A1 | 8/2014 | Rahman et al. |
| 2014/0228649 A1 | 8/2014 | Rayner et al. |
| 2014/0232516 A1 | 8/2014 | Stivoric et al. |
| 2014/0240103 A1 | 8/2014 | Lake et al. |
| 2014/0240122 A1 | 8/2014 | Roberts et al. |
| 2014/0240144 A1 | 8/2014 | Rahman et al. |
| 2014/0240223 A1 | 8/2014 | Lake et al. |
| 2014/0244505 A1 | 8/2014 | Kim |
| 2014/0245161 A1 | 8/2014 | Yuen et al. |
| 2014/0245213 A1 | 8/2014 | Gardenfors et al. |
| 2014/0253412 A1 | 9/2014 | Blaich et al. |
| 2014/0267024 A1 | 9/2014 | Keller et al. |
| 2014/0267543 A1 | 9/2014 | Kerger et al. |
| 2014/0269224 A1 | 9/2014 | Huh et al. |
| 2014/0273848 A1 | 9/2014 | Rahman et al. |
| 2014/0275812 A1 | 9/2014 | Stivoric et al. |
| 2014/0275813 A1 | 9/2014 | Stivoric et al. |
| 2014/0278139 A1 | 9/2014 | Hong et al. |
| 2014/0281956 A1 | 9/2014 | Anderson et al. |
| 2014/0288878 A1 | 9/2014 | Donaldson |
| 2014/0295811 A1 | 10/2014 | Uusitalo et al. |
| 2014/0303523 A1 | 10/2014 | Hong et al. |
| 2014/0310643 A1 | 10/2014 | Karmanenko et al. |
| 2014/0313154 A1 | 10/2014 | Bengtsson et al. |
| 2014/0318699 A1 | 10/2014 | Longinotti-Buitoni et al. |
| 2014/0320381 A1 | 10/2014 | Enzmann et al. |
| 2014/0320435 A1 | 10/2014 | Modarres et al. |
| 2014/0320858 A1 | 10/2014 | Goldring et al. |
| 2014/0321245 A1 | 10/2014 | Sharpe |
| 2014/0323826 A1 | 10/2014 | Wilder-Smith et al. |
| 2014/0325448 A1 | 10/2014 | Han et al. |
| 2014/0328041 A1 | 11/2014 | Rothkopf et al. |
| 2014/0329561 A1 | 11/2014 | Kim et al. |
| 2014/0342782 A1 | 11/2014 | Karmanenko et al. |
| 2014/0347491 A1 | 11/2014 | Connor |
| 2014/0347963 A1 | 11/2014 | El Alej et al. |
| 2014/0349257 A1 | 11/2014 | Connor |
| 2014/0351770 A1 | 11/2014 | Abercrombie |
| 2014/0362020 A1 | 12/2014 | Rothkopf et al. |
| 2014/0368336 A1 | 12/2014 | Felix |
| 2014/0372940 A1 | 12/2014 | Cauwels et al. |
| 2014/0373338 A1 | 12/2014 | O'Connor et al. |
| 2014/0375465 A1 | 12/2014 | Fenuccio et al. |
| 2014/0378786 A1 | 12/2014 | Hong et al. |
| 2014/0378872 A1 | 12/2014 | Hong et al. |
| 2015/0006290 A1 | 1/2015 | Tomkins et al. |
| 2015/0026647 A1 | 1/2015 | Park et al. |
| 2015/0029227 A1 | 1/2015 | Park et al. |
| 2015/0031964 A1 | 1/2015 | Bly et al. |
| 2015/0031967 A1 | 1/2015 | LeBoeuf et al. |
| 2015/0036138 A1 | 2/2015 | Watson et al. |
| 2015/0040282 A1 | 2/2015 | Longinotti-Buitoni et al. |
| 2015/0043770 A1 | 2/2015 | Chen et al. |
| 2015/0045634 A1 | 2/2015 | Goldberg et al. |
| 2015/0057964 A1 | 2/2015 | Albinali |
| 2015/0065893 A1 | 3/2015 | Ye |
| 2015/0091781 A1 | 4/2015 | Yu et al. |
| 2015/0105671 A1 | 4/2015 | Shibuya et al. |
| 2015/0105678 A1 | 4/2015 | Takei et al. |
| 2015/0113473 A1 | 4/2015 | Otsuka et al. |
| 2015/0123647 A1 | 5/2015 | Gisby et al. |
| 2015/0126169 A1 | 5/2015 | Kerger et al. |
| 2015/0126873 A1 | 5/2015 | Connor |
| 2015/0148632 A1 | 5/2015 | Benaron |
| 2015/0148636 A1 | 5/2015 | Benaron |
| 2015/0168365 A1 | 6/2015 | Connor |
| 2015/0302160 A1 | 10/2015 | Muthukumar et al. |
| 2015/0339946 A1* | 11/2015 | Pacione ............... A61B 5/411 434/236 |
| 2016/0026767 A1* | 1/2016 | Sarrafzadeh ........... G06Q 50/22 600/586 |
| 2016/0117952 A1* | 4/2016 | Simons-Nikolova ................... A61B 5/1123 434/127 |

FOREIGN PATENT DOCUMENTS

| | | |
|---|---|---|
| WO | WO2005029242 | 6/2005 |
| WO | WO2010070645 | 6/2010 |
| WO | WO2012170584 | 12/2012 |

* cited by examiner

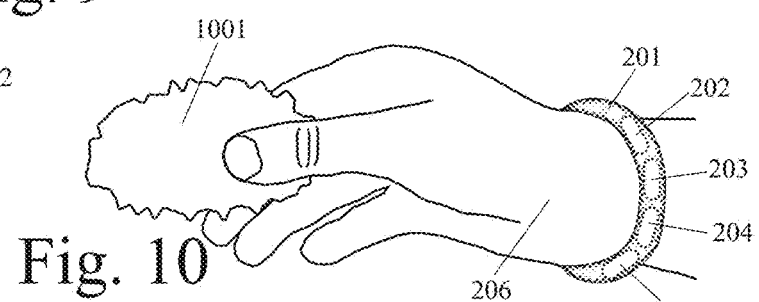
Fig. 9
Fig. 10
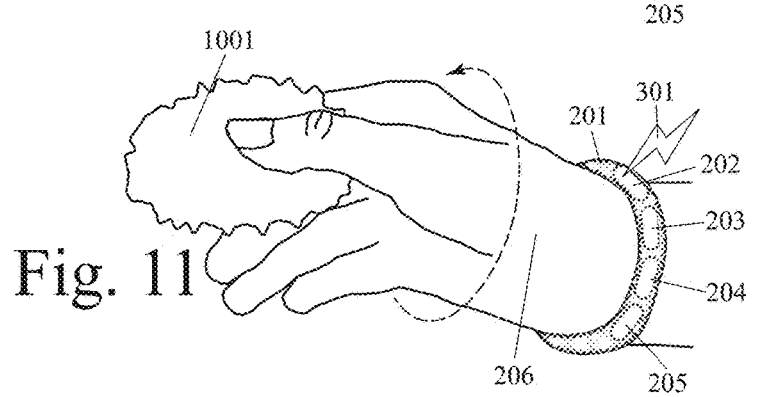
Fig. 11
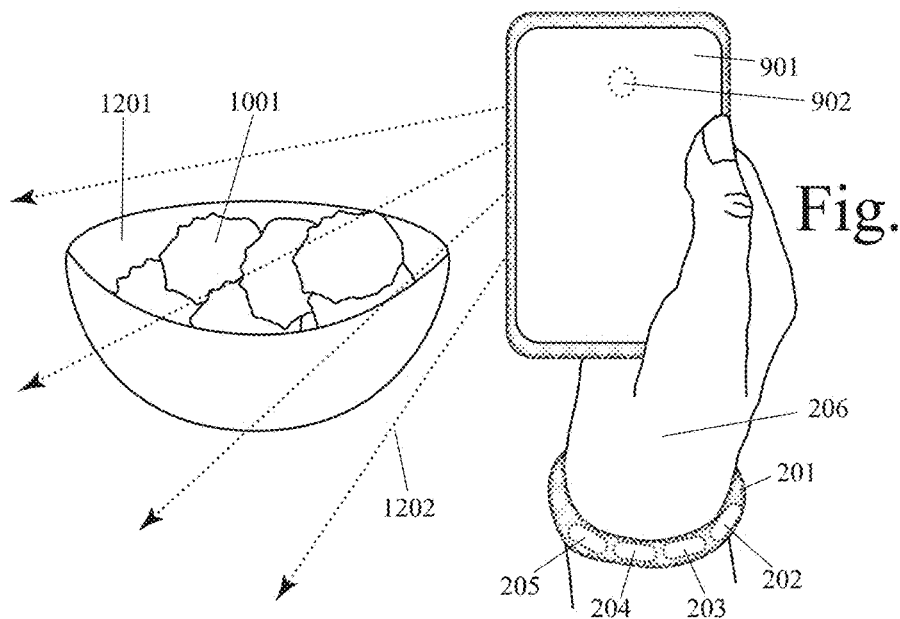
Fig. 12

WEARABLE SPECTROSCOPIC SENSOR TO MEASURE FOOD CONSUMPTION BASED ON INTERACTION BETWEEN LIGHT AND THE HUMAN BODY

CROSS-REFERENCE TO RELATED APPLICATIONS

This patent application: (a) is a continuation in part of U.S. patent application Ser. No. 13/901,131 by Robert A. Connor entitled "Smart Watch and Food Utensil for Monitoring Food Consumption" filed on May 23, 2013; (b) is a continuation in part of U.S. patent application Ser. No. 14/071,112 by Robert A. Connor entitled "Wearable Spectroscopy Sensor to Measure Food Consumption" filed on Nov. 4, 2013; (c) is a continuation in part of U.S. patent application Ser. No. 14/623,337 by Robert A. Connor entitled "Wearable Computing Devices and Methods for the Wrist and/or Forearm" filed on Feb. 16, 2015; and (d) claims the priority benefit of U.S. provisional patent application 62/245,311 by Robert A. Connor entitled "Wearable Device for the Arm with Close-Fitting Biometric Sensors" filed on Oct. 23, 2015. The entire contents of these related applications are incorporated herein by reference.

FEDERALLY SPONSORED RESEARCH

Not Applicable

SEQUENCE LISTING OR PROGRAM

Not Applicable

BACKGROUND

Field of Invention

This invention relates to measuring a person's food consumption with a wearable spectroscopic sensor based on analysis of light reflected from or having passed through body tissue.

Introduction

The United States population has some of the highest prevalence rates of obese and overweight people in the world. Further, these rates have increased dramatically during recent decades. In the late 1990's, around one in five Americans was obese. Today, that figure has increased to around one in three. It is estimated that around one in five American children is now obese. The prevalence of Americans who are generally overweight is estimated to be as high as two out of three. Despite the considerable effort that has been focused on developing new approaches for preventing and treating obesity, the problem is growing. There remains a serious unmet need for new ways to help people to moderate their consumption of unhealthy food, better manage their energy balance, and lose weight in a healthy and sustainable manner.

Since many factors contribute to obesity, good approaches to weight management are comprehensive in nature. Proper nutrition and management of caloric intake are key parts of a comprehensive approach to weight management. Consumption of "junk food" that is high in simple sugars and saturated fats has increased dramatically during the past couple decades, particularly in the United States. This has contributed significantly to the obesity epidemic. For many people, relying on willpower and dieting is not sufficient to moderate their consumption of unhealthy "junk food." The results are dire consequences for their health and well-being.

The invention that is disclosed herein directly addresses this problem by helping a person to monitor and measure their nutritional intake. The invention that is disclosed herein is an innovative technology that can be a key part of a comprehensive system to help a person reduce their consumption of unhealthy types and/or quantities of food.

REVIEW OF THE RELATED ART

The AIRO wristband was generally described in an article entitled "Wearable Tech Company Revolutionizes Health Monitoring" by Nicole Fallon in Business News Daily on Oct. 29, 2013. This article generally describes the wristband as "using light wavelengths to monitor nutrition, exercise, stress and sleep patterns," but does provide many details on device structure or function. A search did not show any related patent applications. The company appears to have subsequently refunded money contributed to it by crowd-funding supporters and does not appear to have launched the wristband yet.

The TellSpec sensor, which raised funds via Indiegogo in 2014, appears to be intended as a hand-held device which uses spectroscopy to measure the nutrient composition of food. The company does not appear to have launched the device yet. Their U.S. patent application 20150036138 by Watson et al. entitled "Analyzing and Correlating Spectra, Identifying Samples and Their Ingredients, and Displaying Related Personalized Information" describes obtaining two spectra from the same sample under two different conditions at about the same time for comparison. Further, this application describes how computing correlations between data related to food and ingredient consumption by users and personal log data (and user entered feedback, user interaction data or personal information related to those users) can be used to detect foods to which a user may be allergic.

The SCiO molecular sensor by Consumer Physics appears to use near-infrared spectroscopy to analyze the composition of nearby objects. It may be used to analyze the composition of food. U.S. patent 20140320858 by Goldring et al. (who appears to be part of the Consumer Physics team) is entitled "Low-Cost Spectrometry System for End-User Food Analysis" and discloses a compact spectrometer that can be used in mobile devices such as cellular telephones.

Application WO 2010/070645 by Einav et al. entitled "Method and System for Monitoring Eating Habits" discloses an apparatus for monitoring eating patterns which can include a spectrometer for detecting nutritious properties of a bite of food. U.S. Pat. No. 8,355,875 by Hyde et al. entitled "Food Content Detector" discloses a utensil, which can include a spectroscopy sensor, for portioning a foodstuff into first and second portions. U.S. patent application 20140061486 by Bao et al. entitled "Spectrometer Devices" discloses a spectrometer including a plurality of semiconductor nanocrystals which can serve as a personal UV exposure tracking device. Other applications include a smartphone or medical device wherein a semiconductor nanocrystal spectrometer is integrated.

U.S. patent application 20150148632 by Benaron entitled "Calorie Monitoring Sensor and Method for Cell Phones, Smart Watches, Occupancy Sensors, and Wearables" discloses a sensor for calorie monitoring in mobile devices, wearables, security, illumination, photography, and other devices and systems which uses an optional phosphor-coated broadband white LED to produce broadband light, which is then transmitted along with any ambient light to a target such as the ear, face, or wrist of a living subject. Calorie monitoring systems incorporating the sensor as well as methods are also disclosed. U.S. patent application 20150148636 by Benaron entitled "Ambient Light Method for Cell Phones, Smart Watches, Occupancy Sensors, and Wearables" discloses a sensor for respiratory and metabolic monitoring in mobile devices, wearables, security, illumination, photography, and other devices and systems that uses a broadband ambient light. The sensor can provide identifying features of type or status of a tissue target, such calories used or ingested.

U.S. patent application 20150302160 by Muthukumar et al. entitled "Method and Apparatus for Monitoring Diet and Activity" discloses a method and apparatus including a camera and spectroscopy module for determining food types and amounts.

U.S. patent application 20140347491 by Connor entitled "Smart Watch and Food-Imaging Member for Monitoring Food Consumption" discloses a device and system for monitoring a person's food consumption comprising: a wearable sensor that automatically collects data to detect probable eating events; an imaging member that is used by the person to take pictures of food wherein the person is prompted to take pictures of food when an eating event is detected by the wearable sensor; and a data analysis component that analyzes these food pictures to estimate the types and amounts of foods, ingredients, nutrients, and/or calories that are consumed by the person.

U.S. patent application 2014034925 by Connor entitled "Smart Watch and Food Utensil for Monitoring Food Consumption" discloses a device and system for monitoring a person's food consumption comprising: a wearable sensor that automatically collects data to detect eating events; a smart food utensil, probe, or dish that collects data concerning the chemical composition of food which the person is prompted to use when an eating event is detected; and a data analysis component that analyzes chemical composition data to estimate the types and amounts of foods, ingredients, nutrients, and/or calories consumed by the person.

U.S. patent application 20150126873 by Connor entitled "Wearable Spectroscopy Sensor to Measure Food Consumption" discloses a wearable device to measure a person's consumption of selected types of food, ingredients, or nutrients comprising: a housing that is configured to be worn on the person's wrist, arm, hand, or finger; a spectroscopy sensor that collects data concerning light energy reflected from the person's body and/or absorbed by the person's body, wherein this data is used to measure the person's consumption of selected types of food, ingredients, or nutrients; a data processing unit; and a power source.

U.S. patent application 20150168365 by Connor entitled "Caloric Intake Measuring System Using Spectroscopic and 3D Imaging Analysis" discloses a caloric intake measuring system comprising: a spectroscopic sensor that collects data concerning light that is absorbed by or reflected from food, wherein this food is to be consumed by a person, and wherein this data is used to estimate the composition of this food; and an imaging device that takes images of this food from different angles, wherein these images from different angles are used to estimate the quantity of this food.

SUMMARY OF THIS INVENTION

This invention is a wearable device to measure a person's food consumption based on the interaction between light energy and the person's body. In an example, a wearable device to measure a person's food consumption based on the interaction between light energy and the person's body can comprise: at least one wearable spectroscopic sensor that collects data concerning the spectrum of light energy reflected from a person's body tissue, absorbed by the person's body tissue, and/or having passed through the person's body tissue, wherein this data is used to measure the person's consumption of one or more selected types of food, ingredients, and/or nutrients; a data processing unit; and a power source. A wearable spectroscopic sensor is not a panacea for good nutrition, energy balance, and weight management. However, such a device can be a useful part of an overall strategy for encouraging good nutrition, energy balance, weight management, and health improvement.

In an example, this invention can be embodied in a finger ring, smart watch, wrist band, wrist bracelet, armlet, cuff, or sleeve. In an example, a spectroscopic sensor can be selected from the group consisting of: white light spectroscopic sensor, infrared light spectroscopic sensor, near-infrared light spectroscopic sensor, and ultraviolet light spectroscopic sensor. In an example, a spectroscopic sensor can be selected from the group consisting of spectrometer, spectrophotometer, ion mobility spectroscopic sensor, and backscattering spectrometry sensor. In an example, measured types of food, ingredients, and/or nutrients can be selected from the group consisting of: food that is high in simple carbohydrates; food that is high in simple sugars; food that is high in saturated or trans fat; fried food; food that is high in Low Density Lipoprotein (LDL); and food that is high in sodium. Food can include consumable liquids, such as water or other beverages, as well as solid food.

In an example, this device can further comprise a first spectroscopic sensor at a first location on the device and a second spectroscopic sensor at a second location on the device, wherein the distance along a circumference of the device from the first location to the second location is at least a quarter inch. In an example, a spectroscopic sensor can be moved along the circumference of the device. In an example, moving the spectroscopic sensor along the circumference of the device changes the location of the spectroscopic sensor relative to the person's body.

In an example, a device can further comprise a first spectroscopic sensor which is configured to project a beam of light onto the surface of a person's body at a first angle and a second spectroscopic sensor which is configured to project a beam of light onto the surface of the person's body at a second angle, wherein the first angle differs from the second angle by at least 10 degrees. In an example, a spectroscopic sensor can be rotated relative to the rest of the device. In an example, rotating the spectroscopic sensor changes the angle at which the spectroscopic sensor projects a beam of light onto the surface of the person's body.

In an example, a device can further comprise an elastic member filled with a flowable substance (such as a gas or liquid) and this elastic member pushes a spectroscopic sensor toward the surface of the person's body. In an example, a device can further comprise an elastic strap (or band) spanning less than 60% of the circumference of the device and this elastic strap (or band) pushes or pulls a spectroscopic sensor toward the surface of the person's body. In an example, a device can further comprise a spring which pushes or pulls a spectroscopic sensor toward the surface of the person's body.

In an example, this device can further comprise: an attachment member which is configured to span at least 60% of the circumference of a person's wrist and/or arm, wherein this attachment member further comprises a first elastic portion with a first elasticity level, a second elastic portion with a second elasticity level, and an inelastic portion with a third elasticity level, wherein the third elasticity level is less than each of the first and second elasticity levels; and an enclosure which is connected between the first and second elastic portions, wherein a spectroscopic sensor is part of the enclosure.

INTRODUCTION TO THE FIGURES

FIGS. 1 through 4 show an example of a device to monitor a person's food consumption comprising a smart watch (with a motion sensor) to detect eating events and a smart spoon (with a built-in chemical composition sensor), wherein the person is prompted to use the smart spoon to eat food when the smart watch detects an eating event.

FIGS. 9 through 12 show an example of a device to monitor a person's food consumption comprising a smart watch (with a motion sensor) to detect eating events and a smart phone (with a built-in camera), wherein the person is prompted to use the smart phone to take pictures of food when the smart watch detects an eating event.

Figure 45:
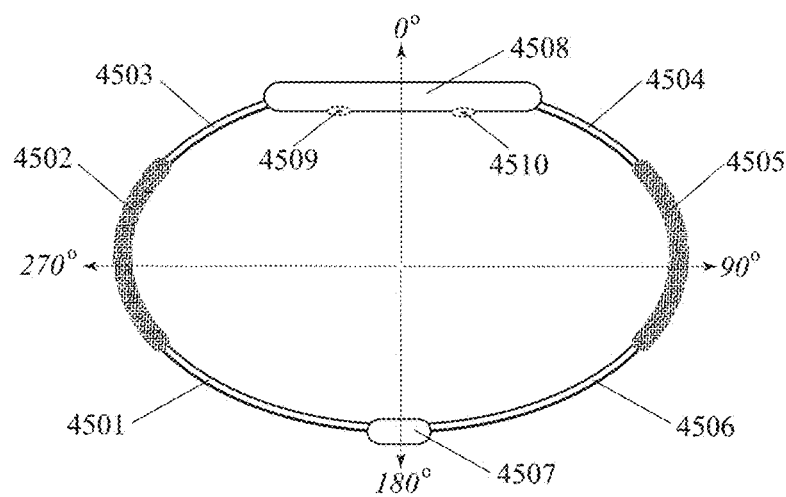

FIG. 45 shows a device with one or more anterior inelastic portions which are configured to span the anterior (upper) surface of a person's arm, one or more posterior inelastic portions which are configured to span the posterior (lower) surface of a person's arm, one or more elastic portions which connect the anterior and posterior inelastic portions, an enclosure which is configured to be worn on the anterior (upper) portion of the arm, and one or more spectroscopic sensors which are part of the enclosure.

Figure 46:
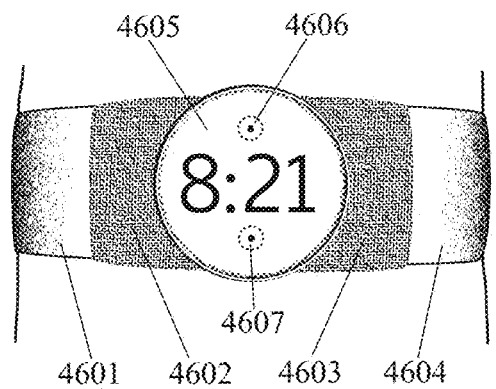

FIG. 46 shows a device with one or more spectroscopic sensors in an enclosure and an attachment member which holds the enclosure on a person's arm, wherein there are rectangular, rounded rectangular, or plano-concave elastic portions of the attachment member which are connected to the enclosure and wherein the rest of the attachment member is inelastic.

Figure 47:
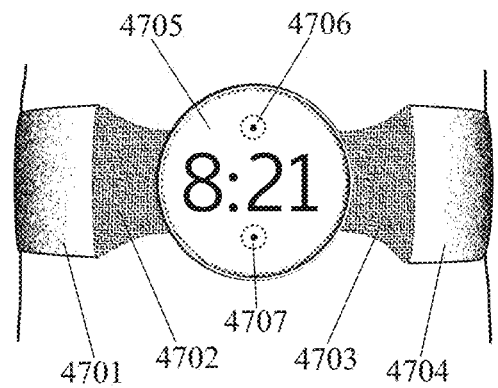

FIG. 47 shows a device with elastic portions which are tapered as they approach an enclosure.

Figure 48:
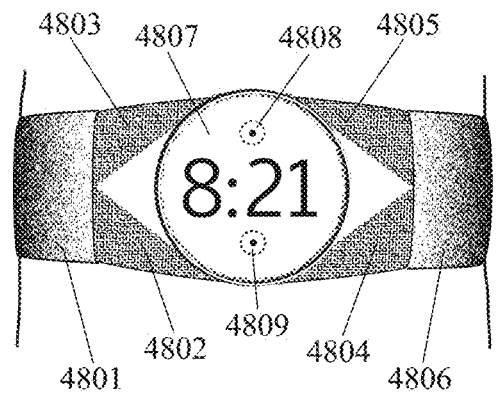

FIG. 48 shows a device with four elastic portions, two connected to each side of an enclosure.

Figure 49:
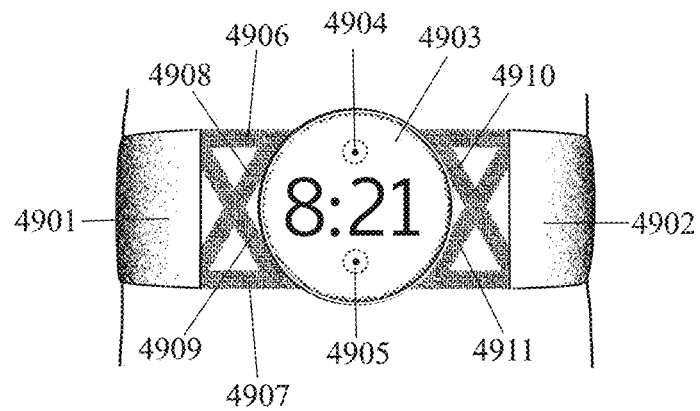

FIG. 49 shows a device with two elastic portions on each side of an enclosure which criss-cross each other, forming an "X" on each side of the enclosure.

Figure 50:
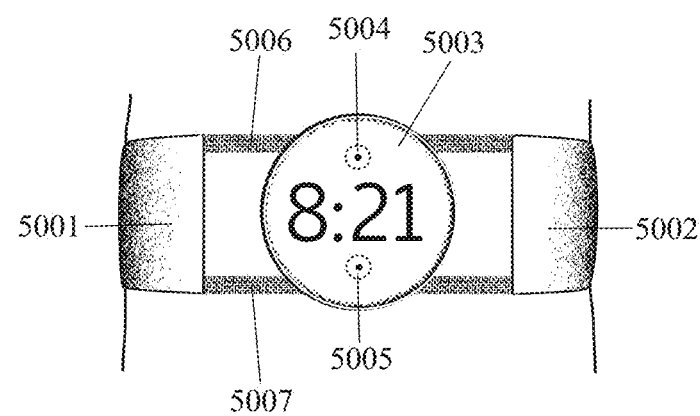

FIG. 50 shows a device with two parallel elastic bands (or straps) connected to an enclosure.

Figure 51:
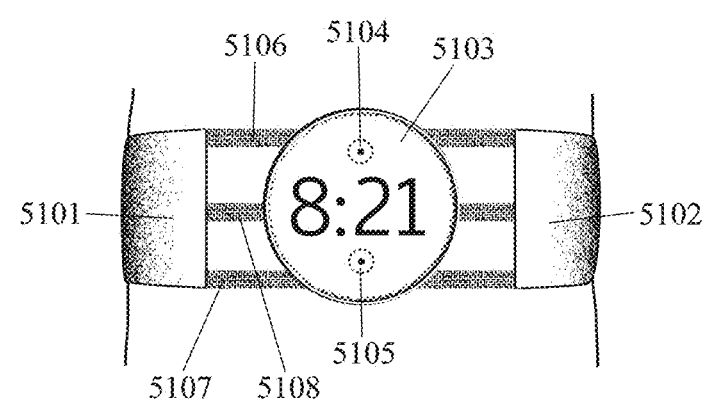

FIG. 51 shows a device with three parallel elastic bands (or straps) connected to an enclosure.

Figure 52:
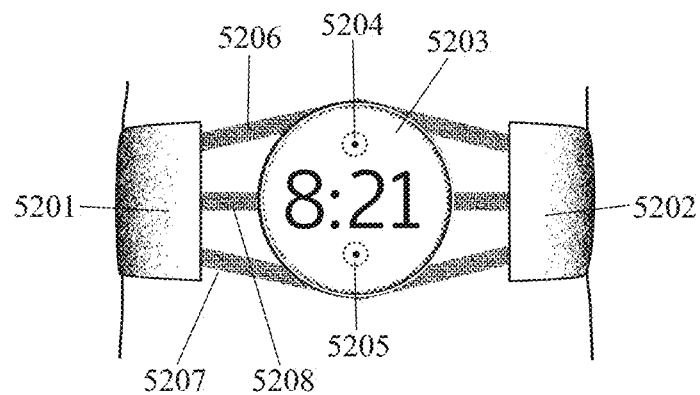

FIG. 52 shows a device wherein three elastic bands (or straps) connected to an enclosure are not parallel.

Figure 53:
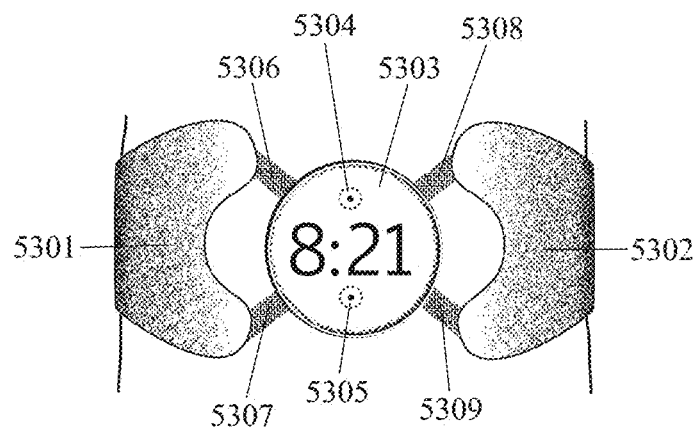

FIG. 53 shows a device with spectroscopic sensors in an enclosure, wherein the enclosure is suspended on the surface of the arm by four elastic bands, and wherein each elastic band is individually connected to one of four points which are equally-spaced around the circumference of the enclosure.

Figure 54:
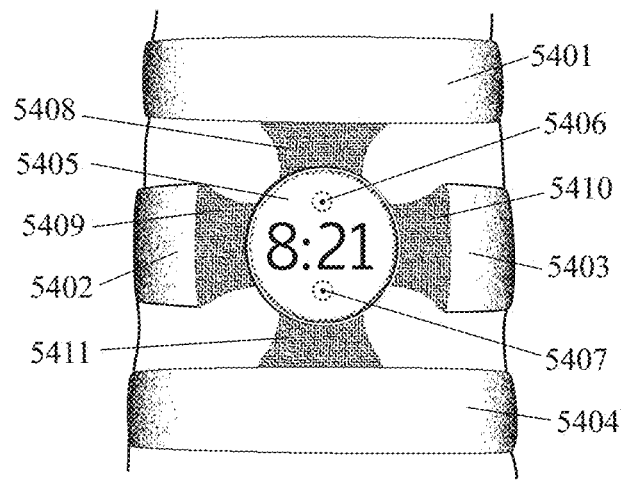

FIG. 54 shows a device with spectroscopic sensors in an enclosure, wherein the enclosure is suspended on the surface of the arm by four elastic suspension bands (or straps) connected to three parallel attachment bands or straps which encircle the arm.

Figure 55:
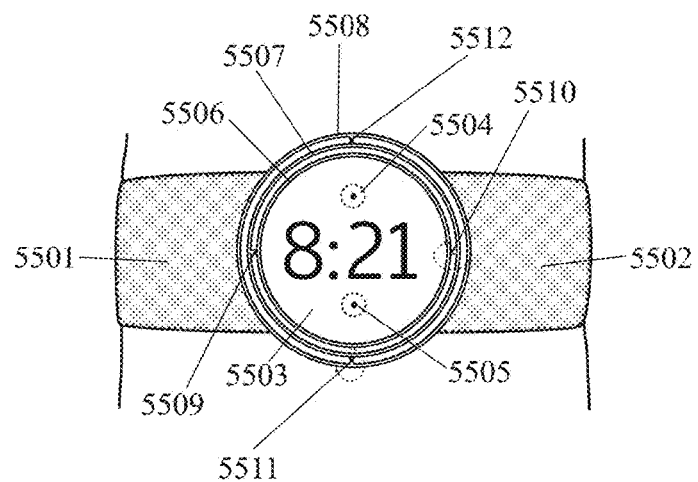

FIG. 55 shows a device with a gimbaled enclosure with one or more spectroscopic sensors.

Figure 56:
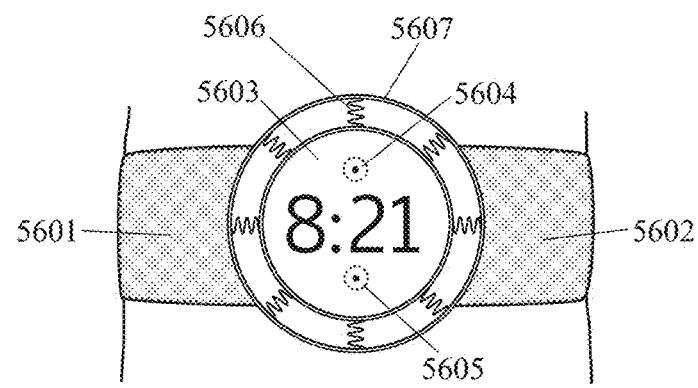

FIG. 56 shows a device with an enclosure containing one or more spectroscopic sensors, wherein this enclosure is suspended by a radial plurality of elastic (and/or stretchable or springy) suspension members which connect to locations on the circumference of the enclosure.

Figure 57:
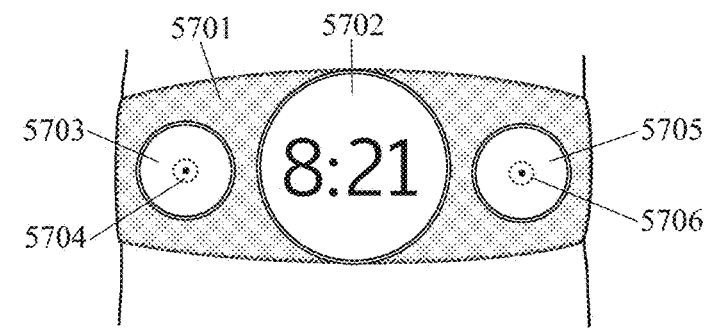

FIG. 57 shows a device with two arcuate enclosures which contain spectroscopic sensors.

Figure 58:
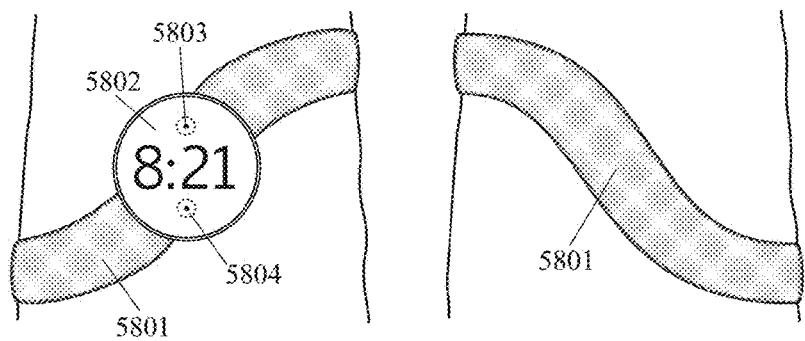

FIG. 58 shows a device with an arcuate enclosure to which a strap or band is connected diagonally.

Figure 59:
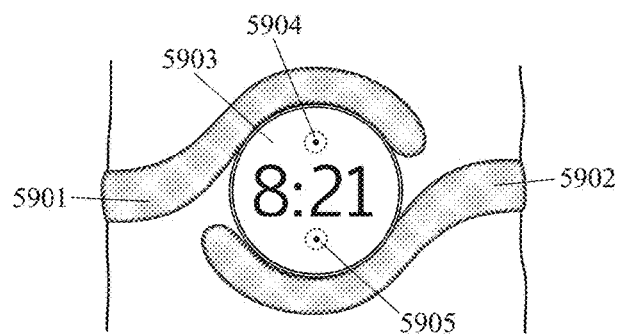

FIG. 59 shows a device that looks like two "gummi worms" crawling in a symmetric manner around portions of the circumference of an enclosure.

Figure 60:
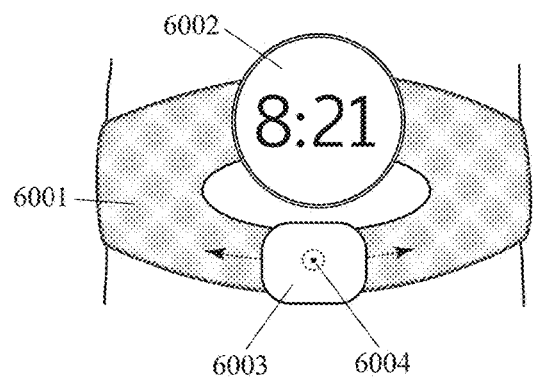

FIG. 60 shows a device with a bifurcating band, wherein one branch of the band is connected to a display screen and the other branch of the band is connected to a circumferentially-sliding enclosure which contains one or more spectroscopic sensors.

Figure 61:
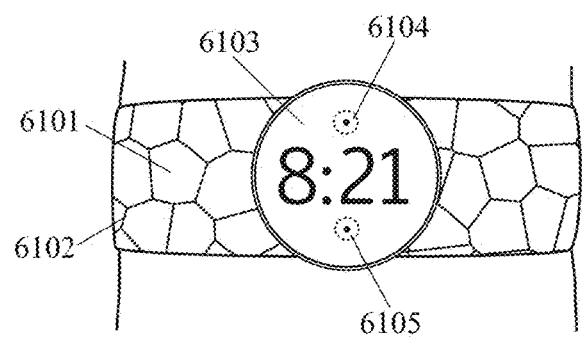

FIG. 61 shows a device with a plurality of various-shaped (rigid) polygons which are inter-connected by flexible strips and/or joints, an enclosure which is connected to the attachment member, and one or more spectroscopic sensors which are part of the enclosure.

Figure 62:
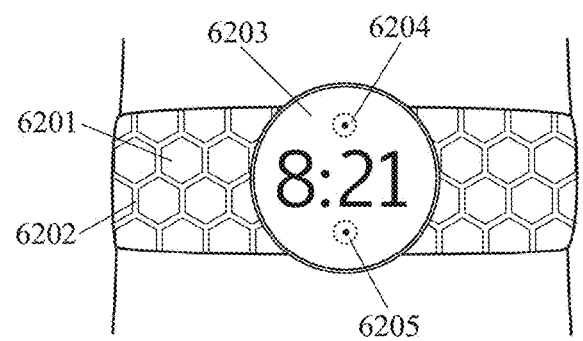

FIG. 62 shows a device with a honeycomb configuration.

Figure 63:
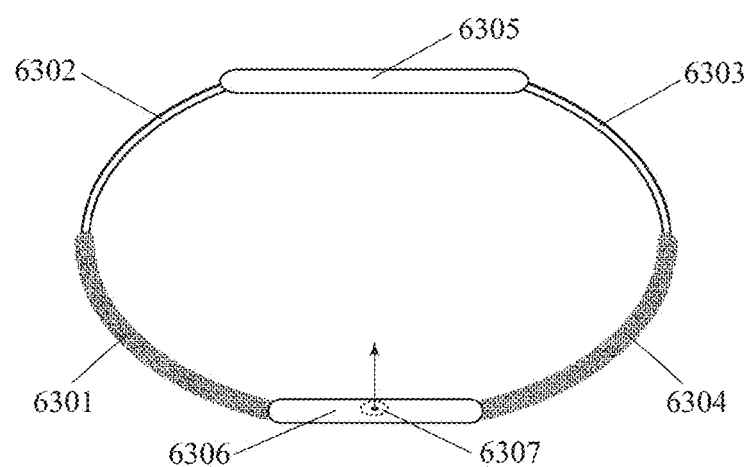

FIG. 63 shows a device comprising: an attachment member which spans at least 60% of the circumference of a person's arm, wherein this attachment member further comprises a first portion with a first elasticity level spanning completely or partially (clockwise) between the 9 o'clock and 3 o'clock (or 270-degree and 90-degree) positions around the device circumference and a second portion with a second elasticity level spanning completely or partially (clockwise) between the 3 o'clock and 9 o'clock (or 90-degree and 270-degree) positions around the device circumference, wherein the second elasticity level is greater than the first elasticity level; a display screen which is part of (or connected to) the first portion of the attachment member; an enclosure which is part of (or connected to) the second portion of the attachment member; and one or more spectroscopic sensors which are configured to collect data concerning arm tissue and which are part of (or attached to) the enclosure.

Figure 64:
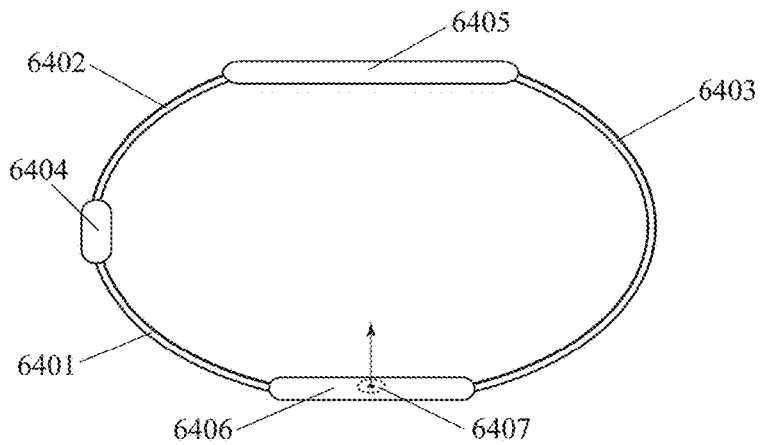

FIG. 64 shows a device with one or more spectroscopic sensors which are located on a portion of the device which is diametrically-opposite from the portion of the device which includes a display screen and there is a connector on the device between the sensors and the screen.

Figure 65:
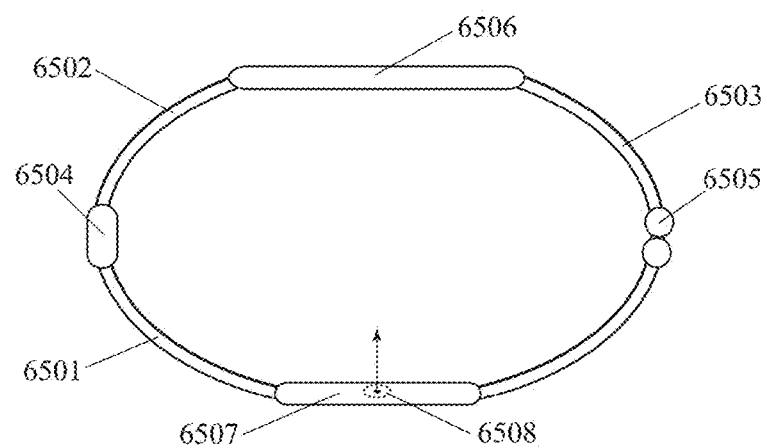

FIG. 65 shows a device with a "clam shell" design.

Figure 66:
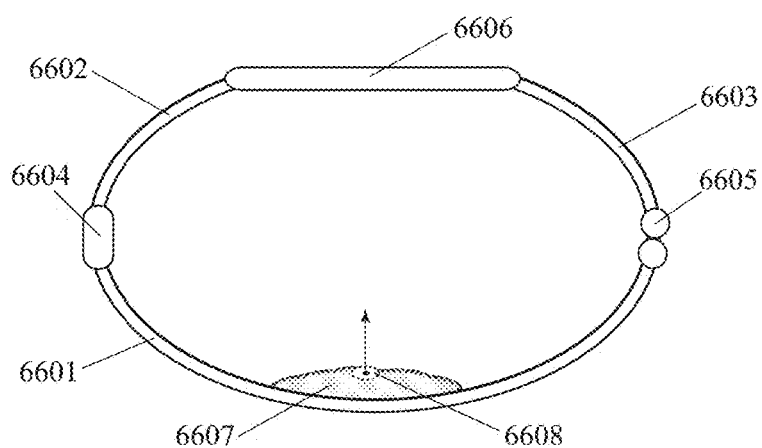

FIG. 66 shows a device with a "clam shell" design and a spectroscopic sensor on the center-facing surface of a compressible member.

Figure 67:
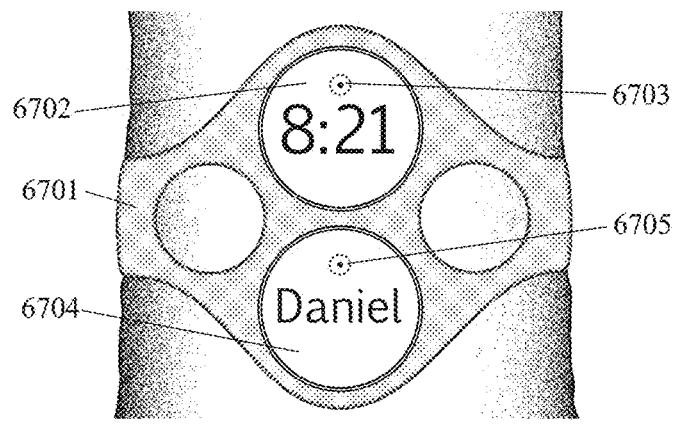

FIG. 67 shows a device with proximal and distal arcuate display screens which are attached to a person's arm by a band, wherein the band has one hole on each side of a virtual line connecting the centers of the two displays.

Figure 68:
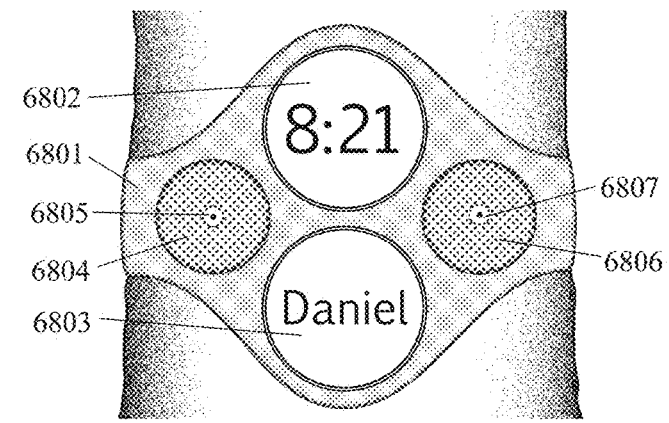

FIG. 68 shows a device with: proximal and distal arcuate display screens; and right and left side enclosures with spectroscopic sensors.

Figure 69:
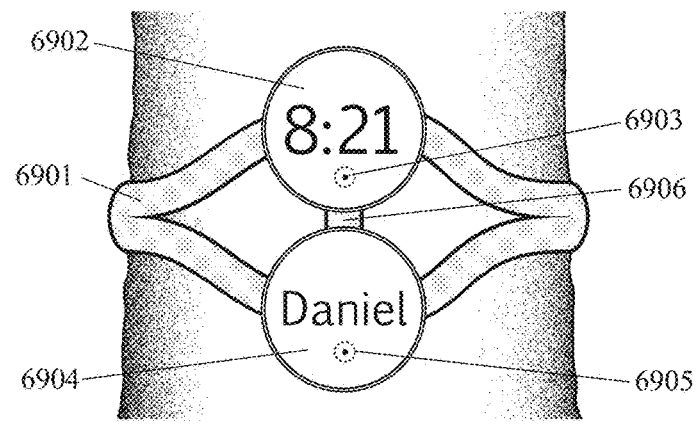

FIG. 69 shows a device with proximal and distal arcuate display screens which are circumferentially attached to an arm by a bifurcating band (or strap) and also connected to each other by a band (or strap) along the central longitudinal axis of the anterior (upper) surface of the arm.

Figure 70:
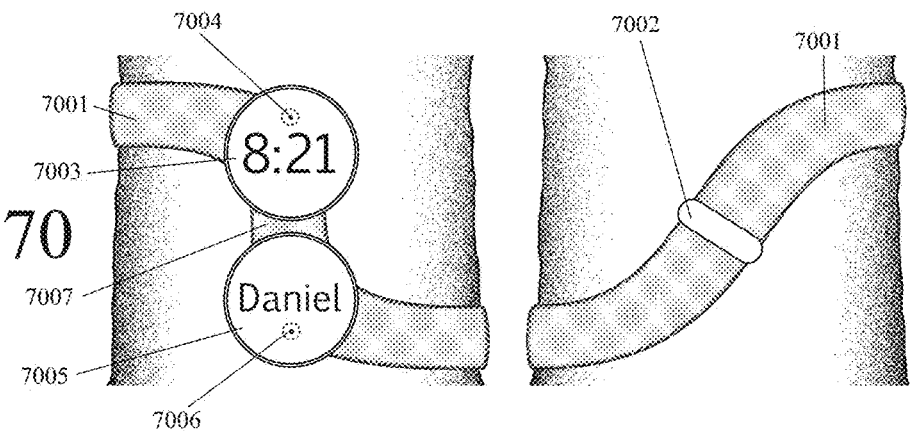

FIG. 70 shows a device with proximal and distal arcuate display screens which are attached to a person's arm by a band with an "S"-shaped portion spanning the anterior (upper) portion of the arm.

Figure 71:
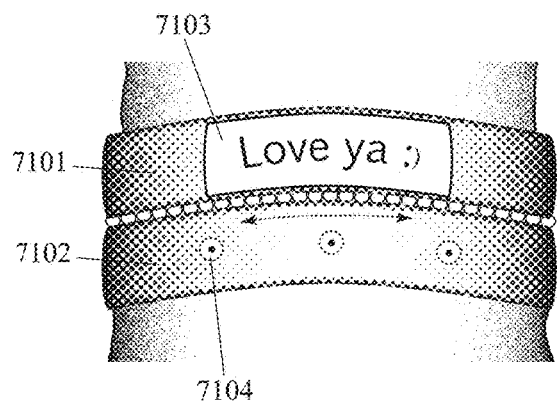

FIG. 71 shows a device with two bands which encircle an arm, wherein these two bands are movably-attached to each other in a manner which allows a second band (with spectroscopic sensors) to be rotated relative to a first band.

Figure 72:
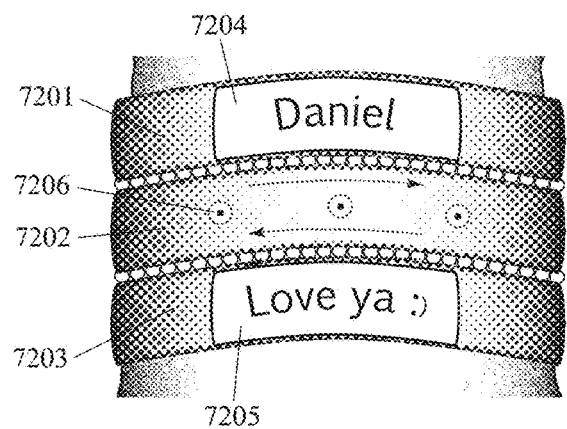

FIG. 72 shows a device with three bands and spectroscopic sensors on a central band which rotates relative to distal and proximal bands.

Figure 73:
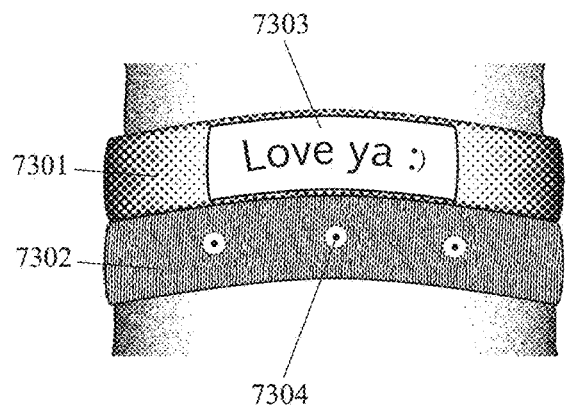

FIG. 73 shows a device with a relatively-rigid band and a relatively-elastic band, wherein each of these bands spans at least 60% of the circumference of a person's arm, wherein these bands are connected to each other, and wherein there are spectroscopic sensors on the relatively-elastic band.

Figure 74:
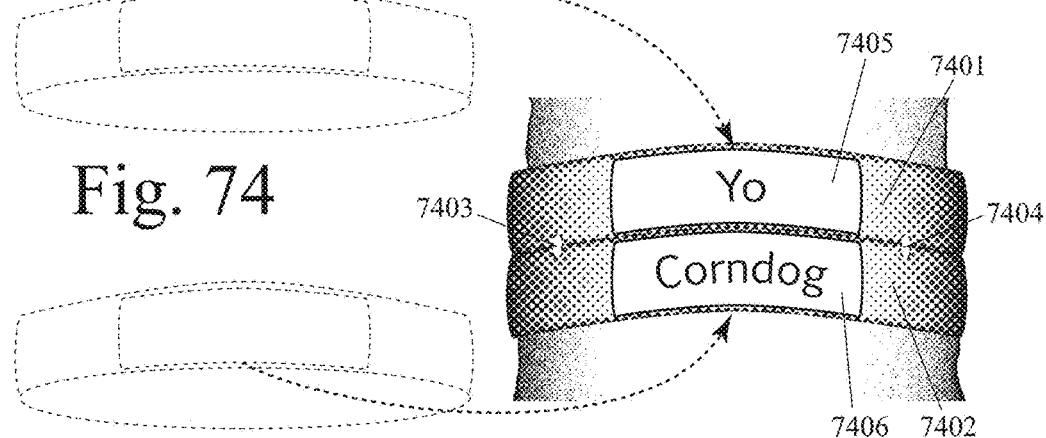

FIG. 74 shows a device with two or more modular and connectable bands, wherein each band spans at least 60% of the circumference of a person's arm, and wherein one or more of these bands house spectroscopic sensors.

Figure 75:
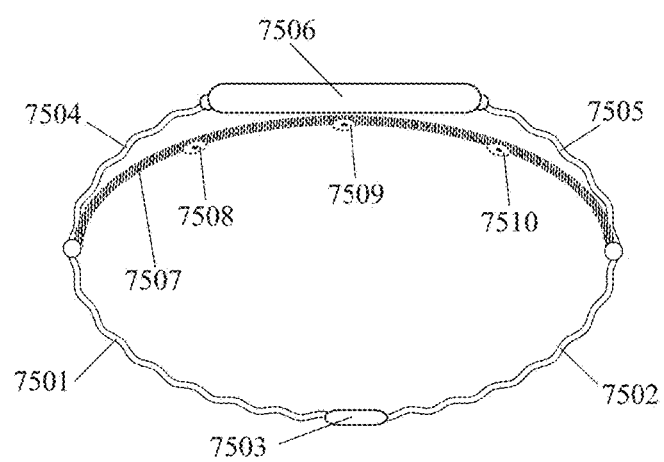

FIG. 75 shows a device with a partial-circumferential inner elastic band and spectroscopic sensors.

Figure 76:
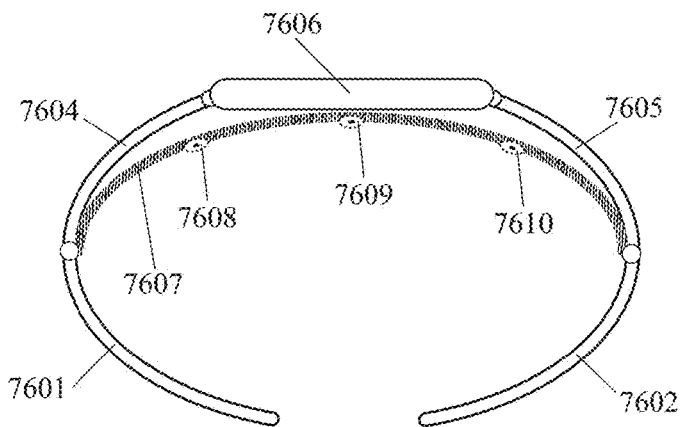

FIG. 76 shows a device wherein an outer inelastic band is sufficiently resilient that its ends hold onto the person's arm without the need for a clasp.

Figure 77:
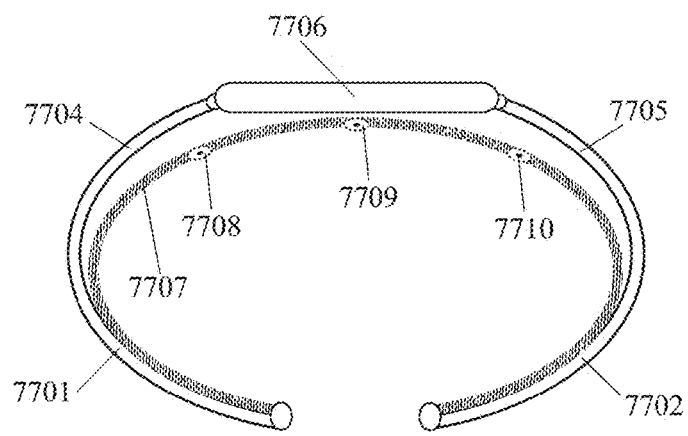

FIG. 77 shows a device with an outer arcuate inelastic band, an inner arcuate elastic band, and spectroscopic sensors which are part of the inner band.

Figure 78:
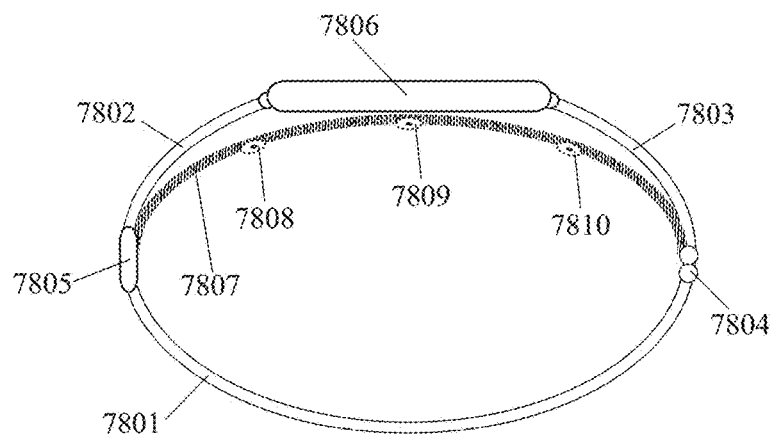

FIG. 78 shows a device with an outer rigid "clam shell" structure to hold a display screen in place and an inner arcuate elastic band to keep spectroscopic sensors close against the surface of the arm.

Figure 79:
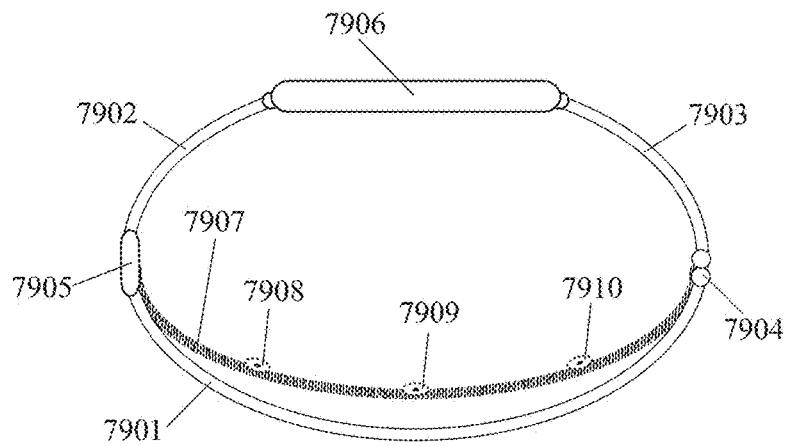

FIG. 79 shows a device with an inner arcuate elastic band which spans the posterior (lower) surface of a person's arm.

Figure 80:
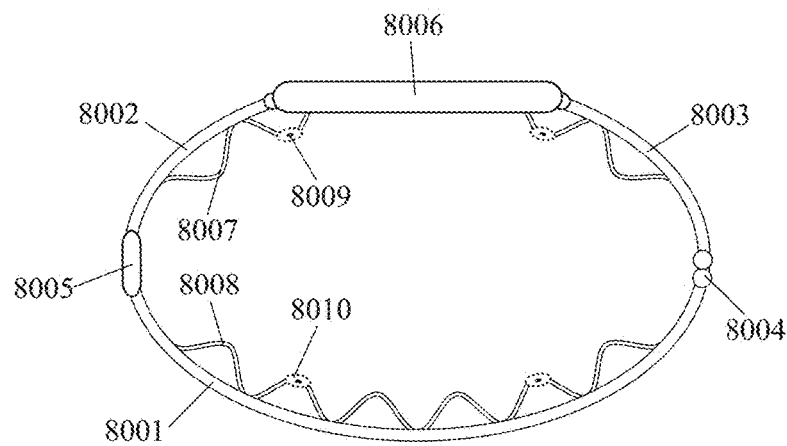

FIG. 80 shows a device with an outer rigid "clam shell" structure and inward-facing flexible undulations to keep spectroscopic sensors close against the surface of the arm.

Figure 81:
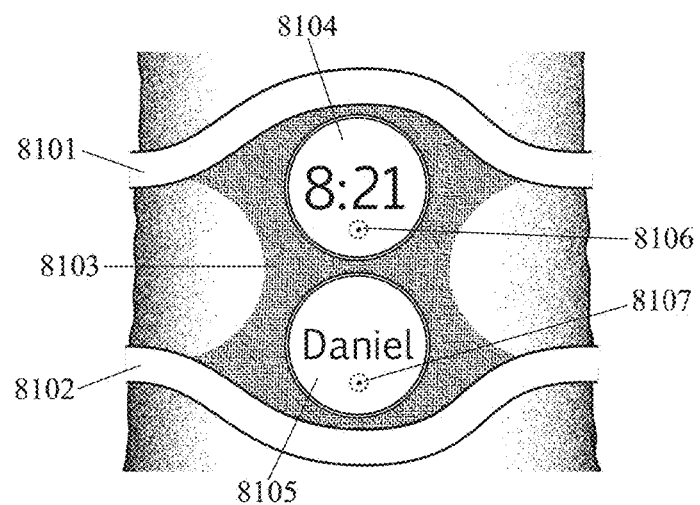

FIG. 81 shows a device with two display screens suspended by an elastic material between two arcuate bands.

Figure 82:
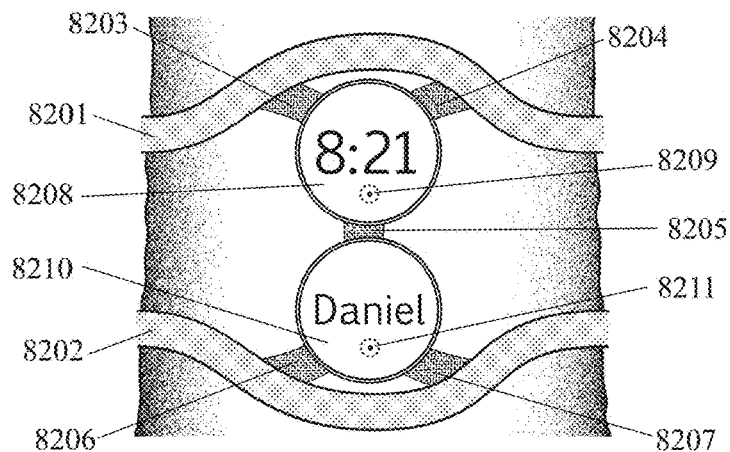

FIG. 82 shows a device with two display screens which are suspended by elastic straps between two arcuate bands.

Figure 83:
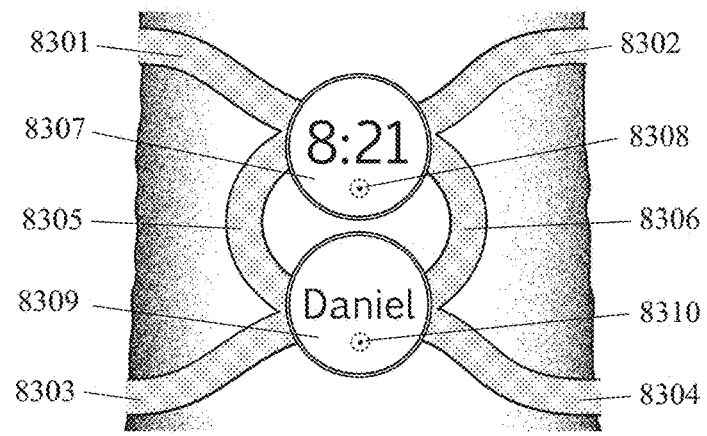

FIG. 83 shows a device with two display screens whose centers are at 12 o'clock and 6 o'clock positions around a circular band on the anterior (upper) surface of an arm.

Figure 84:
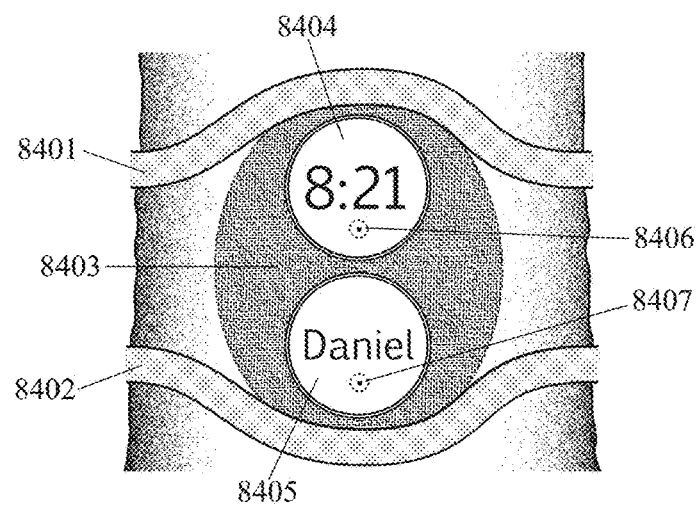

FIG. 84 shows a device with two display screens suspended by an oval (or elliptical or circular) elastic member between two arcuate bands.

DETAILED DESCRIPTION OF THE FIGURES

Overall Strategy for Good Nutrition and Energy Balance:

A device, system, or method for measuring a person's consumption of at least one selected type of food, ingredient, and/or nutrient is not a panacea for good nutrition, energy balance, and weight management, but it can be a useful part of an overall strategy for encouraging good nutrition, energy balance, weight management, and health improvement. Although such a device, system, or method is not sufficient to ensure energy balance and good health, it can be very useful in combination with proper exercise and other good health behaviors. Such a device, system, or method can help a person to track and modify their eating habits as part of an overall system for good nutrition, energy balance, weight management, and health improvement.

In an example, at least one component of such a device can be worn on a person's body or clothing. A wearable food-consumption monitoring device or system can operate in a more-consistent manner than an entirely hand-held food-consumption monitoring device, while avoiding the potential invasiveness and expense of a food-consumption monitoring device that is implanted within the body.

Information from a food-consumption monitoring device that measures a person's consumption of at least one selected type of food, ingredient, and/or nutrient can be combined with information from a separate caloric expenditure monitoring device that measures a person's caloric expenditure to comprise an overall system for energy balance, fitness, weight management, and health improvement. In an example, a food-consumption monitoring device can be in wireless communication with a separate fitness monitoring device. In an example, capability for monitoring food consumption can be combined with capability for monitoring caloric expenditure within a single device. In an example, a single device can be used to measure the types and amounts of food, ingredients, and/or nutrients that a person consumes as well as the types and durations of the calorie-expending activities in which the person engages.

Information from a food-consumption monitoring device that measures a person's consumption of at least one selected type of food, ingredient, and/or nutrient can also be combined with a computer-to-human interface that provides feedback to encourage the person to eat healthy foods and to limit excess consumption of unhealthy foods. In an example, a food-consumption monitoring device can be in wireless communication with a separate feedback device that modifies the person's eating behavior. In an example, capability for monitoring food consumption can be combined with capability for providing behavior-modifying feedback within a single device. In an example, a single device can be used to measure the selected types and amounts of foods, ingredients, and/or nutrients that a person consumes and to provide visual, auditory, tactile, or other feedback to encourage the person to eat in a healthier manner.

A combined device and system for measuring and modifying caloric intake and caloric expenditure can be a useful part of an overall approach for good nutrition, energy balance, fitness, weight management, and good health. As part of such an overall system, a device that measures a person's consumption of at least one selected type of food, ingredient, and/or nutrient can play a key role in helping that person to achieve their goals with respect to proper nutrition, food consumption modification, energy balance, weight management, and good health outcomes.

Selected Types of Foods, Ingredients, and Nutrients:

In order to be really useful for achieving good nutrition and health goals, a device and method for measuring a person's consumption of at least one selected type of food, ingredient, and/or nutrient should be able to differentiate between a person's consumption of healthy foods vs unhealthy foods. This requires the ability to identify consumption of selected types of foods, ingredients, and/or nutrients, as well as estimating the amounts of such consumption. It also requires selection of certain types and/or amounts of food, ingredients, and/or nutrients as healthy vs. unhealthy.

Generally, the technical challenges of identifying consumption of selected types of foods, ingredients, and/or nutrients are greater than the challenges of identifying which types are healthy or unhealthy. Accordingly, while this disclosure covers both food identification and classification, it focuses in greatest depth on identification of consumption of selected types of foods, ingredients, and nutrients. In this disclosure, food consumption is broadly defined to include consumption of liquid beverages and gelatinous food as well as solid food.

In an example, a device can identify consumption of at least one selected type of food. In such an example, selected types of ingredients or nutrients can be estimated indirectly using a database that links common types and amounts of food with common types and amounts of ingredients or nutrients. In another example, a device can directly identify consumption of at least one selected type of ingredient or nutrient. The latter does not rely on estimates from a database, but does require more complex ingredient-specific or nutrient-specific sensors. Since the concepts of food identification, ingredient identification, and nutrient identification are closely related, we consider them together for many portions of this disclosure, although we consider them separately in some sections for greater methodological detail. Various embodiments of the device and method disclosed herein can identify specific nutrients indirectly (through food identification and use of a database) or directly (through the use of nutrient-specific sensors).

Many people consume highly-processed foods whose primary ingredients include multiple types of sugar. The total amount of sugar is often obscured or hidden, even from those who read ingredients on labels. Sometimes sugar is disguised as "evaporated cane syrup." Sometimes different types of sugar are labeled as different ingredients (such as "plain sugar," "brown sugar," "maltose", "dextrose," and "evaporated cane syrup") in a single food item. In such cases, "sugar" does not appear as the main ingredient. However, when one adds up all the different types of sugar in different priority places on the ingredient list, then sugar really is the main ingredient. These highly-processed conglomerations of sugar (often including corn syrup, fats, and/or caffeine) often have colorful labels with cheery terms like "100% natural" or "high-energy." However, they are unhealthy when eaten in the quantities to which many Americans have become accustomed. It is no wonder that there is an obesity epidemic. The device and method disclosed herein is not be fooled by deceptive labeling of ingredients.

In various examples, a device for measuring a person's consumption of one or more selected types of foods, ingredients, and/or nutrients can measure one or more types selected from the group consisting of: a selected type of carbohydrate, a class of carbohydrates, or all carbohydrates; a selected type of sugar, a class of sugars, or all sugars; a selected type of fat, a class of fats, or all fats; a selected type of cholesterol, a class of cholesterols, or all cholesterols; a selected type of protein, a class of proteins, or all proteins; a selected type of fiber, a class of fiber, or all fibers; a specific sodium compound, a class of sodium compounds, or all sodium compounds; high-carbohydrate food, high-sugar food, high-fat food, fried food, high-cholesterol food, high-protein food, high-fiber food, and/or high-sodium food.

In various examples, a device for measuring a person's consumption of one or more selected types of foods, ingredients, and/or nutrients can measure one or more types selected from the group consisting of: simple carbohydrates, simple sugars, saturated fat, trans fat, Low Density Lipoprotein (LDL), and salt. In an example, a device for measuring consumption of a selected nutrient can measure a person's consumption of simple carbohydrates. In an example, a device for measuring consumption of a selected nutrient can measure a person's consumption of simple sugars. In an example, a device for measuring consumption of a selected nutrient can measure a person's consumption of saturated fats. In an example, a device for measuring consumption of a selected nutrient can measure a person's consumption of trans fats. In an example, a device for measuring consumption of a selected nutrient can measure a person's consumption of Low Density Lipoprotein (LDL). In an example, a device for measuring consumption of a selected nutrient can measure a person's consumption of sodium.

In various examples, a food-identifying sensor can detect one or more nutrients selected from the group consisting of: amino acid or protein (a selected type or general class), carbohydrate (a selected type or general class, such as single carbohydrates or complex carbohydrates), cholesterol (a selected type or class, such as HDL or LDL), dairy products (a selected type or general class), fat (a selected type or general class, such as unsaturated fat, saturated fat, or trans fat), fiber (a selected type or class, such as insoluble fiber or soluble fiber), mineral (a selected type), vitamin (a selected type), nuts (a selected type or general class, such as peanuts), sodium compounds (a selected type or general class), sugar (a selected type or general class, such as glucose), and water. In an example, food can be classified into general categories such as fruits, vegetables, or meat.

In an example, a device for measuring a person's consumption of a selected nutrient can measure a person's consumption of food that is high in simple carbohydrates. In an example, a device for measuring consumption of a selected nutrient can measure a person's consumption of food that is high in simple sugars. In an example, a device for measuring consumption of a selected nutrient can measure a person's consumption of food that is high in saturated fats. In an example, a device for measuring consumption of a selected nutrient can measure a person's consumption of food that is high in trans fats. In an example, a device for measuring consumption of a selected nutrient can measure a person's consumption of food that is high in Low Density Lipoprotein (LDL). In an example, a device for measuring consumption of a selected nutrient can measure a person's consumption of food that is high in sodium.

In an example, a device for measuring a person's consumption of a selected nutrient can measure a person's consumption of food wherein a high proportion of its calories comes from simple carbohydrates. In an example, a device for measuring consumption of a selected nutrient can measure a person's consumption of food wherein a high proportion of its calories comes from simple sugars. In an example, a device for measuring consumption of a selected nutrient can measure a person's consumption of food wherein a high proportion of its calories comes from saturated fats. In an example, a device for measuring consumption of a selected nutrient can measure a person's consumption of food wherein a high proportion of its calories comes from trans fats. In an example, a device for measuring consumption of a selected nutrient can measure a person's consumption of food wherein a high proportion of its calories comes from Low Density Lipoprotein (LDL). In an example, a device for measuring consumption of a selected nutrient can measure a person's consumption of food wherein a high proportion of its weight or volume is comprised of sodium compounds.

In an example, a device for measuring nutrient consumption can track the quantities of selected chemicals that a person consumes via food consumption. In various examples, these consumed chemicals can be selected from the group consisting of: carbon, hydrogen, nitrogen, oxygen, phosphorus, and sulfur. In an example, a food-identifying device can selectively detect consumption of one or more types of unhealthy food, wherein unhealthy food is selected from the group consisting of: food that is high in simple carbohydrates; food that is high in simple sugars; food that is high in saturated or trans fat; fried food; food that is high in Low Density Lipoprotein (LDL); and food that is high in sodium.

In a broad range of examples, a food-identifying sensor can measure one or more types selected from the group consisting of: a selected food, ingredient, or nutrient that has been designated as unhealthy by a health care professional organization or by a specific health care provider for a specific person; a selected substance that has been identified as an allergen for a specific person; peanuts, shellfish, or dairy products; a selected substance that has been identified as being addictive for a specific person; alcohol; a vitamin or mineral; vitamin A, vitamin B1, thiamin, vitamin B12, cyanocobalamin, vitamin B2, riboflavin, vitamin C, ascorbic acid, vitamin D, vitamin E, calcium, copper, iodine, iron, magnesium, manganese, niacin, pantothenic acid, phosphorus, potassium, riboflavin, thiamin, and zinc; a selected type of carbohydrate, class of carbohydrates, or all carbohydrates; a selected type of sugar, class of sugars, or all sugars; simple carbohydrates, complex carbohydrates; simple sugars, complex sugars, monosaccharides, glucose, fructose, oligosaccharides, polysaccharides, starch, glycogen, disaccharides, sucrose, lactose, starch, sugar, dextrose, disaccharide, fructose, galactose, glucose, lactose, maltose, monosaccharide, processed sugars, raw sugars, and sucrose; a selected type of fat, class of fats, or all fats; fatty acids, monounsaturated fat, polyunsaturated fat, saturated fat, trans fat, and unsaturated fat; a selected type of cholesterol, a class of cholesterols, or all cholesterols; Low Density Lipoprotein (LDL), High Density Lipoprotein (HDL), Very Low Density Lipoprotein (VLDL), and triglycerides; a selected type of protein, a class of proteins, or all proteins; dairy protein, egg protein, fish protein, fruit protein, grain protein, legume protein, lipoprotein, meat protein, nut protein, poultry protein, tofu protein, vegetable protein, complete protein, incomplete protein, or other amino acids; a selected type of fiber, a class of fiber, or all fiber; dietary fiber, insoluble fiber, soluble fiber, and cellulose; a specific sodium compound, a class of sodium compounds, and all sodium compounds; salt; a selected type of meat, a class of meats, and all meats; a selected type of vegetable, a class of vegetables, and all vegetables; a selected type of fruit, a class of fruits, and all fruits; a selected type of grain, a class of grains, and all grains; high-carbohydrate food, high-sugar food, high-fat food, fried food, high-cholesterol food, high-protein food, high-fiber food, and high-sodium food.

In an example, a device for measuring a person's consumption of at least one specific food, ingredient, and/or nutrient that can analyze food composition can also identify one or more potential food allergens, toxins, or other substances selected from the group consisting of: ground nuts, tree nuts, dairy products, shell fish, eggs, gluten, pesticides, animal hormones, and antibiotics. In an example, a device can analyze food composition to identify one or more types of food whose consumption is prohibited or discouraged for religious, moral, and/or cultural reasons, such as pork or meat products of any kind.

Metrics for Measuring Foods, Ingredients, and Nutrients:

Having discussed different ways to classify types of foods, ingredients, and nutrients, we now turn to different metrics for measuring the amounts of foods, ingredients, and nutrients consumed. Overall, amounts or quantities of food, ingredients, and nutrients consumed can be measured in terms of volume, mass, or weight. Volume measures how much space the food occupies. Mass measures how much matter the food contains. Weight measures the pull of gravity on the food. The concepts of mass and weight are related, but not identical. Food, ingredient, or nutrient density can also be measured, sometimes as a step toward measuring food mass.

Volume can be expressed in metric units (such as cubic millimeters, cubic centimeters, or liters) or U.S. (historically English) units (such as cubic inches, teaspoons, tablespoons, cups, pints, quarts, gallons, or fluid ounces). Mass (and often weight in colloquial use) can be expressed in metric units (such as milligrams, grams, and kilograms) or U.S. (historically English) units (ounces or pounds). The density of specific ingredients or nutrients within food is sometimes measured in terms of the volume of specific ingredients or nutrients per total food volume or measured in terms of the mass of specific ingredients or nutrients per total food mass.

In an example, the amount of a specific ingredient or nutrient within (a portion of) food can be measured directly by a sensing mechanism. In an example, the amount of a specific ingredient or nutrient within (a portion of) food can be estimated indirectly by measuring the amount of food and then linking this amount of food to amounts of ingredients or nutrients using a database that links specific foods with standard amounts of ingredients or nutrients.

In an example, an amount of a selected type of food, ingredient, or nutrient consumed can be expressed as an absolute amount. In an example, an amount of a selected type of food, ingredient, or nutrient consumed can be expressed as a percentage of a standard amount. In an example, an amount of a selected type of food, ingredient, or nutrient consumed can be displayed as a portion of a standard amount such as in a bar chart, pie chart, thermometer graphic, or battery graphic.

In an example, a standard amount can be selected from the group consisting of: daily recommended minimum amount; daily recommended maximum amount or allowance; weekly recommended minimum amount; weekly recommended maximum amount or allowance; target amount to achieve a health goal; and maximum amount or allowance per meal. In an example, a standard amount can be a Reference Daily Intake (RDI) value or a Daily Reference Value.

In an example, the volume of food consumed can be estimated by analyzing one or more pictures of that food. In an example, volume estimation can include the use of a physical or virtual fiduciary marker or object of known size for estimating the size of a portion of food. In an example, a physical fiduciary marker can be placed in the field of view of an imaging system for use as a point of reference or a measure. In an example, this fiduciary marker can be a plate, utensil, or other physical place setting member of known size. In an example, this fiduciary marker can be created virtually by the projection of coherent light beams. In an example, a device can project (laser) light points onto food and, in conjunction with infrared reflection or focal adjustment, use those points to create a virtual fiduciary marker. A fiduciary marker may be used in conjunction with a distance-finding mechanism (such as infrared range finder) that determines the distance from the camera and the food.

In an example, volume estimation can include obtaining video images of food or multiple still pictures of food in order to obtain pictures of food from multiple perspectives. In an example, pictures of food from multiple perspectives can be used to create three-dimensional or volumetric models of that food in order to estimate food volume. In an example, such methods can be used prior to food consumption and again after food consumption, in order to estimate the volume of food consumed based on differences in food volume measured. In an example, food volume estimation can be done by analyzing one or more pictures of food before (and after) consumption. In an example, multiple pictures of food from different angles can enable three-dimensional modeling of food volume. In an example, multiple pictures of food at different times (such as before and after consumption) can enable estimation of the amount of proximal food that is actually consumed vs. just being served in proximity to the person.

In a non-imaging example of food volume estimation, a utensil or other apportioning device can be used to divide food into mouthfuls. Then, the number of times that the utensil is used to bring food up to the person's mouth can be tracked. Then, the number of utensil motions is multiplied times the estimated volume of food per mouthful in order to estimate the cumulative volume of food consumed. In an example, the number of hand motions or mouth motions can be used to estimate the quantity of food consumed. In an example, a motion sensor worn on a person's wrist or incorporated into a utensil can measure the number of hand-to-mouth motions. In an example, a motion sensor, sound sensor, or electromagnetic sensor in communication with a person's mouth can measure the number of chewing motions which, in turn, can be used to estimate food volume.

In an example, a device for measuring a person's consumption of one or more selected types of foods, ingredients, or nutrients can measure the weight or mass of food that the person consumes. In an example, a device and method for measuring consumption of one or more selected types of foods, ingredients, or nutrients can include a food scale that measures the weight of food. In an example a food scale can measure the weight of food prior to consumption and the weight of unconsumed food remaining after consumption in order to estimate the weight of food consumed based on the difference in pre vs. post consumption measurements. In an example, a food scale can be a stand-alone device. In an example, a food scale can be incorporated into a plate, glass, cup, glass coaster, place mat, or other place setting. In an example a plate can include different sections which separately measure the weights of different foods on the plate. In an example, a food scale embedded into a place setting or smart utensil can automatically transmit data concerning food weight to a computer.

In an example, a food scale can be incorporated into a smart utensil. In an example, a food scale can be incorporated into a utensil rest on which a utensil is placed for each bite or mouthful. In an example, a food scale can be incorporated into a smart utensil which tracks the cumulative weight of cumulative mouthfuls of food during an eating event. In an example, a smart utensil can approximate the weight of mouthfuls of food by measuring the effect of food carried by the utensil on an accelerometer or other inertial sensor. In an example, a smart utensil can incorporate a spring between the food-carrying portion and the hand-held portion of a utensil and food weight can be estimated by measuring distension of the spring as food is brought up to a person's mouth.

In an example, a smart utensil can use an inertial sensor, accelerometer, or strain gauge to estimate the weight of the food-carrying end of utensil at a first time (during an upswing motion as the utensil carries a mouthful of food up to the person's mouth), can use this sensor to estimate the weight of the food-carrying end of the utensil at a second time (during a downswing motion as the person lowers the utensil from their mouth), and can estimate the weight of the mouthful of food by calculating the difference in weight between the first and second times.

In an example, a device or system can measure nutrient density or concentration as part of an automatic food, ingredient, or nutrient identification method. In an example, such nutrient density can be expressed as the average amount of a specific ingredient or nutrient per unit of food weight. In an example, such nutrient density can be expressed as the average amount of a specific ingredient or nutrient per unit of food volume. In an example, food density can be estimated by interacting food with light, sound, or electromagnetic energy and measuring the results of this interaction. Such interaction can include energy absorption or reflection.

In an example, nutrient density can be determined by reading a label on packaging associated with food consumed. In an example, nutrient density can be determined by receipt of wirelessly transmitted information from a grocery store display, electronically-functional restaurant menu, or vending machine. In an example, food density can be estimated by ultrasonic scanning of food. In an example, food density and food volume can be jointly analyzed to estimate food weight or mass.

In an example, for some foods with standardized sizes (such as foods that are manufactured in standard sizes at high volume), food weight can be estimated as part of food identification. In an example, information concerning the weight of food consumed can be linked to nutrient quantities in a computer database in order to estimate cumulative consumption of selected types of nutrients.

In an example, a method for measuring a person's consumption of at least one selected type of food, ingredient, or nutrient can comprise monitoring changes in the volume or weight of food at a reachable location near the person. In an example, pictures of food can be taken at multiple times before, during, and after food consumption in order to better estimate the amount of food that the person actually consumes, which can differ from the amount of food served to the person or the amount of food left over after the person eats. In an example, estimates of the amount of food that the person actually consumes can be made by digital image subtraction and/or 3D modeling. In an example, changes in the volume or weight of nearby food can be correlated with hand motions in order to estimate the amount of food that a person actually eats. In an example, a device can track the cumulative number of hand-to-mouth motions, number of chewing motions, or number of swallowing motions. In an example, estimation of food consumed can also involve asking the person whether they ate all the food that was served to them.

In an example, a device and method for measuring a person's consumption of at least one selected type of food, ingredient, or nutrient can collect data that enables tracking the cumulative amount of a type of food, ingredient, or nutrient which the person consumes during a period of time (such as an hour, day, week, or month) or during a particular eating event. In an example, the time boundaries of a particular eating event can be defined by a maximum time between chews or mouthfuls during a meal and/or a minimum time between chews or mouthfuls between meals. In an example, the time boundaries of a particular eating event can be defined by Fourier Transformation analysis of the variable frequencies of chewing, swallowing, or biting during meals vs. between meals.

In an example, a device and method for measuring a person's consumption of at least one selected type of food, ingredient, or nutrient can track the cumulative amount of that food, ingredient, or nutrient consumed by the person and provide feedback to the person based on the person's cumulative consumption relative to a target amount. In an example, a device can provide negative feedback when a person exceeds a target amount of cumulative consumption. In an example, a device and system can sound an alarm or provide other real-time feedback to a person when the cumulative consumed amount of a selected type of food, ingredient, or nutrient exceeds an allowable amount (in total, per meal, or per unit of time).

In various examples, a target amount of consumption can be based on one or more factors selected from the group consisting of: the selected type of selected food, ingredient, or nutrient; amount of this type recommended by a health care professional or governmental agency; specificity or breadth of the selected nutrient type; the person's age, gender, and/or weight; the person's diagnosed health conditions; the person's exercise patterns and/or caloric expenditure; the person's physical location; the person's health goals and progress thus far toward achieving them; one or more general health status indicators; magnitude and/or certainty of the effects of past consumption of the selected nutrient on the person's health; the amount and/or duration of the person's consumption of healthy food or nutrients; changes in the person's weight; time of day; day of the week; occurrence of a holiday or other occasion involving special meals; dietary plan created for the person by a health care provider; input from a social network and/or behavioral support group; input from a virtual health coach; health insurance copay and/or health insurance premium; financial payments, constraints, and/or incentives; cost of food; speed or pace of nutrient consumption; and accuracy of the sensor in detecting the selected nutrient.

Food Consumption and Nutrient Identification Sensors:

A device and method for measuring a person's consumption of at least one selected type of food, ingredient, or nutrient can include: a general food-consumption monitor that detects when a person is probably eating, but does not identify the selected types of foods, ingredients, or nutrients that the person is eating; and a food-identifying sensor that identifies the person's consumption of at least one selected type of food, ingredient, or nutrient.

In an example, operation of a food-identifying sensor can be triggered by the results of a general food-consumption monitor. In an example, a general food-consumption monitor with low privacy intrusion (but low food identification accuracy) can operate continually and trigger the operation of a food-identifying sensor with high privacy intrusion (but high food identification accuracy) when the person is eating. In an example, a general food-consumption monitor with low privacy intrusion (but low power or resource requirements) can operate continually and trigger the operation of a food-identifying sensor with high privacy intrusion (but high power or resource requirements) when the person is eating. In an example, the combination of a general food-consumption monitor and a food-identifying sensor can achieve relatively-high food identification accuracy with relatively-low privacy intrusion or resource requirements.

In an example, a food-consumption monitor or food-identifying sensor can measure food weight, mass, volume, or density. In an example, such a sensor can be a scale, strain gauge, or inertial sensor. In an example, such a sensor can measure the weight or mass of an entire meal, a portion of one type of food within that meal, or a mouthful of a type of food that is being conveyed to a person's mouth. In general, a weight, mass, or volume sensor is more useful for general detection of food consumption and food amount than it is for identification of consumption of selected types of foods, ingredients, and nutrients. However, it can be very useful when used in combination with a specific food-identifying sensor.

In an example, a food-consumption monitor can be a motion sensor. In various examples, a motion sensor can be selected from the group consisting of: bubble accelerometer, dual-axial accelerometer, electrogoniometer, gyroscope, inclinometer, inertial sensor, multi-axis accelerometer, piezoelectric sensor, piezo-mechanical sensor, pressure sensor, proximity detector, single-axis accelerometer, strain gauge, stretch sensor, and tri-axial accelerometer. In an example, a motion sensor can collect data concerning the movement of a person's wrist, hand, fingers, arm, head, mouth, jaw, or neck. In an example, analysis of this motion data can be used to identify when the person is probably eating. In general, a motion sensor is more useful for general detection of food consumption and food amount than it is for identification of consumption of selected types of foods, ingredients, and nutrients. However, it can be very useful when used in combination with a specific food-identifying sensor.

In an example, there can be an identifiable pattern of movement that is highly-associated with food consumption and a motion sensor can monitor a person's movements to identify times when the person is probably eating. In an example, this movement can include repeated movement of a person's hand up to their mouth. In an example, this movement can include a combination of three-dimensional roll, pitch, and yaw by a person's wrist and/or hand. In an example, this movement can include repeated bending of a person's elbow. In an example, this movement can include repeated movement of a person's jaws. In an example, this movement can include peristaltic motion of the person's esophagus that is detectable from contact with a person's neck.

In an example, a motion sensor can be used to estimate the quantity of food consumed based on the number of motion cycles. In an example, a motion sensor can be used to estimate the speed of food consumption based on the speed or frequency of motion cycles. In an example, a proximity sensor can detect when a person's hand gets close to their mouth. In an example, a proximity sensor can detect when a wrist (or hand or finger) is in proximity to a person's mouth. However, a proximity detector can be less useful than a motion detector because it does not identify complex three-dimensional motions that can differentiate eating from other hand-to-mouth motions such as coughing, yawning, smoking, and tooth brushing.

In various examples, a device to measure a person's consumption of at least one selected type of food, ingredient, or nutrient can include a motion sensor that collects data concerning movement of the person's body. In an example, this data can be used to detect when a person is consuming food. In an example, this data can be used to aid in the identification of what types and amounts of food the person is consuming. In an example, analysis of this data can be used to trigger additional data collection to resolve uncertainty concerning the types and amounts of food that the person is consuming.

In an example, a motion sensor can include one or more accelerometers, inclinometers, electrogoniometers, and/or strain gauges. In an example, movement of a person's body that can be monitored and analyzed can be selected from the group consisting of: finger movements, hand movements, wrist movements, arm movements, elbow movements, eye movements, and head movements; tilting movements, lifting movements; hand-to-mouth movements; angles of rotation in three dimensions around the center of mass known as roll, pitch and yaw; and Fourier Transformation analysis of repeated body member movements. In an example, each hand-to-mouth movement that matches a certain pattern can be used to estimate bite or mouthful of food. In an example, the speed of hand-to-mouth movements that match a certain pattern can be used to estimate eating speed. In an example, this pattern can include upward and tilting hand movement, followed by a pause, following by a downward and tilting hand movement.

In an example, a motion sensor that is used to detect food consumption can be worn on a person's wrist, hand, arm, or finger. In an example, a motion sensor can be incorporated into a smart watch, fitness watch, or watch phone. In an example, a fitness watch that already uses an accelerometer to measure motion for estimating caloric expenditure can also use an accelerometer to detect (and estimate the quantity of) food consumption.

Motion-sensing devices that are worn on a person's wrist, hand, arm, or finger can continuously monitor a person's movements to detect food consumption with high compliance and minimal privacy intrusion. They do not require that a person carry a particular piece of electronic equipment everywhere they go and consistently bring that piece of electronic equipment out for activation each time that they eat a meal or snack. However, a motion-detecting device that is worn constantly on a person's wrist, hand, arm, or finger can be subject to false alarms due to motions (such as coughing, yawning, smoking, and tooth brushing) that can be similar to eating motions. To the extent that there is a distinctive pattern of hand and/or arm movement associated with bringing food up to one's mouth, such a device can detect when food consumption is occurring.

In an example, a motion-sensing device that is worn on a person's wrist, hand, arm, or finger can measure how rapidly or often the person brings their hand up to their mouth. A common use of such information is to encourage a person to eat at a slower pace. The idea that a person will eat less if they eat at a slower pace is based on the lag between food consumption and the feeling of satiety from internal gastric organs. If a person eats slower, then they will tend to not overeat past the point of internal identification of satiety.

In an example, a smart watch, fitness watch, watch phone, smart ring, or smart bracelet can measure the speed, pace, or rate at which a person brings food up to their mouth while eating and provide feedback to the person to encourage them to eat slower if the speed, pace, or rate is high. In an example, feedback can be sound-based, such as an alarm, buzzer, or computer-generated voice. In an example, feedback can be tactile, such as vibration or pressure. In an example, such feedback can be visual, such as a light, image, or display screen. In an alternative example, eating speed can be inferred indirectly by a plate, dish, bowl, glass or other place setting member that measures changes in the weight of food on the member. Negative feedback can be provided to the person if the weight of food on the plate, dish, bowl, or glass decreases in a manner that indicates that food consumption is too fast.

In an example, a motion sensor that is used to detect food consumption can be incorporated into, or attached to, a food utensil such as a fork or spoon. A food utensil with a motion sensor can be less prone to false alarms than a motion sensor worn on a person's wrist, hand, arm, or finger because the utensil is only used when the person eats food. Since the utensil is only used for food consumption, analysis of complex motion and differentiation of food consumption actions vs. other hand gestures is less important with a utensil than it is with a device that is worn on the person's body. In an example, a motion sensor can be incorporated into a smart utensil. In an example, a smart utensil can estimate the amount of food consumed by the number of hand-to-mouth motions (combined with information concerning how much food is conveyed by the utensil with each movement). In an example, a smart utensil can encourage a person to eat slower. The idea is that if the person eats more slowly, then they will tend to not overeat past the point of internal identification of satiety.

In an example, a food-consumption monitor or food-identifying sensor can be a light-based sensor that records the interaction between light and food. In an example, a light-based sensor can be a camera, mobile phone, or other conventional imaging device that takes plain-light pictures of food. In an example, a light-based food consumption or identification sensor can comprise a camera that takes video pictures or still pictures of food. In an example, such a camera can take pictures of the interaction between a person and food, including food apportionment, hand-to-mouth movements, and chewing movements.

In an example, a device and method for measuring a person's consumption of at least one selected type of food, ingredient, or nutrient can include a camera, or other picture-taking device, that takes pictures of food. In the following section, we discuss different examples of how a camera or other imaging-device can be used to take pictures of food and how those pictures can be analyzed to identify the types and amounts of food consumed. After that section, we discuss some other light-based approaches to food identification (such as spectroscopy) that do not rely on conventional imaging devices and plain-light food pictures.

A food-consumption monitor or food-identifying sensor can be a camera or other imaging device that is carried and held by a person. In an example, a camera that is used for food identification can be part of a mobile phone, cell phone, electronic tablet, or smart food utensil. In an example, a food-consumption monitor or food-identifying sensor can be a camera or other imaging device that is worn on a person's body or clothing. In an example, a camera can be incorporated into a smart watch, smart bracelet, smart button, or smart necklace.

In an example, a camera that is used for monitoring food consumption and/or identifying consumption of at least one selected type of food, ingredient, or nutrient can be a dedicated device that is specifically designed for this purpose. In an example, a camera that is used for monitoring food consumption and/or identifying consumption of specific foods can be a part of a general purpose device (such as a mobile phone, cell phone, electronic tablet, or digital camera) and in wireless communication with a dedicated device for monitoring food consumption and identifying specific food types.

In an example, use of a hand-held camera, mobile phone, or other imaging device to identify food depends on a person's manually aiming and triggering the device for each eating event. In an example, the person must bring the imaging device with them to each meal or snack, orient it toward the food to be consumed, and activate taking a picture of the food by touch or voice command. In an example, a camera, smart watch, smart necklace or other imaging device that is worn on a person's body or clothing can move passively as the person moves. In an example, the field of vision of an imaging device that is worn on a person's wrist, hand, arm, or finger can move as the person brings food up to their mouth when eating. In an example, such an imaging device can passively capture images of a reachable food source and interaction between food and a person's mouth.

In another example, the imaging vector and/or focal range of an imaging device worn on a person's body or clothing can be actively and deliberately adjusted to better track the person's hands and mouth to better monitor for possible food consumption. In an example, a device can optically scan the space surrounding the person for reachable food sources, hand-to-food interaction, and food-to-mouth interaction. In an example, in the interest of privacy, an imaging device that is worn on a person's body or clothing can only take pictures when some other sensor or information indicates that the person is probably eating.

In an example, a camera that is used for identifying food consumption can have a variable focal length. In an example, the imaging vector and/or focal distance of a camera can be actively and automatically adjusted to focus on: the person's hands, space surrounding the person's hands, a reachable food source, a food package, a menu, the person's mouth, and the person's face. In an example, in the interest of privacy, the focal length of a camera can be automatically adjusted in order to focus on food and not other people.

In an example, a device for measuring a person's consumption of at least one selected type of food, ingredient, or nutrient can include an imaging component that the person must manually aim toward food and manually activate for taking food pictures (such as through touch or voice commands). In an example, the taking of food pictures in this manner requires at least one specific voluntary human action associated with each food consumption event, apart from the actual act of eating, in order to take pictures of food during that food consumption event. In an example, such specific voluntary human actions can be selected from the group consisting of: transporting a mobile imaging device to a meal; aiming an imaging device at food; clicking a button to activate picture taking; touching a screen to activate picture taking; and speaking a voice command to activate picture taking.

In an example, a device for measuring a person's consumption of at least one selected type of food, ingredient, or nutrient can prompt a person to take pictures of food when a non-imaging sensor or other source of information indicates that the person is probably eating. In an alternative example, a device for measuring a person's consumption of at least one selected type of food, ingredient, or nutrient can automatically take pictures of food consumed without the need for specific action by the person in association with a specific eating event apart from the act of eating.

In an example, a device and method for measuring food consumption can include taking multiple pictures of food. In an example, such a device and method can include taking pictures of food from at least two different angles in order to better segment a meal into different types of foods, estimate the three-dimensional volume of each type of food, and control for lighting and shading differences. In an example, a camera or other imaging device can take pictures of food from multiple perspectives to create a virtual three-dimensional model of food in order to determine food volume. In an example, an imaging device can estimate the quantities of specific foods from pictures or images of those foods by volumetric analysis of food from multiple perspectives and/or by three-dimensional modeling of food from multiple perspectives.

In an example, a camera can use an object of known size within its field of view as a fiduciary marker in order to measure the size or scale of food. In an example, a camera can use projected laser beams to create a virtual or optical fiduciary marker in order to measure food size or scale. In an example, pictures of food can be taken at different times. In an example, a camera can be used to take pictures of food before and after consumption. The amount of food that a person actually consumes (not just the amount ordered or served) can be estimated by the difference in observed food volume from the pictures before and after consumption.

In an example, images of food can be automatically analyzed in order to identify the types and quantities of food consumed. In an example, pictures of food taken by a camera or other picture-taking device can be automatically analyzed to estimate the types and amounts of specific foods, ingredients, or nutrients that a person is consumes. In an example, an initial stage of an image analysis system can comprise adjusting, normalizing, or standardizing image elements for better food segmentation, identification, and volume estimation. These elements can include: color, texture, shape, size, context, geographic location, adjacent food, place setting context, and temperature (infrared). In an example, a device can identify specific foods from pictures or images by image segmentation, color analysis, texture analysis, and pattern recognition.

In various examples, automatic identification of food types and quantities can be based on: color and texture analysis; image segmentation; image pattern recognition; volumetric analysis based on a fiduciary marker or other object of known size; and/or three-dimensional modeling based on pictures from multiple perspectives. In an example, a device can collect food images that are used to extract a vector of food parameters (such as color, texture, shape, and size) that are automatically associated with vectors of food parameters in a database of such parameters for food identification.

In an example, a device can collect food images that are automatically associated with images of food in a food image database for food identification. In an example, specific ingredients or nutrients that are associated with these selected types of food can be estimated based on a database linking foods to ingredients and nutrients. In another example, specific ingredients or nutrients can be measured directly. In various examples, a device for measuring consumption of food, ingredient, or nutrients can directly (or indirectly) measure consumption at least one selected type of food, ingredient, or nutrient.

In an example, food image information can be transmitted from a wearable or hand-held device to a remote location where automatic food identification occurs and the results can be transmitted back to the wearable or hand-held device. In an example, identification of the types and quantities of foods, ingredients, or nutrients that a person consumes from pictures of food can be a combination of, or interaction between, automated identification food methods and human-based food identification methods.

We now transition to discussion of light-based methods for measuring food consumption that do not rely of conventional imaging devices and plain-light images. Probably the simplest such method involves identifying food by scanning a barcode or other machine-readable code on the food's packaging (such as a Universal Product Code or European Article Number), on a menu, on a store display sign, or otherwise in proximity to food at the point of food selection, sale, or consumption. In an example, the type of food (and/or specific ingredients or nutrients within the food) can be identified by machine-recognition of a food label, nutritional label, or logo on food packaging, menu, or display sign. However, there are many types of food and food consumption situations in which food is not accompanied by such identifying packaging. Accordingly, a robust imaged-based device and method for measuring food consumption should not rely on bar codes or other identifying material on food packaging.

In an example, selected types of foods, ingredients, and/or nutrients can be identified by the patterns of light that are reflected from, or absorbed by, the food at different wavelengths. In an example, a light-based sensor can detect food consumption or can identify consumption of a specific food, ingredient, or nutrient based on the reflection of light from food or the absorption of light by food at different wavelengths. In an example, an optical sensor can detect fluorescence. In an example, an optical sensor can detect whether food reflects light at a different wavelength than the wavelength of light shone on food. In an example, an optical sensor can be a fluorescence polarization immunoassay sensor, chemiluminescence sensor, thermoluminescence sensor, or piezoluminescence sensor.

In an example, a light-based food-identifying sensor can collect information concerning the wavelength spectra of light reflected from, or absorbed by, food. In an example, an optical sensor can be a chromatographic sensor, spectrographic sensor, analytical chromatographic sensor, liquid chromatographic sensor, gas chromatographic sensor, optoelectronic sensor, photochemical sensor, and photocell. In an example, an optical sensor can analyze modulation of light wave parameters by the interaction of that light with a portion of food. In an example, an optical sensor can detect modulation of light reflected from, or absorbed by, a receptor when the receptor is exposed to food. In an example, an optical sensor can emit and/or detect white light, infrared light, or ultraviolet light.

In an example, a light-based food-identifying sensor can identify consumption of a selected type of food, ingredient, or nutrient with a spectral analysis sensor. In various examples, a food-identifying sensor can identify a selected type of food, ingredient, or nutrient with a sensor that detects light reflection spectra, light absorption spectra, or light emission spectra. In an example, a spectral measurement sensor can be a spectroscopy sensor or a spectrometry sensor. In an example, a spectral measurement sensor can be a white light spectroscopy sensor, an infrared spectroscopy sensor, a near-infrared spectroscopy sensor, an ultraviolet spectroscopy sensor, an ion mobility spectroscopic sensor, a mass spectrometry sensor, a backscattering spectrometry sensor, or a spectrophotometer. In an example, light at different wavelengths can be absorbed by, or reflected off, food and the results can be analyzed in spectral analysis.

In an example, a food-consumption monitor or food-identifying sensor can be a microphone or other type of sound sensor. In an example, a sensor to detect food consumption and/or identify consumption of a selected type of food, ingredient, or nutrient can be a sound sensor. In an example, a sound sensor can be an air conduction microphone or bone conduction microphone. In an example, a microphone or other sound sensor can monitor for sounds associated with chewing or swallowing food. In an example, data collected by a sound sensor can be analyzed to differentiate sounds from chewing or swallowing food from other types of sounds such as speaking, singing, coughing, and sneezing.

In an example, a sound sensor can include speech recognition or voice recognition to receive verbal input from a person concerning food that the person consumes. In an example, a sound sensor can include speech recognition or voice recognition to extract food selecting, ordering, purchasing, or consumption information from other sounds in the environment.

In an example, a sound sensor can be worn or held by a person. In an example, a sound sensor can be part of a general purpose device, such as a cell phone or mobile phone, which has multiple applications. In an example, a sound sensor can measure the interaction of sound waves (such as ultrasonic sound waves) and food in order to identify the type and quantity of food that a person is eating.

In an example, a food-consumption monitor or food-identifying sensor can be a chemical sensor. In an example, a chemical sensor can include a receptor to which at least one specific nutrient-related analyte binds and this binding action creates a detectable signal. In an example, a chemical sensor can include measurement of changes in energy wave parameters that are caused by the interaction of that energy with food. In an example, a chemical sensor can be incorporated into a smart utensil to identify selected types of foods, ingredients, or nutrients. In an example, a chemical sensor can be incorporated into a portable food probe to identify selected types of foods, ingredients, or nutrients. In an example, a sensor can analyze the chemical composition of a person's saliva. In an example, a chemical sensor can be incorporated into an intraoral device that analyzes microsamples of a person's saliva. In an example, such an intraoral device can be adhered to a person's upper palate.

In various examples, a food-consumption monitor or food-identifying sensor can be selected from the group consisting of: receptor-based sensor, enzyme-based sensor, reagent based sensor, antibody-based receptor, biochemical sensor, membrane sensor, pH level sensor, osmolality sensor, nucleic acid-based sensor, or DNA/RNA-based sensor; a biomimetic sensor (such as an artificial taste bud or an artificial olfactory sensor), a chemiresistor, a chemoreceptor sensor, a electrochemical sensor, an electroosmotic sensor, an electrophoresis sensor, or an electroporation sensor; a specific nutrient sensor (such as a glucose sensor, a cholesterol sensor, a fat sensor, a protein-based sensor, or an amino acid sensor); a color sensor, a colorimetric sensor, a photochemical sensor, a chemiluminescence sensor, a fluorescence sensor, a chromatography sensor (such as an analytical chromatography sensor, a liquid chromatography sensor, or a gas chromatography sensor), a spectrometry sensor (such as a mass spectrometry sensor), a spectrophotometer sensor, a spectral analysis sensor, or a spectroscopy sensor (such as a near-infrared spectroscopy sensor); and a laboratory-on-a-chip or microcantilever sensor.

In an example, a food-consumption monitor or food-identifying sensor can be an electromagnetic sensor. In an example, a device for measuring food consumption or identifying specific nutrients can emit and measure electromagnetic energy. In an example, a device can expose food to electromagnetic energy and collect data concerning the effects of this interaction which are used for food identification. In various examples, the results of this interaction can include measuring absorption or reflection of electromagnetic energy by food. In an example, an electromagnetic sensor can detect the modulation of electromagnetic energy that is interacted with food.

In an example, an electromagnetic sensor that detects food or nutrient consumption can detect electromagnetic signals from the body in response to the consumption or digestion of food. In an example, analysis of this electromagnetic energy can help to identify the types of food that a person consumes. In an example, a device can measure electromagnetic signals emitted by a person's stomach, esophagus, mouth, tongue, afferent nervous system, or brain in response to general food consumption. In an example, a device can measure electromagnetic signals emitted by a person's stomach, esophagus, mouth, tongue, afferent nervous system, or brain in response to consumption of selected types of foods, ingredients, or nutrients.

In various examples, a sensor to detect food consumption or identify consumption of a selected type of nutrient can be selected from the group consisting of: neuroelectrical sensor, action potential sensor, ECG sensor, EKG sensor, EEG sensor, EGG sensor, capacitance sensor, conductivity sensor, impedance sensor, galvanic skin response sensor, variable impedance sensor, variable resistance sensor, interferometer, magnetometer, RF sensor, electrophoretic sensor, optoelectronic sensor, piezoelectric sensor, and piezocapacitive sensor.

In an example, a sensor to monitor, detect, or sense food consumption or to identify a selected type of food, ingredient, or nutrient consumed can be pressure sensor or touch sensor. In an example, a pressure or touch sensor can sense pressure or tactile information from contact with food that will be consumed. In an example, a pressure or touch sensor can be incorporated into a smart food utensil or food probe. In an example, a pressure or touch based sensor can be incorporated into a pad on which a food utensil is placed between mouthfuls or when not in use. In an example, a pressure or touch sensor can sense pressure or tactile information from contact with a body member whose internal pressure or external shape is affected by food consumption. In various examples, a pressure or touch sensor can be selected from the group consisting of: food viscosity sensor, blood pressure monitor, muscle pressure sensor, button or switch on a food utensil, jaw motion pressure sensor, and hand-to-mouth contact sensor.

In an example, a food-consumption monitor or food-identifying sensor can be a thermal energy sensor. In an example, a thermal sensor can detect or measure the temperature of food. In an example, a thermal sensor can detect or measure the temperature of a portion of a person's body wherein food consumption changes the temperature of this member. In various examples, a food-consumption monitor can be selected from the group consisting of: a thermometer, a thermistor, a thermocouple, and an infrared energy detector.

In an example, a food-consumption monitor or food-identifying sensor can be a location sensor. In an example, such a sensor can be geographic location sensor or an intra-building location sensor. A device for detecting food consumption and/or indentifying a selected type of food, ingredient, or nutrient consumed can use information concerning a person's location as part of the means for food consumption detection and/or food identification. In an example, a device can identify when a person in a geographic location that is associated with probable food consumption. In an example, a device can use information concerning the person's geographic location as measured by a global positioning system or other geographic location identification system. In an example, if a person is located at a restaurant with a known menu or at a store with a known food inventory, then information concerning this menu or food inventory can be used to narrow down the likely types of food being consumed. In an example, if a person is located at a restaurant, then the sensitivity of automated detection of food consumption can be adjusted. In an example, if a person is located at a restaurant or grocery store, then visual, auditory, or other information collected by a sensor can be interpreted within the context of that location.

In an example, a device can identify when a person is in a location within a building that is associated with probable food consumption. In an example, if a person is in a kitchen or in a dining room within a building, then the sensitivity of automated detection of food consumption can be adjusted. In an example, a food-consumption monitoring system can increase the continuity or level of automatic data collection when a person is in a restaurant, in a grocery store, in a kitchen, or in a dining room. In an example, a person's location can be inferred from analysis of visual signals or auditory signals instead of via a global positioning system. In an example, a person's location can be inferred from interaction between a device and local RF beacons or local wireless networks.

In an example, a food-consumption monitor or food-identifying sensor can have a biological component. In an example, a food-identifying sensor can use biological or biomimetic components to identify specific foods, ingredients, or nutrients. In various examples, a food-identifying sensor can use one or more biological or biomimetic components selected from the group consisting of: biochemical sensor, antibodies or antibody-based chemical receptor, enzymes or enzyme-based chemical receptor, protein or protein-based chemical receptor, biomarker for a specific dietary nutrient, biomembrane or biomembrane-based sensor, porous polymer or filter paper containing a chemical reagent, nucleic acid-based sensor, polynucleotide-based sensor, artificial taste buds or biomimetic artificial tongue, and taste bud cells in communication with an electromagnetic sensor.

In an example, a food-consumption monitor or food-identifying sensor can be a taste or smell sensor. In an example, a sensor can be an artificial taste bud that emulates the function of a natural taste bud. In an example, a sensor can be an artificial olfactory receptor that emulates the function of a natural olfactory receptor. In an example, a sensor can comprise biological taste buds or olfactory receptors that are configured to be in electrochemical communication with an electronic device. In an example, a sensor can be an electronic tongue. In an example, a sensor can be an electronic nose.

In an example, a food-consumption monitor or food-identifying sensor can be a high-energy sensor. In an example, a high-energy sensor can identify a selected type of food, ingredient, or nutrient based on the interaction of microwaves or x-rays with a portion of food. In various examples a high-energy sensor to detect food consumption or identify consumption of a selected type of nutrient can be selected from the group consisting of: a microwave sensor, a microwave spectrometer, and an x-ray detector.

In an example, a person's consumption of food or the identification of a selected type of food, ingredient, or nutrient can be done by a sensor array. A sensor array can comprise multiple sensors of different types. In an example, multiple sensors in a sensor array can operate simultaneously in order to jointly identify food consumption or to jointly identify a selected type of food, ingredient, or nutrient. In an example, a sensor array can comprise multiple cross-reactive sensors. In an example, different sensors in a sensor array can operate independently to identify different types of foods, ingredients, or nutrients. In an example, a single sensor can detect different types of foods, ingredients, or nutrients.

In various examples, a food-consumption monitor or food-identifying sensor can be selected from the group consisting of: chemical sensor, biochemical sensor, amino acid sensor, chemiresistor, chemoreceptor, photochemical sensor, optical sensor, chromatography sensor, fiber optic sensor, infrared sensor, optoelectronic sensor, spectral analysis sensor, spectrophotometer, olfactory sensor, electronic nose, metal oxide semiconductor sensor, conducting polymer sensor, quartz crystal microbalance sensor, electromagnetic sensor, variable impedance sensor, variable resistance sensor, conductance sensor, neural impulse sensor, EEG sensor, EGG sensor, EMG sensor, interferometer, galvanic skin response sensor, cholesterol sensor, HDL sensor, LDL sensor, electrode, neuroelectrical sensor, neural action potential sensor, Micro Electrical Mechanical System (MEMS) sensor, laboratory-on-a-chip, or medichip, micronutrient sensor, osmolality sensor, protein-based sensor or reagent-based sensor, saturated fat sensor or trans fat sensor, action potential sensor, biological sensor, enzyme-based sensor, protein-based sensor, reagent-based sensor, camera, video camera, fixed focal-length camera, variable focal-length camera, pattern recognition sensor, microfluidic sensor, motion sensor, accelerometer, flow sensor, strain gauge, electrogoniometer, inclinometer, peristalsis sensor, multiple-analyte sensor array, an array of cross-reactive sensors, pH level sensor, sodium sensor, sonic energy sensor, microphone, sound-based chewing sensor, sound-based swallow sensor, ultrasonic sensor, sugar sensor, glucose sensor, temperature sensor, thermometer, and thermistor.

In an example, a sensor to monitor, detect, or sense food consumption or to identify consumption of a selected type of food, ingredient, or nutrient can be a wearable sensor that is worn by the person whose food consumption is monitored, detected, or sensed. In an example, a wearable food-consumption monitor or food-identifying sensor can be worn directly on a person's body. In an example a wearable food-consumption monitor or food-identifying sensor can be worn on, or incorporated into, a person's clothing.

In various examples, a wearable sensor can be worn on a person in a location selected from the group consisting of: wrist, neck, finger, hand, head, ear, eyes, nose, teeth, mouth, torso, chest, waist, and leg. In various examples, a wearable sensor can be attached to a person or to a person's clothing by a means selected from the group consisting of: strap, clip, clamp, snap, pin, hook and eye fastener, magnet, and adhesive.

In various examples, a wearable sensor can be worn on a person in a manner like a clothing accessory or piece of jewelry selected from the group consisting of: wristwatch, wristphone, wristband, bracelet, cufflink, armband, armlet, and finger ring; necklace, neck chain, pendant, dog tags, locket, amulet, necklace phone, and medallion; eyewear, eyeglasses, spectacles, sunglasses, contact lens, goggles, monocle, and visor; clip, tie clip, pin, brooch, clothing button, and pin-type button; headband, hair pin, headphones, ear phones, hearing aid, earring; and dental appliance, palatal vault attachment, and nose ring.

In an example, a sensor to monitor, detect, or sense food consumption or to identify consumption of a selected type of food, ingredient or nutrient can be a utensil-based sensor such as a spoon or fork. In an example, a utensil-based food-consumption monitor or food-identifying sensor can be attached to a generic food utensil. In an example, a utensil-based sensor can be incorporated into specialized "smart utensil." In an example, a sensor can be attached to, or incorporated into a smart fork or smart spoon. In an example, a sensor can be attached to, or incorporated into, a beverage holding member such as a glass, cup, mug, or can. In an example, a food-identifying sensor can be incorporated into a portable food probe.

In an example, a device to measure a person's consumption of at least one selected type of food, ingredient, or nutrient can comprise one or more sensors that are integrated into a place setting. In various examples, sensors can be integrated into one or more of the following place setting members: plate, glass, cup, bowl, serving dish, place mat, fork, spoon, knife, and smart utensil. In various examples, a place setting member can incorporate a sensor selected from the group consisting of: scale, camera, chemical receptor, spectroscopy sensor, infrared sensor, electromagnetic sensor. In an example, a place setting member with an integrated food sensor can collect data concerning food with which the place setting member is in contact at different times. In an example, changes in measurements concerning food at different times can be used to estimate the amount of food that a person is served, the amount of food that a person actually eats, and the amount of left-over food that a person does not eat.

In an example, a sensor to detect food consumption or to identify consumption of a selected type of food, ingredient, or nutrient can be incorporated into a multi-purpose mobile electronic device such as a cell phone, mobile phone, smart phone, smart watch, electronic tablet device, electronic book reader, electronically-functional jewelry, or other portable consumer electronics device. In an example, a smart phone application can turn the camera function of a smart phone into a means of food identification. In an example, such a smart phone application can be in wireless communication with a wearable device that is worn by the person whose food consumption is being measured.

In an example, a wearable device can prompt a person to collect information concerning food consumption using a smart phone application. In an example, a wearable device can automatically activate a smart phone or other portable electronic device to collect information concerning food consumption. In an example, a wearable device can automatically trigger a smart phone or other portable electronic device to start recording audio information using the smart phone's microphone when the wearable device detects that the person is probably eating. In an example, a wearable device can automatically trigger a smart phone or other portable electronic device to start recording visual information using the smart phone's camera when the wearable device detects that the person is probably eating.

In an example, a food-consumption monitor or specific food-identifying sensor can monitor, detect, and/or analyze chewing or swallowing actions by a person. In particular, such a monitor or sensor can differentiate between chewing and swallowing actions that are probably associated with eating vs. other activities. In various examples, chewing or swallowing can be monitored, detected, sensed, or analyzed based on sonic energy (differentiated from speaking, talking, singing, coughing, or other non-eating sounds), motion (differentiated from speaking or other mouth motions), imaging (differentiated from other mouth-related activities) or electromagnetic energy (such as electromagnetic signals from mouth muscles). There are differences in food consumed per chew or per swallow between people, and even for the same person over time, based on the type of food, the person's level of hunger, and other variables. This can make it difficult to estimate the amount of food consumed based only on the number of chews or swallows.

In an example, a food-consumption monitor or food-identifying sensor can monitor a particular body member. In various examples, such a monitor or sensor can be selected from the group consisting of: a blood monitor (for example using a blood pressure monitor, a blood flow monitor, or a blood glucose monitor); a brain monitor (such as an electroencephalographic monitor); a heart monitor (such as electrocardiographic monitor, a heartbeat monitor, or a pulse rate monitor); a mouth function monitor (such as a chewing sensor, a biting sensor, a jaw motion sensor, a swallowing sensor, or a saliva composition sensor); a muscle function monitor (such as an electromyographic monitor or a muscle pressure sensor); a nerve monitor or neural monitor (such as a neural action potential monitor, a neural impulse monitor, or a neuroelectrical sensor); a respiration monitor (such as a breathing monitor, an oxygen consumption monitor, an oxygen saturation monitor, a tidal volume sensor, or a spirometry monitor); a skin sensor (such as a galvanic skin response monitor, a skin conductance sensor, or a skin impedance sensor); and a stomach monitor (such as an electrogastrographic monitor or a stomach motion monitor). In various examples, a sensor can monitor sonic energy or electromagnetic energy from selected portions of a person's gastrointestinal tract (ranging from the mouth to the intestines) or from nerves which innervate those portions. In an example, a monitor or sensor can monitor peristaltic motion or other movement of selected portions of a person's gastrointestinal tract.

In an example, a monitor or sensor to detect food consumption or to identify a selected type of food, ingredient, or nutrient can be a micro-sampling sensor. In an example, a micro-sampling sensor can automatically extract and analyze micro-samples of food, intra-oral fluid, saliva, intra-nasal air, chyme, or blood. In an example, a micro-sampling sensor can collect and analyze micro-samples periodically. In an example, a micro-sampling sensor can collect and analyze micro-samples randomly. In an example, a micro-sampling sensor can collect and analyze micro-samples when a different sensor indicates that a person is probably consuming food. In an example, a micro-sampling sensor can be selected from the group consisting of: microfluidic sampling system, microfluidic sensor array, and micropump.

In an example, a sensor to detect food consumption and/or identify consumption of a selected type of food, ingredient, or nutrient can incorporate microscale or nanoscale technology. In various examples, a sensor to detect food consumption or identify a specific food, ingredient, or nutrient can be selected from the group consisting of: micro-cantilever sensor, microchip sensor, microfluidic sensor, nano-cantilever sensor, nanotechnology sensor, Micro Electrical Mechanical System (MEMS) sensor, laboratory-on-a-chip, and medichip.

Smart Watch or Other Wearable Component:

In an example, a food-consumption monitor or food-identifying sensor can be incorporated into a smart watch or other device that is worn on a person's wrist. In an example, a food-consumption monitor or food-identifying sensor can be worn on, or attached to, other members of a person's body or to a person's clothing. In an example, a device for measuring a person's consumption of at least one selected type of food, ingredient, or nutrient can be worn on, or attached to, a person's body or clothing. In an example, a device can be worn on, or attached to, a part of a person's body that is selected from the group consisting of: wrist (one or both), hand (one or both), or finger; neck or throat; eyes (directly such as via contact lens or indirectly such as via eyewear); mouth, jaw, lips, tongue, teeth, or upper palate; arm (one or both); waist, abdomen, or torso; nose; ear; head or hair; and ankle or leg.

In an example, a device for measuring a person's consumption of at least one selected type of food, ingredient, or nutrient can be worn in a manner similar to a piece of jewelry or accessory. In various examples, a food consumption measuring device can be worn in a manner similar to a piece of or accessory selected from the group consisting of: smart watch, wrist band, wrist phone, wrist watch, fitness watch, or other wrist-worn device; finger ring or artificial finger nail; arm band, arm bracelet, charm bracelet, or smart bracelet; smart necklace, neck chain, neck band, or neck-worn pendant; smart eyewear, smart glasses, electronically-functional eyewear, virtual reality eyewear, or electronically-functional contact lens; cap, hat, visor, helmet, or goggles; smart button, brooch, ornamental pin, clip, smart beads; pin-type, clip-on, or magnetic button; shirt, blouse, jacket, coat, or dress button; head phones, ear phones, hearing aid, ear plug, or ear-worn bluetooth device; dental appliance, dental insert, upper palate attachment or implant; tongue ring, ear ring, or nose ring; electronically-functional skin patch and/or adhesive patch; undergarment with electronic sensors; head band, hair band, or hair clip; ankle strap or bracelet; belt or belt buckle; and key chain or key ring.

In an example, a device for measuring a person's consumption of at least one selected type of food, ingredient, or nutrient can be incorporated or integrated into an article of clothing or a clothing-related accessory. In various examples, a device for measuring food consumption can be incorporated or integrated into one of the following articles of clothing or clothing-related accessories: belt or belt buckle; neck tie; shirt or blouse; shoes or boots; underwear, underpants, briefs, undershirt, or bra; cap, hat, or hood; coat, jacket, or suit; dress or skirt; pants, jeans, or shorts; purse; socks; and sweat suit.

In an example, a device for measuring a person's consumption of at least one selected type of food, ingredient, or nutrient can be attached to a person's body or clothing. In an example, a device to measure food consumption can be attached to a person's body or clothing using an attachment means selected from the group consisting of: band, strap, chain, hook and eye fabric, ring, adhesive, bracelet, buckle, button, clamp, clip, elastic band, eyewear, magnet, necklace, piercing, pin, string, suture, tensile member, wrist band, and zipper. In an example, a device can be incorporated into the creation of a specific article of clothing. In an example, a device to measure food consumption can be integrated into a specific article of clothing by a means selected from the group consisting of: adhesive, band, buckle, button, clip, elastic band, hook and eye fabric, magnet, pin, pocket, pouch, sewing, strap, tensile member, and zipper.

In an example, a wearable device for measuring a person's consumption of at least one selected type of food, ingredient, or nutrient can comprise one or more sensors selected from the group consisting of: motion sensor, accelerometer (single multiple axis), electrogoniometer, or strain gauge; optical sensor, miniature still picture camera, miniature video camera, miniature spectroscopy sensor; sound sensor, miniature microphone, speech recognition software, pulse sensor, ultrasound sensor; electromagnetic sensor, skin galvanic response (Galvanic Skin Response) sensor, EMG sensor, chewing sensor, swallowing sensor; temperature sensor, thermometer, infrared sensor; and chemical sensor, chemical sensor array, miniature spectroscopy sensor, glucose sensor, cholesterol sensor, or sodium sensor.

In an example, a device and system for measuring a person's consumption of at least one selected type of food, ingredient, or nutrient can be entirely wearable or include a wearable component. In an example, a wearable device or component can be worn directly on a person's body, can be worn on a person's clothing, or can be integrated into a specific article of clothing. In an example, a wearable device for measuring food consumption can be in wireless communication with an external device. In various examples, a wearable device for measuring food consumption can be in wireless communication with an external device selected from the group consisting of: a cell phone, an electronic tablet, electronically-functional eyewear, a home electronics portal, an internet portal, a laptop computer, a mobile phone, a remote computer, a remote control unit, a smart phone, a smart utensil, a television set, and a virtual menu system.

In an example, a wearable device for measuring a person's consumption of at least one selected type of food, ingredient, or nutrient can comprise multiple components selected from the group consisting of: Central Processing Unit (CPU) or microprocessor; food-consumption monitoring component (motion sensor, electromagnetic sensor, optical sensor, and/or chemical sensor); graphic display component (display screen and/or coherent light projection); human-to-computer communication component (speech recognition, touch screen, keypad or buttons, and/or gesture recognition); memory component (flash, RAM, or ROM); power source and/or power-transducing component; time keeping and display component; wireless data transmission and reception component; and strap or band.

Smart Utensil, Mobile Phone, or Other Hand-Held Component:

In an example, a device, method, and system for measuring consumption of selected types of foods, ingredients, or nutrients can include a hand-held component in addition to a wearable component. In an example, a hand-held component can be linked or combined with a wearable component to form an integrated system for measuring a person's consumption of at least one selected type of food, ingredient, or nutrient. In an example, the combination and integration of a wearable member and a hand-held member can provide advantages that are not possible with either a wearable member alone or a hand-held member alone. In an example, a wearable member of such a system can be a food-consumption monitor. In an example, a hand-held member of such a system can be a food-identifying sensor.

In an example, a wearable member can continually monitor to detect when the person is consuming food, wherein this continual monitoring does not significantly intrude on the person's privacy. In an example, a hand-held member may be potentially more intrusive with respect to privacy when it operates, but is only activated to operate when food consumption is detected by the wearable member. In an example, wearable and hand-held components of such a system can be linked by wireless communication. In an example, wearable and held-held components of such a system can be physically linked by a flexible wire. In an example, a hand-held component can be removably attached to the wearable member and detached for use in identifying at least one selected type of food, ingredient, or nutrient.

In an example, a hand-held component of a device or system for measuring a person's consumption of at least one selected type of food, ingredient, or nutrient can be a hand-held smart food utensil or food probe. In an example, a hand-held component of a device or system for measuring a person's consumption of at least one selected type of food, ingredient, or nutrient can be a hand-held mobile phone or other general consumer electronics device that performs multiple functions. In an example, a mobile phone application can link or integrate the operation of the mobile phone with the operation of a wearable component of a system for measuring a person's consumption of at least one selected type of food, ingredient, or nutrient.

In various examples, a hand-held component can be selected from the group consisting of: smart utensil, smart spoon, smart fork, smart food probe, smart bowl, smart chop stick, smart dish, smart glass, smart plate, electronically-functional utensil, electronically-functional spoon, electronically-functional fork, electronically-functional food probe, electronically-functional bowl, electronically-functional chop stick, electronically-functional dish, electronically-functional glass, electronically-functional plate, smart phone, mobile phone, cell phone, electronic tablet, and digital camera.

In various examples, a food-consumption monitoring and nutrient identifying system can comprise a combination of a wearable component and a hand-held component that is selected from the group consisting of: smart watch and smart food utensil; smart watch and food probe; smart watch and mobile phone; smart watch and electronic tablet; smart watch and digital camera; smart bracelet and smart food utensil; smart bracelet and food probe; smart bracelet and mobile phone; smart bracelet and electronic tablet; smart bracelet and digital camera; smart necklace and smart food utensil; smart necklace and food probe; smart necklace and mobile phone; smart necklace and electronic tablet; and smart necklace and digital camera.

In an example, a wearable food-consumption monitor (such as may be embodied in a smart watch, smart bracelet, or smart necklace) and a hand-held food-identifying sensor (such as may be embodied in a smart utensil, food probe, or smart phone) can be linked or combined together into an integrated system for measuring a person's consumption of at least one selected type of food, ingredient, or nutrient. In an example, wearable and held-held components such a system can be separate components that are linked by wireless communication. In an example, wearable and held-held components of such a system can be physically connected by a flexible element. In an example, wearable and hand-held components can be physically attached or detached for use. In an example, a hand-held component can be a removable part of a wearable component for easier portability and increased user compliance for all eating events. In an example, a smart utensil or food probe can be removed from a wearable component to identify food prior to, or during consumption. This can increase ease of use and user compliance with food identification for all eating events.

A smart food utensil can be a food utensil that is specifically designed to help measure a person's consumption of at least one selected type of food, ingredient, or nutrient. In an example, a smart utensil can be a food utensil that is equipped with electronic and/or sensory functionality. In an example, a smart food utensil can be designed to function like a regular food utensil, but is also enhanced with sensors in order to detect food consumption and/or identify consumption of selected types of foods, ingredients, or nutrients.

A regular food utensil can be narrowly defined as a tool that is commonly used to convey a single mouthful of food up to a person's mouth. In this narrow definition, a food utensil can be selected from the group consisting of: fork, spoon, spork, and chopstick. In an example, a food utensil can be more broadly defined as a tool that is used to apportion food into mouthfuls during food consumption or to convey a single mouthful of food up to a person's mouth during food consumption. This broader definition includes cutlery and knives used at the time of food consumption in addition to forks, spoons, sporks, and chopsticks.

In an example, a food utensil may be more broadly defined to also include tools and members that are used to convey amounts of food that are larger than a single mouthful and to apportion food into servings prior to food consumption by an individual. Broadly defined in such a manner, a food utensil can be selected from the group consisting of: fork, spoon, spork, knife, chopstick, glass, cup, mug, straw, can, tablespoon, teaspoon, ladle, scoop, spatula, tongs, dish, bowl, and plate. In an example, a smart utensil is an electronically-functional utensil. In an example, a smart utensil can be a utensil with one or built-in functions selected from the group consisting of: detecting use to convey food; detecting food consumption; measuring the speed, rate, or pace of food consumption; measuring the amount of food consumed; identifying the type of food consumed; and communicating information concerning food consumption to other devices or system components.

In an example, a food-consumption monitor or food-identifying sensor can be incorporated into, or attached to, a food utensil. In an example, such a sensor can be an integral part of a specialized smart utensil that is specifically designed to measure food consumption or detect consumption of at least one selected type of food, ingredient, or nutrient. In an example, such a sensor can be designed to be removably attached to a generic food utensil so that any generic utensil can be used. In an example, a sensor can be attached to a generic utensil by tension, a clip, an elastic band, magnetism, or adhesive.

In an example, such a sensor, or a smart utensil of which this sensor is a part, can be in wireless communication with a smart watch or other member that is worn on a person's wrist, hand, or arm. In this manner, a system or device can tell if a person is using the smart utensil when they eat based on the relative movements and/or proximity of a smart utensil to a smart watch. In an example, a smart utensil can be a component of a multi-component system to measure of person's consumption of at least one selected type of food, ingredient, or nutrient.

In an example, a smart food utensil or food probe can identify the types and amounts of consumed foods, ingredients, or nutrients by being in optical communication with food. In an example, a smart food utensil can identify the types and amounts of food consumed by taking pictures of food. In an example, a smart food utensil can take pictures of food that is within a reachable distance of a person. In an example, a smart food utensil can take pictures of food on a plate. In an example, a smart food utensil can take pictures of a portion of food as that food is conveyed to a person's mouth via the utensil.

In an example, a smart food utensil can identify the type of food by optically analyzing food being consumed. In an example, a smart food utensil can identify the types and amounts of food consumed by recording the effects light that is interacted with food. In an example, a smart food utensil can identify the types and amounts of food consumed via spectroscopy. In an example, a smart food utensil can perform spectroscopic analysis of a portion of food as that food is conveyed to a person's mouth via the utensil. In an example, a smart food utensil can measure the amount of food consumed using a photo-detector.

In an example, a smart food utensil or food probe can identify the types and amounts of consumed foods, ingredients, or nutrients by performing chemical analysis of food. In an example, a smart food utensil can identify the types and amounts of food consumed by performing chemical analysis of the chemical composition of food. In an example, a smart food utensil can collect data that is used to analyze the chemical composition of food by direct contact with food. In an example, a smart food utensil can identify the type of food, ingredient, or nutrient being consumed by being in fluid or gaseous communication with food. In an example, a smart food utensil can include an array of chemical sensors with which a sample of food interacts.

In an example, a smart food utensil can collect data that is used to analyze the chemical composition of food by measuring the absorption of light, sound, or electromagnetic energy by food that is in proximity to the person whose consumption is being monitored. In an example, a smart food utensil can collect data that is used to analyze the chemical composition of food by measuring the reflection of light, sound, or electromagnetic energy by food that is in proximity to the person whose consumption is being monitored. In an example, a smart food utensil can collect data that is used to analyze the chemical composition of food by measuring the reflection of different wavelengths of light, sound, or electromagnetic energy by food that is in proximity to the person whose consumption is being monitored.

In an example, a smart food utensil can identify the types and amounts of food consumed by measuring the effects of interacting food with electromagnetic energy. In an example, a smart food utensil can estimate the amount of food that a person consumes by tracking utensil motions with an accelerometer. In various examples, one or more sensors that are part of, or attached to, a smart food utensil can be selected from the group consisting of: motion sensor, accelerometer, strain gauge, inertial sensor, scale, weight sensor, or pressure sensor; miniature camera, video camera, optical sensor, optoelectronic sensor, spectrometer, spectroscopy sensor, or infrared sensor; chemical sensor, chemical receptor array, or spectroscopy sensor; microphone, sound sensor, or ultrasonic sensor; and electromagnetic sensor, capacitive sensor, inductance sensor, or piezoelectric sensor.

In an example, a wearable member (such as a smart watch) can continually monitor for possible food consumption, but a smart utensil is only used when the person is eating. In an example, a device or system for measuring food consumption can compare the motion of a smart utensil with the motion of a wearable member (such as a smart watch) in order to detect whether the smart utensil is being properly used whenever the person is eating food. In an example, a device or system for measuring food consumption can track the movement of a smart utensil that a person should use consistently to eat food, track the movement of a wearable motion sensor (such as a smart watch) that a person wears continuously, and compare the movements to determine whether the person always uses the smart utensil to eat. In an example, this device or system can prompt the person to use the smart utensil when comparison of the motion of the smart utensil with the motion of a wearable motion sensor (such as a smart watch) indicates that the person is not using the smart utensil when they are eating.

In an example, a device or system for measuring food consumption can monitor the proximity of a smart utensil to a wearable member (such as a smart watch) in order to detect whether the smart utensil is being properly used whenever the person is eating food. In an example, this device or system can prompt the person to use the smart utensil when lack of proximity between the smart utensil and a wearable member (such as a smart watch) indicates that the person is not using the smart utensil when they are eating. In an example, a device or system for measuring food consumption can detect if a smart utensil is attached to, or near to, a smart watch. In an example, a device or system for measuring food consumption can prompt a person to use a smart utensil if the smart utensil is not attached to, or near to, a smart watch when the person is eating.

In an example, a food-consumption monitoring and nutrient identifying system can include a hand-held component that is selected from the group consisting of: smart phone, mobile phone, cell phone, holophone, or application of such a phone; electronic tablet, other flat-surface mobile electronic device, Personal Digital Assistant (PDA), or laptop; digital camera; and smart eyewear, electronically-functional eyewear, or augmented reality eyewear. In an example, such a hand-held component can be in wireless communication with a wearable component of such a system. In an example, a device, method, or system for detecting food consumption or measuring consumption of a selected type of food, ingredient, or nutrient can include integration with a general-purpose mobile device that is used to collects data concerning food consumption. In an example, the hand-held component of such a system can be a general purpose device, of which collecting data for food identification is only one among many functions that it performs. In an example, a system for measuring a person's consumption of at least one selected type of food, ingredient, or nutrient can comprise: a wearable member that continually monitors for possible food consumption; a hand-held smart phone that is used to take pictures of food that will be consumed; wireless communication between the wearable member and the smart phone; and software that integrates the operation of the wearable member and the smart phone.

In an example, the hand-held component of a food-consumption monitoring and nutrient identifying system can be a general purpose smart phone which collects information concerning food by taking pictures of food. In an example, this smart phone can be in wireless communication with a wearable component of the system, such as a smart watch. In an example, the hand-held component of such a system must be brought into physical proximity with food that will be consumed in order to measure the results of interaction between food and light, sound, or electromagnetic energy.

In an example, a hand-held component of such a system requires voluntary action by a person in order to collect data for food identification in association with each eating event apart from the actual act of eating. In an example, a mobile phone must be pointed toward food by a person and triggered to take pictures of that food. In an example, a hand-held component of such a system must be brought into fluid or gaseous communication with food in order to chemically analyze the composition of food. In an example, a wearable member (such as a smart watch) can continually monitor for possible food consumption, but a smart phone is only used for food identification when the person is eating. In an example, this device or system can prompt the person to use a smart phone for food identification when the person is eating.

In an example, a smart phone can identify the types and amounts of consumed foods, ingredients, or nutrients by being in optical communication with food. In an example, a smart phone can collect information for identifying the types and amounts of food consumed by taking pictures of food. In an example, a smart phone can take pictures of food that is within a reachable distance of a person. In an example, a smart phone can take pictures of food on a plate.

In an example, a smart phone can collect data that is used to analyze the chemical composition of food by measuring the absorption of light, sound, or electromagnetic energy by food that is in proximity to the person whose consumption is being monitored. In an example, a smart phone can collect data that is used to analyze the chemical composition of food by measuring the reflection of different wavelengths of light, sound, or electromagnetic energy by food that is in proximity to the person whose consumption is being monitored. In various examples, one or more sensors that are part of, or attached to, a smart phone can be selected from the group consisting of: miniature camera, video camera, optical sensor, optoelectronic sensor, spectrometer, spectroscopy sensor, and infrared sensor.

User Interface:

In an example, a device for measuring a person's consumption of at least one selected type of food, ingredient, or nutrient can include a human-to-computer interface for communication from a human to a computer. In various examples, a device for measuring a person's consumption of at least one selected type of food, ingredient, or nutrient can include a human-to-computer interface selected from the group consisting of: speech recognition or voice recognition interface; touch screen or touch pad; physical keypad/keyboard, virtual keypad or keyboard, control buttons, or knobs; gesture recognition interface or holographic interface; motion recognition clothing; eye movement detector, smart eyewear, and/or electronically-functional eyewear; head movement tracker; conventional flat-surface mouse, 3D blob mouse, track ball, or electronic stylus; graphical user interface, drop down menu, pop-up menu, or search box; and neural interface or EMG sensor.

In an example, such a human-to-computer interface can enable a user to directly enter information concerning food consumption. In an example, such direct communication of information can occur prior to food consumption, during food consumption, and/or after food consumption. In an example, such a human-to-computer interface can enable a user to indirectly collect information concerning food consumption. In an example, such indirect collection of information can occur prior to food consumption, during food consumption, and/or after food consumption.

In an example, a device for measuring a person's consumption of at least one selected type of food, ingredient, or nutrient can include a computer-to-human interface for communication from a computer to a human. In an example, a device and method for monitoring and measuring a person's food consumption can provide feedback to the person. In an example, a computer-to-human interface can communicate information about the types and amounts of food that a person has consumed, should consume, or should not consume. In an example, a computer-to-human interface can provide feedback to a person concerning their eating habits and the effects of those eating habits. In an example, this feedback can prompt the person to collect more information concerning the types and amounts of food that the person is consuming. In an example, a computer-to-human interface can be used to not just provide information concerning eating behavior, but also to change eating behavior.

In various examples, a device for measuring a person's consumption of at least one selected type of food, ingredient, or nutrient can provide feedback to the person that is selected from the group consisting of: auditory feedback (such as a voice message, alarm, buzzer, ring tone, or song); feedback via computer-generated speech; mild external electric charge or neural stimulation; periodic feedback at a selected time of the day or week; phantom taste or smell; phone call; pre-recorded audio or video message by the person from an earlier time; television-based messages; and tactile, vibratory, or pressure-based feedback.

In various examples, a device for measuring a person's consumption of at least one selected type of food, ingredient, or nutrient can provide feedback to the person that is selected from the group consisting of: feedback concerning food consumption (such as types and amounts of foods, ingredients, and nutrients consumed, calories consumed, calories expended, and net energy balance during a period of time); information about good or bad ingredients in nearby food; information concerning financial incentives or penalties associated with acts of food consumption and achievement of health-related goals; information concerning progress toward meeting a weight, energy-balance, and/or other health-related goal; information concerning the calories or nutritional components of specific food items; and number of calories consumed per eating event or time period.

In various examples, a device for measuring a person's consumption of at least one selected type of food, ingredient, or nutrient can provide feedback to the person that is selected from the group consisting of: augmented reality feedback (such as virtual visual elements superimposed on foods within a person's field of vision); changes in a picture or image of a person reflecting the likely effects of a continued pattern of food consumption; display of a person's progress toward achieving energy balance, weight management, dietary, or other health-related goals; graphical display of foods, ingredients, or nutrients consumed relative to standard amounts (such as embodied in pie charts, bar charts, percentages, color spectrums, icons, emoticons, animations, and morphed images); graphical representations of food items; graphical representations of the effects of eating particular foods; holographic display; information on a computer display screen (such as a graphical user interface); lights, pictures, images, or other optical feedback; touch screen display; and visual feedback through electronically-functional eyewear.

In various examples, a device for measuring a person's consumption of at least one selected type of food, ingredient, or nutrient can provide feedback to the person that is selected from the group consisting of: advice concerning consumption of specific foods or suggested food alternatives (such as advice from a dietician, nutritionist, nurse, physician, health coach, other health care professional, virtual agent, or health plan); electronic verbal or written feedback (such as phone calls, electronic verbal messages, or electronic text messages); live communication from a health care professional; questions to the person that are directed toward better measurement or modification of food consumption; real-time advice concerning whether to eat specific foods and suggestions for alternatives if foods are not healthy; social feedback (such as encouragement or admonitions from friends and/or a social network); suggestions for meal planning and food consumption for an upcoming day; and suggestions for physical activity and caloric expenditure to achieve desired energy balance outcomes.

Power Source and Wireless Communication:

In an example, a wearable and/or hand-held member of a device for measuring a person's consumption of at least one selected type of food, ingredient, or nutrient can comprise multiple components selected from the group consisting of: a food-consumption monitor or food-identifying sensor; a central processing unit (CPU) such as a microprocessor; a database of different types of food and food attributes; a memory to store, record, and retrieve data such as the cumulative amount consumed for at least one selected type of food, ingredient, or nutrient; a communications member to transmit data to from external sources and to receive data from external sources; a power source such as a battery or power transducer; a human-to-computer interface such as a touch screen, keypad, or voice recognition interface; and a computer-to-human interface such as a display screen or voice-producing interface.

In an example, the power source for a wearable and/or hand-held member of a device for measuring a person's consumption of at least one selected type of food, ingredient, or nutrient can be selected from the group consisting of: power from a power source that is internal to the device during regular operation (such as an internal battery, capacitor, energy-storing microchip, or wound coil or spring); power that is obtained, harvested, or transduced from a power source other than the person's body that is external to the device (such as a rechargeable battery, electromagnetic inductance from external source, solar energy, indoor lighting energy, wired connection to an external power source, ambient or localized radiofrequency energy, or ambient thermal energy); and power that is obtained, harvested, or transduced from the person's body (such as kinetic or mechanical energy from body motion, electromagnetic energy from the person's body, blood flow or other internal fluid flow, glucose metabolism, or thermal energy from the person's body.

In an example, a device or system for measuring a person's consumption of at least one selected type of food, ingredient, or nutrient can include one or more communications components for wireless transmission and reception of data. In an example, multiple communications components can enable wireless communication (including data exchange) between separate components of such a device and system. In an example, a communications component can enable wireless communication with an external device or system. In various examples, the means of this wireless communication can be selected from the group consisting of: radio transmission, Bluetooth transmission, Wi-Fi, and infrared energy.

In various examples, a device and system for measuring food consumption can be in wireless communication with an external device or system selected from the group consisting of: internet portal; smart phone, mobile phone, cell phone, holophone, or application of such a phone; electronic tablet, other flat-surface mobile electronic device, Personal Digital Assistant (PDA), remote control unit, or laptop; smart eyewear, electronically-functional eyewear, or augmented reality eyewear; electronic store display, electronic restaurant menu, or vending machine; and desktop computer, television, or mainframe computer. In various examples, a device can receive food-identifying information from a source selected from the group consisting of: electromagnetic transmissions from a food display or RFID food tag in a grocery store, electromagnetic transmissions from a physical menu or virtual user interface at a restaurant, and electromagnetic transmissions from a vending machine.

In an example, data concerning food consumption that is collected by a wearable or hand-held device can be analyzed by a data processing unit within the device in order to identify the types and amounts of foods, ingredients, or nutrients that a person consumes. In an example, data concerning food consumption that is collected by a smart watch can be analyzed within the housing of the watch. In an example, data concerning food consumption that is collected by a smart food utensil can be analyzed within the housing of the utensil.

In another example, data concerning food consumption that is collected by a wearable or hand-held device can be transmitted to an external device or system for analysis at a remote location. In an example, pictures of food can be transmitted to an external device or system for food identification at a remote location. In an example, chemical analysis results can be transmitted to an external device or system for food identification at a remote location. In an example, the results of analysis at a remote location can be transmitted back to a wearable or hand-held device.

Automatic Food Identification:

In an example, a device for measuring a person's consumption of at least one selected type of food, ingredient, or nutrient can identify and track the selected types and amounts of foods, ingredients, or nutrients that the person consumes in an entirely automatic manner. In an example, such identification can occur in a partially automatic manner in which there is interaction between automated and human identification methods.

In an example, a device for measuring a person's consumption of at least one selected type of food, ingredient, or nutrient can identify and track food consumption at the point of selection or point of sale. In an example, a device for monitoring food consumption or consumption of selected types of foods, ingredients, or nutrients can approximate such measurements by tracking a person's food selections and purchases at a grocery store, at a restaurant, or via a vending machine. Tracking purchases can be relatively easy to do, since financial transactions are already well-supported by existing information technology. In an example, such tracking can be done with specific methods of payment, such as a credit card or bank account. In an example, such tracking can be done with electronically-functional food identification means such as bar codes, RFID tags, or electronically-functional restaurant menus. Electronic communication for food identification can also occur between a food-consumption monitoring device and a vending machine.

In an example, a device for measuring a person's consumption of at least one selected type of food, ingredient, or nutrient can identify food using information from a food's packaging or container. In an example, this information can be detected optically by means of a picture or optical scanner. In an example, food can be identified directly by automated optical recognition of information on food packaging, such as a logo, label, or barcode. In various examples, optical information on a food's packaging or container that is used to identify the type and/or amount of food can be selected from the group consisting of: bar code, food logo, food trademark design, nutritional label, optical text recognition, and UPC code. With respect to meals ordered at restaurants, some restaurants (especially fast-food restaurants) have standardized menu items with standardized food ingredients. In such cases, identification of types and amounts of food, ingredients, or nutrients can be conveyed at the point of ordering (via an electronically-functional menu) or purchase (via purchase transaction). In an example, food can be identified directly by wireless information received from a food display, RFID tag, electronically-functional restaurant menu, or vending machine. In an example, food or its nutritional composition can be identified directly by wireless transmission of information from a food display, menu, food vending machine, food dispenser, or other point of food selection or sale and a device that is worn, held, or otherwise transported with a person.

However, there are limitations to estimating food consumption based on food selections or purchases in a store or restaurant. First, a person might not eat everything that they purchase through venues that are tracked by the system. The person might purchase food that is eaten by their family or other people and might throw out some of the food that they purchase. Second, a person might eat food that they do not purchase through venues that are tracked by the system. The person might purchase some food with cash or in venues that are otherwise not tracked. The person might eat food that someone else bought, as when eating as a guest or family member. Third, timing differences between when a person buys food and when they eat it, especially for non-perishable foods, can confound efforts to associate caloric intake with caloric expenditure to manage energy balance during a defined period of time. For these reasons, a robust device for measuring food consumption should (also) be able to identify food at the point of consumption.

In an example, a device, method, or system for measuring a person's consumption of at least one selected type of food, ingredient, or nutrient can identify and track a person's food consumption at the point of consumption. In an example, such a device, method, or system can include a database of different types of food. In an example, such a device, method, or system can be in wireless communication with an externally-located database of different types of food. In an example, such a database of different types of food and their associated attributes can be used to help identify selected types of foods, ingredients, or nutrients. In an example, a database of attributes for different types of food can be used to associate types and amounts of specific ingredients, nutrients, and/or calories with selected types and amounts of food.

In an example, such a database of different types of foods can include one or more elements selected from the group consisting of: food color, food name, food packaging bar code or nutritional label, food packaging or logo pattern, food picture (individually or in combinations with other foods), food shape, food texture, food type, common geographic or intra-building locations for serving or consumption, common or standardized ingredients (per serving, per volume, or per weight), common or standardized nutrients (per serving, per volume, or per weight), common or standardized size (per serving), common or standardized number of calories (per serving, per volume, or per weight), common times or special events for serving or consumption, and commonly associated or jointly-served foods.

In an example, a picture of a meal as a whole can be automatically segmented into portions of different types of food for comparison with different types of food in a food database. In an example, the boundaries between different types of food in a picture of a meal can be automatically determined to segment the meal into different food types before comparison with pictures in a food database. In an example, a picture of a meal with multiple types of food can be compared as a whole with pictures of meals with multiple types of food in a food database. In an example, a picture of a food or a meal comprising multiple types of food can be compared directly with pictures of food in a food database.

In an example, a picture of food or a meal comprising multiple types of food can be adjusted, normalized, or standardized before it is compared with pictures of food in a food database. In an example, food color can be adjusted, normalized, or standardized before comparison with pictures in a food database. In an example, food size or scale can be adjusted, normalized, or standardized before comparison with pictures in a food database. In an example, food texture can be adjusted, normalized, or standardized before comparison with pictures in a food database. In an example, food lighting or shading can be adjusted, normalized, or standardized before comparison with pictures in a food database.

In an example, a food database can be used to identify the amount of calories that are associated with an indentified type and amount of food. In an example, a food database can be used to identify the type and amount of at least one selected type of food that a person consumes. In an example, a food database can be used to identify the type and amount of at least one selected type of ingredient that is associated with an identified type and amount of food. In an example, a food database can be used to identify the type and amount of at least one selected type of nutrient that is associated with an identified type and amount of food. In an example, an ingredient or nutrient can be associated with a type of food on a per-portion, per-volume, or per-weight basis.

In an example, a vector of food characteristics can be extracted from a picture of food and compared with a database of such vectors for common foods. In an example, analysis of data concerning food consumption can include comparison of food consumption parameters between a specific person and a reference population. In an example, data analysis can include analysis of a person's food consumption patterns over time. In an example, such analysis can track the cumulative amount of at least one selected type of food, ingredient, or nutrient that a person consumes during a selected period of time.

In various examples, data concerning food consumption can be analyzed to identify and track consumption of selected types and amounts of foods, ingredients, or nutrient consumed using one or more methods selected from the group consisting of: linear regression and/or multivariate linear regression, logistic regression and/or probit analysis, Fourier transformation and/or fast Fourier transform (FFT), linear discriminant analysis, non-linear programming, analysis of variance, chi-squared analysis, cluster analysis, energy balance tracking, factor analysis, principal components analysis, survival analysis, time series analysis, volumetric modeling, neural network and machine learning.

In an example, a device for measuring a person's consumption of at least one selected type of food, ingredient, or nutrient can identify the types and amounts of food consumed in an automated manner based on images of that food. In various examples, food pictures can be analyzed for automated food identification using methods selected from the group consisting of: image attribute adjustment or normalization; inter-food boundary determination and food portion segmentation; image pattern recognition and comparison with images in a food database to identify food type; comparison of a vector of food characteristics with a database of such characteristics for different types of food; scale determination based on a fiduciary marker and/or three-dimensional modeling to estimate food quantity; and association of selected types and amounts of ingredients or nutrients with selected types and amounts of food portions based on a food database that links common types and amounts of foods with common types and amounts of ingredients or nutrients. In an example, automated identification of selected types of food based on images and/or automated association of selected types of ingredients or nutrients with that food can occur within a wearable or hand-held device. In an example, data collected by a wearable or hand-held device can be transmitted to an external device where automated identification occurs and the results can then be transmitted back to the wearable or hand-held device.

In an example, a device and system for measuring a person's consumption of at least one selected type of food, ingredient, or nutrient can take pictures of food using a digital camera. In an example, a device and system for measuring a person's consumption of at least one selected type of food, ingredient, or nutrient can take pictures of food using an imaging device selected from the group consisting of: smart watch, smart bracelet, fitness watch, fitness bracelet, watch phone, bracelet phone, wrist band, or other wrist-worn device; arm bracelet; and smart ring or finger ring. In an example, a device and system for measuring a person's consumption of at least one selected type of food, ingredient, or nutrient can take pictures of food using an imaging device selected from the group consisting of: smart phone, mobile phone, cell phone, holophone, and electronic tablet.

In an example, a device and system for measuring a person's consumption of at least one selected type of food, ingredient, or nutrient can take pictures of food using an imaging device selected from the group consisting of: smart glasses, visor, or other eyewear; electronically-functional glasses, visor, or other eyewear; augmented reality glasses, visor, or other eyewear; virtual reality glasses, visor, or other eyewear; and electronically-functional contact lens. In an example, a device and system for measuring a person's consumption of at least one selected type of food, ingredient, or nutrient can take pictures of food using an imaging device selected from the group consisting of: smart utensil, fork, spoon, food probe, plate, dish, or glass; and electronically-functional utensil, fork, spoon, food probe, plate, dish, or glass. In an example, a device and system for measuring a person's consumption of at least one selected type of food, ingredient, or nutrient can take pictures of food using an imaging device selected from the group consisting of: smart necklace, smart beads, smart button, neck chain, and neck pendant.

In an example, an imaging device can take multiple still pictures or moving video pictures of food. In an example, an imaging device can take multiple pictures of food from different angles in order to perform three-dimensional analysis or modeling of the food to better determine the volume of food. In an example, an imaging device can take multiple pictures of food from different angles in order to better control for differences in lighting and portions of food that are obscured from some perspectives. In an example, an imaging device can take multiple pictures of food from different angles in order to perform three-dimensional modeling or volumetric analysis to determine the three-dimensional volume of food in the picture. In an example, an imaging device can take multiple pictures of food at different times, such as before and after an eating event, in order to better determine how much food the person actually ate (as compared to the amount of food served). In an example, changes in the volume of food in sequential pictures before and after consumption can be compared to the cumulative volume of food conveyed to a person's mouth by a smart utensil to determine a more accurate estimate of food volume consumed. In various examples, a person can be prompted by a device to take pictures of food from different angles or at different times.

In an example, a device that indentifies a person's food consumption based on images of food can receive food images from an imaging component or other imaging device that the person holds in their hand to operate. In an example, a device that indentifies a person's food consumption based on images of food can receive food images from an imaging component or other imaging device that the person wears on their body or clothing. In an example, a wearable imaging device can be worn in a relatively fixed position on a person's neck or torso so that it always views the space in front of a person. In an example, a wearable imaging device can be worn on a person's wrist, arm, or finger so that the field of vision of the device moves as the person moves their arm, wrist, and/or fingers. In an example, a device with a moving field of vision can monitor both hand-to-food interaction and hand-to-mouth interaction as the person moves their arm, wrist, and/or hand. In an example, a wearable imaging device can comprise a smart watch with a miniature camera that monitors the space near a person's hands for possible hand-to-food interaction and monitors the near a person's mouth for hand-to-mouth interaction.

In an example, selected attributes or parameters of a food image can be adjusted, standardized, or normalized before the food image is compared to images in a database of food images or otherwise analyzed for identifying the type of food. In various examples, these image attributes or parameters can be selected from the group consisting of: food color, food texture, scale, image resolution, image brightness, and light angle.

In an example, a device and system for identifying types and amounts of food consumed based on food images can include the step of automatically segmenting regions of a food image into different types or portions of food. In an example, a device and system for identifying types and amounts of food consumed based on food images can include the step of automatically identifying boundaries between different types of food in an image that contains multiple types or portions of food. In an example, the creation of boundaries between different types of food and/or segmentation of a meal into different food types can include edge detection, shading analysis, texture analysis, and three-dimensional modeling. In an example, this process can also be informed by common patterns of jointly-served foods and common boundary characteristics of such jointly-served foods.

In an example, estimation of specific ingredients or nutrients consumed from information concerning food consumed can be done using a database that links specific foods (and quantities thereof) with specific ingredients or nutrients (and quantities thereof). In an example, food in a picture can be classified and identified based on comparison with pictures of known foods in a food image database. In an example, such food identification can be assisted by pattern recognition software. In an example, types and quantities of specific ingredients or nutrients can be estimated from the types and quantities of food consumed.

In an example, attributes of food in an image can be represented by a multi-dimensional food attribute vector. In an example, this food attribute vector can be statistically compared to the attribute vector of known foods in order to automate food identification. In an example, multivariate analysis can be done to identify the most likely identification category for a particular portion of food in an image. In various examples, a multi-dimensional food attribute vector can include attributes selected from the group consisting of: food color; food texture; food shape; food size or scale; geographic location of selection, purchase, or consumption; timing of day, week, or special event; common food combinations or pairings; image brightness, resolution, or lighting direction; infrared light reflection; spectroscopic analysis; and person-specific historical eating patterns.

Primary and Secondary Data Collection:

In an example, a method for measuring a person's consumption of at least one selected type of food, ingredient, or nutrient can comprise collecting primary data concerning food consumption and collecting secondary data concerning food consumption. In an example, a device and system for measuring a person's consumption of at least one selected type of food, ingredient, or nutrient can comprise a primary data collection component and a secondary data collection component. In an example, primary data and secondary data can be jointly analyzed to identify the types and amounts of foods, ingredients, or nutrients that a person consumes.

In an example, primary data collection can occur automatically, without the need for any specific action by a person in association with a specific eating event, apart from the actual act of eating. In an example, a primary data component can operate automatically, without the need for any specific action by the person in association with a specific eating event apart from the actual act of eating. In an example, primary data is collected continuously, but secondary data is only collected when primary data indicates that a person is probably eating food. In an example, a primary data collection component operates continuously, but a secondary data collection component only operates when primary data indicates that a person is probably eating food.

In an example, primary data is collected automatically, but secondary data is only collected when triggered, activated, or operated by a person via a specific action in association with a specific eating event other than the act of eating. In an example, a primary data collection component operates automatically, but a secondary data collection component only operates when it is triggered, activated, or operated by a person via a specific action in association with a specific eating event other than the act of eating.

In an example, collection of secondary data can require a specific triggering or activating action by a person, apart from the act of eating, for each specific eating event. In an example, a device to measure food consumption can prompt a person to trigger, activate, or operate secondary data collection in association with a specific eating event when analysis of primary data indicates that this person is probably eating. In an example, a device to measure food consumption can prompt a person to trigger, activate, or operate a secondary data collection component in association with a specific eating event when analysis of primary data indicates that this person is probably eating. In an example, a component of this device that automatically collects primary data to detect when a person is probably eating can prompt the person to collect secondary data to identify food consumed when the person is probably eating. In an example, a device can prompt a person to collect secondary data in association with a specific eating event when analysis of primary data indicates that the person is probably eating and the person has not yet collected secondary data.

In an example, primary data can be collected by a wearable member and secondary data can be collected by a hand-held member. In an example, a person can be prompted to use a hand-held member to collect secondary data when primary data indicates that this person is probably eating. In an example, the wearable member can detect when a person is eating something, but is not very good at identifying what selected types of food the person is eating. In an example, the hand-held member is better at identifying what selected types of food the person is eating, but only when the hand-held member is used, which requires specific action by the person for each eating event.

In an example, a device and system can prompt a person to use a hand-held member (such as a mobile phone or smart utensil) to take pictures of food when a wearable member (such as a smart watch or smart bracelet) indicates that the person is probably eating. In an example, a person can be prompted to use a digital camera to take pictures of food when a wearable food-consumption monitor detects that the person is consuming food.

In an example, a person can be prompted to use a smart utensil to take pictures of food when a wearable food-consumption monitor detects that the person is consuming food. In an example, a device and system can prompt a person to use a hand-held member (such as a smart utensil or food probe) to analyze the chemical composition of food when a wearable member (such as a smart watch or smart bracelet) indicates that the person is probably eating. In an example, a person can be prompted to use a smart utensil for chemical analysis of food when a wearable food-consumption monitor detects that the person is consuming food.

In an example, a device for measuring food consumption can prompt a person to collect secondary data in real time, while a person is eating, when food consumption is indicated by primary data. In an example, a device for measuring food consumption can prompt a person to collect secondary data after food consumption, after food consumption has been indicated by primary data. In various examples, a device can prompt a person to take one or more actions to collect secondary data that are selected from the group consisting of: use a specific smart utensil for food consumption; use a specific set of smart place setting components (dish, plate, utensils, glass, etc) to record information about types and quantities of food; use a special food scale; touch food with a food probe or smart utensil; take a still picture or multiple still pictures of food from different angles; record a video of food from different angles; and expose food to light, electromagnetic, microwave, sonic, or other energy and record the results of interaction between food and this energy.

In an example, the process of collecting primary data can be less intrusive than the process of collecting secondary data with respect to a person's privacy. In an example, secondary data can enable more accurate food identification than primary data with respect to measuring a person's consumption of at least one selected type of food, ingredient, or nutrient. In an example, a coordinated system of primary and secondary data collection can achieve a greater level of measurement accuracy for a selected level of privacy intrusion than either primary data collection or secondary data collection alone. In an example, a coordinated system of primary and secondary data collection can achieve a lower level of privacy intrusion for a selected level of measurement accuracy than either primary data collection or secondary data collection alone.

In an example, primary data can be collected by a device or device component that a person wears on their body or clothing. In an example, primary data can be collected by a smart watch, smart bracelet, or other wrist-worn member. In an example, primary data can be collected by a smart necklace or other neck-worn member. In an example, primary data can be collected by smart glasses or other electronically-functional eyewear. In an example, primary data can be data concerning a person's movements that is collected using a motion detector. In an example, a primary data collection component can monitor a person's movements for movements that indicate that the person is probably eating food. In an example, primary data can be data concerning electromagnetic signals from a person's body. In an example, a primary data collection component can monitor electromagnetic signals from the person's body for signals that indicate that the person is probably eating food.

In an example, secondary data can be collected by a device or device component that a person holds in their hand. In an example, secondary data can be collected by a smart phone, mobile phone, smart utensil, or smart food probe. In an example, secondary data can be images of food. In an example, collection of secondary data can require that the person aim a camera at food and take one or more pictures of food. In an example, a camera-based food-identifying sensor automatically starts taking pictures when data collected by the monitor indicates that a person is probably consuming food, but the person is prompted to manually aim the camera toward food being consumed when data collected by the monitor indicates that a person is probably consuming food.

In an example, secondary data can be the results of chemical analysis of food. In an example, collection of secondary data can require that the person bring a nutrient-identifying utensil or sensor into physical contact with food. In an example, collection of secondary data can require that the person speak into a voice-recognizing device and verbally identify the food that they are eating. In an example, collection of secondary data can require that the person use a computerized menu-interface to identify the food that they are eating.

In an example, a device for measuring a person's consumption of at least one selected type of food, ingredient, or nutrient can collect primary data concerning food consumption without the need for a specific action by the person in association with an eating event apart from the act of eating. In an example, a device for measuring a person's consumption of at least one selected type of food, ingredient, or nutrient can collect primary data automatically. In an example, a device for measuring a person's consumption of at least one selected type of food, ingredient, or nutrient can collect primary data continually.

In an example, a device for measuring a person's consumption of at least one selected type of food, ingredient, or nutrient automatically collects secondary data concerning food consumption during a specific eating event, but only when analysis of primary data indicates that the person is eating. In an example, a device for measuring a person's consumption of at least one selected type of food, ingredient, or nutrient only collects secondary data concerning food consumption during a specific eating when it is triggered, activated, or operated by the person for that eating event by an action apart from the act of eating. In an example, a device can prompt the person to trigger, activate, or operate secondary data collection when primary data indicates that the person is eating.

In an example, a device for measuring a person's food consumption can automatically start collecting secondary data when primary data detects: reachable food sources; hand-to-food interaction; physical location in a restaurant, kitchen, dining room, or other location associated with probable food consumption; hand or arm motions associated with bringing food up to the person's mouth; physiologic responses by the person's body that are associated with probable food consumption; smells or sounds that are associated with probable food consumption; and/or speech patterns that are associated with probable food consumption.

In an example, a device for measuring a person's food consumption can prompt a person to collect secondary data when primary data detects: reachable food sources; hand-to-food interaction; physical location in a restaurant, kitchen, dining room, or other location associated with probable food consumption; hand or arm motions associated with bringing food up to the person's mouth; physiologic responses by the person's body that are associated with probable food consumption; smells or sounds that are associated with probable food consumption; and/or speech patterns that are associated with probable food consumption.

In an example, a device for measuring a person's consumption of at least one selected type of food, ingredient, or nutrient can include a combination of food identification methods or steps that are performed automatically by a computer and food identification methods or steps that are performed by a human. In an example, a device and method for detecting food consumption and identifying consumption of specific ingredients or nutrients can comprise multiple types of data collection and analysis involving interaction between automated analysis and human entry of information. In an example, a person can play a role in segmenting an image of a multi-food meal into different types of food by creating a virtual boundary between foods, such as by moving their finger across a touch-screen image of the meal. In an example, the person may review images of food consumed after an eating event and manually enter food identification information. In an example, a person can select one or more food types and/or quantities from a menu provided in response to a picture or other recorded evidence of an eating event.

In an example, redundant food identification can be performed by both a computer and a human during a calibration period, after which food identification is performed only by a computer. In an example, a device and system can automatically calibrate sensors and responses based on known quantities and outcomes. In an example, a person can eat food with known amounts of specific ingredients or nutrients. In an example, measured amounts can be compared to known amounts in order to calibrate device or system sensors. In an example, a device and system can track actual changes in a person's weight or Body Mass Index (BMI) and use these actual changes to calibrate device or system sensors. In an example, a device or system for measuring a person's consumption of at least one specific food, ingredient, or nutrient can be capable of adaptive machine learning. In an example, such a device or system can include a neural network. In an example, such a device and system can iteratively adjust the weights given to human responses based on feedback and health outcomes In an example, initial estimates of the types and amounts of food consumed can be made by a computer in an automated manner and then refined by human review as needed. In an example, if automated methods for identification of the types and amounts of food consumed do not produce results with a required level of certainty, then a device and system can prompt a person to collect and/or otherwise provide supplemental information concerning the types of food that the person is consuming. In an example, a device and system can track the accuracy of food consumption information provided by an automated process vs. that provided by a human by comparing predicted to actual changes in a person's weight. In an example, the relative weight which a device and system places on information from automated processes vs. information from human input can be adjusted based on their relatively accuracy in predicting weight changes. Greater weight can be given to the information source which is more accurate based on empirical validation.

In an example, a device can ask a person clarifying questions concerning food consumed. In an example, a device can prompt the person with queries to refine initial automatically-generated estimates of the types and quantities of food consumed. In an example, these questions can be asked in real time, as a person is eating, or in a delayed manner, after a person has finished eating or at a particular time of the day. In an example, the results of preliminary automated food identification can be presented to a human via a graphical user interface and the human can then refine the results using a touch screen. In an example, the results of automated food identification can be presented to a human via verbal message and the human can refine the results using a speech recognition interface. In an example, data can be transmitted (such as by the internet) to a review center where food is identified by a dietician or other specialist. In various examples, a human-to-computer interface for entering information concerning food consumption can comprise one or more interface elements selected the group consisting of: microphone, speech recognition, and/or voice recognition interface; touch screen, touch pad, keypad, keyboard, buttons, or other touch-based interface; camera, motion recognition, gesture recognition, eye motion tracking, or other motion detection interface; interactive food-identification menu with food pictures and names; and interactive food-identification search box.

In an example, a device and method for measuring consumption of a selected type of food, ingredient, or nutrient can comprise: a wearable motion sensor that is worn by a person that automatically collects data concerning the person's body motion, wherein this body motion data is used to determine when this person is consuming food; and a user interface that prompts the person to provide additional information concerning the selected types of foods, ingredients, or nutrients that the person is eating when the body motion data indicates that the person is consuming food.

In an example, a device and method for measuring consumption of a selected type of food, ingredient, or nutrient can comprise: a wearable sound sensor that is worn by a person that automatically collects data concerning sounds from the person's body or the environment, wherein this sound data is used to determine when this person is consuming food; and a user interface that prompts the person to provide additional information concerning the selected types of foods, ingredients, or nutrients that the person is eating when the sound data indicates that the person is consuming food.

In an example, a device and method for measuring consumption of a selected type of food, ingredient, or nutrient can comprise: a wearable imaging sensor that is worn by a person that automatically collects image data, wherein this image data is used to determine when this person is consuming food; and a user interface that prompts the person to provide additional information concerning the selected types of foods, ingredients, or nutrients that the person is eating when the imaging data indicates that the person is consuming food.

In an example, a device for measuring a person's consumption of at least one selected type of food, ingredient, or nutrient can comprise a wearable camera that continually takes pictures of the space surrounding a person. In an example, a camera can continually track the locations of a person's hands and only focus on the space near those hands to detect possible hand-and-food interaction. In an example, a device for monitoring a person's food consumption can optically monitor the space around a person for reachable food sources that may result in food consumption. In an example, a device for monitoring a person's food consumption can monitor the person's movements for hand-to-mouth gestures that may indicate food consumption.

In an example, a device can automatically recognize people within its range of vision and restrict picture focal range or content to not record pictures of people. In an example, this camera can automatically defocus images of other people for the sake of privacy. As an alternative way to address privacy issues, this camera can only be triggered to take record pictures when there are visual, sonic, olfactory, or locational indicators that the person is eating food or likely to eat food. As another way to address privacy issues, this camera can have a manual shut-off that the person can use to shut off the camera.

In an example, a wearable device and system for measuring a person's consumption of at least one selected type of food, ingredient, or nutrient can be tamper resistant. In an example, a wearable device can detect when it has been removed from the person's body by monitoring signals from the body such as pulse, motion, heat, skin electromagnetism, or proximity to an implanted device. In an example, a wearable device for measuring food consumption can detect if it has been removed from the person's body by detecting a lack of motion, lack of a pulse, and/or lack of electromagnetic response from skin. In various examples, a wearable device for measuring food consumption can continually monitor optical, electromagnetic, temperature, pressure, or motion signals that indicate that the device is properly worn by a person. In an example, a wearable device can trigger feedback if the device is removed from the person and the signals stop.

In an example, a wearable device for measuring food consumption can detect if its mode of operation becomes impaired. In an example, a wearable device for measuring food consumption that relies on taking pictures of food can detect if its line-of-sight to a person's hands or mouth is blocked. In an example, a wearable device can automatically track the location of a person's hands or mouth and can trigger feedback if this tracking is impaired. In an example, wrist-worn devices can be worn on both wrists to make monitoring food consumption more inclusive and to make it more difficult for a person to circumvent detection of food consumption by the combined devices or system. In an example, a wearable device for measuring food consumption that relies on a smart food utensil can detect if a person is consuming food without using the smart utensil. In an example, a device or system can detect when a utensil or food probe is not in functional linkage with wearable member. In an example, functional linkage can be monitored by common movement, common sound patterns, or physical proximity. In an example, a device or system can trigger feedback or behavioral modification if its function is impaired.

In an example, a person can be prompted to use a hand-held food-identifying sensor to identify the type of food being consumed when a smart watch detects that the person is consuming food and the hand-held food-identifying sensor is not already being used. In an example, a device and system for monitoring, sensing, detecting, and/or tracking a person's consumption of one or more selected types of foods, ingredients, or nutrients can comprise a wearable food-consumption monitor (such as a smart watch or smart necklace) and a hand-held food-identifying sensor (such as a smart utensil or smart phone), wherein data collected by the monitor and sensor are jointly analyzed to measure the types and amounts of specific foods, ingredients, and/or nutrients that the person consumes.

In an example, a person can be prompted to use a hand-held food-identifying sensor for chemical analysis of food when a smart watch detects that the person is consuming food. In an example, a person can be prompted to use a smart utensil for chemical analysis of food when a smart watch detects that the person is consuming food. In an example, a person can be prompted to use a food probe for chemical analysis of food when a smart watch detects that the person is consuming food.

In an example, a person can be prompted to use a hand-held food-identifying sensor to take pictures of food when a smart watch detects that the person is consuming food. In an example, a person can be prompted to use a mobile phone to take pictures of food when a smart watch detects that the person is consuming food. In an example, a person can be prompted to use a smart utensil to take pictures of food when a smart watch detects that the person is consuming food. In an example, a person can be prompted to use a digital camera to take pictures of food when a smart watch detects that the person is consuming food.

In an example, a device and method for monitoring, sensing, detecting, and/or tracking a person's consumption of one or more selected types of foods, ingredients, or nutrients can comprise a wearable device with primary and second modes, mechanisms, or levels of data collection concerning a person's food consumption. The primary mode of data collection can be continuous, not requiring action by the person in association with an eating event apart from the act of eating, and be more useful for general detection of food consumption than it is for identification of consumption of selected types of foods, ingredients, and/or nutrients by the person. The secondary mode of data collection can be non-continuous, requiring action by the person in association with an eating event apart from the act of eating, and can be very useful for identification of consumption of selected types of foods, ingredients, and/or nutrients by the person.

In an example, both primary and secondary data collection can be performed by a device that a person wears on their wrist (such as a smart watch or watch phone). In example, both primary and secondary data collection can be performed by a device that a person wears around their neck (such as a smart necklace or necklace phone). In an example, primary and secondary data can be jointly analyzed to measure the types and amounts of specific foods, ingredients, and/or nutrients that the person consumes. In an example, a person can be prompted to collect secondary data when primary data indicates that the person is probably consuming food.

In an example, data collection by a hand-held food-identifying sensor (such as a smart utensil, food probe, or smart phone) concerning a particular eating event requires action by a person in association with this eating event apart from the actual act of eating. In an example, the person can be prompted to collect data using the hand-held food-identifying sensor when: data that is automatically collected by a wearable food-consumption monitor indicates that the person is probably consuming food; and the person has not already collected data concerning this particular eating event.

In an example, data collection by a hand-held food-identifying sensor can require that a person bring a food-identifying sensor into contact with food, wherein the person is prompted to bring the food-identifying sensor into contact with food when: data that is automatically collected by a wearable food-consumption monitor indicates that the person is probably consuming food; and the person has not already brought the food-identifying sensor into contact with this food. In an example, data collection by a hand-held food-identifying sensor can require that the person aim a camera and take a picture of food, wherein the person is prompted to aim a camera and take a picture of food when: data that is automatically collected by a wearable food-consumption monitor indicates that the person is probably consuming food; and the person has not already taken a picture of this food.

In an example, data collection by a hand-held food-identifying sensor can require that a person enter information concerning food consumed into a hand-held member by touch, keyboard, speech, or gesture. The person can be prompted to enter information concerning food consumed into a hand-held member by touch, keyboard, speech, or gesture when: data that is automatically collected by a wearable food-consumption monitor indicates that the person is probably consuming food; and the person has not already entered information concerning this food.

Some Devices and Methods for Measuring Food Consumption:

In an example, a device for measuring a person's consumption of at least one selected type of food, ingredient, or nutrient can comprise: a wearable food-consumption monitor that detects when the person is probably consuming food; and a hand-held food-identifying sensor that detects the person's consumption of at least one selected type of food, ingredient, or nutrient. In an example, the person can be prompted to use the hand-held food-identifying sensor when the wearable consumption monitor indicates that the person is consuming food. In an example, the hand-held food-identifying sensor can be automatically activated or triggered when the food-consumption monitor indicates that the person is consuming food.

In an example, a device for measuring, monitoring, sensing, detecting, and/or tracking a person's consumption of at least one selected type of food, ingredient, or nutrient can comprise: a wearable food-consumption monitor that automatically monitors and detects when the person consumes food, wherein operation of this monitor to detect food consumption does not require any action associated with a particular eating event by the person apart from the actual act of eating; and a hand-held food-identifying sensor that identifies the selected types of foods, ingredients, and/or nutrients that the person consumes, wherein operation of this sensor to identify foods, ingredients, and/or nutrients during a particular eating event requires action by the person apart associated with that eating event apart from the actual act of eating, and wherein the person is prompted to use the hand-held food-identifying sensor when the wearable consumption monitor indicates that the person is consuming food.

In an example, a method for measuring a person's consumption of at least one selected type of food, ingredient, or nutrient can comprise: collecting primary data concerning food consumption using a wearable food-consumption monitor to detect when a person is consuming food; and collecting secondary data concerning food consumption using a hand-held food-identifying sensor when analysis of primary data indicates that the person is consuming food. In an example, collection of secondary data can be automatic when primary data indicates that the person is consuming food. In an example, collection of secondary data can require a triggering action by the person in association with a particular eating event apart from the actual act of eating. In an example, the person can be prompted to take the triggering action necessary to collect secondary data when primary data indicates that the person is consuming food.

In an example, a method for measuring, monitoring, sensing, detecting, and/or tracking a person's consumption of at least one selected type of food, ingredient, or nutrient can comprise: collecting primary data using a wearable food-consumption monitor to detect when a person is probably consuming food, wherein this detector is worn on the person, and wherein primary data collection does not require action by the person at the time of food consumption apart from the act of consuming food; and collecting secondary data using a hand-held food-identifying sensor to identify the selected types of foods, ingredients, or nutrients that the person is consuming, wherein secondary data collection by the hand-held food-identifying sensor requires action by the person at the time of food consumption apart from the act of consuming food, and wherein the person is prompted to take this action when primary data indicates that the person is consuming food and secondary data has not already been collected.

In an example, a method for measuring a person's consumption of at least one selected type of food, ingredient, or nutrient can comprise: (a) having the person wear a motion sensor that is configured to be worn on at least one body member selected from the group consisting of wrist, hand, finger, and arm; wherein this motion sensor continually monitors body motion to provide primary data that is used to detect when a person is consuming food; (b) prompting the person to collect secondary data concerning food consumption when this primary data indicates that the person is consuming food; wherein secondary data is selected from the group consisting of: data from the interaction between food and reflected, absorbed, or emitted light energy including pictures, chromatographic results, fluorescence results, absorption spectra, reflection spectra, infrared radiation, and ultraviolet radiation; data from the interaction between food and electromagnetic energy including electrical conductivity, electrical resistance, and magnetic interaction; data from the interaction between food and sonic energy including ultrasonic energy; data from the interaction between food and chemical receptors including reagents, enzymes, biological cells, and microorganisms; and data from the interaction between food and mass measuring devices including scales and inertial sensors; and (c) using both primary and secondary data to identify the types and quantities of food consumed in a manner that is at least a partially-automatic; wherein the identification of food type and quantity includes one or more methods selected from the group consisting of: motion pattern analysis and identification; image pattern analysis and identification; chromatography; electromagnetic energy pattern analysis and identification; sound pattern analysis and identification; mass, weight, and/or density; and chemical composition analysis.

In an example, a device for measuring a person's consumption of at least one selected type of food, ingredient, or nutrient can comprise: a wearable motion sensor that automatically collects data concerning body motion, wherein this body motion data is used to determine when a person is consuming food; and an imaging sensor that collects images of food, wherein these food images are used to identify the type and quantity of food, ingredients, or nutrients that a person is consuming food. In an example, an imaging sensor that requires action by the person to pictures of food during an eating event. In an example, the device can prompt the person to use the imaging sensor to take pictures of food when body motion data indicates that the person is consuming food. In an example, a device for measuring a person's consumption of at least one selected type of food, ingredient, or nutrient can comprise: a wearable motion sensor that is worn by a person, wherein this motion sensor automatically and continuously collects data concerning the person's body motion, and wherein the body motion data is used to determine when a person is consuming food; and a wearable imaging sensor that is worn by the person, wherein this imaging sensor does not continuously take pictures, but rather only collects images of eating activity when body motion data indicates that the person is consuming food.

In an example, an imaging sensor need not collect images continuously, but rather requires specific action by the person to initiate imaging at the time of food consumption apart from the actual action of eating. In an example, a person can be prompted to take pictures of food when body motion data collected by a wearable motion sensor indicates that the person is consuming food. In an example, a person can be prompted to take pictures of food when sound data collected by a wearable sound sensor indicates that the person is consuming food.

In an example, a device for measuring a person's consumption of at least one selected type of food, ingredient, or nutrient can comprise: a wearable motion sensor that automatically collects data concerning body motion, wherein this body motion data is used to determine when a person is consuming food; and a chemical composition sensor that analyzes the chemical composition of food, wherein results of this chemical analysis are used to identify the type and quantity of food, ingredients, or nutrients that a person is consuming food. In an example, a device for measuring a person's consumption of at least one selected type of food, ingredient, or nutrient can comprise: a wearable motion sensor that is worn by a person, wherein this motion sensor automatically and continuously collects data concerning the person's body motion, and wherein the body motion data is used to determine when a person is consuming food; and a chemical composition sensor, wherein this chemical composition sensor does not continuously monitor the chemical composition of material within the person's mouth or gastrointestinal tract, but rather only collects information concerning the chemical composition of material within the person's mouth or gastrointestinal tract when body motion data indicates that the person is consuming food.

In an example, a chemical composition sensor can identify the type of food, ingredient, or nutrient based on: physical contact between the sensor and food; or the effects of interaction between food and electromagnetic energy or light energy. In an example, a chemical composition sensor need not collect chemical information continuously, but rather requires specific action by the person to initiate chemical analysis at the time of food consumption apart from the actual action of consuming food. In an example, a person can be prompted to activate a sensor to perform chemical analysis of food when body motion data collected by a wearable motion sensor indicates that the person is consuming food. In an example, a person can be prompted to activate a sensor to perform chemical analysis of food when sound data collected by a wearable sound sensor indicates that the person is consuming food.

In an example, a device for measuring a person's consumption of at least one selected type of food, ingredient, or nutrient can comprise: a wearable sound sensor that automatically collects data concerning body or environmental sounds, wherein this sound data is used to determine when a person is consuming food; and an imaging sensor that collects images of food, wherein these food images are used to identify the type and quantity of food, ingredients, or nutrients that a person is consuming food. In an example, this imaging sensor can require action by the person to pictures of food during an eating event. In an example, the person can be prompted to use the imaging sensor to take pictures of food when sound data indicates that the person is consuming food. In an example, a device for measuring a person's consumption of at least one selected type of food, ingredient, or nutrient can comprise: a wearable sound sensor that is worn by a person, wherein this sound sensor automatically and continuously collects data concerning sounds from the person's body, and wherein this sound data is used to determine when a person is consuming food; and a wearable imaging sensor that is worn by the person, wherein this imaging sensor does not continuously take pictures, but rather only collects images of eating activity when sound data indicates that the person is consuming food.

In an example, a device for measuring a person's consumption of at least one selected type of food, ingredient, or nutrient can comprise: a wearable sound sensor that automatically collects data concerning body or environmental sound, wherein this sound data is used to determine when a person is consuming food; and a chemical composition sensor that analyzes the chemical composition of food, wherein results of this chemical analysis are used to identify the type and quantity of food, ingredients, or nutrients that a person is consuming food. In an example, a device for measuring a person's consumption of at least one selected type of food, ingredient, or nutrient can comprise: a wearable sound sensor that is worn by a person, wherein this motion sensor automatically and continuously collects data concerning sound from the person's body, and wherein this sound data is used to determine when a person is consuming food; and a chemical composition sensor, wherein this chemical composition sensor does not continuously monitor the chemical composition of material within the person's mouth or gastrointestinal tract, but rather only collects information concerning the chemical composition of material within the person's mouth or gastrointestinal tract when sound data indicates that the person is consuming food.

In an example, a method for measuring a person's consumption of at least one selected type of food, ingredient, or nutrient can comprise: collecting a first set of data to detect when a person is probably consuming food in an automatic and continuous manner that does not require action by the person at the time of food consumption apart from the act of consuming food; collecting a second set of data to identify what selected types of foods, ingredients, or nutrients a person is consuming when the first set of data indicates that the person is probably consuming food; and jointly analyzing both the first and second sets of data to estimate consumption of at least one specific food, ingredient, or nutrient by the person.

In an example, a device or system for measuring a person's consumption of at least one selected type of food, ingredient, or nutrient can comprise: (a) a wearable food-consumption monitor that is configured to be worn on a person's body or clothing, wherein this monitor automatically collects primary data that is used to detect when the person is consuming food; (b) a food-identifying sensor that collects secondary data that is used to measure the person's consumption of at least one selected type of food, ingredient, or nutrient, and wherein secondary data collection in association with a specific food consumption event requires a specific action by the person in association with that specific food consumption event apart from the act of consuming food; and (c) a computer-to-human prompting interface, wherein this interface prompts the person to take the specific action required for secondary data collection in association with a specific food consumption event when the primary data indicates that the person is consuming food and the person has not already taken this specific action. In an example, primary data can be body movement data or data concerning electromagnetic signals from the person's body. In an example, secondary data can be collected by a mobile phone, smart utensil, food probe, smart necklace, smart eyewear, or a smart watch.

In an example, a device or system for measuring a person's consumption of at least one selected type of food, ingredient, or nutrient can comprise: (a) a wearable food-consumption monitor that is configured to be worn on a person's body or clothing, wherein this monitor automatically collects primary data that is used to detect when the person is consuming food; (b) an imaging component that collects secondary data that is used to measure the person's consumption of at least one selected type of food, ingredient, or nutrient, wherein this secondary data comprises pictures of food, and wherein taking pictures of food in association with a specific food consumption event requires a specific action by the person in association with that specific food consumption event apart from the act of consuming food; and (c) a computer-to-human prompting interface, wherein this interface prompts the person to take pictures of food in association with a specific food consumption event when the primary data indicates that the person is consuming food and pictures of this food have not already been taken. In an example, primary data can be body movement data or data concerning electromagnetic signals from the person's body. In an example, secondary data can be collected by a mobile phone, smart utensil, food probe, smart necklace, smart eyewear, or a smart watch.

In an example, a device or system for measuring a person's consumption of at least one selected type of food, ingredient, or nutrient can comprise: (a) a wearable food-consumption monitor that is configured to be worn on a person's body or clothing, wherein this monitor automatically collects primary data that is used to detect when the person is consuming food; (b) an chemical-analyzing component that collects secondary data that is used to measure the person's consumption of at least one selected type of food, ingredient, or nutrient, wherein this secondary data comprises chemical analysis of food, and wherein performing chemical analysis of food in association with a specific food consumption event requires a specific action by the person in association with that specific food consumption event apart from the act of consuming food; and (c) a computer-to-human prompting interface, wherein this interface prompts the person to take the action required to perform chemical analysis of food in association with a specific food consumption event when the primary data indicates that the person is consuming food and chemical analysis of this food has not already been performed. In an example, primary data can be body movement data or data concerning electromagnetic signals from the person's body. In an example, secondary data can be collected by a mobile phone, smart utensil, food probe, smart necklace, smart eyewear, or a smart watch.

In an example, a device or system for measuring a person's consumption of at least one selected type of food, ingredient, or nutrient can comprise: (a) a wearable food-consumption monitor that is configured to be worn on a person's body or clothing, wherein this monitor automatically collects primary data that is used to detect when the person is consuming food; (b) a computer-to-human prompting interface which a person uses to enter secondary data concerning the person's consumption of at least one selected type of food, ingredient, or nutrient, wherein this interface selected from the group consisting of: speech or voice recognition, touch or gesture recognition, motion recognition or eye tracking, and buttons or keys, and wherein this interface prompts the person to enter secondary data in association with a specific food consumption event when the primary data indicates that the person is consuming food and the person has not already entered this data. In an example, primary data can be body movement data or data concerning electromagnetic signals from the person's body. In an example, secondary data can be collected by a mobile phone, smart utensil, food probe, smart necklace, smart eyewear, or a smart watch.

In an example, a device or system for measuring a person's consumption of at least one selected type of food, ingredient, or nutrient can comprise: (a) a wearable food-consumption monitor that is configured to be worn on a person's body or clothing, wherein this monitor automatically collects primary data that is used to detect when the person is consuming food; (b) a food-identifying sensor that automatically collects secondary data that is used to measure the person's consumption of at least one selected type of food, ingredient, or nutrient in association with a specific food consumption event when the primary data indicates that the person is consuming food. In an example, primary data can be body movement data or data concerning electromagnetic signals from the person's body. In an example, secondary data can be collected by a mobile phone, smart utensil, food probe, smart necklace, smart eyewear, or a smart watch.

In an example, a device or system for measuring a person's consumption of at least one selected type of food, ingredient, or nutrient can comprise: (a) a smart watch that is configured to be worn on a person's wrist, hand, or arm, wherein this smart watch automatically collects primary data that is used to detect when the person is consuming food; (b) a food-identifying sensor that collects secondary data that is used to measure the person's consumption of at least one selected type of food, ingredient, or nutrient, and wherein secondary data collection in association with a specific food consumption event requires a specific action by the person in association with that specific food consumption event apart from the act of consuming food; and (c) a computer-to-human prompting interface, wherein this interface prompts the person to take the specific action required for secondary data collection in association with a specific food consumption event when the primary data indicates that the person is consuming food and the person has not already taken this specific action. In an example, primary data can be body movement data or data concerning electromagnetic signals from the person's body. In an example, secondary data can be collected by a mobile phone, smart utensil, food probe, smart necklace, smart eyewear, or the smart watch.

In an example, a device or system for measuring a person's consumption of at least one selected type of food, ingredient, or nutrient can comprise: (a) a smart watch that is configured to be worn on a person's wrist, hand, or arm, wherein this smart watch automatically collects primary data that is used to detect when the person is consuming food; (b) an imaging component that collects secondary data that is used to measure the person's consumption of at least one selected type of food, ingredient, or nutrient, wherein this secondary data comprises pictures of food, and wherein taking pictures of food in association with a specific food consumption event requires a specific action by the person in association with that specific food consumption event apart from the act of consuming food; and (c) a computer-to-human prompting interface, wherein this interface prompts the person to take pictures of food in association with a specific food consumption event when the primary data indicates that the person is consuming food and pictures of this food have not already been taken. In an example, primary data can be body movement data or data concerning electromagnetic signals from the person's body. In an example, secondary data can be collected by a mobile phone, smart utensil, food probe, smart necklace, smart eyewear, or the smart watch.

In an example, a device or system for measuring a person's consumption of at least one selected type of food, ingredient, or nutrient can comprise: (a) a smart watch that is configured to be worn on a person's wrist, hand, or arm, wherein this smart watch automatically collects primary data that is used to detect when the person is consuming food; (b) an chemical-analyzing component that collects secondary data that is used to measure the person's consumption of at least one selected type of food, ingredient, or nutrient, wherein this secondary data comprises chemical analysis of food, and wherein performing chemical analysis of food in association with a specific food consumption event requires a specific action by the person in association with that specific food consumption event apart from the act of consuming food; and (c) a computer-to-human prompting interface, wherein this interface prompts the person to take the action required to perform chemical analysis of food in association with a specific food consumption event when the primary data indicates that the person is consuming food and chemical analysis of this food has not already been performed. In an example, primary data can be body movement data or data concerning electromagnetic signals from the person's body. In an example, secondary data can be collected by a mobile phone, smart utensil, food probe, smart necklace, smart eyewear, or the smart watch.

In an example, a device or system for measuring a person's consumption of at least one selected type of food, ingredient, or nutrient can comprise: (a) a smart watch that is configured to be worn on a person's wrist, hand, or arm, wherein this smart watch automatically collects primary data that is used to detect when the person is consuming food; (b) a computer-to-human prompting interface which a person uses to enter secondary data concerning the person's consumption of at least one selected type of food, ingredient, or nutrient, wherein this interface selected from the group consisting of: speech or voice recognition, touch or gesture recognition, motion recognition or eye tracking, and buttons or keys, and wherein this interface prompts the person to enter secondary data in association with a specific food consumption event when the primary data indicates that the person is consuming food and the person has not already entered this data. In an example, primary data can be body movement data or data concerning electromagnetic signals from the person's body. In an example, the interface can comprise a mobile phone, smart utensil, food probe, smart necklace, smart eyewear, or the smart watch.

In an example, a device or system for measuring a person's consumption of at least one selected type of food, ingredient, or nutrient can comprise: (a) a smart watch that is configured to be worn on a person's wrist, hand, or arm, wherein this smart watch automatically collects primary data that is used to detect when the person is consuming food; (b) a food-identifying sensor that automatically collects secondary data that is used to measure the person's consumption of at least one selected type of food, ingredient, or nutrient in association with a specific food consumption event when the primary data indicates that the person is consuming food. In an example, primary data can be body movement data or data concerning electromagnetic signals from the person's body. In an example, secondary data can be collected by a mobile phone, smart utensil, food probe, smart necklace, smart eyewear, or the smart watch.

Narrative to Accompany FIGS. 1 Through 4:

First we will provide an introductory overview to FIGS. 1 through 4. FIGS. 1 through 4 show an example of a device and system for measuring a person's consumption of at least one specific type of food, ingredient, or nutrient, wherein this device and system has two components. The first component is a wearable food-consumption monitor that is worn on a person's body or clothing. In this example, the wearable food-consumption monitor is a smart watch that is worn on a person's wrist. The smart watch automatically collects primary data that is used to detect when a person is consuming food. The second component is a hand-held food-identifying sensor. In this example, the hand-held food-identifying sensor is a smart spoon. The smart spoon collects secondary data that is used to identify the person's consumption of at least one specific type of food, ingredient, or nutrient.

In the example shown in FIGS. 1 through 4, the smart watch collects primary data automatically, without requiring any specific action by the person in association with a specific eating event apart from the actual act of eating. As long as the person continues to wear the smart watch, the smart watch collects the primary data that is used to detect food consumption. In an example, primary data can be motion data concerning the person's wrist movements. In an example, primary data can be up-and-down and tilting movements of the wrist that are generally associated with eating food. In contrast to primary data collection by the smart watch, which is automatic and relatively-continuous, secondary data collection by the smart spoon depends on the person using that particular spoon to eat. In other words, secondary data collection by the smart spoon requires specific action by the person in association with a specific eating event apart from the actual act of eating.

This device and system includes both a smart watch and a smart spoon that work together as an integrated system. Having the smart watch and smart spoon work together provides advantages over use of either a smart watch or a smart spoon by itself. The smart watch provides superior capability for food consumption monitoring (as compared to a smart spoon) because the person wears the smart watch all the time and the smart watch monitors for food consumption continually. The smart spoon provides superior capability for food identification (as compared to a smart watch) because the spoon has direct contact with the food and can directly analyze the chemical composition of food in a manner that is difficult to do with a wrist-worn member. Having both the smart watch and smart spoon work together as an integrated system can provide better monitoring compliance and more-accurate food identification than either working alone.

As FIGS. 1 through 4 collectively show, an integrated device and system that comprises both a smart watch and a smart spoon, working together, can measure a person's consumption of at least one selected type of food, ingredient, or nutrient in a more consistent and accurate manner than either a smart watch or a smart spoon operating alone. One way in which the smart watch and smart spoon can work together is for the smart watch to track whether or not the smart spoon is being used when the smart watch detects that the person is eating food. If the smart spoon is not being used when the person eats, then the smart watch can prompt the person to use the smart spoon. This prompt can range from a relatively-innocuous tone or vibration (which the person can easily ignore) to a more-substantive aversive stimulus, depending on the strength of the person's desire for measurement accuracy and self-control.

Figure 1:
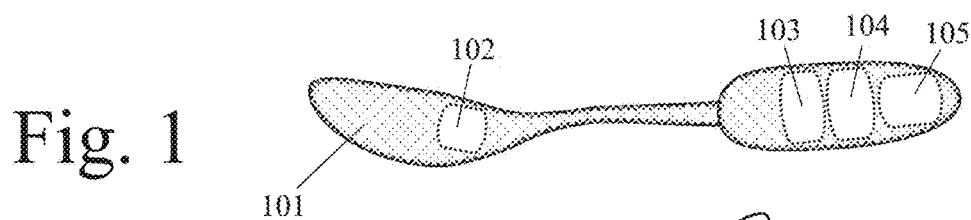
FIGS. 1 through 84 show examples of a wearable spectroscopic sensor to measure food consumption based on the interaction between light and the human body, but they do not limit the full generalizability of the claims.
Figure 2:
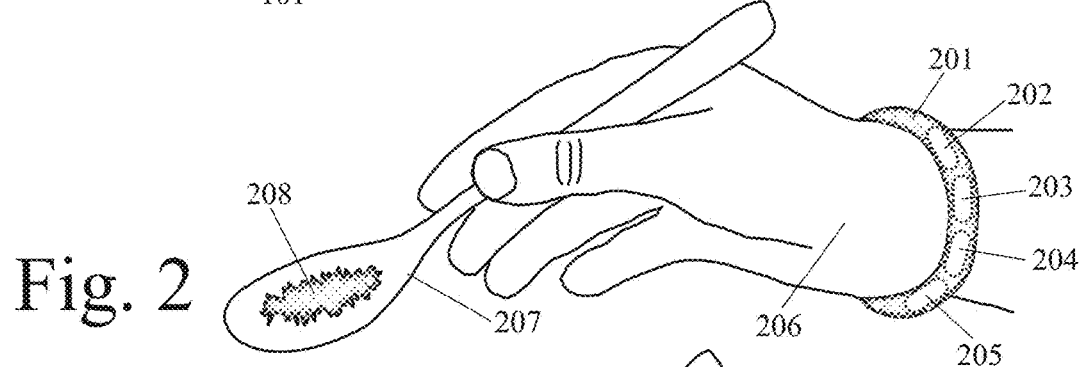
Figure 3:
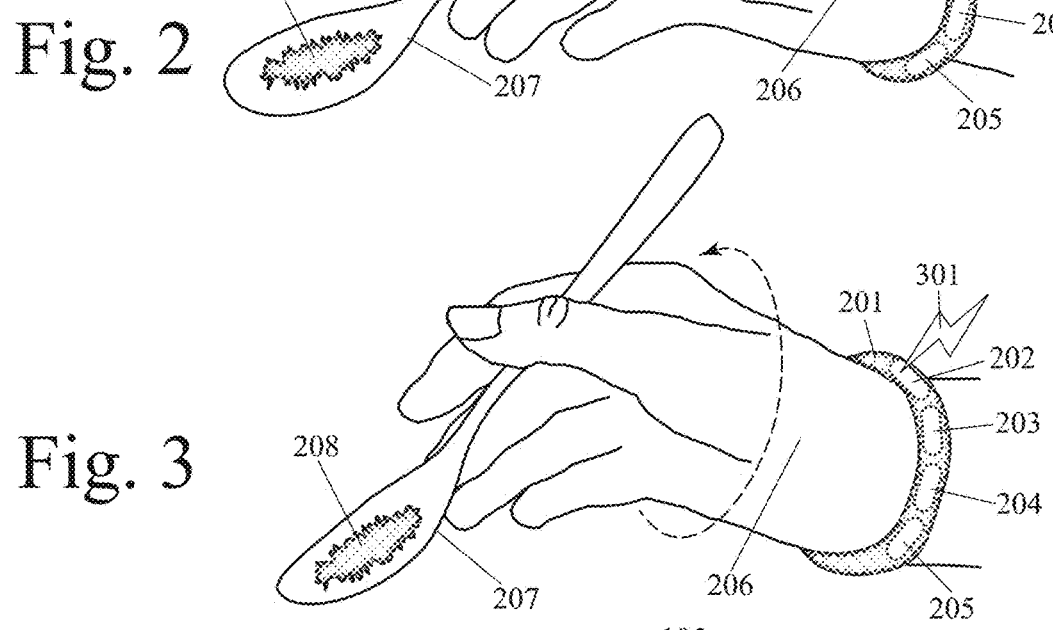
Figure 4:
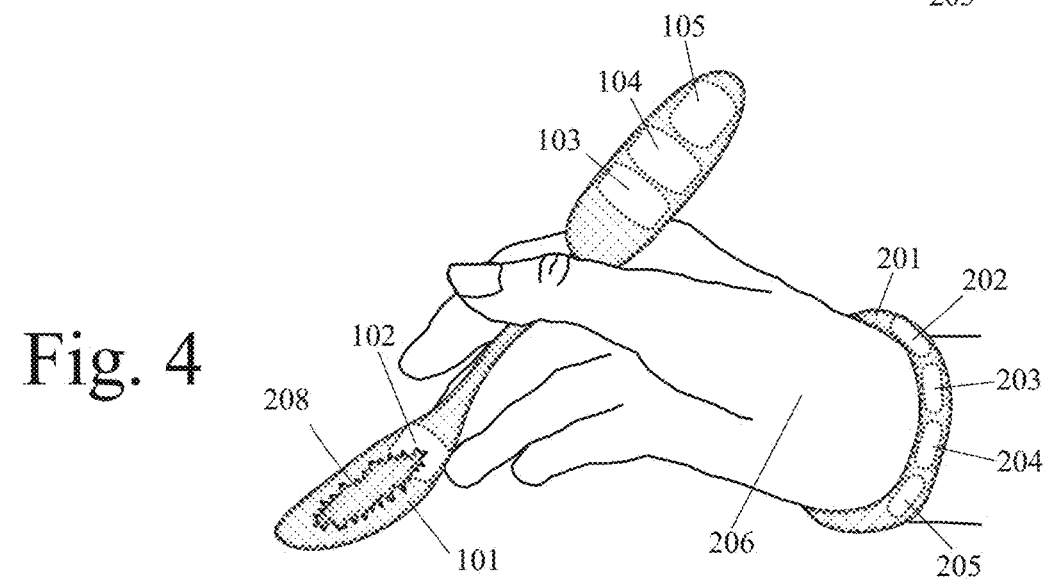

Having provided an introductory overview for FIGS. 1 through 4 collectively, we now discuss them individually. FIG. 1 introduces the hand-held food-identifying sensor of this device, which is a smart spoon in this example. In this example, a smart spoon is a specialized electronic spoon that includes food sensors as well as wireless data communication capability. In this example, the smart spoon includes a chemical sensor which analyzes the chemical composition of food with which the spoon comes into contact. FIG. 2 introduces the wearable food-consumption monitor of this device, which is a smart watch in this example. In this example, a smart watch is a wrist-worn electronic device that includes body sensors, a data processing unit, and wireless data communication capability. In this example, the body sensor is a motion sensor. FIGS. 3 and 4 show how the smart spoon and smart watch work together as an integrated system to monitor and measure a person's consumption of at least one selected type of food, ingredient, or nutrient. We now discuss FIGS. 1 through 4 individually in more detail.

FIG. 1 shows that the hand-held food-identifying sensor in this device is a smart spoon 101 that comprises at least four operational components: a chemical composition sensor 102; a data processing unit 103; a communication unit 104; and a power supply and/or transducer 105. In other examples, the hand-held food-identifying sensor component of this device can be a different kind of smart utensil, such as a smart fork, or can be a hand-held food probe. In an example, smart spoon 101 can include other components, such as a motion sensor or camera. The four operational components 102-105 of smart spoon 101 in this example are in electronic communication with each other. In an example, this electronic communication can be wireless. In another example, this electronic communication can be through wires. Connecting electronic components with wires is well-known in the prior art and the precise configuration of possible wires is not central to this invention, so connecting wires are not shown.

In an example, power supply and/or transducer 105 can be selected from the group consisting of: power from a power source that is internal to the device during regular operation (such as an internal battery, capacitor, energy-storing microchip, or wound coil or spring); power that is obtained, harvested, or transduced from a power source other than the person's body that is external to the device (such as a rechargeable battery, electromagnetic inductance from external source, solar energy, indoor lighting energy, wired connection to an external power source, ambient or localized radiofrequency energy, or ambient thermal energy); and power that is obtained, harvested, or transduced from the person's body (such as kinetic or mechanical energy from body motion.

In the example shown in FIG. 1, chemical composition sensor 102 on the food-carrying scoop end of smart spoon 101 can identify at least one selected type of food, ingredient, or nutrient by analyzing the chemical composition of food that is carried by smart spoon 101. In this example, chemical composition sensor 102 analyzes the chemical composition of food by being in direct fluid communication with food that is carried in the scoop end of smart spoon 101. In this example, chemical composition sensor 102 includes at least one chemical receptor to which chemicals in a selected type of food, ingredient, or nutrient bind. This binding action creates a signal that is detected by the chemical composition sensor 102, received by the data processing unit 103, and then transmitted to a smart watch or other location via communication unit 104.

In another example, chemical composition sensor 102 can analyze the chemical composition of food by measuring the effects of the interaction between food and light energy. In an example, this interaction can comprise the degree of reflection or absorption of light by food at different light wavelengths. In an example, this interaction can include spectroscopic analysis.

In an example, chemical composition sensor 102 can directly identify at least one selected type of food by chemical analysis of food contacted by the spoon. In an example, chemical composition sensor 102 can directly identify at least one selected type of ingredient or nutrient by chemical analysis of food. In an example, at least one selected type of ingredient or nutrient can be indentified indirectly by: first identifying a type and amount of food; and then linking that identified food to common types and amounts of ingredients or nutrients, using a database that links specific foods to specific ingredients or nutrients. In various examples, such a food database can be located in the data processing unit 103 of smart spoon 101, in the data processing unit 204 of a smart watch 201, or in an external device with which smart spoon 101 and/or a smart watch 201 are in wireless communication.

In various examples, a selected type of food, ingredient, or nutrient that is identified by chemical composition sensor 102 can be selected from the group consisting of: a specific type of carbohydrate, a class of carbohydrates, or all carbohydrates; a specific type of sugar, a class of sugars, or all sugars; a specific type of fat, a class of fats, or all fats; a specific type of cholesterol, a class of cholesterols, or all cholesterols; a specific type of protein, a class of proteins, or all proteins; a specific type of fiber, a class of fiber, or all fiber; a specific sodium compound, a class of sodium compounds, and all sodium compounds; high-carbohydrate food, high-sugar food, high-fat food, fried food, high-cholesterol food, high-protein food, high-fiber food, and high-sodium food.

In various examples, chemical composition sensor 102 can analyze food composition to identify one or more potential food allergens, toxins, or other substances selected from the group consisting of: ground nuts, tree nuts, dairy products, shell fish, eggs, gluten, pesticides, animal hormones, and antibiotics. In an example, a device can analyze food composition to identify one or more types of food (such as pork) whose consumption is prohibited or discouraged for religious, moral, and/or cultural reasons.

In various examples, chemical composition sensor 102 can be selected from the group of sensors consisting of: receptor-based sensor, enzyme-based sensor, reagent based sensor, antibody-based receptor, biochemical sensor, membrane sensor, pH level sensor, osmolality sensor, nucleic acid-based sensor, or DNA/RNA-based sensor; biomimetic sensor (such as an artificial taste bud or an artificial olfactory sensor), chemiresistor, chemoreceptor sensor, electrochemical sensor, electroosmotic sensor, electrophoresis sensor, or electroporation sensor; specific nutrient sensor (such as a glucose sensor, a cholesterol sensor, a fat sensor, a protein-based sensor, or an amino acid sensor); color sensor, colorimetric sensor, photochemical sensor, chemiluminescence sensor, fluorescence sensor, chromatography sensor (such as an analytical chromatography sensor, a liquid chromatography sensor, or a gas chromatography sensor), spectrometry sensor (such as a mass spectrometry sensor), spectrophotometer sensor, spectral analysis sensor, or spectroscopy sensor (such as a near-infrared spectroscopy sensor); and laboratory-on-a-chip or microcantilever sensor.

In an example, smart spoon 101 can measure the quantities of foods, ingredients, or nutrients consumed as well as the specific types of foods, ingredients, or nutrients consumed. In an example, smart spoon 101 can include a scale which tracks the individual weights (and cumulative weight) of mouthfuls of food carried and/or consumed during an eating event. In an example, smart spoon 101 can approximate the weights of mouthfuls of food carried by the spoon by measuring the effect of those mouthfuls on the motion of the spoon as a whole or the relative motion of one part of the spoon relative to another. In an example, smart spoon 101 can include a motion sensor and/or inertial sensor. In an example, smart spoon 101 can include one or more accelerometers in different, motion-variable locations along the length of the spoon. In an example, smart spoon 101 can include a spring and/or strain gauge between the food-carrying scoop of the spoon and the handle of the spoon. In an example, food weight can estimated by measuring distension of the spring and/or strain gauge as food is brought up to a person's mouth.

In an example, smart spoon 101 can use a motion sensor or an inertial sensor to estimate the weight of the food-carrying scoop of the spoon at a first point in time (such as during an upswing motion as the spoon carries a mouthful of food up to the person's mouth) and also at a second point in time (such as during a downswing motion as the person lowers the spoon from their mouth). In an example, smart spoon 101 can estimate the weight of food actually consumed by calculating the difference in food weights between the first and second points in time. In an example, a device can track cumulative food consumption by tracking the cumulative weights of multiple mouthfuls of (different types of) food during an eating event or during a defined period of time (such as a day or week).

FIG. 2 shows that, in this embodiment, the wearable food-consumption monitor component of the device is a smart watch 201. Smart watch 201 is configured to be worn around the person's wrist, adjoining the person's hand 206. In other examples, the wearable food-consumption monitor component of this device can be embodied in a smart bracelet, smart arm band, or smart finger ring. In this example, smart watch 201 includes four operational components: a communication unit 202; a motion sensor 203; a data processing unit 204; and a power supply and/or transducer 205. In other examples, a wearable food-consumption monitor component of this device can be embodied in a smart necklace. In the case of a smart necklace, monitoring for food consumption would more likely be done with a sound sensor rather than a motion sensor. In the case of a smart necklace, food consumption can be monitored and detected by detecting swallowing and/or chewing sounds, rather than monitoring and detecting hand-to-mouth motions.

The four components 202-205 of smart watch 201 are in electronic communication with each other. In an example, this electronic communication can be wireless. In another example, this electronic communication can be through wires. Connecting electronic components with wires is well-known in the prior art and the precise configuration of possible wires is not central to this invention, so a configuration of connecting wires is not shown.

In an example, power supply and/or transducer 205 can be selected from the group consisting of: power from a power source that is internal to the device during regular operation (such as an internal battery, capacitor, energy-storing microchip, or wound coil or spring); power that is obtained, harvested, or transduced from a power source other than the person's body that is external to the device (such as a rechargeable battery, electromagnetic inductance from external source, solar energy, indoor lighting energy, wired connection to an external power source, ambient or localized radiofrequency energy, or ambient thermal energy); and power that is obtained, harvested, or transduced from the person's body (such as kinetic or mechanical energy from body motion.

In an example, motion sensor 203 of smart watch 201 can be selected from the group consisting of: bubble accelerometer, dual-axial accelerometer, electrogoniometer, gyroscope, inclinometer, inertial sensor, multi-axis accelerometer, piezoelectric sensor, piezo-mechanical sensor, pressure sensor, proximity detector, single-axis accelerometer, strain gauge, stretch sensor, and tri-axial accelerometer. In an example, motion sensor 203 can collect primary data concerning movements of a person's wrist, hand, or arm.

In an example, there can be an identifiable pattern of movement that is highly-associated with food consumption. Motion sensor 203 can continuously monitor a person's wrist movements to identify times when this pattern occurs to detect when the person is probably eating. In an example, this movement can include repeated movement of the person's hand 206 up to their mouth. In an example, this movement can include a combination of three-dimensional roll, pitch, and yaw by a person's wrist. In an example, motion sensor 203 can also be used to estimate the quantity of food consumed based on the number of motion cycles. In an example, motion sensor 203 can be also used to estimate the speed of food consumption based on the speed or frequency of motion cycles.

In various examples, movements of a person's body that can be monitored and analyzed can be selected from the group consisting of: hand movements, wrist movements, arm movements, tilting movements, lifting movements, hand-to-mouth movements, angles of rotation in three dimensions around the center of mass known as roll, pitch and yaw, and Fourier Transformation analysis of repeated body member movements.

In various examples, smart watch 201 can include a sensor to monitor for possible food consumption other than a motion sensor. In various examples, smart watch 201 can monitor for possible food consumption using one or more sensors selected from the group consisting of: electrogoniometer or strain gauge; optical sensor, miniature still picture camera, miniature video camera, miniature spectroscopy sensor; sound sensor, miniature microphone, speech recognition software, pulse sensor, ultrasound sensor; electromagnetic sensor, skin galvanic response (Galvanic Skin Response) sensor, EMG sensor, chewing sensor, swallowing sensor; and temperature sensor, thermometer, or infrared sensor.

In addition to smart watch 201 that is worn around the person's wrist, FIG. 2 also shows that the person's hand 206 holding a regular spoon 207 that is carrying a mouthful of food 208. It is important to note that this is a regular spoon 207 (with no sensor or data transmission capability), not the smart spoon 101 that was introduced in FIG. 1. There are multiple possible reasons for use of a regular spoon 207 rather than smart spoon 101. In various examples, the person may simply have forgotten to use the smart spoon, may be intentionally trying to "cheat" on dietary monitoring by not using the smart spoon, or may be in dining setting where they are embarrassed to use the smart spoon.

In any event, if the person continues to use the regular spoon 207 instead of the smart spoon 101, then the device and system will not be able to accurately identify the amounts and types of food that they are eating. If the person were not wearing smart watch 201, then the person could continue eating with regular spoon 207 and the device would be completely blind to the eating event. This would lead to low accuracy and low consistency in measuring food consumption. This highlights the accuracy, consistency, and compliance problems that occur if a device relies only on a hand-held food-identifying sensor (without integration with a wearable food-consumption monitor). FIGS. 3 and 4 show how the embodiment disclosed here, comprising both a wearable food-consumption monitor (smart watch 201) and a hand-held food-identification sensor (smart spoon 101) that work together, can correct these problems.

In FIG. 3, motion sensor 203 of smart watch 201 detects the distinctive pattern of wrist and/or arm movement (represented symbolically by the rotational dotted line arrow around hand 206) that indicates that the person is probably consuming food. In an example, a three-dimensional accelerometer on smart watch 201 can detect a distinctive pattern of upward (hand-up-to-mouth) arm movement, followed by a distinctive pattern of tilting or rolling motion (food-into-mouth) wrist movement, followed by a distinctive pattern of downward (hand-down-from-mouth) movement.

If smart watch 201 detects a distinctive pattern of body movements that indicates that the person is probably eating and smart watch 201 has not yet received food identifying secondary data from the use of smart spoon 101, then smart watch 201 can prompt the person to start using smart spoon 101. In an example, this prompt can be relatively-innocuous and easy for the person to ignore if they wish to ignore it. In an example, this prompt can be a quiet tone, gentle vibration, or modest text message to a mobile phone. In another example, this prompt can be a relatively strong and aversive negative stimulus. In an example, this prompt can be a loud sound, graphic warning, mild electric shock, and/or financial penalty.

In the example shown in FIG. 3, the person is not using smart spoon 101 (as they should). This is detected by smart watch 201, which prompts the person to start using smart spoon 101. In FIG. 3, this prompt 301 is represented by a "lightning bolt symbol". In this example, the prompt 301 represented by the lightning bolt symbol is a mild vibration. In an example, a prompt 301 can be more substantive and/or adverse. In an example, the prompt 301 can involve a wireless signal that to a mobile phone or other intermediary device. In an example, the prompt to the person be communicated through an intermediary device and result in an automated text message or phone call (through a mobile phone, for example) to the person to prompt them to use the smart spoon.

In an example, communication unit 202 of smart watch 201 comprises a computer-to-human interface. In an example, part of this computer-to-human interface 202 can include having the computer prompt the person to collect secondary data concerning food consumption when primary data indicates that the person is probably consuming food. In various examples, communication unit 202 can use visual, auditory, tactile, electromagnetic, gustatory, and/or olfactory signals to prompt the person to use the hand-held food-identifying sensor (smart spoon 101 in this example) to collect secondary data (food chemical composition data in this example) when primary data (motion data in this example) collected by the smart watch indicates that the person is probably eating and the person has not already collected secondary data in association with a specific eating event.

In this example, the person's response to the prompt 301 from smart watch 201 is entirely voluntary; the person can ignore the prompt and continue eating with a regular spoon 207 if they wish. However, if the person wishes to have a stronger mechanism for self-control and measurement compliance, then the person can select (or adjust) a device to make the prompt stronger and less voluntary. In an example, a stronger prompt can be a graphic display showing the likely impact of excessive food consumption, a mild electric shock, an automatic message to a health care provider, and an automatic message to a supportive friend or accountability partner. In an example, the prompt can comprise playing the latest inane viral video song that is sweeping the internet—which the person finds so annoying that they comply and switch from using regular spoon 207 to using smart spoon 101. The strength of the prompt can depend on how strongly the person feels about self-constraint and self-control in the context of monitoring and modifying their patterns of food consumption.

In an example, even if a person's response to prompt 301 is entirely voluntary and the person ignores prompt 301 to use the smart spoon to collect detailed secondary data concerning the meal or snack that the person is eating, the device can still be aware that a meal or snack has occurred. In this respect, even if the person's response to prompt 301 is voluntary, the overall device and system disclosed herein can still track all eating events. This disclosed device provides greater compliance and measurement information than is likely with a hand-held device only. With a hand-held device only, if the person does not use the hand-held member for a particular eating event, then the device is completely oblivious to that eating event. For example, if a device relies on taking pictures from a smart phone to measure food consumption and a person just keeps the phone in their pocket or purse when they eat a snack or meal, then the device is oblivious to that snack or meal. The device disclosed herein corrects this problem. Even if the person does not respond to the prompt, the device still knows that an eating event has occurred.

In an example, there are other ways by which smart watch 201 can detect if smart spoon 101 is being properly used or not. In an example, both smart watch 201 and smart spoon 101 can have integrated motion sensors (such as paired accelerometers) and their relative motions can be compared. If the movements of smart watch 201 and smart spoon 101 are similar during a time when smart watch 201 detects that the person is probably consuming food, then smart spoon 101 is probably being properly used to consume food. However, if smart spoon is not moving when smart watch 201 detects food consumption, then smart spoon 101 is probably just lying somewhere unused and smart watch 201 can prompt the person to use smart spoon 101.

In a similar manner, there can be a wireless (or non-wireless physical linkage) means of detecting physical proximity between smart watch 201 and smart spoon 101. When the person is eating and the smart spoon 101 is not close to smart watch 201, then smart watch 201 can prompt the person to use smart spoon 101. In an example, physical proximity between smart watch 201 and smart spoon 101 can be detected by electromagnetic signals. In an example, physical proximity between smart watch 201 and smart spoon 101 can be detected by optical signals.

If a person feels very strongly about the need for self-constraint and self-control in the measurement and modification of their food consumption, then a device for measuring consumption of at least one selected type of food, ingredient, or nutrient can be made tamper-resistant. In the example shown in FIGS. 1 through 4, smart watch 201 can include a mechanism for detecting when it is removed from the person's body. This can help make it tamper-resistant. In an example, smart watch 201 can monitor signals related to the person's body selected from the group consisting of: pulse, motion, heat, electromagnetic signals, and proximity to an implanted device. In an example, smart watch 201 can detect when it is been removed from the person's wrist by detecting a lack of motion, lack of a pulse, and/or lack of electromagnetic response from skin. In various examples, smart watch 201 can continually monitor optical, electromagnetic, temperature, pressure, or motion signals that indicate that smart watch 201 is properly worn by a person. In an example, smart watch 201 can trigger feedback if it is removed from the person.

In the final figure of this sequence, FIG. 4 shows that the person has responded positively to prompting signal 301 and has switched from using regular spoon 207 (without food sensing and identification capability) to using smart spoon 101 (with food sensing and identification capability). In FIG. 4, the mouthful of food 208 that is being carried by smart spoon 101 is now in fluid or optical communication with chemical composition sensor 102. This enables identification of at least one selected type of food, ingredient, or nutrient by chemical composition sensor 102 as part of smart spoon 101.

In an example, secondary data concerning the type of food, ingredient, or nutrient carried by smart spoon 101 can be wirelessly transmitted from communication unit 104 on smart spoon 101 to communication unit 202 on smart watch 201. In an example, the data processing unit 204 on smart watch 201 can track the cumulative amount consumed of at least one selected type of food, ingredient, or nutrient. In an example, smart watch 201 can convey this data to an external device, such as through the internet, for cumulative tracking and analysis.

In some respects there can be a tradeoff between the accuracy and consistency of food consumption measurement and a person's privacy. The device disclosed herein offers good accuracy and consistency of food consumption measurement, with relatively-low privacy intrusion. In contrast, consider a first method of measuring food consumption that is based only on voluntary use of a hand-held smart phone or smart utensil, apart from any wearable food consumption monitor. This first method can offer relatively-low privacy intrusion, but the accuracy and consistency of measurement depends completely on the person's remembering to use it each time that the person eats a meal or snack—which can be problematic. Alternatively, consider a second method of measuring food consumption that is based only on a wearable device that continually records video pictures of views (or continually records sounds) around the person. This second method can offer relatively high accuracy and consistency of food consumption measurement, but can be highly intrusive with respect to the person's privacy.

The device disclosed herein provides a good solution to this problem of accuracy vs. privacy and is superior to either the first or second methods discussed above. This embodiment of this device that is shown in FIGS. 1 through 4 comprises a motion-sensing smart watch 201 and a chemical-detecting smart spoon 101 that work together to offer relatively-high food measurement accuracy with relatively-low privacy intrusion. Consistent use of the smart watch 201 does not require that a person remember to carry, pack, or otherwise bring a particular piece of portable electronic equipment like methods that rely exclusively on use of mobile phone or utensil. As long as the person does not remove the smart watch, the smart watch goes with them where ever they go and continually monitors for possible food consumption activity. Also, continually monitoring wrist motion is far less-intrusive with respect to a person's privacy than continually monitoring what the person sees (video monitoring) or hears (sound monitoring).

In this example, a smart watch 201 collects primary data concerning probable food consumption and prompts the person to collect secondary for food identification when primary data indicates that the person is probably eating food and the person has not yet collected secondary data. In this example, primary data is body motion data and secondary data comprises chemical analysis of food. In this example, smart watch 201 is the mechanism for collection of primary data and smart spoon 101 is the mechanism for collection of secondary data. In this example, collection of primary data is automatic, not requiring any action by the person in association with a particular eating event apart from the actual act of eating, but collection of secondary data requires a specific action (using the smart spoon to carry food) in association with a particular eating event apart from the actual act of eating. In this example, this combination of automatic primary data collection and non-automatic secondary data collection combine to provide relatively high-accuracy and high-compliance food consumption measurement with relatively low privacy intrusion. This is an advantage over food consumption devices and methods in the prior art.

In an example, information concerning a person's consumption of at least one selected type of food, ingredient, and/or nutrient can be combined with information from a separate caloric expenditure monitoring device that measures a person's caloric expenditure to comprise an overall system for energy balance, fitness, weight management, and health improvement. In an example, a food-consumption monitoring device (such as this smart watch) can be in wireless communication with a separate fitness monitoring device. In an example, capability for monitoring food consumption can be combined with capability for monitoring caloric expenditure within a single smart watch device. In an example, a smart watch device can be used to measure the types and amounts of food, ingredients, and/or nutrients that a person consumes as well as the types and durations of the calorie-expending activities in which the person engages.

FIGS. 1 through 4 also show an example of a device for monitoring food consumption comprising: (a) a wearable sensor that is configured to be worn on a person's body or clothing, wherein this wearable sensor automatically collects data that is used to detect probable eating events without requiring action by the person in association with a probable eating event apart from the act of eating, and wherein a probable eating event is a period of time during which the person is probably eating; (b) a smart food utensil, probe, or dish, wherein this food utensil, probe, or dish collects data that is used to analyze the chemical composition of food that the person eats, wherein this collection of data by the food utensil, probe, or dish requires that the person use the utensil, probe, or dish when eating, and wherein the person is prompted to use the food utensil, probe, or dish when data collected by the wearable sensor indicates a probable eating event; and (c) a data analysis component, wherein this component analyzes data collected by the food utensil, probe, or dish to estimate the types and amounts of foods, ingredients, nutrients, and/or calories that are consumed by the person. In this example, the wearable sensor is motion sensor 203. In this example, the smart food utensil is smart spoon 101. In this example, the data analysis component is data processing unit 204.

In the example shown in FIGS. 1 through 4, motion sensor 203 automatically collects data that is used to detect probable eating events. In this example, this data comprises hand motion. When data collected by motion sensor 203 indicates a probable eating event, then communication unit 202 sends a signal that prompts the person to start using smart spoon 101 to eat. When prompted, the person starts using smart spoon 101 which collects data concerning the chemical composition of food 208 using chemical composition sensor 102. Then, data analysis component 204 analyzes this chemical composition data to estimate the types and amounts of foods, ingredients, nutrients, and/or calories that are consumed by the person.

In this example, analysis of chemical composition data occurs in a wrist-based data analysis component. In other examples, analysis of chemical composition data can occur in other locations. In an example, analysis of chemical composition data can occur in data processing unit 103 in smart spoon 101. In another example, analysis of chemical composition data can occur in a remote computer with which communication unit 104 or communication unit 202 is in wireless communication.

In the example shown in FIGS. 1 through 4, a wearable sensor is worn on the person's wrist. In other examples, a wearable sensor can be worn on a person's hand, finger, or arm. In this example, a wearable sensor is part of an electronically-functional wrist band or smart watch. In another example, a wearable sensor can be an electronically-functional adhesive patch that is worn on a person's skin. In another example, a sensor can be worn on a person's clothing.

In the example shown in FIGS. 1 through 4, the smart food utensil, probe, or dish is a smart spoon 101 with chemical composition sensor 102. In another example, a smart food utensil, probe, or dish can be a fork with a chemical composition sensor. In another example, the smart food utensil, probe, or dish can be a food probe with a chemical composition sensor. In another example, the smart food utensil, probe, or dish can be a plate with a chemical composition sensor. In another example, the smart food utensil, probe, or dish can be a bowl with a chemical composition sensor.

In this example, a wearable sensor and a smart food utensil, probe, or dish are separate but in wireless communication with each other. In another example, a wearable sensor and a food probe can be connectable and detachable. In this example, a chemical composition sensor is an integral part of a smart food utensil, food probe, or food dish. In another example, a chemical composition data can be connectable to, and detachable from, a food utensil, such as for washing the utensil. In an example, a wearable sensor and a smart food utensil, probe, or dish can be physically linked.

In the example shown in FIGS. 1 through 4, a wearable sensor automatically collects data concerning motion of the person's body. In another example, a wearable sensor can automatically collect data concerning electromagnetic energy that is emitted from the person's body or transmitted through the person's body. In another example, a wearable sensor can automatically collect data concerning thermal energy that is emitted from the person's body. In another example, a wearable sensor can automatically collect data concerning light energy that is reflected from the person's body or absorbed by the person's body. In various examples, food events can be detected by monitoring selected from the group consisting of: monitoring motion of the person's body; monitoring electromagnetic energy that is emitted from the person's body or transmitted through the person's body; monitoring thermal energy that is emitted from the person's body; and monitoring light energy that is reflected from the person's body or absorbed by the person's body.

In the example shown in FIGS. 1 through 4, the person is prompted to use a smart food utensil, probe, or dish when data collected by a wearable sensor indicates a probable eating event and the person does not start using the smart food utensil, probe, or dish for this probable eating event before a selected length of time after the start of the probable eating event. In another example, the person can be prompted to use the smart food utensil, probe, or dish when data collected by the wearable sensor indicates a probable eating event and the person does not start using the smart food utensil, probe, or dish for this probable eating event before a selected quantity of eating-related actions occurs during the probable eating event. In another example, the person can be prompted to use the smart food utensil, probe, or dish when data collected by the wearable sensor indicates a probable eating event and the person does not use the smart food utensil, probe, or dish throughout the entire probable eating event.

In a variation on this example, a device for monitoring food consumption can comprise: (a) a wearable sensor that is configured to be worn on a person's wrist, hand, finger, or arm, wherein this wearable sensor automatically collects data that is used to detect probable eating events without requiring action by the person in association with a probable eating event apart from the act of eating, and wherein a probable eating event is a period of time during which the person is probably eating; (b) a smart food utensil, probe, or dish, wherein this food utensil, probe, or dish collects data that is used to analyze the chemical composition of food that the person eats, wherein this collection of data by the food utensil, probe, or dish requires that the person use the utensil, probe, or dish when eating, and wherein the person is prompted to use the food utensil, probe, or dish when data collected by the wearable sensor indicates a probable eating event; and (c) a data analysis component, wherein this component analyzes data collected by the food utensil, probe, or dish to estimate the types and amounts of foods, ingredients, nutrients, and/or calories that are consumed by the person.

In an variation on this example, a device for monitoring food consumption can comprise: (a) a wearable sensor that is configured to be worn on a person's wrist, hand, finger, or arm, wherein this wearable sensor automatically collects data that is used to detect probable eating events without requiring action by the person in association with a probable eating event apart from the act of eating, wherein a probable eating event is a period of time during which the person is probably eating, and wherein this data is selected from the group consisting of data concerning motion of the person's body, data concerning electromagnetic energy emitted from or transmitted through the person's body, data concerning thermal energy emitted from the person's body, and light energy reflected from or absorbed by the person's body; (b) a smart food utensil, probe, or dish, wherein this food utensil, probe, or dish collects data that is used to analyze the chemical composition of food that the person eats, wherein this collection of data by the food utensil, probe, or dish requires that the person use the utensil, probe, or dish when eating, wherein the person is prompted to use the food utensil, probe, or dish when data collected by the wearable sensor indicates a probable eating event; and (c) a data analysis component, wherein this component analyzes data collected by the food utensil, probe, or dish to estimate the types and amounts of foods, ingredients, nutrients, and/or calories that are consumed by the person, and wherein this component analyzes data received from the sensor and data collected by the food utensil, probe, or dish to evaluate the completeness of data collected by the food utensil, probe, or dish for tracking the person's total food consumption.

Narrative to Accompany FIGS. 5 Through 8:

The device that is shown in FIGS. 5 through 8 is similar to the one that was just shown in FIGS. 1 through 4, except that now food is identified by taking pictures of food rather than by chemical analysis of food. In FIGS. 5 through 8, smart spoon 501 of this device and system has a built-in camera 502. In an example, camera 502 can be used to take pictures of a mouthful of food 208 in the scoop portion of smart spoon 501. In another example, camera 502 can be used to take pictures of food before it is apportioned by the spoon, such as when food is still on a plate, in a bowl, or in original packaging. In an example, the types and amounts of food consumed can be identified, in a manner that is at least partially automated, by analysis of food pictures.

Like the example that was just shown in FIGS. 1 through 4, the example that is now shown in FIGS. 5 through 8 shows how device and system for measuring a person's consumption that includes both a wearable food-consumption monitor (a smart watch in this example) and a hand-held food-identifying sensor (a smart spoon in this example). However, in this present example, instead of smart spoon 101 having a chemical composition sensor 102 that analyzes the chemical composition of food, smart spoon 501 has a camera 502 to take plain-light pictures of food. These pictures are then analyzed, in a manner that is at least partially automated, in order to identify the amounts and types of foods, ingredients, and/or nutrients that the person consumes. In an example, these pictures of food can be still-frame pictures. In an example, these pictures can be motion (video) pictures.

Figure 5:
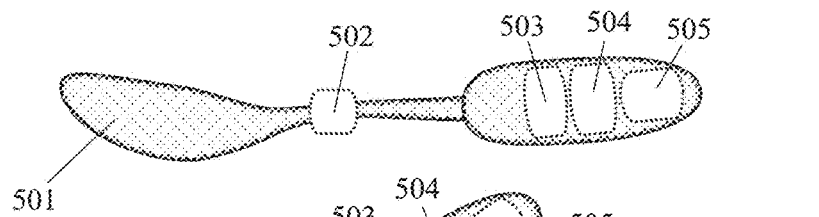
FIGS. 5 through 8 show an example of a device to monitor a person's food consumption comprising a smart watch (with a motion sensor) to detect eating events and a smart spoon (with a built-in camera), wherein the person is prompted to use the smart spoon to take pictures of food when the smart watch detects an eating event.

We now discuss the components of the example shown in FIGS. 5 through 8 in more detail. In FIG. 5, smart spoon 501 includes camera 502 in addition to a data processing unit 503, a communication unit 504, and a power supply and/or transducer 50. The latter three components are like those in the prior example, but the food-identifying sensor (camera 502 vs. chemical composition sensor 102) is different. In this example, camera 502 is built into smart spoon 501 and is located on the portion of smart spoon 501 between the spoon's scoop and the portion of the handle that is held by the person's hand 206.

In this example, camera 502 can be focuses in different directions as the person moves smart spoon 501. In an example, camera 502 can take a picture of a mouthful of food 208 in the scoop of spoon 501. In an example, camera 502 can be directed to take a picture of food on a plate, in a bowl, or in packaging. In this example, camera 502 is activated by touch. In an example, camera 502 can be activated by voice command or by motion of smart spoon 501.

Figure 6:
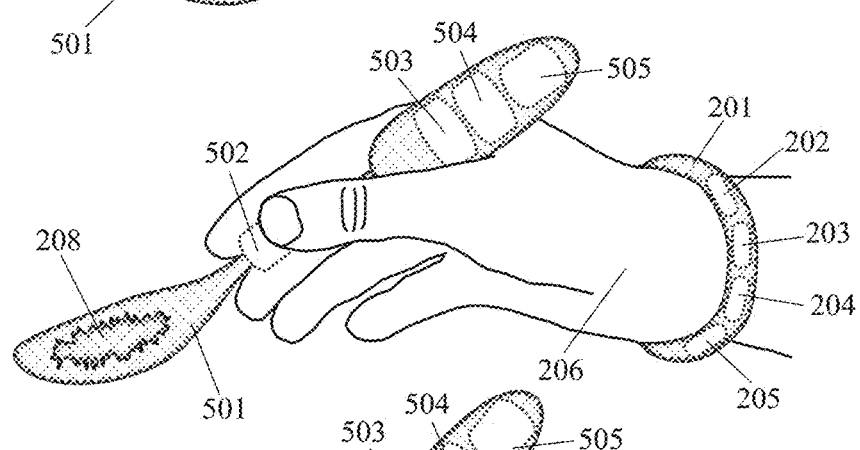
Figure 7:
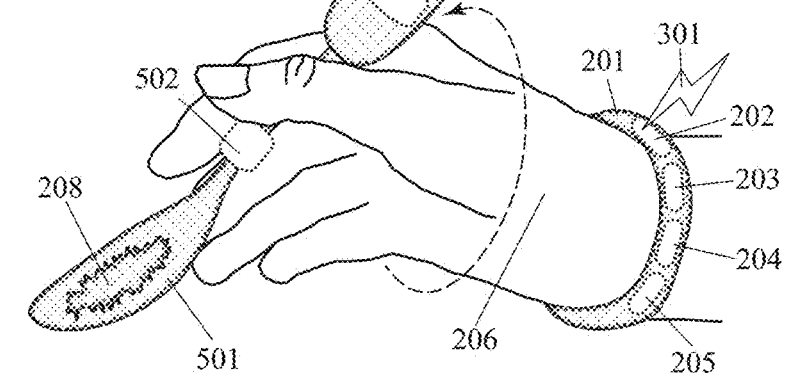
Figure 8:
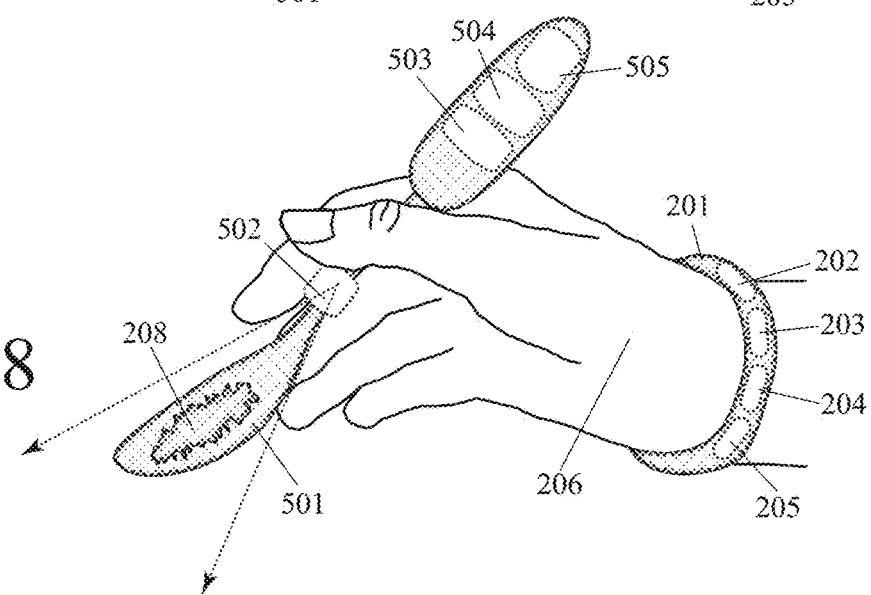

FIG. 6 shows smart spoon 501 in use for food consumption, along with smart watch 201. Smart watch 201 in this example is like smart watch 201 shown in the previous example in FIGS. 1 through 4. As in the last example, smart watch 201 in FIG. 6 includes communication unit 202, motion sensor 203, data processing unit 204, and power supply and/or transducer 205. As in the last example, when the person starts moving their wrist and arm in the distinctive movements that are associated with food consumption, then these movements are recognized by motion sensor 203 on smart watch 201. This is shown in FIG. 7.

If the person has not already used camera 502 on smart spoon 501 to take pictures of food during a particular eating event detected by smart watch 201, then smart watch 201 prompts the person to take a picture of food using camera 502 on smart spoon 501. In this example, this prompt 301 is represented by a "lightning bolt" symbol in FIG. 7. In this example, the person complies with prompt 301 and activates camera 502 by touch in FIG. 8. In this example, a picture is taken of a mouthful of food 208 in the scoop of smart spoon 501. In another example, the person could aim camera 502 on smart spoon 501 toward food on a plate, food in a bowl, or food packaging to take a picture of food before it is apportioned by spoon 501.

In this example, smart watch 201 collects primary data concerning probable food consumption and prompts the person to collect secondary for food identification when primary data indicates that the person is probably eating food and the person has not yet collected secondary data. In this example, primary data is body motion data and secondary data comprises pictures of food. In this example, smart watch 201 is the mechanism for collecting primary data and smart spoon 101 is the mechanism for collecting secondary data. In this example, collection of primary data is automatic, not requiring any action by the person in association with a particular eating event apart from the actual act of eating, but collection of secondary data requires a specific action (triggering and possibly aiming the camera) in association with a particular eating event apart from the actual act of eating. In this example, automatic primary data collection and non-automatic secondary data collection combine to provide relatively high-accuracy and high-compliance food consumption measurement with relatively low privacy intrusion. This is an advantage over food consumption devices and methods in the prior art.

In an example, this device and system can prompt a person to use smart spoon 501 for eating and once the person is using smart spoon 501 for eating this spoon can automatically take pictures of mouthfuls of food that are in the spoon's scoop. In an example, such automatic picture taking can be triggered by infrared reflection, other optical sensor, pressure sensor, electromagnetic sensor, or other contact sensor in the spoon scoop. In another example, this device can prompt a person to manually trigger camera 502 to take a picture of food in the spoon's scoop. In another example, this device can prompt a person to aim camera 502 toward food on a plate, in a bowl, or in original packaging to take pictures of food before it is apportioned into mouthfuls by the spoon. In an example, food on a plate, in a bowl, or in original packaging can be easier to identify by analysis of its shape, texture, scale, and colors than food apportioned into mouthfuls.

In an example, use of camera 502 in smart spoon 501 can rely on having the person manually aim and trigger the camera for each eating event. In an example, the taking of food pictures in this manner requires at least one specific voluntary human action associated with each food consumption event, apart from the actual act of eating, in order to take pictures of food during that food consumption event. In an example, such specific voluntary human actions can be selected from the group consisting of: bringing smart spoon 501 to a meal or snack; using smart spoon 501 to eat food; aiming camera 502 of smart spoon 501 at food on a plate, in a bowl, or in original packaging; triggering camera 502 by touching a button, screen, or other activation surface; and triggering camera 502 by voice command or gesture command.

In an example, camera 502 of smart spoon 501 can be used to take multiple still-frame pictures of food. In an example, camera 502 of smart spoon 501 can be used to take motion (video) pictures of food from multiple angles. In an example, camera 502 can take pictures of food from at least two different angles in order to better segment a picture of a multi-food meal into different types of foods, better estimate the three-dimensional volume of each type of food, and better control for differences in lighting and shading. In an example, camera 502 can take pictures of food from multiple perspectives to create a virtual three-dimensional model of food in order to determine food volume. In an example, quantities of specific foods can be estimated from pictures of those foods by volumetric analysis of food from multiple perspectives and/or by three-dimensional modeling of food from multiple perspectives.

In an example, pictures of food on a plate, in a bowl, or in packaging can be taken before and after consumption. In an example, the amount of food that a person actually consumes (not just the amount ordered by the person or served to the person) can be estimated by measuring the difference in food volume from pictures before and after consumption. In an example, camera 502 can image or virtually create a fiduciary market to better estimate the size or scale of food. In an example, camera 502 can be used to take pictures of food which include an object of known size. This object can serve as a fiduciary marker in order to estimate the size and/or scale of food. In an example, camera 502, or another component on smart spoon 501, can project light beams within the field of vision to create a virtual fiduciary marker. In an example, pictures can be taken of multiple sequential mouthfuls of food being transported by the scoop of smart spoon 501 and used to estimate the cumulative amount of food consumed.

In an example, there can be a preliminary stage of processing or analysis of food pictures wherein image elements and/or attributes are adjusted, normalized, or standardized. In an example, a food picture can be adjusted, normalized, or standardized before it is compared with food pictures in a food database. This can improve segmentation of a meal into different types of food, identification of foods, and estimation of food volume or mass. In an example, food size or scale can be adjusted, normalized, or standardized before comparison with pictures in a food database. In an example, food texture can be adjusted, normalized, or standardized before comparison with pictures in a food database. In an example, food lighting or shading can be adjusted, normalized, or standardized before comparison with pictures in a food database. In various examples, a preliminary stage of food picture processing and/or analysis can include adjustment, normalization, or standardization of food color, texture, shape, size, context, geographic location, adjacent foods, place setting context, and temperature.

In an example, a food database can be used as part of a device and system for identifying types and amounts of food, ingredients, or nutrients. In an example, a food database can include one or more elements selected from the group consisting of: food name, food picture (individually or in combinations with other foods), food color, food packaging bar code or nutritional label, food packaging or logo pattern, food shape, food texture, food type, common geographic or intra-building locations for serving or consumption, common or standardized ingredients (per serving, per volume, or per weight), common or standardized nutrients (per serving, per volume, or per weight), common or standardized size (per serving), common or standardized number of calories (per serving, per volume, or per weight), common times or special events for serving or consumption, and commonly associated or jointly-served foods.

In an example, the boundaries between different types of food in a picture of a meal can be automatically determined to segment the meal into different food types before comparison with pictures in a food database. In an example, individual portions of different types of food within a multi-food meal can be compared individually with images of portions of different types of food in a food database. In an example, a picture of a meal including multiple types of food can be automatically segmented into portions of different types of food for comparison with different types of food in a food database. In an example, a picture of a meal with multiple types of food can be compared as a whole with pictures of meals with multiple types of food in a food database.

In an example, a food database can also include average amounts of specific ingredients and/or nutrients associated with specific types and amounts of foods for measurement of at least one selected type of ingredient or nutrient. In an example, a food database can be used to identify the type and amount of at least one selected type of ingredient that is associated with an identified type and amount of food. In an example, a food database can be used to identify the type and amount of at least one selected type of nutrient that is associated with an identified type and amount of food. In an example, an ingredient or nutrient can be associated with a type of food on a per-portion, per-volume, or per-weight basis.

In an example, automatic identification of food amounts and types can include extracting a vector of food parameters (such as color, texture, shape, and size) from a food picture and comparing this vector with vectors of these parameters in a food database. In various examples, methods for automatic identification of food types and amounts from food pictures can include: color analysis, image pattern recognition, image segmentation, texture analysis, three-dimensional modeling based on pictures from multiple perspectives, and volumetric analysis based on a fiduciary marker or other object of known size.

In various examples, food pictures can be analyzed in a manner which is at least partially automated in order to identify food types and amounts using one or more methods selected from the group consisting of: analysis of variance; chi-squared analysis; cluster analysis; comparison of a vector of food parameters with a food database containing such parameters; energy balance tracking; factor analysis; Fourier transformation and/or fast Fourier transform (FFT); image attribute adjustment or normalization; pattern recognition; comparison with food images with food images in a food database; inter-food boundary determination and food portion segmentation; linear discriminant analysis; linear regression and/or multivariate linear regression; logistic regression and/or probit analysis; neural network and machine learning; non-linear programming; principal components analysis; scale determination using a physical or virtual fiduciary marker; three-dimensional modeling to estimate food quantity; time series analysis; and volumetric modeling.

In an example, attributes of food in an image can be represented by a multi-dimensional food attribute vector. In an example, this food attribute vector can be statistically compared to the attribute vector of known foods in order to automate food identification. In an example, multivariate analysis can be done to identify the most likely identification category for a particular portion of food in an image. In various examples, a multi-dimensional food attribute vector can include attributes selected from the group consisting of: food color; food texture; food shape; food size or scale; geographic location of selection, purchase, or consumption; timing of day, week, or special event; common food combinations or pairings; image brightness, resolution, or lighting direction; infrared light reflection; spectroscopic analysis; and person-specific historical eating patterns. In an example, in some situations the types and amounts of food can be identified by analysis of bar codes, brand logos, nutritional labels, or other optical patterns on food packaging.

In an example, analysis of data concerning food consumption can include comparison of food consumption parameters between a specific person and a reference population. In an example, data analysis can include analysis of a person's food consumption patterns over time. In an example, such analysis can track the cumulative amount of at least one selected type of food, ingredient, or nutrient that a person consumes during a selected period of time.

In an example, pictures of food can be analyzed within the data processing unit of a hand-held device (such as a smart spoon) or a wearable device (such as a smart watch). In an example, pictures of food can be wirelessly transmitted from a hand-held or wearable device to an external device, wherein these food pictures are automatically analyzed and food identification occurs. In an example, the results of food identification can then be wirelessly transmitted back to the wearable or hand-held device. In an example, identification of the types and quantities of foods, ingredients, or nutrients that a person consumes can be a combination of, or interaction between, automated identification food methods and human-based food identification methods.

In the example shown in FIGS. 5 through 8, food-imaging camera 502 is built into smart spoon 501. In various alternative examples, a device and system for measuring a person's consumption of at least one selected type of food, ingredient, or nutrient can take pictures of food with an imaging device or component that is selected from the group consisting of: smart food utensil and/or electronically-functional utensil, smart spoon, smart fork, food probe, smart chop stick, smart plate, smart dish, or smart glass; smart phone, mobile phone, or cell phone; smart watch, watch cam, smart bracelet, fitness watch, fitness bracelet, watch phone, or bracelet phone; smart necklace, necklace cam, smart beads, smart button, neck chain, or neck pendant; smart finger ring or ring cam; electronically-functional or smart eyewear, smart glasses, visor, augmented or virtual reality glasses, or electronically-functional contact lens; digital camera; and electronic tablet.

Narrative to Accompany FIGS. 9 Through 12:

The device that is shown in FIGS. 9 through 12 is similar to the one that was just shown in FIGS. 5 through 8, except that now food pictures are taken by a general-purpose mobile electronic device (such as a smart phone) rather than by a specialized food utensil (such as a smart spoon). In this example, the general-purpose mobile electronic device is a smart phone. In other examples, a general-purpose mobile electronic device can be an electronic tablet or a digital camera.

The wearable food-monitoring component of the example shown in FIGS. 9 through 12 is again a smart watch with a motion sensor, like the one in previous examples. The smart watch and smart phone components of this example work together in FIGS. 9 through 12 in a similar manner to the way in which the smart watch and smart spoon components worked together in the example shown in FIGS. 5 through 8. We do not repeat the methodological detail of possible ways to identify food based on food pictures here because this was already discussed in the narrative accompanying the previous example.

FIG. 9 shows a rectangular general-purpose smart phone 901 that includes a camera (or other imaging component) 902. FIG. 10 shows a person grasping food item 1001 in their hand 206. FIG. 10 also shows that this person is wearing a smart watch 201 that includes communication unit 202, motion sensor 203, data processing unit 204, and power supply and/or transducer 205. In an example, food item 1001 can be a deep-fried pork rind. In another example, food item 1001 can be a blob of plain tofu; however, it is unlikely that any person who eats a blob of plain tofu would even need a device like this.

FIG. 11 shows this person bringing food item 1001 up to their mouth with a distinctive rotation of their wrist that is represented by the dotted-line arrow around hand 206. This indicates that the person is probably eating food. Using motion sensor 203, smart watch 201 detects this pattern of movement and detects that the person is probably eating something. Since the person has not yet taken a picture of food in association with this eating event, smart watch 201 prompts the person to take a picture of food using smart phone 901. This prompt 301 is represented in FIG. 11 by a "lightning bolt" symbol coming out from communication unit 202. We discussed a variety of possible prompts in earlier examples and do not repeat them here.

FIG. 12 shows that this person responds positively to prompt 301. This person responds by taking a picture of food items 1001 in bowl 1201 using camera 902 in smart phone 901. The field of vision of camera 902 is represented by dotted-line rays 1202 that radiate from camera 902 toward bowl 1201. In an example, the person manually aims camera 902 of smart phone 901 toward the food source (bowl 1201 in this example) and then triggers camera 902 to take a picture by touching the screen of smart phone 901. In another example, the person could trigger camera 902 with a voice command or a gesture command.

In this example, smart watch 201 and smart phone 901 share wireless communication. In an example, communication with smart watch 201 can be part of a smart phone application that runs on smart phone 901. In an example, smart watch 201 and smart phone 901 can comprise part of an integrated system for monitoring and modifying caloric intake and caloric expenditure to achieve energy balance, weight management, and improved health.

In an example, smart watch 201 and/or smart phone 901 can also be in communication with an external computer. An external computer can provide advanced data analysis, data storage and memory, communication with health care professionals, and/or communication with a support network of friends. In an example, a general purpose smart phone can comprise the computer-to-human interface of a device and system for measuring a person's consumption of at least one selected type of food, ingredient, or nutrient. In an example, such a device and system can communicate with a person by making calls or sending text messages through a smart phone. In an alternative example, an electronic tablet can serve the role of a hand-held imaging and interface device instead of smart phone 901.

FIGS. 9 through 12 show an embodiment of a device for measuring a person's consumption of at least one selected type of food, ingredient, or nutrient comprising a wearable food-consumption monitor (a smart watch in this example) that is configured to be worn on the person's wrist, arm, hand or finger and a hand-held food-identifying sensor (a smart phone in this example). The person is prompted to use the smart phone to take pictures of food when the smart watch indicates that the person is consuming food. In this example, primary data concerning food consumption that is collected by a smart watch includes data concerning movement of the person's body and secondary data for food identification that is collected by a smart phone includes pictures of food. In this example, the person is prompted to take pictures of food when they are moving in a manner that indicates that they are probably eating and secondary data has not already been collected.

The system for measuring food consumption that is shown in FIGS. 9 through 12 combines continual motion monitoring by a smart watch and food imaging by a smart phone. It is superior to prior art that relies only on a smart phone. A system for measuring food consumption that depends only on the person using a smart phone to take a picture of every meal and every snack they eat will probably have much lower compliance and accuracy than the system disclosed herein. With the system disclosed herein, as long as the person wears the smart watch (which can be encouraged by making it comfortable and tamper resistant), the system disclosed herein continually monitors for food consumption. A system based on a stand-alone smart phone offers no such functionality.

Ideally, if the smart watch 201 herein is designed to be sufficiently comfortable and unobtrusive, it can be worn all the time. Accordingly, it can even monitor for night-time snacking. It can monitor food consumption at times when a person would be unlikely to bring out their smart phone to take pictures (at least not without prompting). The food-imaging device and system that is shown here in FIGS. 9 through 12, including the coordinated operation of a motion-sensing smart watch and a wirelessly-linked smart phone, can provide highly-accurate food consumption measurement with relatively-low privacy intrusion.

Figure 13:
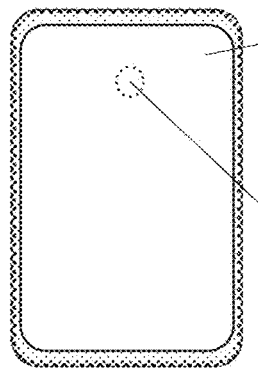
FIGS. 13 through 15 show an example of a device to monitor a person's food consumption comprising a smart necklace (with a microphone) to detect eating events and a smart phone (with a built-in camera), wherein the person is prompted to use the smart phone to take pictures of food when the smart necklace detects an eating event.
Figure 14:
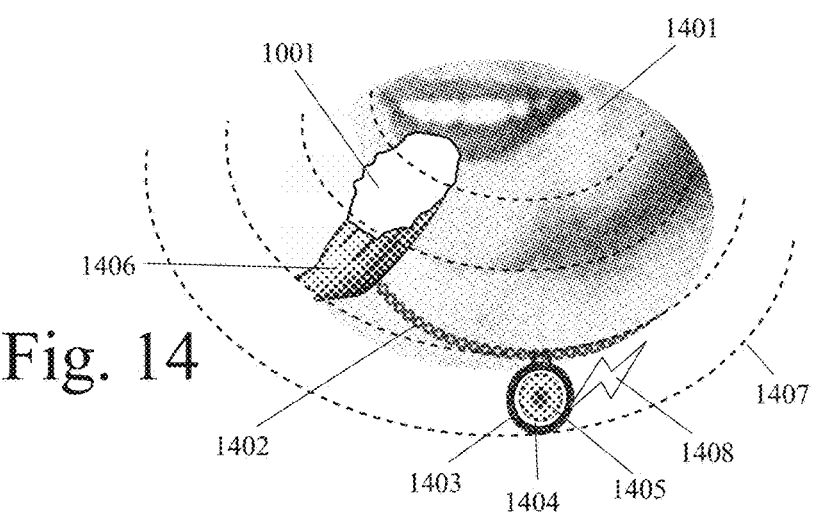
Figure 15:
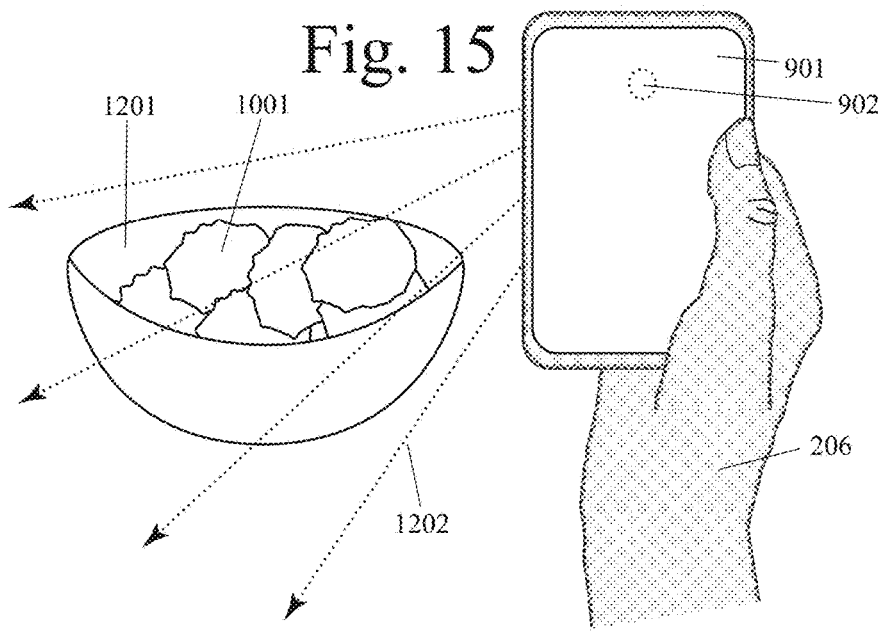

Narrative to Accompany FIGS. 13 Through 18:

The device that is shown in FIGS. 13 through 15 is similar to the one that was just shown in FIGS. 9 through 12, except that the wearable food-monitoring component is now a smart necklace instead of a smart watch. The smart necklace in this example monitors for food consumption by monitoring sounds instead of motion. In this example, the smart necklace detects food consumption by detecting chewing or swallowing sounds.

FIG. 13 shows the smart phone 901 with camera 902 that was introduced in the previous example. FIG. 14 shows that the person 1401 is wearing smart necklace 1402 including communication unit 1403, data processing unit and power supply 1404, and microphone 1405. FIG. 14 also shows that the person is eating food item 1001 using fork 1406.

In FIG. 14, microphone 1405 of smart necklace 1402 detects that the person is consuming food based on chewing or swallowing sounds. In FIG. 14, chewing or swallowing sounds are represented by dotted-line curves 1407 expanding outwardly from the person's mouth. Smart necklace 1402 then prompts the person to take a picture of food using camera 902 on smart phone 901. In FIG. 14, this prompt 1408 is represented by a "lightning bolt" symbol coming out from communication unit 1403.

FIG. 15 shows that the person responds to prompt 1408 by aiming camera 902 of smart phone 901 toward bowl 1201 containing food items 1001. The field of vision of camera 902 is represented by dotted-line rays 1202 that radiate outwards from camera 902 toward bowl 1201.

Figure 16:
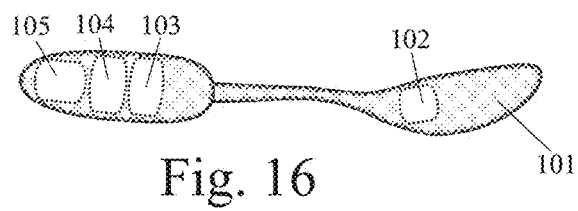
FIGS. 16 through 18 show an example of a device to monitor a person's food consumption comprising a smart necklace (with a microphone) to detect eating events and a smart spoon (with a built-in chemical composition sensor), wherein the person is prompted to use the smart spoon to eat food when the smart necklace detects an eating event.
Figure 17:
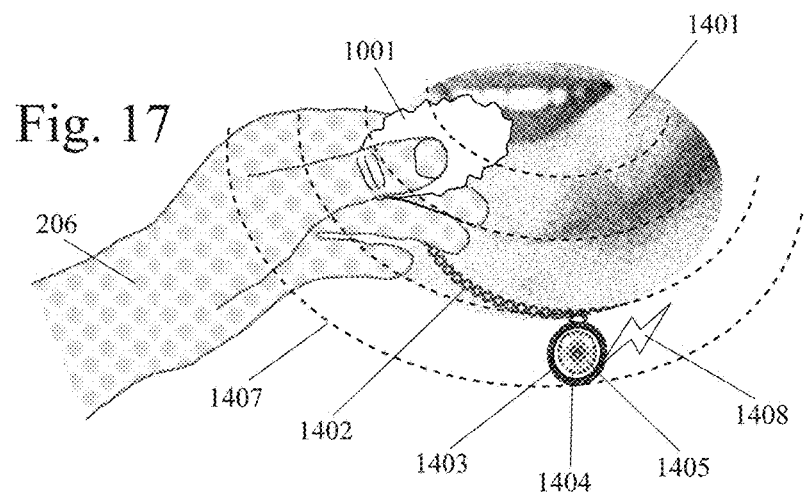
Figure 18:
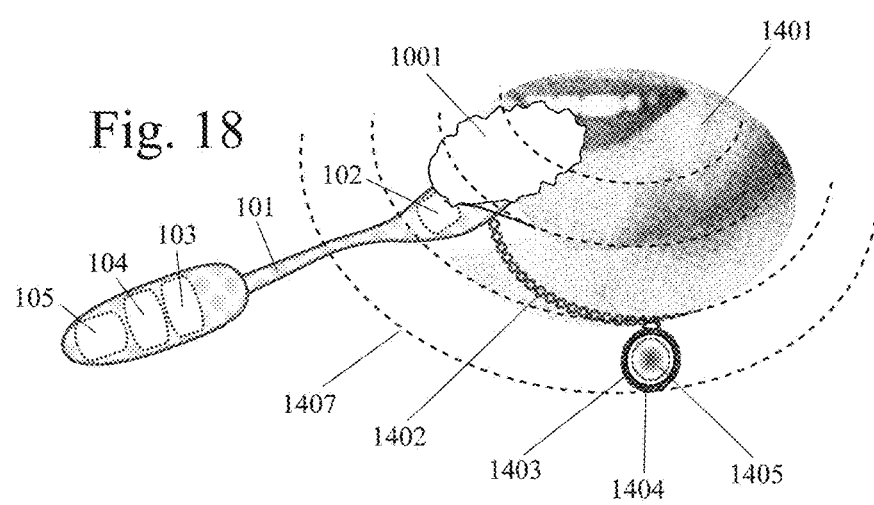

The device that is shown in FIGS. 16 through 18 is similar to the one that was just shown in FIGS. 13 through 15, except that hand-held food-identifying component is the smart spoon that was introduced earlier instead of a smart phone. FIG. 16 shows smart spoon 101 with chemical composition sensor 102, data processing unit 103, communication unit 104, and power supply and/or transducer 105.

FIG. 17 shows that the person is eating food item 1001 without using smart spoon 101. In FIG. 17, microphone 1405 of smart necklace 1402 detects that the person is consuming food based on chewing or swallowing sounds 1407. In FIG. 14, chewing or swallowing sounds are represented by dotted-line curves 1407 expanding outwardly from the person's mouth. Smart necklace 1402 then prompts the person to use smart spoon 101 to eat food item 1001. In FIG. 14, this prompt 1408 is represented by a "lightning bolt" symbol coming out from communication unit 1403.

FIG. 18 shows that the person responds to prompt 1408 by using smart spoon 101. Use of smart spoon 101 brings food item 1001 into contact with chemical composition sensor 102 on smart spoon 101. This contact enables identification of food item 1001.

FIGS. 1 through 18 show various examples of a device for measuring a person's consumption of at least one selected type of food, ingredient, or nutrient comprising: a wearable food-consumption monitor, wherein this food-consumption monitor is configured to be worn on a person's body or clothing, and wherein this food-consumption monitor automatically collects primary data that is used to detect when a person is consuming food, without requiring any specific action by the person in association with a specific eating event with the exception of the act of eating; and a hand-held food-identifying sensor, wherein this food-identifying sensor collects secondary data that is used to identify the person's consumption of at least one selected type of food, ingredient, or nutrient.

In FIGS. 1 through 18, the collection of secondary data by a hand-held food-identifying sensor requires a specific action by the person in association with a specific eating event apart from the act of eating. Also in FIGS. 1 through 18, the person whose food consumption is monitored is prompted to perform a specific action to collect secondary data when primary data collected by a food-consumption monitor indicates that the person is probably eating and the person has not already collected secondary data in association with a specific eating event.

FIGS. 1 through 12 show various examples of a device wherein a wearable food-consumption monitor is a smart watch or smart bracelet. FIGS. 9 through 15 show various examples of a device wherein a hand-held food-identifying sensor is a smart phone, cell phone, or mobile phone. FIGS. 1 through 8 and also FIGS. 16 through 18 show various examples of a device wherein a hand-held food-identifying sensor is a smart fork, smart spoon, other smart utensil, or food probe.

FIGS. 1 through 4 show an example of a device wherein a wearable food-consumption monitor is a smart watch or other electronic member that is configured to be worn on the person's wrist, arm, hand or finger; wherein a hand-held food-identifying sensor is a smart food utensil or food probe; and wherein a person is prompted to use the smart food utensil or food probe to analyze the chemical composition of food when the smart watch indicates that the person is consuming food.

FIGS. 1 through 4 show an example of a device wherein a wearable food-consumption monitor is a smart watch or other electronic member that is configured to be worn on the person's wrist, arm, hand or finger; wherein primary data collected by the smart watch or other electronic member that is configured to be worn on the person's wrist, arm, hand or finger includes data concerning movement of the person's body; wherein a hand-held food-identifying sensor is a smart food utensil or food probe; and wherein a person is prompted to use the smart food utensil or food probe to analyze the chemical composition of food when the smart watch indicates that the person is consuming food.

FIGS. 9 through 12 show an example of a device wherein a wearable food-consumption monitor is a smart watch or other electronic member that is configured to be worn on the person's wrist, arm, hand or finger; wherein a hand-held food-identifying sensor is a smart phone, cell phone, or mobile phone; and wherein a person is prompted to use the smart phone, cell phone, or mobile phone to take pictures of food or food packaging when the smart watch indicates that the person is consuming food.

FIGS. 9 through 12 show an example of a device wherein a wearable food-consumption monitor is a smart watch or other electronic member that is configured to be worn on the person's wrist, arm, hand or finger; wherein primary data collected by the smart watch or other electronic member that is configured to be worn on the person's wrist, arm, hand or finger includes data concerning movement of the person's body; wherein a hand-held food-identifying sensor is a smart phone, cell phone, or mobile phone; and wherein a person is prompted to use the smart phone, cell phone, or mobile phone to take pictures of food or food packaging when primary data indicates that the person is consuming food.

In another example: a wearable food-consumption monitor can be a smart watch or other electronic member that is configured to be worn on the person's wrist, arm, hand or finger wherein primary data collected by the smart watch or other electronic member that is configured to be worn on the person's wrist, arm, hand or finger includes data concerning electromagnetic energy received from the person's body; a hand-held food-identifying sensor can be a smart food utensil or food probe; and a person can be prompted to use the smart food utensil or food probe to analyze the chemical composition of food when the smart watch indicates that the person is consuming food.

In another example: a wearable food-consumption monitor can be a smart watch or other electronic member that is configured to be worn on the person's wrist, arm, hand or finger wherein primary data collected by the smart watch or other electronic member that is configured to be worn on the person's wrist, arm, hand or finger includes data concerning electromagnetic energy received from the person's body; a hand-held food-identifying sensor can be a smart phone, cell phone, or mobile phone; and a person can be prompted to use the smart phone, cell phone, or mobile phone to take pictures of food or food packaging when primary data indicates that the person is consuming food.

In another example: a wearable food-consumption monitor can be a smart watch or other electronic member that is configured to be worn on the person's wrist, arm, hand or finger wherein primary data collected by the smart watch or other electronic member that is configured to be worn on the person's wrist, arm, hand or finger includes images; a hand-held food-identifying sensor can be a smart food utensil or food probe; and a person can be prompted to use the smart food utensil or food probe to analyze the chemical composition of food when the smart watch indicates that the person is consuming food.

In another example: a wearable food-consumption monitor can be a smart watch or other electronic member that is configured to be worn on the person's wrist, arm, hand or finger wherein primary data collected by the smart watch or other electronic member that is configured to be worn on the person's wrist, arm, hand or finger includes images; a hand-held food-identifying sensor can be a smart phone, cell phone, or mobile phone; and a person can be prompted to use the smart phone, cell phone, or mobile phone to take pictures of food or food packaging when primary data indicates that the person is consuming food.

In another example: a wearable food-consumption monitor is a smart necklace or other electronic member that is configured to be worn on the person's neck, head, or torso wherein primary data collected by the smart watch or other electronic member that is configured to be worn on the person's wrist, arm, hand or finger includes patterns of sonic energy; a hand-held food-identifying sensor can be a smart food utensil or food probe; and a person can be prompted to use the smart food utensil or food probe to analyze the chemical composition of food when the smart watch indicates that the person is consuming food.

In another example: a wearable food-consumption monitor is a smart necklace or other electronic member that is configured to be worn on the person's neck, head, or torso wherein primary data collected by the smart watch or other electronic member that is configured to be worn on the person's wrist, arm, hand or finger includes patterns of sonic energy; a hand-held food-identifying sensor can be a smart phone, cell phone, or mobile phone; and a person can be prompted to use the smart phone, cell phone, or mobile phone to take pictures of food or food packaging when primary data indicates that the person is consuming food.

In an example, at least one selected type of food, ingredient, or nutrient for these examples can be selected from the group consisting of: a specific type of carbohydrate, a class of carbohydrates, or all carbohydrates; a specific type of sugar, a class of sugars, or all sugars; a specific type of fat, a class of fats, or all fats; a specific type of cholesterol, a class of cholesterols, or all cholesterols; a specific type of protein, a class of proteins, or all proteins; a specific type of fiber, a class of fiber, or all fiber; a specific sodium compound, a class of sodium compounds, and all sodium compounds; high-carbohydrate food, high-sugar food, high-fat food, fried food, high-cholesterol food, high-protein food, high-fiber food, and high-sodium food.

In an example, at least one selected type of food, ingredient, or nutrient can be selected from the group consisting of: a selected food, ingredient, or nutrient that has been designated as unhealthy by a health care professional organization or by a specific health care provider for a specific person; a selected substance that has been identified as an allergen for a specific person; peanuts, shellfish, or dairy products; a selected substance that has been identified as being addictive for a specific person; alcohol; a vitamin or mineral; vitamin A, vitamin B1, thiamin, vitamin B12, cyanocobalamin, vitamin B2, riboflavin, vitamin C, ascorbic acid, vitamin D, vitamin E, calcium, copper, iodine, iron, magnesium, manganese, niacin, pantothenic acid, phosphorus, potassium, riboflavin, thiamin, and zinc; a specific type of carbohydrate, class of carbohydrates, or all carbohydrates; a specific type of sugar, class of sugars, or all sugars; simple carbohydrates, complex carbohydrates; simple sugars, complex sugars, monosaccharides, glucose, fructose, oligosaccharides, polysaccharides, starch, glycogen, disaccharides, sucrose, lactose, starch, sugar, dextrose, disaccharide, fructose, galactose, glucose, lactose, maltose, monosaccharide, processed sugars, raw sugars, and sucrose; a specific type of fat, class of fats, or all fats; fatty acids, monounsaturated fat, polyunsaturated fat, saturated fat, trans fat, and unsaturated fat; a specific type of cholesterol, a class of cholesterols, or all cholesterols; Low Density Lipoprotein (LDL), High Density Lipoprotein (HDL), Very Low Density Lipoprotein (VLDL), and triglycerides; a specific type of protein, a class of proteins, or all proteins; dairy protein, egg protein, fish protein, fruit protein, grain protein, legume protein, lipoprotein, meat protein, nut protein, poultry protein, tofu protein, vegetable protein, complete protein, incomplete protein, or other amino acids; a specific type of fiber, a class of fiber, or all fiber; dietary fiber, insoluble fiber, soluble fiber, and cellulose; a specific sodium compound, a class of sodium compounds, and all sodium compounds; salt; a specific type of meat, a class of meats, and all meats; a specific type of vegetable, a class of vegetables, and all vegetables; a specific type of fruit, a class of fruits, and all fruits; a specific type of grain, a class of grains, and all grains; high-carbohydrate food, high-sugar food, high-fat food, fried food, high-cholesterol food, high-protein food, high-fiber food, and high-sodium food.

FIGS. 1 through 18 show various examples of a device for measuring a person's consumption of at least one selected type of food, ingredient, or nutrient comprising: (a) a wearable food-consumption monitor, wherein this food-consumption monitor is configured to be worn on a person's body or clothing, and wherein this food-consumption monitor automatically collects primary data that is used to detect when a person is consuming food, without requiring any specific action by the person in association with a specific eating event with the exception of the act of eating; (b) a hand-held food-identifying sensor, wherein this food-identifying sensor collects secondary data that is used to identify the person's consumption of at least one selected type of food, ingredient, or nutrient; wherein collection of secondary data by this hand-held food-identifying sensor requires a specific action by the person in association with a specific eating event apart from the act of eating; and (c) a computer-to-human interface, wherein this interface uses visual, auditory, tactile, electromagnetic, gustatory, and/or olfactory communication to prompt the person to use the hand-held food-identifying sensor to collect secondary data when primary data collected by the food-consumption monitor indicates that the person is probably eating and the person has not already collected secondary data in association with a specific eating event.

FIGS. 1 through 18 also show various examples of a method for measuring a person's consumption of at least one selected type of food, ingredient, or nutrient comprising: (a) automatically collecting primary data using a food-consumption monitor that a person wears on their body or clothing without requiring any specific action by the person in association with a specific eating event with the possible exception of the act of eating, wherein this primary data is used to detect when the person is consuming food; (b) collecting secondary data using a hand-held food-identifying sensor wherein collection of secondary data requires a specific action by the person in association with a specific eating event apart from the act of eating, and wherein this secondary data is used to identify the person's consumption of at least one selected type of food, ingredient, or nutrient; and (c) prompting the person to use a hand-held food-identifying sensor to collect secondary data when primary data collected by a food-consumption monitor indicates that the person is eating and the person has not already collected secondary data in association with a specific eating event.

Figures shown and discussed herein disclose a device for monitoring food consumption comprising: (a) a wearable sensor that is configured to be worn on a person's body or clothing, wherein this wearable sensor automatically collects data that is used to detect probable eating events without requiring action by the person in association with a probable eating event apart from the act of eating, and wherein a probable eating event is a period of time during which the person is probably eating; (b) a smart food utensil, probe, or dish, wherein this food utensil, probe, or dish collects data that is used to analyze the chemical composition of food that the person eats, wherein this collection of data by the food utensil, probe, or dish requires that the person use the utensil, probe, or dish when eating, and wherein the person is prompted to use the food utensil, probe, or dish when data collected by the wearable sensor indicates a probable eating event; and (c) a data analysis component, wherein this component analyzes data collected by the food utensil, probe, or dish to estimate the types and amounts of foods, ingredients, nutrients, and/or calories that are consumed by the person.

Figures shown and discussed herein disclose a device for monitoring food consumption wherein the wearable sensor is worn on a person's wrist, hand, finger, or arm. Figures shown and discussed herein disclose a device for monitoring food consumption wherein the wearable sensor is part of an electronically-functional wrist band or smart watch. In another example, the wearable sensor can be part of an electronically-functional adhesive patch that is worn on a person's skin.

Figures shown and discussed herein disclose a device for monitoring food consumption wherein the smart food utensil, probe, or dish is a spoon with a chemical composition sensor. In another example, the smart food utensil, probe, or dish can be a fork with a chemical composition sensor. In another example, the smart food utensil, probe, or dish can be a food probe with a chemical composition sensor. In another example, the smart food utensil, probe, or dish can be a plate with a chemical composition sensor. In another example, the smart food utensil, probe, or dish can be a bowl with a chemical composition sensor.

Figures shown and discussed herein disclose a device for monitoring food consumption wherein the wearable sensor and the smart food utensil, probe, or dish are in wireless communication with each other. In another example, the wearable sensor and the smart food utensil, probe, or dish can be physically linked.

Figures shown and discussed herein disclose a device for monitoring food consumption wherein the wearable sensor automatically collects data concerning motion of the person's body. In another example, the wearable sensor can automatically collect data concerning electromagnetic energy emitted from the person's body or transmitted through the person's body. In another example, the wearable sensor can automatically collect data concerning thermal energy emitted from the person's body. In another example, the wearable sensor can automatically collect data concerning light energy reflected from the person's body or absorbed by the person's body.

Figures shown and discussed herein disclose a device for monitoring food consumption wherein the person is prompted to use the smart food utensil, probe, or dish when data collected by the wearable sensor indicates a probable eating event and the person does not start using the smart food utensil, probe, or dish for this probable eating event before a selected length of time after the start of the probable eating event. In another example, the person can be prompted to use the smart food utensil, probe, or dish when data collected by the wearable sensor indicates a probable eating event and the person does not start using the smart food utensil, probe, or dish for this probable eating event before a selected quantity of eating-related actions occurs during the probable eating event. In another example, the person can be prompted to use the smart food utensil, probe, or dish when data collected by the wearable sensor indicates a probable eating event and the person does not use the smart food utensil, probe, or dish throughout the entire probable eating event.

Figures shown and discussed herein disclose a device for monitoring food consumption comprising: (a) a wearable sensor that is configured to be worn on a person's wrist, hand, finger, or arm, wherein this wearable sensor automatically collects data that is used to detect probable eating events without requiring action by the person in association with a probable eating event apart from the act of eating, and wherein a probable eating event is a period of time during which the person is probably eating; (b) a smart food utensil, probe, or dish, wherein this food utensil, probe, or dish collects data that is used to analyze the chemical composition of food that the person eats, wherein this collection of data by the food utensil, probe, or dish requires that the person use the utensil, probe, or dish when eating, and wherein the person is prompted to use the food utensil, probe, or dish when data collected by the wearable sensor indicates a probable eating event; and (c) a data analysis component, wherein this component analyzes data collected by the food utensil, probe, or dish to estimate the types and amounts of foods, ingredients, nutrients, and/or calories that are consumed by the person.

Figures shown and discussed herein disclose a device for monitoring food consumption comprising: (a) a wearable sensor that is configured to be worn on a person's wrist, hand, finger, or arm, wherein this wearable sensor automatically collects data that is used to detect probable eating events without requiring action by the person in association with a probable eating event apart from the act of eating, wherein a probable eating event is a period of time during which the person is probably eating, and wherein this data is selected from the group consisting of data concerning motion of the person's body, data concerning electromagnetic energy emitted from or transmitted through the person's body, data concerning thermal energy emitted from the person's body, and light energy reflected from or absorbed by the person's body; (b) a smart food utensil, probe, or dish, wherein this food utensil, probe, or dish collects data that is used to analyze the chemical composition of food that the person eats, wherein this collection of data by the food utensil, probe, or dish requires that the person use the utensil, probe, or dish when eating, wherein the person is prompted to use the food utensil, probe, or dish when data collected by the wearable sensor indicates a probable eating event; and (c) a data analysis component, wherein this component analyzes data collected by the food utensil, probe, or dish to estimate the types and amounts of foods, ingredients, nutrients, and/or calories that are consumed by the person, and wherein this component analyzes data received from the sensor and data collected by the food utensil, probe, or dish to evaluate the completeness of data collected by the food utensil, probe, or dish for tracking the person's total food consumption.

In an example, a wearable spectroscopic sensor to measure food consumption based on the interaction between light and the human body can comprise a wearable food-consumption monitor that is configured to be worn on the person's wrist, arm, hand or finger. In an example, a wearable spectroscopic sensor to measure food consumption based on the interaction between light and the human body can monitor light energy that is reflected from a person's body, absorbed by the person's body, or having passed through a person's body. In an example, a wearable spectroscopic sensor to measure food consumption based on the interaction between light and the human body can identify consumption of a selected type of food, ingredient, or nutrient with a spectral analysis sensor. In an example, a spectral measurement sensor can be a spectroscopic sensor or a spectrometry sensor. In an example, a spectral measurement sensor can be a white light spectroscopic sensor, an infrared spectroscopic sensor, a near-infrared spectroscopic sensor, an ultraviolet spectroscopic sensor, an ion mobility spectroscopic sensor, a mass spectrometry sensor, a backscattering spectrometry sensor, or a spectrophotometer.

In an example, wearable spectroscopic sensor to measure food consumption based on the interaction between light and the human body can comprise: a spectroscopic sensor that collects data concerning light energy reflected from the person's body and/or absorbed by the person's body, wherein this data is used to measure the person's consumption of one or more selected types of food, ingredients, or nutrients; a data processing unit; and a power source. In an example, a spectroscopic sensor can be worn on a person's wrist. In an example, a spectroscopic sensor can be worn on a person's arm. In an example, a spectroscopic sensor can be worn on a person's hand. In an example, a spectroscopic sensor can be worn on a person's finger.

In an example, a spectroscopic sensor can be a spectral analysis sensor. In an example, a spectroscopic sensor can detect light reflection spectra. In an example, a spectroscopic sensor can detect light absorption spectra. In an example, a spectroscopic sensor can be a white light spectroscopic sensor. In an example, a spectroscopic sensor can be an infrared or near-infrared spectroscopic sensor. In an example, a spectroscopic sensor can be an ultraviolet spectroscopic sensor. In an example, a spectroscopic sensor can be a spectrometer. In an example, a spectroscopic sensor can be a spectrophotometer. In an example, a spectroscopic sensor can be an ion mobility spectroscopic sensor. In an example, a spectroscopic sensor can be a backscattering spectrometry sensor.

In an example, a one or more selected types of food, ingredients, or nutrients can be selected from the group consisting of: food that is high in simple carbohydrates; food that is high in simple sugars; food that is high in saturated or trans fat; fried food; food that is high in Low Density Lipoprotein (LDL); and food that is high in sodium. In an example, a one or more selected types of foods, ingredients, or nutrients can be selected from the group consisting of: a selected food, ingredient, or nutrient that has been designated as unhealthy by a health care professional organization or by a specific health care provider for a specific person; a selected substance that has been identified as an allergen for a specific person; peanuts, shellfish, or dairy products; a selected substance that has been identified as being addictive for a specific person; alcohol; a vitamin or mineral; vitamin A, vitamin B1, thiamin, vitamin B12, cyanocobalamin, vitamin B2, riboflavin, vitamin C, ascorbic acid, vitamin D, vitamin E, calcium, copper, iodine, iron, magnesium, manganese, niacin, pantothenic acid, phosphorus, potassium, riboflavin, thiamin, and zinc; a selected type of carbohydrate, class of carbohydrates, or all carbohydrates; a selected type of sugar, class of sugars, or all sugars; simple carbohydrates, complex carbohydrates; simple sugars, complex sugars, monosaccharides, glucose, fructose, oligosaccharides, polysaccharides, starch, glycogen, disaccharides, sucrose, lactose, starch, sugar, dextrose, disaccharide, fructose, galactose, glucose, lactose, maltose, monosaccharide, processed sugars, raw sugars, and sucrose; a selected type of fat, class of fats, or all fats; fatty acids, monounsaturated fat, polyunsaturated fat, saturated fat, trans fat, and unsaturated fat; a selected type of cholesterol, a class of cholesterols, or all cholesterols; Low Density Lipoprotein (LDL), High Density Lipoprotein (HDL), Very Low Density Lipoprotein (VLDL), and triglycerides; a selected type of protein, a class of proteins, or all proteins; dairy protein, egg protein, fish protein, fruit protein, grain protein, legume protein, lipoprotein, meat protein, nut protein, poultry protein, tofu protein, vegetable protein, complete protein, incomplete protein, or other amino acids; a selected type of fiber, a class of fiber, or all fiber; dietary fiber, insoluble fiber, soluble fiber, and cellulose; a specific sodium compound, a class of sodium compounds, and all sodium compounds; salt; a selected type of meat, a class of meats, and all meats; a selected type of vegetable, a class of vegetables, and all vegetables; a selected type of fruit, a class of fruits, and all fruits; a selected type of grain, a class of grains, and all grains; high-carbohydrate food, high-sugar food, high-fat food, fried food, high-cholesterol food, high-protein food, high-fiber food, and high-sodium food.

In an example, wearable spectroscopic sensor to measure food consumption based on the interaction between light and the human body can comprise: a housing that is configured to be worn on a person's wrist, arm, hand, or finger; a spectroscopic sensor that collects data concerning light energy reflected from the person's body and/or absorbed by the person's body, wherein this data is used to measure the person's consumption of one or more selected types of food, ingredients, or nutrients; a data processing unit; and a power source. In an example, a method to measure a person's consumption of one or more selected types of food, ingredients, or nutrients can comprise: configuring a housing containing a spectroscopic sensor to be worn on a person's wrist, arm, hand, or finger; using the spectroscopic sensor to collect data concerning light energy reflected from the person's body and/or absorbed by the person's body; and analyzing this data to measure the person's consumption of one or more selected types of food, ingredients, or nutrients. Narrative to Accompany FIGS. 19 Through 84:

In an example, a wearable spectroscopic sensor to measure food consumption based on the interaction between light and the human body can comprise a wearable food-consumption monitor that is configured to be worn on a person's wrist, arm, hand or finger. In an example, a wearable spectroscopic sensor to measure food consumption based on the interaction between light and the human body can monitor light energy that is reflected from a person's body tissue, absorbed by the person's body tissue, or has passed through the person's body tissue. In an example, a wearable spectroscopic sensor to measure food consumption based on the interaction between light and the human body can identify consumption of a selected type of food, ingredient, or nutrient using spectral analysis. In an example, a spectroscopic sensor can be a white light spectroscopic sensor, an infrared spectroscopic sensor, a near-infrared spectroscopic sensor, an ultraviolet spectroscopic sensor, an ion mobility spectroscopic sensor, a mass spectrometry sensor, a backscattering spectrometry sensor, or a spectrophotometer.

Figure 19:
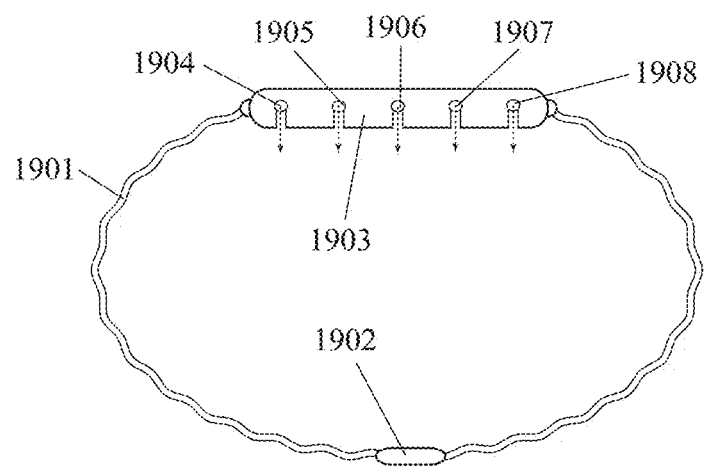
FIG. 19 shows a device with spectroscopic sensors at different locations on the device circumference.

FIG. 19 shows an example of a wearable device for the arm with a plurality of close-fitting biometric sensors. This figure shows the device from a side perspective, as it would appear encircling a lateral cross-section of a person's wrist (or other portion of the person's arm). Described generally, the example shown in FIG. 19 is an arcuate wrist-worn device with a circumferentially-distributed array of biometric sensors. A series of circumference-center-facing biometric sensors are distributed along different locations on a portion of the circumference of the device. In this example, the array of sensors is distributed along the circumference-center-facing surface of an enclosure which is on the anterior (upper) portion of the device. In another example, an array of sensors can be distributed along the circumference-center-facing surface of a band or strap.

Having a circumferentially-distributed array of sensors allows a wearable device to record biometric measurements from different locations along the circumference of a person's wrist. This can help to find the best location on a person's wrist from which to most-accurately record biometric measurements. Having a circumferentially-distributed array of sensors can also enable a device to record biometric measurements from substantially the same location on a person's wrist, even if the device is unintentionally slid, shifted, and/or partially-rotated around the person's wrist. A different primary sensor can selected to record data when the device slides, shifts, and/or rotates. This can help to reduce biometric measurement errors when the device is slid, shifted, and/or partially-rotated around a person's wrist.

More specifically, the example shown in FIG. 19 is a wearable device for the arm with a plurality of close-fitting biometric sensors comprising: (a) an attachment member, such as a strap or band, which is configured to span at least a portion of the circumference of a person's arm; (b) an enclosure which is part of (or attached to) the attachment member; (c) a first biometric sensor at a first location in the enclosure which is configured to record biometric data concerning the person's arm tissue; and (d) a second biometric sensor at a second location in the enclosure which is configured to record biometric data concerning the person's arm tissue, wherein the distance along the circumference of the device from the first location to second location is at least a quarter inch.

In an example, an attachment member can be a strap, band, bracelet, ring, armlet, cuff, or sleeve. In an example, an attachment member can be attached to a person's arm by connecting two ends of the attachment member with a clasp, clip, buckle, hook, pin, plug, or hook-and-eye mechanism. In an example, the attachment member can be attached to a person's arm by stretching and sliding it over the person's hand onto the arm. In an example, the attachment member can be attached to a person's arm by applying force to pull two ends apart to slip the member over the arm, wherein the two ends retract back towards each other when the force is removed.

In an example, the circumference-center-facing surface of an enclosure can be substantially flat. In an example, the circumference-center-facing surface of an enclosure can be curved. In an example, a plurality of sensors can be housed within a single enclosure. In another example, different sensors can be housed in different enclosures. In another example, sensors can be located along the circumference-center-facing surface of an attachment member. In an example, there can be a display screen on the outward-facing surface of an enclosure.

In an example, first and second biometric sensors can be spectroscopic sensors which are each configured to measure the spectrum of light energy reflected from (and/or absorbed by) tissue of the person's arm. In an example, first and second biometric sensors can be electromagnetic energy sensors which are each configured to measure parameters and/or patterns of electromagnetic energy passing through (and/or emitted by) tissue of the person's arm. In an example, measured parameters and/or patterns of electromagnetic energy can be selected from the group consisting of: impedance, resistance, conductivity, and electromagnetic wave pattern.

With respect to specific components, the example shown in FIG. 19 includes: strap (or band) 1901, strap (or band) connector 1902, enclosure 1903, and spectroscopic sensors 1904, 1905, 1906, 1907, and 1908. In an example, this device can further comprise one or more components selected from the group consisting of: a data processor; a battery and/or energy harvesting unit; a display screen; a data transmitter; and a data receiver. In an example, relevant embodiment variations discussed elsewhere in this disclosure can also apply to this example.

Figure 20:
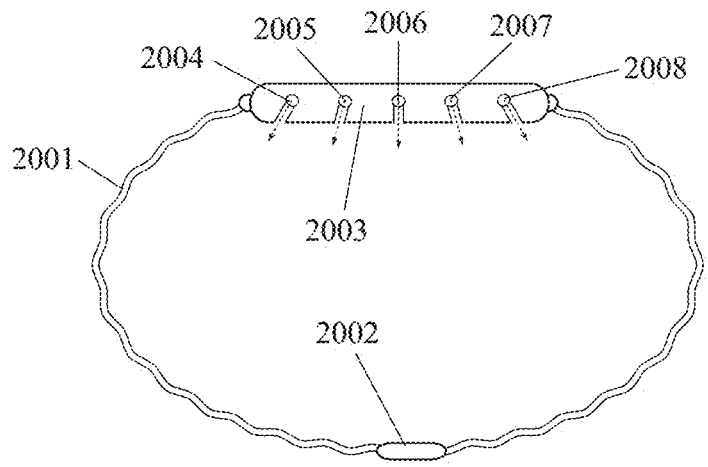
FIG. 20 shows a device with spectroscopic sensors with different light-projection angles.

FIG. 20 shows another example of a wearable device for the arm with a plurality of close-fitting biometric sensors. This figure shows the device from a side perspective, as it would appear encircling a lateral cross-section of a person's wrist (or other portion of the person's arm).

The example shown in FIG. 20 is like the one shown in FIG. 19 except that different sensors in the array of sensors direct light energy onto the surface of an arm at different angles relative to an enclosure. Having an array of sensors which direct light energy onto the surface of the arm at different angles relative to an enclosure can enable a device to record biometric measurements with substantially the same angle of incidence, even if the enclosure is tilted with respect to the surface of the person's wrist. A different primary sensor with a different angle of light projection can be selected to record data when the enclosure is tilted. For example, when an enclosure is parallel to the surface of the person's wrist, then a sensor with a 90-degree light projection angle (relative to the enclosure) can be selected so that light is projected onto the surface of the arm in a perpendicular manner. However, when the enclosure is tilted at a 20-degree angle relative to the surface of the person's wrist, then a sensor with a 70-degree angle (relative to the enclosure) can be selected so that light is again projected onto the surface of the arm in a perpendicular manner.

The example shown in FIG. 20 is a wearable device for the arm with a plurality of close-fitting biometric sensors comprising: (a) an attachment member, such as a strap or band, which is configured to span at least a portion of the circumference of a person's arm; (b) an enclosure which is part of (or attached to) the attachment member; (c) a first spectroscopic sensor in the enclosure which is configured to project a beam of light onto the arm surface at a first angle relative to the enclosure; and (d) a second spectroscopic sensor in the enclosure which is configured to project a beam of light onto the arm surface at a second angle relative to the enclosure, wherein the first angle differs from the second angle by at least 10 degrees.

In an example, an attachment member can be a strap, band, bracelet, ring, armlet, cuff, or sleeve. In an example, an attachment member can be attached to a person's arm by connecting two ends of the attachment member with a clasp, clip, buckle, hook, pin, plug, or hook-and-eye mechanism. In an example, the attachment member can be attached to a person's arm by stretching and sliding it over the person's hand onto the arm. In an example, the attachment member can be attached to a person's arm by applying force to pull two ends apart to slip the member over the arm, wherein the two ends retract back towards each other when the force is removed.

In an example, the circumference-center-facing surface of an enclosure can be substantially flat. In an example, the circumference-center-facing surface of an enclosure can be curved. In an example, a plurality of sensors can be housed within a single enclosure. In another example, different sensors can be housed in different enclosures. In another example, sensors can be located along the circumference-center-facing surface of an attachment member. In an example, there can be a display screen on the outward-facing surface of an enclosure.

With respect to specific components, the example shown in FIG. 20 includes: strap (or band) 2001, strap (or band) connector 2002, enclosure 2003, and spectroscopic sensors 2004, 2005, 2006, 2007, and 2008. In an example, this device can further comprise one or more components selected from the group consisting of: a data processor; a battery and/or energy harvesting unit; a display screen; a data transmitter; and a data receiver. In an example, relevant embodiment variations discussed elsewhere in this disclosure can also apply to this example.

Figure 21:
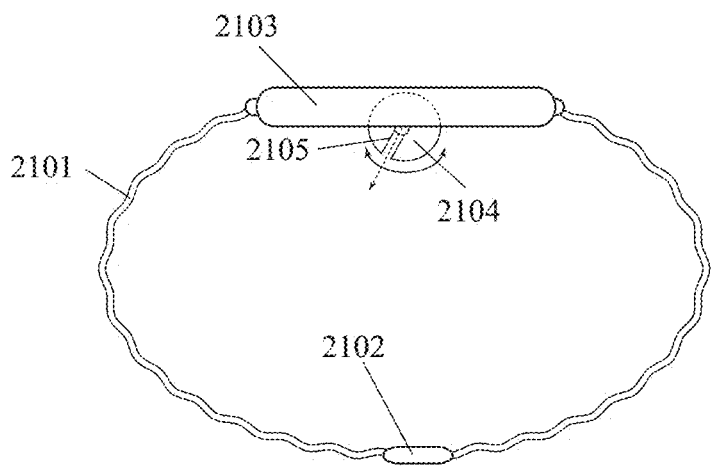
FIG. 21 shows a device with a rotating spectroscopic sensor.

FIG. 21 shows an example of a wearable device for the arm with a close-fitting biometric sensor. This figure shows the device from a side perspective, as it would appear encircling a lateral cross-section of a person's wrist (or other portion of the person's arm).

Described generally, the example shown in FIG. 21 is an arcuate wrist-worn device with a rotating light-projecting spectroscopic sensor, wherein rotation of this sensor changes the angle at which it projects light onto the surface of a person's arm. In this example, the rotating light-projecting spectroscopic sensor is on the circumference-center-facing surface of an enclosure which is on the anterior (upper) portion of the device. In another example, such a sensor can be on the circumference-center-facing surface of a band or strap.

Having a rotating light-projecting spectroscopic sensor can enable a device to record biometric measurements with substantially the same angle of incidence, even if an enclosure is tilted with respect to the surface of the person's wrist. For example, when the enclosure is parallel to the surface of the person's wrist, then the rotating sensor is automatically rotated to project light at a 90-degree angle (relative to the enclosure) so that light is projected onto the surface of the arm in a perpendicular manner. However, when the enclosure is tilted at a 20-degree angle relative to the surface of the person's wrist, then the rotating sensor is automatically rotated to project light at a 70-degree angle (relative to the enclosure) so that light is again projected onto the surface of the arm in a perpendicular manner.

The example shown in FIG. 21 is a wearable device for the arm with a close-fitting biometric sensor comprising: (a) an attachment member, such as a strap or band, which is configured to span at least a portion of the circumference of a person's arm; (b) an enclosure which is part of (or attached to) the attachment member; and (c) a rotating light-projecting spectroscopic sensor, wherein this sensor can be rotated relative to the enclosure and wherein rotation of this sensor relative to the enclosure changes the angle at which the sensor projects light onto the surface of a person's arm.

In an example, an attachment member can be a strap, band, bracelet, ring, armlet, cuff, or sleeve. In an example, an attachment member can be attached to a person's arm by connecting two ends of the attachment member with a clasp, clip, buckle, hook, pin, plug, or hook-and-eye mechanism. In an example, the attachment member can be attached to a person's arm by stretching and sliding it over the person's hand onto the arm. In an example, the attachment member can be attached to a person's arm by applying force to pull two ends apart to slip the member over the arm, wherein the two ends retract back towards each other when the force is removed.

In an example, the circumference-center-facing surface of an enclosure can be substantially flat. In an example, the circumference-center-facing surface of an enclosure can be curved. In an example, there can be a display screen on the outward-facing surface of an enclosure.

With respect to specific components, the example shown in FIG. 21 includes: strap (or band) 2101, strap (or band) connector 2102, enclosure 2103, rotating member 2104, and light-projecting spectroscopic sensor 2105. In an example, this device can further comprise one or more components selected from the group consisting of: a data processor; a battery and/or energy harvesting unit; a display screen; a data transmitter; and a data receiver. In an example, relevant embodiment variations discussed elsewhere in this disclosure can also apply to this example.

Figure 22:
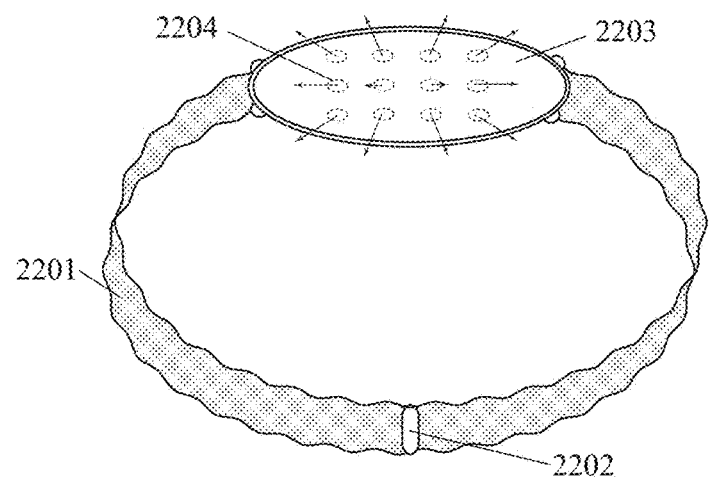
FIG. 22 shows a device with a two-dimensional array of spectroscopic sensors.

FIG. 22 shows another example of a wearable device for the arm with a plurality of close-fitting biometric sensors. This figure shows the device from a non-perpendicular lateral perspective, as it would appear encircling a lateral cross-section of a person's wrist (or other portion of the person's arm).

Described generally, the example shown in FIG. 22 is an arcuate wrist-worn device with a two-dimensional array of spectroscopic sensors. Sensors in this two-dimensional array differ in location circumferentially (they are at different locations around the circumference of the device) and laterally (they are at different locations along axes which are perpendicular to the circumference of the device). In this example, the two-dimensional sensor array is part of the circumference-center-facing surface of an enclosure which is on the anterior (upper) portion of the device. In another example, a two-dimensional sensor array can be on the circumference-center-facing surface of a band or strap.

Having a two-dimensional sensor array allows a wearable device to record biometric measurements from multiple locations on a person's wrist. This can help to find the best location on a person's wrist from which to most-accurately record biometric measurements. Having a two-dimensional sensor array can also enable a device to record biometric measurements from substantially the same location on a person's wrist even if the device is rotated around the person's wrist or slid up or down the person's arm. A different primary sensor can be automatically selected to record data when the device rotates or slides.

More specifically, the example shown in FIG. 22 is a wearable device for the arm with a plurality of close-fitting biometric sensors comprising: (a) an attachment member, such as a strap or band, which is configured to span at least a portion of the circumference of a person's arm; (b) an enclosure which is part of (or attached to) the attachment member; and (c) a two-dimensional sensor array which is part of the enclosure, wherein sensors in this two-dimensional array differ in location along a portion of the circumference of the device, and wherein sensors in this two-dimensional array differ in location along axes which are perpendicular to the circumference of the device.

In an example, an attachment member can be a strap, band, bracelet, ring, armlet, cuff, or sleeve. In an example, an attachment member can be attached to a person's arm by connecting two ends of the attachment member with a clasp, clip, buckle, hook, pin, plug, or hook-and-eye mechanism. In an example, the attachment member can be attached to a person's arm by stretching and sliding it over the person's hand onto the arm. In an example, the attachment member can be attached to a person's arm by applying force to pull two ends apart to slip the member over the arm, wherein the two ends retract back towards each other when the force is removed.

In an example, the circumference-center-facing surface of an enclosure can be substantially flat. In an example, the circumference-center-facing surface of an enclosure can be curved. In an example, there can be a display screen on the outward-facing surface of an enclosure.

In an example, sensors in a two-dimensional sensor array can be spectroscopic sensors which are each configured to measure the spectrum of light energy reflected from (and/or absorbed by) tissue of the person's arm. In an example, sensors in a two-dimensional sensor array can be electromagnetic energy sensors which are each configured to measure parameters and/or patterns of electromagnetic energy passing through (and/or emitted by) tissue of the person's arm. In an example, measured parameters and/or patterns of electromagnetic energy can be selected from the group consisting of: impedance, resistance, conductivity, and electromagnetic wave pattern.

With respect to specific components, the example shown in FIG. 22 includes: a strap (or band) 2201, a strap (or band) connector 2202, an enclosure 2203, and a two-dimensional spectroscopic sensor array which includes sensor 2204. In an example, this device can further comprise one or more components selected from the group consisting of: a data processor; a battery and/or energy harvesting unit; a display screen; a data transmitter; and a data receiver. In an example, relevant embodiment variations discussed elsewhere in this disclosure can also apply to this example.

Figure 23:
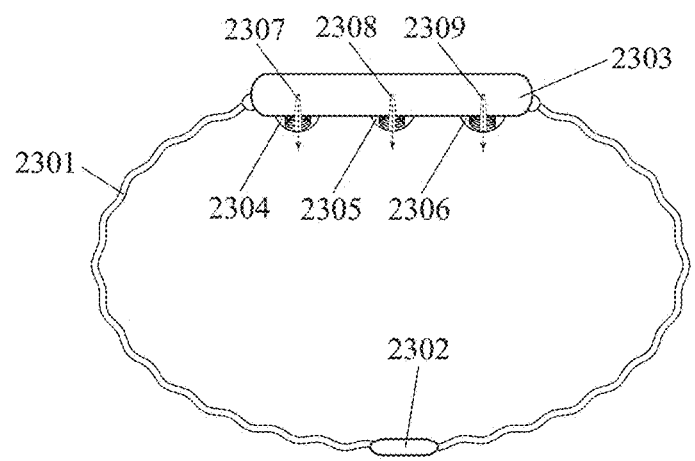
FIG. 23 shows a device with spectroscopic sensors pushed inward by hydraulic, pneumatic, or electromagnetic mechanisms.

FIG. 23 shows another example of a wearable device for the arm with a plurality of close-fitting biometric sensors. This figure shows the device from a side perspective, as it would appear encircling a lateral cross-section of a person's wrist (or other portion of the person's arm).

Described generally, the example shown in FIG. 23 is an arcuate wrist-worn device with a plurality of spectroscopic sensors, wherein each of these sensors is pushed toward the surface of an arm in order to stay in close contact with the surface of the arm even if the enclosure is shifted or tilted away from the surface of the arm. In this example, the spectroscopic sensors are on the circumference-center-facing portion of an enclosure. In this example, each of the spectroscopic sensors is pushed toward the surface of the arm by a spring mechanism. In another example, each of the spectroscopic sensors can be pushed toward the surface by a hydraulic mechanism, a pneumatic mechanism, or a microscale electromagnetic actuator.

More specifically, the example shown in FIG. 23 is a wearable device for the arm with a plurality of close-fitting biometric sensors comprising: (a) an attachment member, such as a strap or band, which is configured to span at least a portion of the circumference of a person's arm; (b) an enclosure which is part of (or attached to) the attachment member; and (c) a plurality of sensors which are part of the enclosure, wherein each sensor in this plurality of sensors is configured to be pushed toward the surface of the arm by a spring mechanism in order to keep the sensor in close contact with the surface of the arm.

In an example, an attachment member can be a strap, band, bracelet, ring, armlet, cuff, or sleeve. In an example, an attachment member can be attached to a person's arm by connecting two ends of the attachment member with a clasp, clip, buckle, hook, pin, plug, or hook-and-eye mechanism. In an example, the attachment member can be attached to a person's arm by stretching and sliding it over the person's hand onto the arm. In an example, the attachment member can be attached to a person's arm by applying force to pull two ends apart to slip the member over the arm, wherein the two ends retract back towards each other when the force is removed.

In an example, sensors of this device can be spectroscopic sensors which are each configured to measure the spectrum of light energy reflected from (and/or absorbed by) tissue of the person's arm. In an example, sensors of this device can be electromagnetic energy sensors which are each configured to measure parameters and/or patterns of electromagnetic energy passing through (and/or emitted by) tissue of the person's arm. In an example, measured parameters and/or patterns of electromagnetic energy can be selected from the group consisting of: impedance, resistance, conductivity, and electromagnetic wave pattern.

With respect to specific components, the example shown in FIG. 23 includes: a strap (or band) 2301; a strap (or band) connector 2302; an enclosure 2303; a plurality of spectroscopic sensors (2307, 2308, and 2309); and a plurality of spring mechanisms (2304, 2305, and 2306) which are configured to push the sensors inward toward the center of the device. In an example, this device can further comprise one or more components selected from the group consisting of: a data processor; a battery and/or energy harvesting unit; a display screen; a data transmitter; and a data receiver. In an example, relevant embodiment variations discussed elsewhere in this disclosure can also apply to this example.

Figure 24:
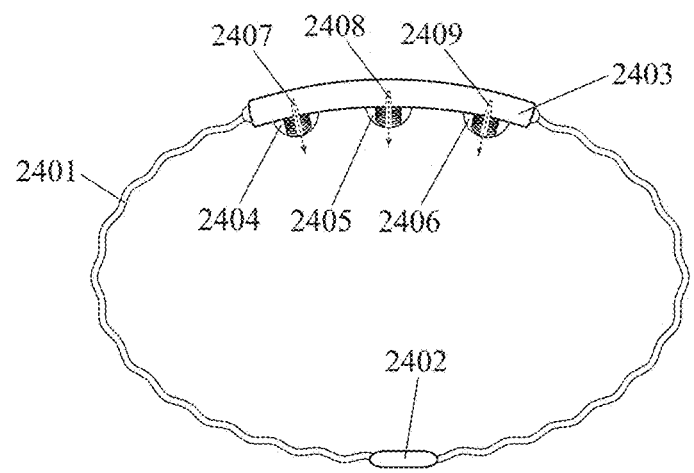
FIG. 24 shows a device with spectroscopic sensors pushed inward by individual springs.

FIG. 24 shows another example of a wearable device for the arm with a plurality of close-fitting biometric sensors. This figure shows the device from a side perspective, as it would appear encircling a lateral cross-section of a person's wrist (or other portion of the person's arm). The example shown in FIG. 24 is similar to the one shown in FIG. 23, except that the enclosure housing biometric sensors in FIG. 24 has a curved circumference-center-facing surface rather than a flat circumference-center-facing surface.

With respect to specific components, the example shown in FIG. 24 includes: a strap (or band) 2401; a strap (or band) connector 2402; an enclosure 2403; a plurality of spectroscopic sensors (2407, 2408, and 2409); and a plurality of spring mechanisms (2404, 2405, and 2406) which are configured to push the sensors inward toward the center of the device. In an example, this device can further comprise one or more components selected from the group consisting of: a data processor; a battery and/or energy harvesting unit; a display screen; a data transmitter; and a data receiver. In an example, relevant embodiment variations discussed elsewhere in this disclosure can also apply to this example.

Figure 25:
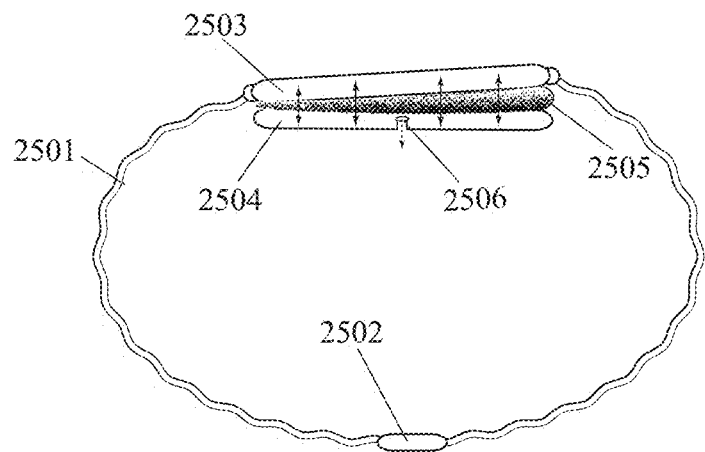
FIG. 25 shows a device with spectroscopic sensors on an inward-facing surface connected to an elastic compartment.

FIG. 25 shows another example of a wearable device for the arm with one or more close-fitting biometric sensors. This figure shows the device from a side perspective, as it would appear encircling a lateral cross-section of a person's wrist (or other portion of the person's arm). Described generally, the example shown in FIG. 25 is an arcuate wrist-worn device with a biometric sensor which is located on a circumference-center-facing portion of an enclosure, wherein this circumference-center-facing portion tilts on a central inflated portion of the enclosure so that the sensor remains in close contact with the surface of a person's arm even if the device tilts with respect to the arm surface. In this example, an enclosure is positioned on the anterior (upper) portion of the device circumference. In this example, the enclosure has an outward-facing portion (which can include a display screen), a central inflated portion (which can be a balloon), and an inner-facing portion (which houses the biometric sensor). In an example, a central inflated portion can be sandwiched between a rigid outward-facing portion and a rigid circumference-center-facing portion. In an example, the circumference-center-facing portion can tilt with respect to the outward-facing portion as the device tilts with respect to the surface of the person's arm.

Having a biometric sensor located on a circumference-center-facing portion of an enclosure which tilts on a central inflated portion can help to keep the biometric sensor in close proximity to the surface of the person's arm and at substantially the same angle with respect to the surface of a person's arm. This can be particularly important for a spectroscopic sensor, wherein it is desirable to maintain the same projection angle (and/or reflection angle) of a beam of light which is directed toward (and/or reflected from) the surface of a person's arm.

More specifically, the example shown in FIG. 25 is a wearable device for the arm with one or more close-fitting biometric sensors comprising: (a) an attachment member, such as a strap or band, which is configured to span at least a portion of the circumference of a person's arm; (b) an enclosure which is part of (or attached to) the attachment member, wherein this enclosure further comprises a rigid outward facing portion, an inflated central portion, and a rigid circumference-center-facing portion, wherein the rigid circumference-center-facing portion tilts relative to the rigid outward facing portion; and (c) a biometric sensor in the circumference-center-facing portion which is configured to record biometric data concerning the person's arm tissue.

In an example, there can be a display screen on the outward-facing surface of the enclosure. In an example, the central portion of an enclosure can be filled with a liquid or gel rather than inflated with a gas. In an example, there can be more than one biometric sensor on the rigid circumference-center-facing portion. In an example, a biometric sensor can be a spectroscopic sensor which is configured to measure the spectrum of light energy reflected from (and/or absorbed by) tissue of the person's arm. In an example, a biometric sensor can be an electromagnetic energy sensor which is configured to measure parameters and/or patterns of electromagnetic energy passing through (and/or emitted by) tissue of the person's arm. In an example, measured parameters and/or patterns of electromagnetic energy can be selected from the group consisting of: impedance, resistance, conductivity, and electromagnetic wave pattern.

With respect to specific components, the example shown in FIG. 25 includes: strap (or band) 2501, strap (or band) connector 2502, outward facing portion 2503 of an enclosure, circumference-center-facing portion 2504 of the enclosure, inflated central portion 2505 of the enclosure, and a biometric sensor 2506 on the circumference-center-facing portion of the enclosure. In an example, this device can further comprise one or more components selected from the group consisting of: a data processor; a battery and/or energy harvesting unit; a display screen; a data transmitter; and a data receiver. In an example, relevant embodiment variations discussed elsewhere in this disclosure can also apply to this example.

Figure 26:
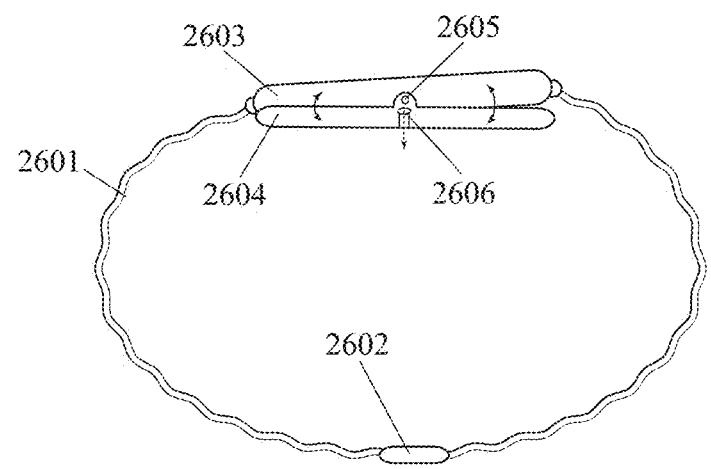
FIG. 26 shows a device with spectroscopic sensors on an inward-facing surface that pivots around a joint.

FIG. 26 shows another example of a wearable device for the arm with one or more close-fitting biometric sensors. This figure shows the device from a side perspective, as it would appear encircling a lateral cross-section of a person's wrist (or other portion of the person's arm). Described generally, the example shown in FIG. 26 is an arcuate wrist-worn device with a biometric sensor which is located on a circumference-center-facing portion of an enclosure, wherein this circumference-center-facing portion pivots around an axis so that the sensor remains in close contact with the surface of a person's arm even if the device tilts with respect to the arm surface. In this example, an enclosure is positioned on the anterior (upper) portion of the device circumference. In this example, the enclosure has an outward-facing portion (which can include a display screen) and an inner-facing portion (which houses the biometric sensor).

In this example, a circumference-center-facing portion which houses a biometric sensor pivots around a central axis when the device tilts with respect to the surface of the person's arm. Having a biometric sensor located on a circumference-center-facing portion of an enclosure which pivots around an axis can help to keep the biometric sensor in close proximity to the surface of the person's arm and at substantially the same angle with respect to the surface of a person's arm. This can be particularly important for a spectroscopic sensor, wherein it is desirable to maintain the same projection angle (and/or reflection angle) of a beam of light which is directed toward (and/or reflected from) the surface of a person's arm.

More specifically, the example shown in FIG. 26 is a wearable device for the arm with one or more close-fitting biometric sensors comprising: (a) an attachment member, such as a strap or band, which is configured to span at least a portion of the circumference of a person's arm; (b) an enclosure which is part of (or attached to) the attachment member, wherein this enclosure further comprises an outward facing portion and a circumference-center-facing portion, wherein the rigid inward (or center) pivots around a central axis with respect to the outward facing portion; and (c) a biometric sensor in the circumference-center-facing portion which is configured to record biometric data concerning the person's arm tissue.

In this example, the central axis around which the circumference-center-facing portion pivots is perpendicular to the circumference of the device. In another example, the central axis around which the circumference-center-facing portion pivots can be parallel or tangential to the circumference of the device. In an example, there can be a display screen on the outward-facing surface of the enclosure. In an example, there can be more than one biometric sensor on the circumference-center-facing portion of the enclosure.

In an example, a biometric sensor can be a spectroscopic sensor which is configured to measure the spectrum of light energy reflected from (and/or absorbed by) tissue of the person's arm. In an example, a biometric sensor can be an electromagnetic energy sensor which is configured to measure parameters and/or patterns of electromagnetic energy passing through (and/or emitted by) tissue of the person's arm. In an example, measured parameters and/or patterns of electromagnetic energy can be selected from the group consisting of: impedance, resistance, conductivity, and electromagnetic wave pattern.

With respect to specific components, the example shown in FIG. 26 includes: strap (or band) 2601, strap (or band) connector 2602, outward facing portion 2603 of an enclosure, circumference-center-facing portion 2604 of the enclosure, axis 2605 around which circumference-center-facing portion 2604 pivots; and a biometric sensor 2606 on the circumference-center-facing portion of the enclosure. In an example, this device can further comprise one or more components selected from the group consisting of: a data processor; a battery and/or energy harvesting unit; a display screen; a data transmitter; and a data receiver. In an example, relevant embodiment variations discussed elsewhere in this disclosure can also apply to this example.

Figure 27:
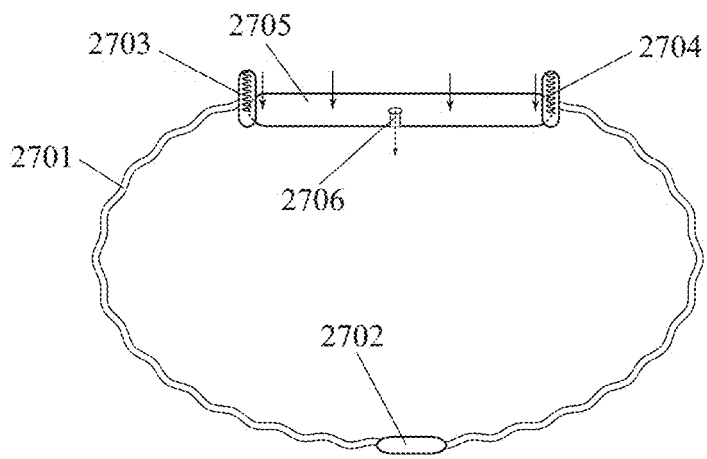
FIG. 27 shows a device with spectroscopic sensors on an inward-facing surface pressed inward by springs.

FIG. 27 shows another example of a wearable device for the arm with one or more close-fitting biometric sensors. This figure shows the device from a side perspective, as it would appear encircling a lateral cross-section of a person's wrist (or other portion of the person's arm). Described generally, the example shown in FIG. 27 is a wrist-worn device with a biometric sensor located on an enclosure, wherein the enclosure is pushed toward the surface of a person's arm by spring mechanisms so that the sensor remains in close contact with the arm's surface even if the rest of the device shifts away from the arm's surface. In this example, the enclosure is on the anterior (upper) portion of the device circumference.

The example shown in FIG. 27 can also be expressed as a wearable device for the arm with one or more close-fitting biometric sensors comprising: (a) an attachment member, such as a strap or band, which is configured to span at least a portion of the circumference of a person's arm; (b) an enclosure which is part of (or attached to) the attachment member; (c) one or more spring mechanisms which push the enclosure inward toward the circumference center of the device; and (d) a biometric sensor in the enclosure which is configured to record biometric data concerning the person's arm tissue.

In this example, there are two spring mechanisms which push the enclosure inward toward the surface of a person's arm. In this example, these spring mechanisms are located at the places where the enclosure is connected to a strap or band. In an example, there can be a display screen on the outward-facing surface of the enclosure. In an example, there can be more than one biometric sensor on the circumference-center-facing portion of the enclosure. In an example, a biometric sensor can be a spectroscopic sensor which is configured to measure the spectrum of light energy reflected from (and/or absorbed by) tissue of the person's arm. In an example, a biometric sensor can be an electromagnetic energy sensor which is configured to measure parameters and/or patterns of electromagnetic energy passing through (and/or emitted by) tissue of the person's arm. In an example, measured parameters and/or patterns of electromagnetic energy can be selected from the group consisting of: impedance, resistance, conductivity, and electromagnetic wave pattern.

With respect to specific components, the example shown in FIG. 27 includes: strap (or band) 2701, strap (or band) connector 2702, first spring mechanism 2703, second spring mechanism 2704, enclosure 2705 which is pushed inward (toward the circumference center of the device) by spring mechanisms 2703 and 2704, and biometric sensor 2706. In an example, this device can further comprise one or more components selected from the group consisting of: a data processor; a battery and/or energy harvesting unit; a display screen; a data transmitter; and a data receiver. In an example, relevant embodiment variations discussed elsewhere in this disclosure can also apply to this example.

Figure 28:
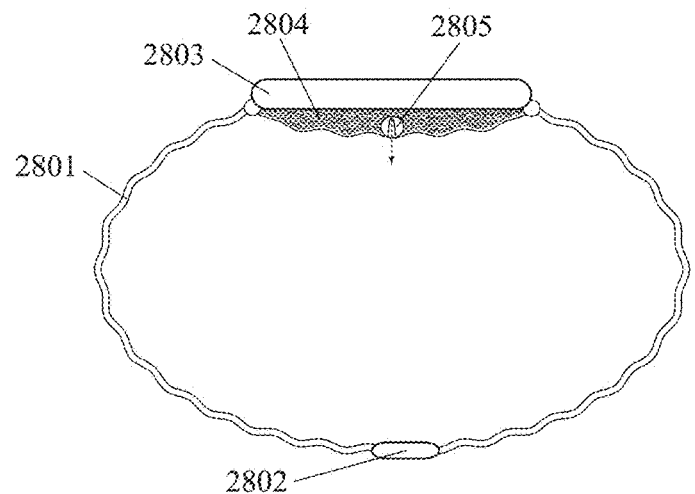
FIG. 28 shows a device with a spectroscopic sensor on an elastic compartment.

FIG. 28 shows another example of a wearable device for the arm with one or more close-fitting biometric sensors. This figure shows the device from a side perspective, as it would appear encircling a lateral cross-section of a person's wrist (or other portion of the person's arm). Described generally, this example is a wrist-worn device with an elastic member (such as a balloon) that is filled with a fluid, gel, or gas and a biometric sensor which is attached to the circumference-center-facing wall of this elastic member. Having a biometric sensor attached to the circumference-center-facing wall of an elastic member can help to keep the sensor in close contact with the surface of a person's arm, even if other components of the device are shifted or tilted away from the arm's surface. In an example, an elastic member can be part of an enclosure which is attached to an arm by a strap. In an example, such an enclosure can be positioned on the anterior (upper) portion of the device circumference.

The example shown in FIG. 28 can also be expressed as a wearable device for the arm with one or more close-fitting biometric sensors comprising: (a) an attachment member, such as a strap or band, which is configured to span at least a portion of the circumference of a person's arm; (b) an enclosure which is part of (or attached to) the attachment member; (c) an elastic member filled with a fluid, gel, or gas which is attached to (or part of) the enclosure; and (d) a biometric sensor which is configured to record biometric data concerning the person's arm tissue, wherein this sensor is attached to a circumference-center-facing wall of the elastic member.

In an example, there can be a display screen on the outward facing surface of an enclosure. In an example, there can be more than one biometric sensor on the circumference-center-facing wall of an elastic member. In an example, a biometric sensor can be a spectroscopic sensor which is configured to measure the spectrum of light energy reflected from (and/or absorbed by) tissue of the person's arm. In an example, a biometric sensor can be an electromagnetic energy sensor which is configured to measure parameters and/or patterns of electromagnetic energy passing through (and/or emitted by) tissue of the person's arm. In an example, measured parameters and/or patterns of electromagnetic energy can be selected from the group consisting of: impedance, resistance, conductivity, and electromagnetic wave pattern.

With respect to specific components, the example shown in FIG. 28 includes: strap (or band) 2801; strap (or band) connector 2802; enclosure 2803; elastic member 2804 which is filled with a fluid, gel, or gas; and biometric sensor 2805 which is attached to the circumference-center-facing wall of the elastic member. In an example, this device can further comprise one or more components selected from the group consisting of: a data processor; a battery and/or energy harvesting unit; a display screen; a data transmitter; and a data receiver. In an example, relevant embodiment variations discussed elsewhere in this disclosure can also apply to this example.

Figure 29:
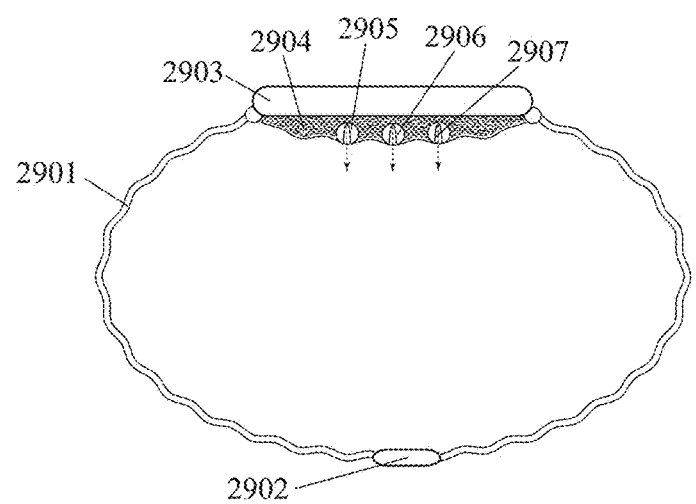
FIG. 29 shows a device with multiple spectroscopic sensors on an elastic compartment.

FIG. 29 shows another example of a wearable device for the arm with one or more close-fitting biometric sensors. This figure shows the device from a side perspective, as it would appear encircling a lateral cross-section of a person's wrist (or other portion of the person's arm). The example shown in FIG. 29 is like the one shown in FIG. 28, except that in FIG. 29 there are multiple biometric sensors on the circumference-center-facing wall of an elastic member. In FIG. 29, there are three biometric sensors.

With respect to specific components, the example shown in FIG. 29 includes: strap (or band) 2901; strap (or band) connector 2902; enclosure 2903; elastic member 2904 which is filled with a fluid, gel, or gas; and biometric sensors 2905, 2906, and 2907 which are attached to the circumference-center-facing wall of the elastic member. In an example, this device can further comprise one or more components selected from the group consisting of: a data processor; a battery and/or energy harvesting unit; a display screen; a data transmitter; and a data receiver. In an example, relevant embodiment variations discussed elsewhere in this disclosure can also apply to this example.

Figure 30:
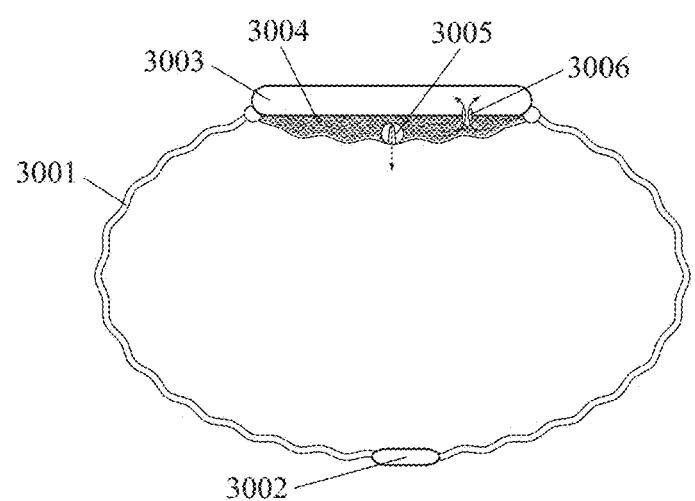
FIG. 30 shows a device with a spectroscopic sensor on an elastic compartment with adjustable pressure.

FIG. 30 shows another example of a wearable device for the arm with one or more close-fitting biometric sensors.

This figure shows the device from a side perspective, as it would appear encircling a lateral cross-section of a person's wrist (or other portion of the person's arm). The example shown in FIG. 30 is like the one shown in FIG. 28, except that in FIG. 30 there is also a micropump which can pump fluid, gel, or gas into (or out of) the elastic member. This enables (automatic) adjustment of the size and/or internal pressure of the elastic member in order to better maintain proximity of the sensor to the surface of the person's arm.

With respect to specific components, the example shown in FIG. 30 includes: strap (or band) 3001; strap (or band) connector 3002; enclosure 3003; elastic member 3004 which is filled with a fluid, gel, or gas; biometric sensor 3005 which is attached to the circumference-center-facing wall of the elastic member; and micropump 3006 which pumps fluid, gel, or gas into (or out of) the elastic member. In an example, this device can further comprise one or more components selected from the group consisting of: a data processor; a battery and/or energy harvesting unit; a display screen; a data transmitter; and a data receiver. In an example, relevant embodiment variations discussed elsewhere in this disclosure can also apply to this example.

Figure 31:
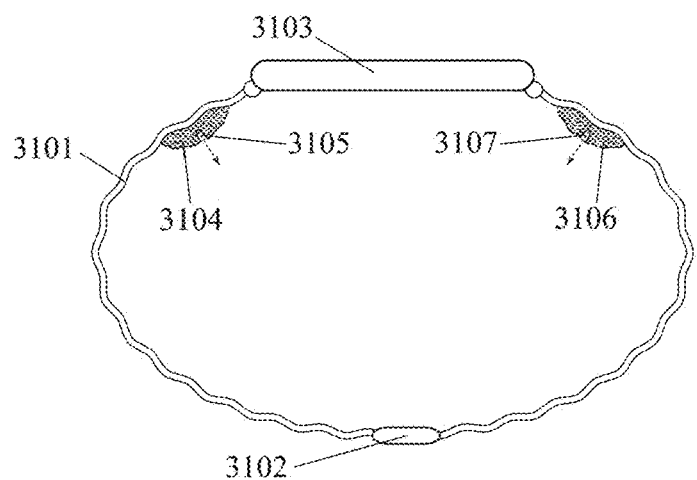
FIG. 31 shows a device with spectroscopic sensors on elastic compartments on a strap or band.

FIG. 31 shows another example of a wearable device for the arm with one or more close-fitting biometric sensors. This figure shows the device from a side perspective, as it would appear encircling a lateral cross-section of a person's wrist (or other portion of the person's arm). This wrist-worn device comprises: an attachment member which is configured to span at least a portion of the circumference of a person's arm; one or more elastic members filled with a flowable substance, wherein these elastic members are part of (or attached to) the circumference-center-facing surface of the attachment member; and one or more biometric sensors, wherein each sensor is part of (or attached to) a circumference-center-facing wall of an elastic member.

The design of this device keeps biometric sensors close to the surface of a person's arm, even if portions of the device shift away from the surface of the person's arm. The interiors of the elastic members on which these sensors are located are under modest pressure so that these elastic members expand when they are moved away from the arm surface and these elastic members are compressed when they are moved toward the arm surface.

In an example, an attachment member can be a strap, band, bracelet, ring, armlet, cuff, or sleeve. In an example, an attachment member can be attached to a person's arm by connecting two ends of the attachment member with a clasp, clip, buckle, hook, pin, plug, or hook-and-eye mechanism. In an example, an attachment member can be attached to a person's arm by stretching it circumferentially and sliding it over the person's hand onto the arm. In an example, an attachment member can be attached to a person's arm by applying force to pull two ends of the member apart in order to slip the member over the arm; the two ends then retract back towards each other when device is on the arm and the force is removed.

In an example, an elastic member can be a balloon or other elastic substance-filled compartment. In an example, the flowable substance inside an elastic member can be a fluid, gel, or gas. In this example, there are two elastic members on the attachment member. In this example, the elastic members are symmetrically located with respect to a central cross-section of the device. In an example, there can be a plurality of elastic members (with attached biometric sensors) which are distributed around the circumference of an attachment member and/or the device. In this example, a device can also include an enclosure which further comprises a display screen.

In an example, a biometric sensor can be a spectroscopic sensor which is configured to measure the spectrum of light energy reflected from (and/or absorbed by) tissue of the person's arm. In an example, a biometric sensor can be an electromagnetic energy sensor which is configured to measure parameters and/or patterns of electromagnetic energy passing through (and/or emitted by) tissue of the person's arm. In an example, measured parameters and/or patterns of electromagnetic energy can be selected from the group consisting of: impedance, resistance, conductivity, and electromagnetic wave pattern.

With respect to specific components, the example shown in FIG. 31 includes: band 3101; band connector 3102; enclosure 3103; first elastic member 3104 which is filled with a fluid, gel, or gas; first biometric sensor 3105 which is attached to the circumference-center-facing wall of the first elastic member; second elastic member 3106 which is filled with a fluid, gel, or gas; and second biometric sensor 3107 which is attached to the circumference-center-facing wall of the second elastic member. In an example, this device can further comprise one or more components selected from the group consisting of: a data processor; a battery and/or energy harvesting unit; a display screen; a data transmitter; and a data receiver. In an example, relevant embodiment variations discussed elsewhere in this disclosure can also apply to this example.

Figure 32:
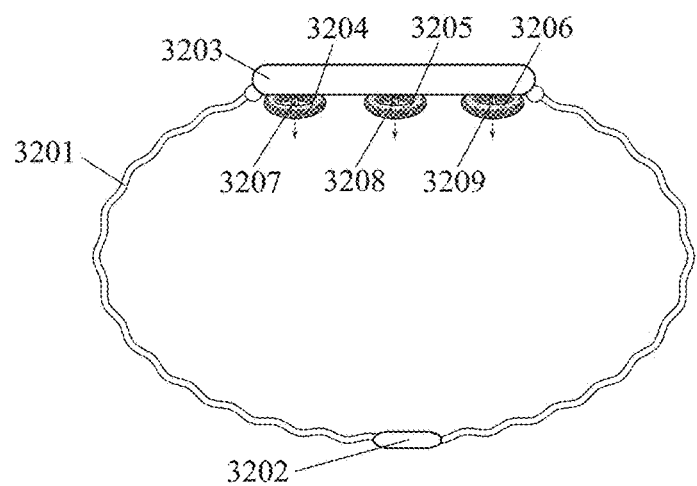
FIG. 32 shows a device with spectroscopic sensors on toroidal elastic compartments.

FIG. 32 shows another example of a wearable device for the arm with one or more close-fitting biometric sensors. This figure shows the device from a side perspective, as it would appear encircling a lateral cross-section of a person's wrist (or other portion of the person's arm). This wrist-worn device comprises: (a) an attachment member which is configured to span at least a portion of the circumference of a person's arm; (b) an enclosure which is part of (or attached to) the attachment member; (c) one or more torus-shaped elastic members filled with a flowable substance, wherein these elastic members are part of (or attached to) the enclosure; and (d) one or more biometric sensors, wherein each sensor is located in the central hole of a torus-shaped elastic member.

In an example, an attachment member can be a strap, band, bracelet, ring, armlet, cuff, or sleeve. In an example, an enclosure can further comprise a display screen on its outer surface. In an example, a torus-shaped elastic member can be a balloon which is filled with a fluid, gel, or gas. In an example, a biometric sensor can be a spectroscopic sensor which is configured to measure the spectrum of light energy reflected from (and/or absorbed by) tissue of the person's arm. In an example, a biometric sensor can be an electromagnetic energy sensor which is configured to measure parameters and/or patterns of electromagnetic energy passing through (and/or emitted by) tissue of the person's arm. In an example, measured parameters and/or patterns of electromagnetic energy can be selected from the group consisting of: impedance, resistance, conductivity, and electromagnetic wave pattern.

With respect to specific components, the example shown in FIG. 32 includes: band 3201; band connector 3202; enclosure 3203; torus-shaped elastic members 3204, 3205, and 3206; and biometric sensors 3207, 3208, and 3209 which are each located in the central opening (or hole) of a torus-shaped elastic member. In an example, this device can further comprise one or more components selected from the group consisting of: a data processor; a battery and/or energy harvesting unit; a display screen; a data transmitter; and a data receiver. In an example, relevant embodiment variations discussed elsewhere in this disclosure can also apply to this example.

Figure 33:
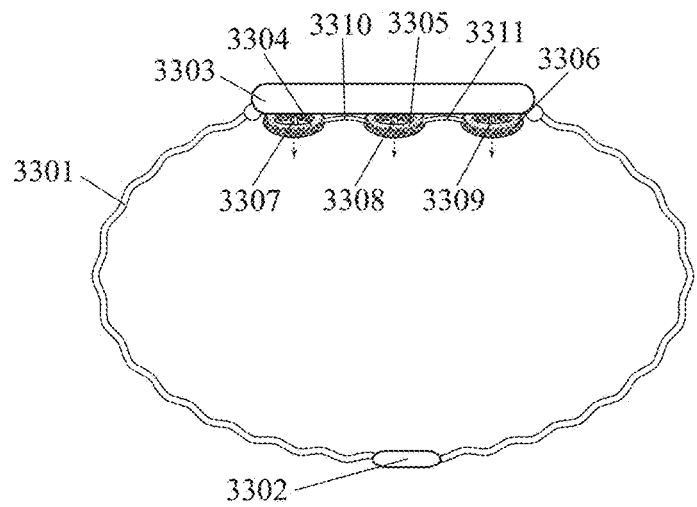
FIG. 33 shows a device with spectroscopic sensors on interconnected toroidal elastic compartments.

FIG. 33 shows another example of a wearable device for the arm with one or more close-fitting biometric sensors. This figure shows the device from a side perspective, as it would appear encircling a lateral cross-section of a person's wrist (or other portion of the person's arm). The example in FIG. 33 like the one shown in FIG. 32, except that the example in FIG. 33 also includes channels through which a fluid, gel, or gas can flow between the torus-shaped elastic members.

With respect to specific components, the example shown in FIG. 33 includes: band 3301; band connector 3302; enclosure 3303; torus-shaped elastic members 3304, 3305, and 3306; biometric sensors 3307, 3308, and 3309 which are each located in the central opening (or hole) of a torus-shaped elastic member; and channels 3310 and 3311 through which fluid, gel, or gas can flow between the torus-shaped elastic members. In an example, this device can further comprise one or more components selected from the group consisting of: a data processor; a battery and/or energy harvesting unit; a display screen; a data transmitter; and a data receiver. In an example, relevant embodiment variations discussed elsewhere in this disclosure can also apply to this example.

Figure 34:
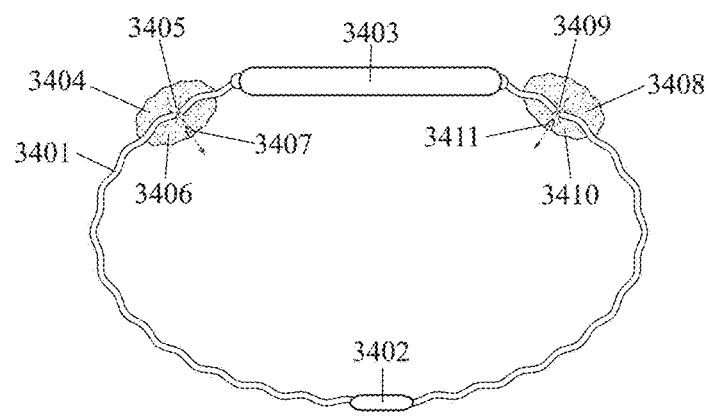
FIG. 34 shows a device with spectroscopic sensors on inner elastic compartments connected to outer elastic compartments.

FIG. 34 shows another example of a wearable device for the arm with one or more close-fitting biometric sensors. This figure shows the device from a side perspective, as it would appear encircling a lateral cross-section of a person's wrist (or other portion of the person's arm). The example in FIG. 34 like the one shown in FIG. 31, except that the example in FIG. 34 also includes elastic members on the outward-facing surface of the attachment member and channels through which fluid, gel, or gas can flow from circumference-center-facing elastic members to outward-facing elastic members, or vice versa.

This wrist-worn device comprises: (a) an attachment member which is configured to span at least a portion of the circumference of a person's arm; (b) at least one circumference-center-facing elastic member, wherein this member is filled with a flowable substance, and wherein this elastic member is part of (or attached to) the circumference-center-facing surface of the attachment member; (c) at least one outward-facing elastic member, wherein this member is filled with the flowable substance, and wherein this elastic member is part of (or attached to) the outward-facing surface of the attachment member; (d) a channel through which the flowable substance can flow between the circumference-center-facing elastic member and the outward-facing elastic member; and (e) a biometric sensor which is part of (or attached to) the circumference-center-facing wall of the circumference-center-facing elastic member.

In an example, an attachment member can be a strap, band, bracelet, ring, armlet, cuff, or sleeve. In an example, one or both of the elastic members can be a balloon or other elastic substance-filled compartment. In an example, the flowable substance inside an elastic member can be a fluid, gel, or gas. In an example, a biometric sensor can be a spectroscopic sensor which is configured to measure the spectrum of light energy reflected from (and/or absorbed by) tissue of the person's arm. In an example, a biometric sensor can be an electromagnetic energy sensor which is configured to measure parameters and/or patterns of electromagnetic energy passing through (and/or emitted by) tissue of the person's arm. In an example, measured parameters and/or patterns of electromagnetic energy can be selected from the group consisting of: impedance, resistance, conductivity, and electromagnetic wave pattern.

With respect to specific components, the example shown in FIG. 34 includes: band 3401; band connector 3402; enclosure 3403; outward-facing elastic members 3404 and 3408, which are filled with a fluid, gel, or gas; circumference-center-facing elastic members 3406 and 3410, which are filled with the fluid, gel, or gas; channels 3405 and 3409 through which the fluid, gel, or gas can flow from an outward-facing elastic member to a circumference-center-facing elastic member, or vice versa; and biometric sensors 3407 and 3411 which are each attached to a circumference-center-facing wall of a circumference-center-facing elastic member. In an example, this device can further comprise one or more components selected from the group consisting of: a data processor; a battery and/or energy harvesting unit; a display screen; a data transmitter; and a data receiver. In an example, relevant embodiment variations discussed elsewhere in this disclosure can also apply to this example.

Figure 35:
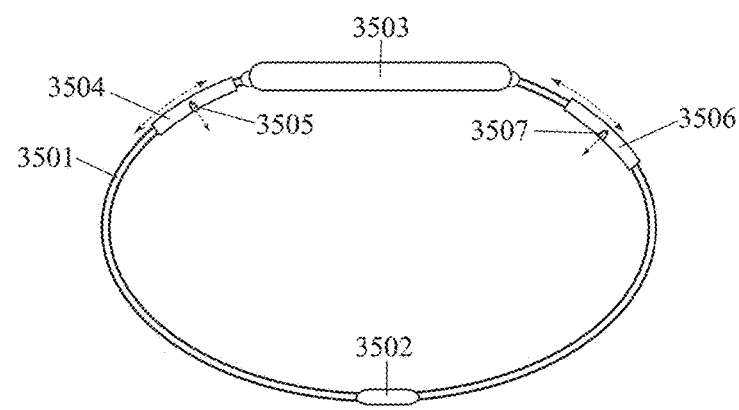
FIG. 35 shows a device with spectroscopic sensors which can adjustably slide around the circumference of the device.

FIG. 35 shows another example of a wearable device for the arm with one or more close-fitting biometric sensors. This figure shows the device from a side perspective, as it would appear encircling a lateral cross-section of a person's wrist (or other portion of the person's arm). A general description of the example in FIG. 35 can be expressed as a wrist-worn device with biometric sensors on circumferentially-sliding members, wherein these circumferentially-sliding members are slid along the circumference of the device in order to adjust the positions from which the biometric sensors measure data concerning arm tissue. Such moveable sensors enable a user to find the best positions around the circumference of the device from which to collect biometric data for a selected application.

This wrist-worn device comprises: (a) an attachment member which is configured to span at least a portion of the circumference of a person's arm; (b) at least one circumferentially-sliding member, wherein this member is slid along the circumference of the attachment member; and (c) at least one a biometric sensor which is part of (or attached to) the circumferentially-sliding member and collects data concerning arm tissue.

In an example, a sliding member can laterally-encircle an attachment member in order to keep the sliding member on the attachment member. In an example, the ends of a sliding member can curve around the sides of an attachment member in order to keep the sliding member on the attachment member. In an example, there can be a circumferential track on an attachment member into which a sliding member fits in order to keep the sliding member on the attachment member. In an example, a spring or other compressive mechanism on a sliding member can engage the attachment member in order to keep the sliding member on the attachment member. In an example, pressing on the top or sides of a sliding member frees it to slide along the attachment member and releasing this pressure causes the sliding member to stop sliding (and remain at a selected location on the attachment member). In an example, data from a biometric sensor on the sliding member can be analyzed in real time in order to identify the optimal location along the circumference of the attachment member from which to collect data.

In an example, an attachment member can be a strap, band, bracelet, ring, armlet, cuff, or sleeve. In an example, a biometric sensor can be a spectroscopic sensor which is configured to measure the spectrum of light energy reflected from (and/or absorbed by) tissue of the person's arm. In an example, a biometric sensor can be an electromagnetic energy sensor which is configured to measure parameters and/or patterns of electromagnetic energy passing through (and/or emitted by) tissue of the person's arm. In an example, measured parameters and/or patterns of electromagnetic energy can be selected from the group consisting of: impedance, resistance, conductivity, and electromagnetic wave pattern.

With respect to specific components, the example shown in FIG. 35 includes: band 3501; band connector 3502; enclosure 3503; circumferentially-sliding members 3504 and 3506, wherein these members slide along the circumference of the band; and biometric sensors 3505 and 3507 which are each part of (or attached to) a circumferentially-sliding member. In an example, this device can further comprise one or more components selected from the group consisting of: a data processor; a battery and/or energy harvesting unit; a display screen; a data transmitter; and a data receiver. In an example, relevant embodiment variations discussed elsewhere in this disclosure can also apply to this example.

Figure 36:
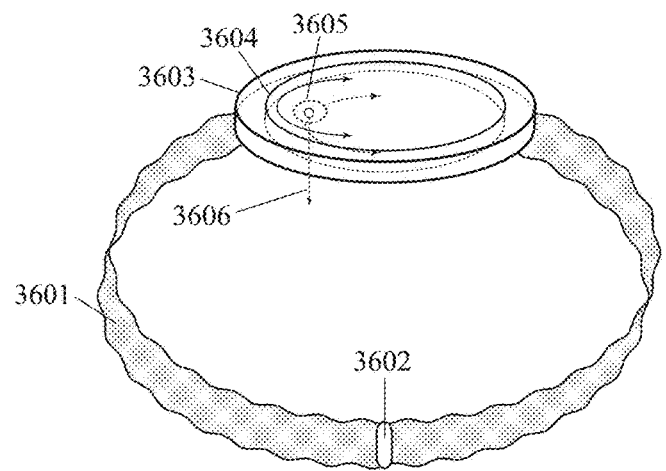
FIG. 36 shows a device with a spectroscopic sensor on a laterally-rotating enclosure.

FIG. 36 shows another example of a wearable device for the arm with one or more close-fitting biometric sensors. This figure shows the device from a non-perpendicular lateral perspective, as it would appear encircling a lateral cross-section of a person's wrist (or other portion of the person's arm).

A general description of the example in FIG. 36 can be expressed as a wrist-worn device with a biometric sensor on a rotating member, wherein rotation of the rotating member moves the biometric sensor in a circular manner. In an example, the circular path in which a sensor moves is configured to be in a plane which is substantially tangential to the surface of a person's arm. In an example, a user can manually rotate the rotating member in order to find the optimal location from which to have the sensor collect biometric data. In an example, a device can automatically rotate the rotating member in order to find the optimal location from which to have the sensor collect biometric data. In an example, a device can automatically rotate the rotating member in order to maintain the optimal sensor location if the device is unintentionally shifted with respect to the arm's surface. In an example, a device can automatically rotate the rotating member in order to collect data from multiple locations for more comprehensive and/or accurate analysis.

In this example, a wearable device for the arm with one or more close-fitting biometric sensors comprises: (a) an attachment member which is configured to span at least a portion of the circumference of a person's arm; (b) an enclosure which is part of (or attached to) the attachment member; (c) a rotating member which is part of (or attached to) the enclosure; and (d) a biometric sensor which is part of (or attached to) the rotating member, wherein this biometric sensor is configured to collect data concerning a person's arm tissue, and wherein this biometric sensor moves in a circular path when the rotating member is rotated.

In an example, an attachment member can be a strap, band, bracelet, ring, armlet, cuff, or sleeve. In an example, a rotating member can be a circular member which fits into a hole or recess in an enclosure. In an example, a rotating member can be manually moved by a user in order to find the best location from which to have a sensor collect biometric data. In an example, a rotating member can be automatically moved by an actuator in the device in order to find the best location from which to have a sensor collect biometric data. In an example, a rotating member can be automatically moved by an actuator in the device in order to maintain the best sensor location when an enclosure is unintentionally shifted with respect to the arm's surface. In an example, a rotating member can be automatically moved by an actuator in order to collect data from multiple locations for more comprehensive and/or accurate analysis.

In an example, a biometric sensor can be a spectroscopic sensor which is configured to measure the spectrum of light energy reflected from (and/or absorbed by) tissue of the person's arm. In an example, a biometric sensor can be an electromagnetic energy sensor which is configured to measure parameters and/or patterns of electromagnetic energy passing through (and/or emitted by) tissue of the person's arm. In an example, measured parameters and/or patterns of electromagnetic energy can be selected from the group consisting of: impedance, resistance, conductivity, and electromagnetic wave pattern.

With respect to specific components, the example shown in FIG. 36 includes: band 3601; band connector 3602; enclosure 3603; rotating member 3604 which is part of (or attached to) the enclosure; and biometric sensor 3605 which is part of (or attached to) the rotating member. In an example, this device can further comprise one or more components selected from the group consisting of: a data processor; a battery and/or energy harvesting unit; a display screen; a data transmitter; and a data receiver. In an example, relevant embodiment variations discussed elsewhere in this disclosure can also apply to this example.

Figure 37:
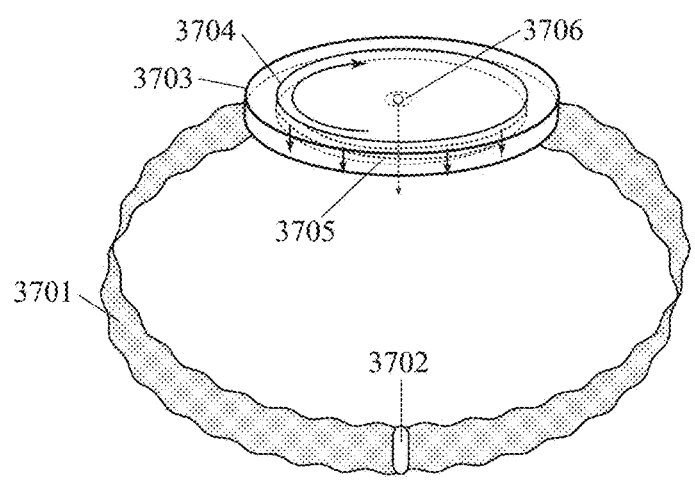
FIG. 37 shows a device with a spectroscopic sensor on a threaded rotating enclosure.

FIG. 37 shows another example of a wearable device for the arm with one or more close-fitting biometric sensors. This figure shows the device from a non-perpendicular lateral perspective, as it would appear encircling a lateral cross-section of a person's wrist (or other portion of the person's arm).

A general description of the example shown in FIG. 37 can be expressed as a wrist-worn device with a biometric sensor on a threaded rotating member, wherein rotation of the threaded rotating member adjusts the distance between the biometric sensor and the surface of a person's arm. In an example, a user can manually rotate the rotating member in order to find the optimal distance between the sensor and the arm's surface from which to have the sensor collect biometric data. In an example, a device can automatically (e.g. with an actuator) rotate the rotating member in order to find the optimal distance between the sensor and the arm's surface from which to have the sensor collect biometric data. In an example, a device can automatically (e.g. with an actuator) rotate the rotating member to maintain the optimal distance between a sensor and the arm's surface if the enclosure is unintentionally shifted with respect to the arm's surface.

In this example, a wearable device for the arm with one or more close-fitting biometric sensors comprises: (a) an attachment member which is configured to span at least a portion of the circumference of a person's arm; (b) an enclosure which is attached to (or part of) the attachment member; (c) a threaded rotating member which is attached to (or part of) the enclosure, wherein rotation of the threaded rotating member changes the distance between the threaded rotating member and the circumferential center of the device; and (d) a biometric sensor which is attached to (or part of) the threaded rotating member, wherein this biometric sensor is configured to collects data concerning a person's arm tissue, and wherein rotation of the threaded rotating member changes the distance between the biometric sensor and the circumferential center of the device. In an example, rotation of the threaded rotating member is also configured to change the distance between the biometric sensor and the surface of the person's arm.

In an example, an attachment member can be a strap, band, bracelet, ring, armlet, cuff, or sleeve. In an example, a threaded rotating member can have a spiral thread around its circumference which fits into a complementary spiral thread in a hole or recess in the enclosure. In an example, a threaded rotating member can be manually moved by a user in order to find the best distance between a sensor and the arm's surface from which to collect biometric data. In an example, a threaded rotating member can be automatically moved by an actuator in the device in order to find the best distance between a sensor and the arm's surface from which to collect biometric data. In an example, a threaded rotating member can be automatically moved by an actuator in the device in order to maintain the best distance between a sensor and the arm's surface when the location of an enclosure with respect to the arm's surface is unintentionally shifted.

In an example, a biometric sensor can be a spectroscopic sensor which is configured to measure the spectrum of light energy reflected from (and/or absorbed by) tissue of the person's arm. In an example, a biometric sensor can be an electromagnetic energy sensor which is configured to measure parameters and/or patterns of electromagnetic energy passing through (and/or emitted by) tissue of the person's arm. In an example, measured parameters and/or patterns of electromagnetic energy can be selected from the group consisting of: impedance, resistance, conductivity, and electromagnetic wave pattern.

With respect to specific components, the example shown in FIG. 37 includes: band 3701; band connector 3702; enclosure 3703; threaded rotating member 3704 with spiral thread 3705 which is part of (or attached to) the enclosure; and biometric sensor 3706 which is part of (or attached to) the rotating member. In an example, this device can further comprise one or more components selected from the group consisting of: a data processor; a battery and/or energy harvesting unit; a display screen; a data transmitter; and a data receiver. In an example, relevant embodiment variations discussed elsewhere in this disclosure can also apply to this example.

Figure 38:
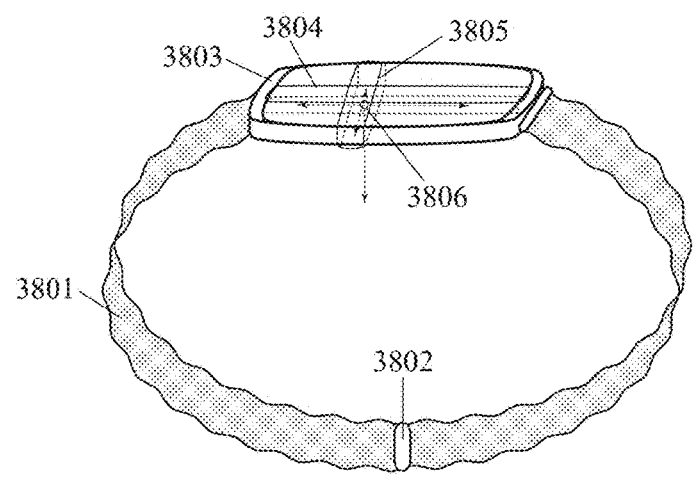
FIG. 38 shows a device with a two-way location-adjustable spectroscopic sensor.

FIG. 38 shows another example of a wearable device for the arm with one or more close-fitting biometric sensors. This figure shows the device from a non-perpendicular lateral perspective, as it would appear encircling a lateral cross-section of a person's wrist (or other portion of the person's arm). The example shown in FIG. 38 can be described as a wrist-worn device with a biometric sensor, wherein the location of this sensor can be moved along an X axis and/or along a Y axis, wherein the X axis is substantially tangential to the circumference of the device, and wherein the Y axis is perpendicular to the X axis.

In an example, a user can manually move a sensor along these X and/or Y axes in order to find the optimal location from which to collect biometric data concerning arm tissue. In an example, the device can automatically move a sensor (e.g. with an actuator) along these X and/or Y axes in order to find the optimal location from which to collect biometric data concerning arm tissue. In an example, the device can automatically move a sensor (e.g. with an actuator) along these X and/or Y axes in order to keep the sensor at the optimal location even if the device is unintentionally shifted with respect to the arm's surface. In an example, the device can automatically move a sensor (e.g. with an actuator) along these X and/or Y axes in order to collect data from various locations for more comprehensive or accurate analysis.

In this example, a wearable device for the arm with one or more close-fitting biometric sensors comprises: (a) an attachment member which is configured to span at least a portion of the circumference of a person's arm; (b) an enclosure which is attached to (or part of) the attachment member; (c) a biometric sensor which is configured to collect data concerning arm tissue; (d) a first moving member whose movement moves the biometric sensor along an X axis, wherein this X axis is substantially tangential to the circumference of the device; and (e) a second moving member whose movement moves the biometric sensor along an Y axis, wherein this Y axis is perpendicular to the X axis.

In an example, an attachment member can be a strap, band, bracelet, ring, armlet, cuff, or sleeve. In an example, a biometric sensor can be attached to a circumference-center-facing portion of an enclosure. In an example, first and second moving members can be sliding members. In an example, a first moving member can be a strip on an enclosure which slides along the X axis. In an example, a second moving member can be a strip on an enclosure which slides along the Y axis. In another example, first and second moving members can be rotating members.

In an example, a biometric sensor can be a spectroscopic sensor which is configured to measure the spectrum of light energy reflected from (and/or absorbed by) tissue of the person's arm. In an example, a biometric sensor can be an electromagnetic energy sensor which is configured to measure parameters and/or patterns of electromagnetic energy passing through (and/or emitted by) tissue of the person's arm. In an example, measured parameters and/or patterns of electromagnetic energy can be selected from the group consisting of: impedance, resistance, conductivity, and electromagnetic wave pattern.

With respect to specific components, the example shown in FIG. 38 includes: band 3801; band connector 3802; enclosure 3803; first sliding member 3804 which slides along an X axis, wherein the X axis is substantially tangential to the circumference of the device; second sliding member 3805 which slides along an Y axis, wherein the Y axis is substantially perpendicular to the X axis; and biometric sensor 3806 which is configured to collect data concerning arm tissue, wherein the X and Y coordinates of biometric sensor 3806 are changed by moving the first and second sliding members, respectively. In a variation on this example, both an enclosure and Y axis can be arcuate. In an example, this device can further comprise one or more components selected from the group consisting of: a data processor; a battery and/or energy harvesting unit; a display screen; a data transmitter; and a data receiver. In an example, relevant embodiment variations discussed elsewhere in this disclosure can also apply to this example.

Figure 39:
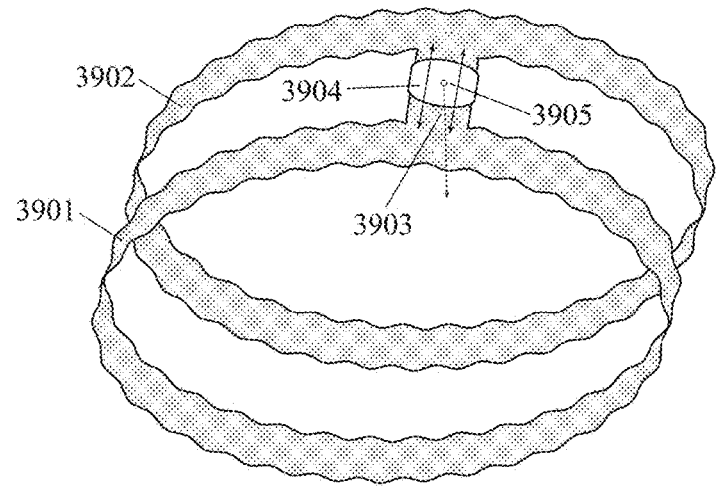
FIG. 39 shows a device with two parallel bands and a spectroscopic sensor that adjustably slides between them.

FIG. 39 shows another example of a wearable device for the arm with one or more close-fitting biometric sensors. This figure shows the device from a non-perpendicular lateral perspective, as it would appear encircling a lateral cross-section of a person's wrist (or other portion of the person's arm). The example shown in FIG. 39 can be described as a wrist-worn device with: two parallel bands which are connected to each other on the anterior (upper) surface of the wrist; and a biometric sensor which slides (back and forth) along the strip which connects the two bands.

In an example, a user can manually slide the biometric sensor (back and forth) along the strip connecting the two bands in order to find the optimal location from which to collect biometric data concerning arm tissue. In an example, the device can automatically slide the biometric sensor (back and forth) along the strip connecting the two bands in order to find the optimal location from which to collect biometric data concerning arm tissue. In an example, the device can automatically slide the biometric sensor (back and forth) along the strip connecting the two bands in order to collect data from different locations for more comprehensive or accurate analysis.

In this example, a wearable device for the arm with one or more close-fitting biometric sensors comprises: (a) two substantially-parallel bands which are each configured to span at least a portion of the circumference of a person's arm; (b) a connecting strip which is configured to connect the two bands to each other on the anterior (upper) surface of the arm; (c) a moving enclosure which slides (back and forth) along the connecting strip; and (d) a biometric sensor which is configured to collect data concerning arm tissue, wherein this biometric sensor is part of (or attached to) the moving enclosure.

In an example, a biometric sensor can be a spectroscopic sensor which is configured to measure the spectrum of light energy reflected from (and/or absorbed by) tissue of the person's arm. In an example, a biometric sensor can be an electromagnetic energy sensor which is configured to measure parameters and/or patterns of electromagnetic energy passing through (and/or emitted by) tissue of the person's arm. In an example, measured parameters and/or patterns of electromagnetic energy can be selected from the group consisting of: impedance, resistance, conductivity, and electromagnetic wave pattern.

With respect to specific components, the example shown in FIG. 39 includes: first band 3901; second band 3902; connecting strip 3903 which connects the first and second bands; sliding enclosure 3904 which slides (back and forth) along the connecting strip; and biometric sensor 3905 which is configured to collect data concerning arm tissue, wherein this biometric sensor is part of (or attached to) the sliding enclosure. In an example, this device can further comprise one or more components selected from the group consisting of: a data processor; a battery and/or energy harvesting unit; a display screen; a data transmitter; and a data receiver. In an example, relevant embodiment variations discussed elsewhere in this disclosure can also apply to this example.

Figure 40:
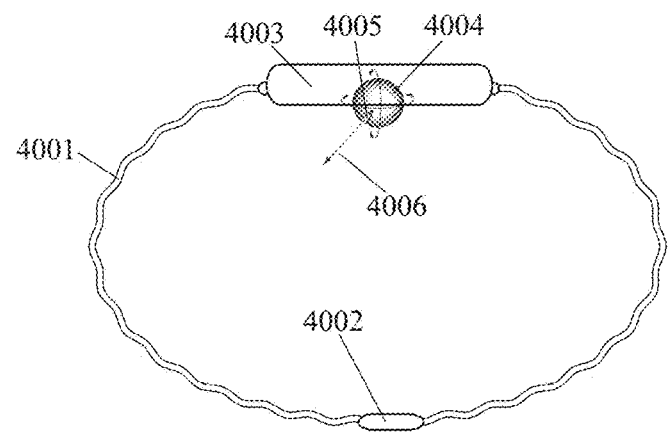
FIG. 40 shows a device with a spectroscopic sensor on a rotating ball.

FIG. 40 shows another example of a wearable device for the arm with one or more close-fitting biometric sensors. This figure shows the device from a side perspective, as it would appear encircling a lateral cross-section of a person's wrist (or other portion of the person's arm). Described generally, the example shown in FIG. 40 is an arcuate wrist-worn device with a light-projecting spectroscopic sensor on a rotating ball. Rotating the ball changes the angle at which the spectroscopic sensor projects light onto the surface of a person's arm. The ball can be rotated in different directions so that the range of possible projection beams comprises a conic or frustal shape in three-dimensional space. Having a light-projecting spectroscopic sensor on a rotating ball can enable a device to record biometric measurements with substantially the same angle of incidence, even if an enclosure is tilted with respect to the surface of the person's arm.

The example shown in FIG. 40 is a wearable device for the arm with a close-fitting biometric sensor comprising: (a) an attachment member, such as a strap or band, which is configured to span at least a portion of the circumference of a person's arm; (b) an enclosure which is part of (or attached to) the attachment member; (c) a rotating ball which is part of (or attached to) the enclosure; and (d) a light-projecting spectroscopic sensor which is part of (or attached to) the rotating ball.

In an example, an attachment member can be a strap, band, bracelet, ring, armlet, cuff, or sleeve. In an example, the circumference-center-facing surface of an enclosure can be substantially flat. In an example, the circumference-center-facing surface of an enclosure can be curved. In an example, there can be a display screen on the outward-facing surface of an enclosure. In an example, the rotating ball can fit into the enclosure like a ball-and-socket joint. In an example, the device can further comprise one or more actuators which move the rotating ball.

With respect to specific components, the example shown in FIG. 40 includes: strap 4001, strap connector 4002, enclosure 4003, rotating ball 4004, and spectroscopic sensor 4005 which emits beam of light 4006. In an example, this device can further comprise one or more components selected from the group consisting of: a data processor; a battery and/or energy harvesting unit; a display screen; a data transmitter; and a data receiver. In an example, relevant embodiment variations discussed elsewhere in this disclosure can also apply to this example.

Figure 41:
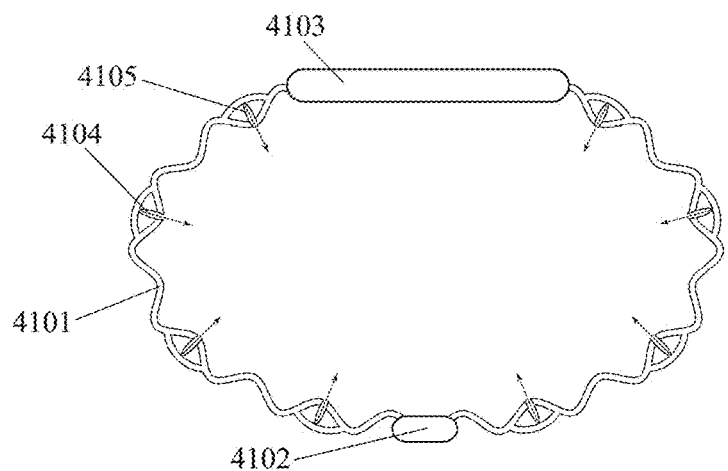
FIG. 41 shows a device with an undulating band with spectroscopic sensors.

FIG. 41 shows another example of a wearable device for the arm with one or more close-fitting biometric sensors. This figure shows the device from a side perspective, as it would appear encircling a lateral cross-section of a person's wrist (or other portion of the person's arm). Described generally, the example shown in FIG. 41 is a wearable device for the arm with a flexible circumferentially-undulating band with biometric sensors on the proximal portions of undulating waves. A band with such a flexible circumferentially-undulating structure can help to keep a plurality of biometric sensors in close proximity to the surface of a person's arm. In an example, an attachment member can be a strap, band, bracelet, ring, or armlet. In an example, a circumferentially-undulating attachment member can have a repeating wave pattern. In an example, a circumferentially-undulating attachment member can have a sinusoidal wave pattern.

The example shown in FIG. 41 is a wearable device for the arm with a close-fitting biometric sensor comprising: (a) a circumferentially-undulating attachment member which is configured to span at least a portion of the circumference of a person's arm; and (b) a plurality of biometric sensors which collect data concerning arm tissue, wherein each biometric sensor is located at the proximal portion of an undulation, and wherein the proximal portion of an undulation is the portion of an undulating wave which is closest to the circumferential center of the device.

With respect to specific components, the example shown in FIG. 41 includes: circumferentially-undulating band 4101, band connector 4102, enclosure 4103, first biometric sensor 4104 at the proximal portion of a first wave in the circumferentially-undulating band, and second biometric sensor 4105 at the proximal portion of a second wave in the circumferentially-undulating band. In an example, this device can further comprise one or more components selected from the group consisting of: a data processor; a battery and/or energy harvesting unit; a display screen; a data transmitter; and a data receiver. In an example, relevant embodiment variations discussed elsewhere in this disclosure can also apply to this example.

Figure 42:
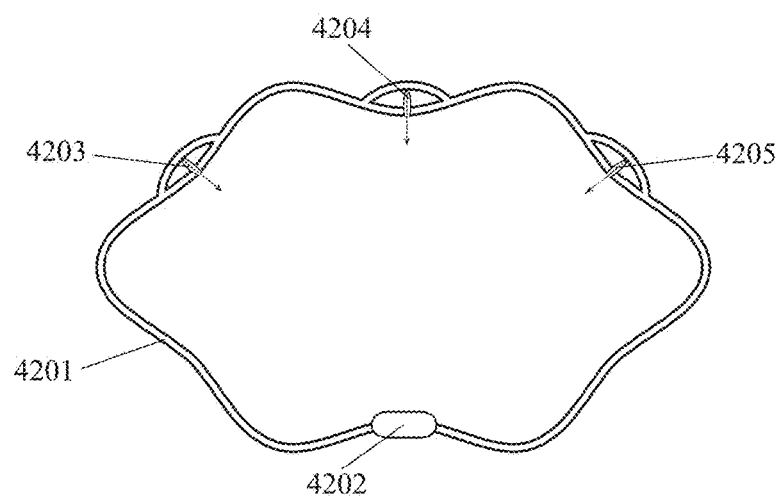
FIG. 42 shows a device with an undulating band with six undulations and spectroscopic sensors.

FIG. 42 shows another example of a wearable device for the arm with one or more close-fitting biometric sensors. This figure shows the device from a side perspective, as it would appear encircling a lateral cross-section of a person's wrist (or other portion of the person's arm). Described generally, the example shown in FIG. 42 is a wearable device for the arm with a flexible circumferentially-undulating band with six waves and biometric sensors on the proximal portions of some or all of these waves.

A band with a circumferentially-undulating structure can help to keep a plurality of biometric sensors in close proximity to the surface of a person's arm. Further, a band with six waves can engage the sides of a person's wrist with two symmetrically-opposite waves to resist rotational shifting better than a circular or oval band. This can help to reduce measurement errors caused by movement of biometric sensors. In an example, a circumferentially-undulating attachment member can be a strap, band, bracelet, ring, or armlet. In an example, a circumferentially-undulating attachment member can have a repeating wave pattern. In an example, a circumferentially-undulating attachment member can have a sinusoidal wave pattern.

The example shown in FIG. 42 is a wearable device for the arm with one or more close-fitting biometric sensors comprising: (a) a circumferentially-undulating attachment member with six waves which is configured to span the circumference of a person's arm; and (b) a plurality of biometric sensors which collect data concerning arm tissue, wherein each biometric sensor is located at the proximal portion of an undulation, and wherein the proximal portion of an undulation is the portion of an undulating wave which is closest to the circumferential center of the device.

With respect to specific components, the example shown in FIG. 42 includes: circumferentially-undulating band 4201 with six waves, band connector 4202, a first biometric sensor 4203 at the proximal portion of a first wave in the circumferentially-undulating band, a second biometric sensor 4205 at the proximal portion of a second wave in the circumferentially-undulating band, and a third biometric sensor 4206 at the proximal portion of a third wave in the circumferentially-undulating band. In an example, this device can further comprise one or more components selected from the group consisting of: a data processor; a battery and/or energy harvesting unit; a display screen; a data transmitter; and a data receiver. In an example, relevant embodiment variations discussed elsewhere in this disclosure can also apply to this example.

Figure 43:
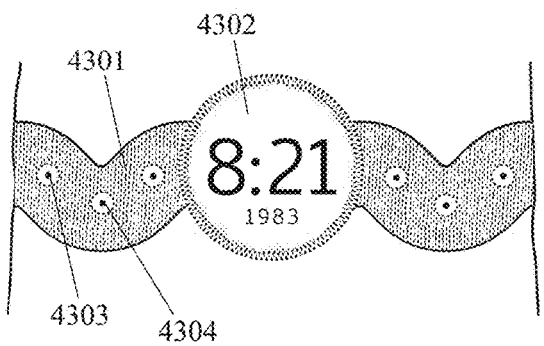
FIG. 43 shows a device with a laterally-undulating band with spectroscopic sensors.

FIG. 43 shows another example of a wearable device for the arm with one or more close-fitting biometric sensors. This figure shows the device from a top-down perspective, as it would appear spanning the anterior (upper) surface of a person's wrist (or other portion of the person's arm) in a circumferential manner. Described generally, the example shown in FIG. 43 is a wearable device for the arm with a laterally-undulating band and biometric sensors. Lateral undulations are waves which are substantially perpendicular to the plane containing the band circumference. In an example, a band can have sinusoidal lateral undulations.

The example shown in FIG. 43 is a wearable device for the arm with one or more close-fitting biometric sensors comprising: (a) a laterally-undulating attachment member which is configured to span at least a portion of the circumference of a person's arm, wherein lateral undulations are waves which are substantially perpendicular to the plane containing the circumference of the attachment member; and (b) one or more biometric sensors which collect data concerning arm tissue, wherein these biometric sensors are part of (or attached to) the laterally-undulating attachment member.

With respect to specific components, the example shown in FIG. 43 includes: laterally-undulating strap 4301; display screen 4302; and biometric sensors including 4303 and 4304. In an example, this device can further comprise one or more components selected from the group consisting of: a data processor; a battery and/or energy harvesting unit; a display screen; a data transmitter; and a data receiver. In an example, relevant embodiment variations discussed elsewhere in this disclosure can also apply to this example.

Figure 44:
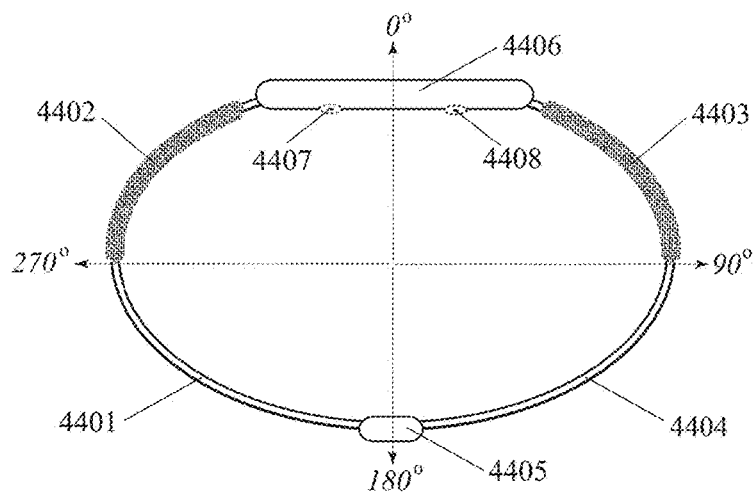
FIG. 44 shows a device with one or more elastic portions which are configured to span the anterior (upper) surface of a person's arm, one or more inelastic portions which are configured to span the posterior (lower) surface of the person's arm, an enclosure which is connected to the elastic portions, and one or more spectroscopic sensors which are part of the enclosure.

FIG. 44 shows another example of a wearable device for the arm with one or more close-fitting biometric sensors. This figure shows the device from a side perspective, as it would appear encircling a lateral cross-section of a person's wrist (or other portion of the person's arm). Described generally, the example shown in FIG. 44 is a wearable device for an arm with one or more biometric sensors in an enclosure and an attachment member (such as a strap, band, bracelet, or cuff) which attaches the enclosure to the arm, wherein this attachment member has relatively-elastic portions connected to the enclosure and relatively-inelastic portions elsewhere. This structure can help to keep the enclosure and sensors fitting closely against the arm. This, in turn, can enable more-consistent collection of data concerning arm tissue.

In an example, the device in FIG. 44 can be specified as a wearable device for the arm with one or more close-fitting biometric sensors comprising: (a) an attachment member which is configured to span at least 60% of the circumference of a person's arm, wherein this attachment member further comprises—one or more elastic portions which are configured to span the anterior (upper) surface of a person's arm and one or more inelastic portions which are configured to span the posterior (lower) surface of the person's arm; (b) an enclosure which is connected to the elastic portions of the attachment member; and (c) one or more biometric sensors which collect data concerning arm tissue which are part of (or attached to) the enclosure.

In an alternative example, a wearable device for the arm with one or more close-fitting biometric sensors can comprise: (a) an attachment member which is configured to span at least 60% of the circumference of a person's arm, wherein this attachment member further comprises—one or more elastic portions which are configured to span the posterior (lower) surface of a person's arm and one or more inelastic portions which are configured to span the anterior (upper) surface of the person's arm; (b) an enclosure which is connected to the elastic portions of the attachment member; and (c) one or more biometric sensors which collect data concerning arm tissue which are part of (or attached to) the enclosure.

In an example, an elastic portion of an attachment member can be an elastic strap or band. In an example, an elastic portion of an attachment member can be made from elastic fabric. In an example, an elastic portion of an attachment member can have a first elasticity level, an inelastic portion of an attachment member can have a second elasticity level, and the first elasticity level can be greater than the second elasticity level. In an example, a first elastic portion of an attachment member can be directly connected to a first side of an enclosure and a second elastic portion of an attachment member can be directly connected to a second (opposite) side of the enclosure. In an example, a first elastic portion of an attachment member can be indirectly connected to a first side of an enclosure and a second elastic portion of an attachment member can be indirectly connected to a second (opposite) side of the enclosure.

In an example, the device in FIG. 44 can be specified as a wearable device for the arm with one or more close-fitting biometric sensors comprising: (a) an attachment member which is configured to span at least 60% of the circumference of a person's arm wherein this attachment member further comprises: two elastic portions which are configured to span a first portion of the circumference of a person's arm; and two inelastic portions which are configured to span a second portion of the circumference of the person's arm; (b) an enclosure which is connected between the two elastic portions; (c) a clip, buckle, clasp, pin, or hook-and-eye mechanism between the two inelastic portions; and d) one or more biometric sensors which collect data concerning arm tissue which are part of (or attached to) the enclosure.

In an example, the device in FIG. 44 can be specified as a wearable device for the arm with one or more close-fitting biometric sensors comprising: (a) an attachment member which is configured to span at least 60% of the circumference of a person's arm wherein this attachment member further comprises: two elastic portions of the attachment member which are configured to span a portion of the circumference of a person's arm; and one or more inelastic portions which comprise the remainder of the attachment member; (b) an enclosure which is connected between the two elastic portions; (c) one or more biometric sensors which collect data concerning arm tissue which are part of (or attached to) the enclosure.

In an example, a single elastic portion can be configured to span at least 10% of the circumference of a person's arm. In an example, a single elastic portion can be configured to span at least 10% of the circumference of an attachment member. In an example, a single inelastic portion can be configured to span at least 10% of the circumference of a person's arm. In an example, a single inelastic portion can be configured to span at least 10% of the circumference of an attachment member. In an example, two elastic portions can be configured to collectively span at least 20% of the circumference of a person's arm. In an example, two elastic portions can be configured to collectively span at least 20% of the circumference of an attachment member. In an example, two inelastic portions can be configured to collectively span at least 20% of the circumference of a person's arm. In an example, two inelastic portions can be configured to collectively span at least 20% of the circumference of an attachment member.

In an example, a first definition of polar (or compass) coordinates can be defined for a device relative to how the device is configured to be worn on a person's arm. A 0-degree position can be defined as the position on a device circumference which is configured to intersect the longitudinal mid-line of the anterior (upper) surface of the arm. A 180-degree position is diametrically opposite (through the circumferential center) the 0-degree position. A 90-degree position is (clockwise) midway between the 0-degree and 180-degree positions. A 270-degree position is diametrically opposite the 90-degree position.

Using this first definition of polar coordinates, the device in FIG. 44 can be specified as a wearable device for the arm with one or more close-fitting biometric sensors comprising: (a) an attachment member which is configured to span at least 60% of the circumference of a person's arm wherein this attachment member further comprises—an elastic first portion with a first level of elasticity which spans at least 35 degrees (clockwise) between the 270-degree and 0-degree positions; an elastic second portion with a second level of elasticity which spans at least 35 degrees (clockwise) between the 0-degree and 90-degree positions, an inelastic third portion with a third level of elasticity which spans at least 35 degrees (clockwise) between the 90-degree and 180-degree positions, an inelastic fourth portion with a fourth level of elasticity which spans at least 35 degrees (clockwise) between the 180-degree and 270-degree positions, and wherein each of the first and second elasticity levels is greater than each of the third and fourth elasticity levels; (b) an enclosure that is configured to be worn (clockwise) between the 270-degree and 90-degree positions; and (c) one or more biometric sensors which collect data concerning arm tissue which are part of (or attached to) the enclosure.

Using this first definition of polar coordinates, the device in FIG. 44 can also be specified as a wearable device for the arm with one or more close-fitting biometric sensors comprising: (a) an attachment member which is configured to span at least 60% of the circumference of a person's arm wherein this attachment member further comprises—an elastic first portion with a first level of elasticity which spans at least 35 degrees (clockwise) between the 270-degree and 0-degree positions; an elastic second portion with a second level of elasticity which spans at least 35 degrees (clockwise) between the 0-degree and 90-degree positions, an inelastic third portion with a third level of elasticity which spans at least 35 degrees (clockwise) between the 90-degree and 180-degree positions, an inelastic fourth portion with a fourth level of elasticity which spans at least 35 degrees (clockwise) between the 180-degree and 270-degree positions, and wherein each of the first and second elasticity levels is greater than each of the third and fourth elasticity levels; (b) an enclosure that is connected between the elastic first and second portions; and (c) one or more biometric sensors which collect data concerning arm tissue which are part of (or attached to) the enclosure.

Alternatively, a second definition of polar (or compass) coordinates can be defined for the circumference of such a device relative to the position of an enclosure. The 0-degree position can be defined as the position on the device circumference which intersects the (lateral) mid-line of the enclosure. The 180-degree position is diametrically opposite (through the circumferential center) the 0-degree position. The 90-degree position is clockwise midway between the 0-degree and 180-degree positions. The 270-degree position is diametrically opposite the 90-degree position.

Using this second definition of polar coordinates, the device in FIG. 44 can be specified as a wearable device for the arm with one or more close-fitting biometric sensors comprising: (a) an attachment member which is configured to span at least 60% of the circumference of a person's arm wherein this attachment member further comprises—an elastic first portion with a first level of elasticity which spans at least 35 degrees (clockwise) between the 270-degree and 0-degree positions; an elastic second portion with a second level of elasticity which spans at least 35 degrees (clockwise) between the 0-degree and 90-degree positions, an inelastic third portion with a third level of elasticity which spans at least 35 degrees (clockwise) between the 90-degree and 180-degree positions, an inelastic fourth portion with a fourth level of elasticity which spans at least 35 degrees (clockwise) between the 180-degree and 270-degree positions, and wherein each of the first and second elasticity levels is greater than each of the third and fourth elasticity levels; (b) an enclosure that is connected between the elastic first and second portions of the attachment member; and (c) one or more biometric sensors which collect data concerning arm tissue which are part of (or attached to) the enclosure.

In an example, a biometric sensor can be a spectroscopic sensor which is configured to measure the spectrum of light energy reflected from (and/or absorbed by) tissue of the person's arm. In an example, a biometric sensor can be an electromagnetic energy sensor which is configured to measure parameters and/or patterns of electromagnetic energy passing through (and/or emitted by) tissue of the person's arm. In an example, measured parameters and/or patterns of electromagnetic energy can be selected from the group consisting of: impedance, resistance, conductivity, and electromagnetic wave pattern.

With respect to specific components, the example shown in FIG. 44 includes: inelastic portion 4401 of an attachment member; elastic portion 4402 of an attachment member; elastic portion 4403 of an attachment member; inelastic portion 4404 of an attachment member; attachment member connector 4405; enclosure 4406; and biometric sensors 4407 and 4408. In an example, this device can further comprise one or more components selected from the group consisting of: a data processor; a battery and/or energy harvesting unit; a display screen; a data transmitter; and a data receiver. In an example, relevant embodiment variations discussed elsewhere in this disclosure can also apply to this example.

FIG. 45 shows another example of a wearable device for the arm with one or more close-fitting biometric sensors. This figure shows the device from a side perspective, as it would appear encircling a lateral cross-section of a person's wrist (or other portion of the person's arm). Described generally, the example shown in FIG. 45 is a wearable device for the arm with one or more biometric sensors in an enclosure and an attachment member (such as a strap, band, bracelet, or cuff) which attaches the enclosure to the arm, wherein the attachment member is configured to have elastic portions spanning the lateral surfaces of the arm and inelastic portions spanning the anterior (upper) and posterior (lower) surfaces of the arm. This structure can help to keep the enclosure and sensors from rotating around the arm. This, in turn, can enable more-consistent collection of data concerning arm tissue.

In an example, the device in FIG. 45 can be specified as a wearable device for the arm with one or more close-fitting biometric sensors comprising: (a) an attachment member which is configured to span at least 60% of the circumference of a person's arm wherein this attachment member further comprises—one or more anterior inelastic portions which are configured to span the anterior (upper) surface of a person's arm, one or more posterior inelastic portions which are configured to span the posterior (lower) surface of a person's arm, and one or more elastic portions which connect the anterior and posterior inelastic portions; (b) an enclosure which is configured to be worn on the anterior (upper) portion of the arm; and (c) one or more biometric sensors which collect data concerning arm tissue which are part of (or attached to) the enclosure.

In another example, a wearable device for the arm with one or more close-fitting biometric sensors can comprise: (a) an attachment member which is configured to span at least 60% of the circumference of a person's arm wherein this attachment member further comprises—one or more anterior inelastic portions which are configured to span the anterior (upper) surface of a person's arm, one or more posterior inelastic portions which are configured to span the posterior (lower) surface of a person's arm, and one or more elastic portions which connect the anterior and posterior inelastic portions; (b) an enclosure which is configured to be worn on the posterior (lower) portion of the arm; and (c) one or more biometric sensors which collect data concerning arm tissue which are part of (or attached to) the enclosure.

In an example, a first inelastic portion of an attachment member can be connected to a first side of an enclosure and a second inelastic portion of an attachment member can be connected to a second side of the enclosure. In an example, an elastic portion can have a first level of elasticity, an inelastic portion can have a second level of elasticity, and the first level is greater than the second level. In an example, a single elastic portion can be configured to span at least 10% of the circumference of a person's arm. In an example, a single elastic portion can be configured to span at least 10% of the circumference of an attachment member. In an example, a single inelastic portion can be configured to span at least 10% of the circumference of a person's arm. In an example, a single inelastic portion can be configured to span at least 10% of the circumference of an attachment member.

In an example, polar (or compass) coordinates can be defined for a device relative to how the device is configured to be worn on a person's arm. A 0-degree position can be defined as the position on a device circumference which is configured to intersect the longitudinal mid-line of the anterior (upper) surface of the arm. A 180-degree position is diametrically opposite (through the circumferential center) the 0-degree position. A 90-degree position is clockwise midway between the 0-degree and 180-degree positions. A 270-degree position is diametrically opposite the 90-degree position.

In an example, the device in FIG. 45 can be specified as a wearable device for the arm with one or more close-fitting biometric sensors comprising: (a) an attachment member which is configured to span at least 60% of the circumference of a person's arm wherein this attachment member further comprises—a inelastic first portion with a first level of elasticity which spans at least 35 degrees (clockwise) between the 270-degree and 90-degree positions; an inelastic second portion with a second level of elasticity which spans at least 35 degrees (clockwise) between the 90-degree and 270-degree positions, an elastic third portion with a third level of elasticity which spans at least 35 degrees (clockwise) between the 180-degree and 0-degree positions, an elastic fourth portion with a fourth level of elasticity which spans at least 35 degrees (clockwise) between the 0-degree and 180-degree positions, and wherein each of the first and second elasticity levels is lower than each of the third and fourth elasticity levels; (b) an enclosure that is connected between the inelastic first portion and the inelastic second portion; and (c) one or more biometric sensors which collect data concerning arm tissue which are part of (or attached to) the enclosure.

In an alternative example, polar (or compass) coordinates can be defined for the circumference of such a device relative to the position of an enclosure on the device. The 0-degree position can be defined as the position on the device circumference which intersects the (lateral) mid-line of the enclosure. The 180-degree position is diametrically opposite (through the circumferential center) the 0-degree position. The 90-degree position is clockwise midway between the 0-degree and 180-degree positions. The 270-degree position is diametrically opposite the 90-degree position.

In an example, a biometric sensor can be a spectroscopic sensor which is configured to measure the spectrum of light energy reflected from (and/or absorbed by) tissue of the person's arm. In an example, a biometric sensor can be an electromagnetic energy sensor which is configured to measure parameters and/or patterns of electromagnetic energy passing through (and/or emitted by) tissue of the person's arm. In an example, measured parameters and/or patterns of electromagnetic energy can be selected from the group consisting of: impedance, resistance, conductivity, and electromagnetic wave pattern.

With respect to specific components, the example shown in FIG. 45 includes: inelastic portion 4501 of an attachment member; elastic portion 4502 of an attachment member; inelastic portion 4503 of an attachment member; inelastic portion 4504 of an attachment member; elastic portion 4505 of an attachment member; inelastic portion 4506 of an attachment member; attachment member connector 4507; enclosure 4508; and biometric sensors 4509 and 4510. In an example, this device can further comprise one or more components selected from the group consisting of: a data processor; a battery and/or energy harvesting unit; a display screen; a data transmitter; and a data receiver. In an example, relevant embodiment variations discussed elsewhere in this disclosure can also apply to this example.

FIG. 46 shows another example of a wearable device for the arm with one or more close-fitting biometric sensors. This figure shows the device from a top-down perspective, as it would appear spanning the anterior (upper) surface of a person's wrist (or other portion of the person's arm) in a circumferential manner. This can be seen as a top-down view of a further-specified variation of the example that was shown from a side perspective in FIG. 44.

The example shown in FIG. 46 can be described generally as a wearable device for the arm with one or more biometric sensors in an enclosure and an attachment member (such as a band, strap, bracelet, or cuff) which holds the enclosure on a person's arm, wherein there are rectangular, rounded rectangular, or plano-concave elastic portions of the attachment member which are connected to the enclosure and wherein the rest of the attachment member is inelastic. Such a structure can help to keep the enclosure and sensors close against the arm surface. This, in turn, can enable more-consistent collection of data concerning arm tissue.

In an example, the device in FIG. 46 can be specified as a wearable device for the arm with one or more close-fitting biometric sensors comprising: (a) an attachment member which is configured to span at least 60% of the circumference of a person's arm, wherein this attachment member further comprises—a first elastic portion with a first elasticity level, a second elastic portion with a second elasticity level, and an inelastic portion with a third elasticity level, wherein the third elasticity level is less than each of the first and second elasticity levels; (b) an enclosure which is connected between the first and second elastic portions; and (c) one or more biometric sensors which collect data concerning arm tissue which are part of (or attached to) the enclosure.

In an example, the device in FIG. 46 can be specified as a wearable device for the arm with one or more close-fitting biometric sensors comprising: (a) an attachment member which is configured to span at least 60% of the circumference of a person's arm, wherein this attachment member further comprises—a first plano-concave elastic portion with a first elasticity level, a second plano-concave elastic portion with a second elasticity level, and an inelastic portion with a third elasticity level, wherein the third elasticity level is less than each of the first and second elasticity levels; (b) an enclosure which is connected between the first and second plano-concave elastic portions; and (c) one or more biometric sensors which collect data concerning arm tissue which are part of (or attached to) the enclosure.

In an example, the device in FIG. 46 can be specified as a wearable device for the arm with one or more close-fitting biometric sensors comprising: (a) an enclosure which is configured to be worn on a person's arm; (b) one or more biometric sensors which collect data concerning arm tissue which are part of (or attached to) the enclosure; (c) two elastic members which are attached to the enclosure, wherein these elastic members are configured to collectively span at least 20% of the circumference of the arm, and wherein these elastic attachment members have first and second elasticity levels, respectively; and (d) one or more inelastic members which are attached to the two elastic attachment members, wherein these inelastic members collectively span at least 40% of the circumference of the arm, and wherein these inelastic members have a third elasticity level which is less than each of the first and second elasticity levels.

In an example, an elastic member can have a shape which is selected from the group consisting of: rectangular; rounded rectangle; plano-concave; and section of a cylinder. In an example, the device in FIG. 46 can be specified as a wearable device for the arm with one or more close-fitting biometric sensors comprising: (a) an attachment member which is configured to span at least 60% of the circumference of a person's arm, wherein this attachment member further comprises—two symmetric plano-concave elastic portions, with first and second elasticity levels respectively, and an inelastic portion with a third elasticity level, wherein the third elasticity level is less than each of the first and second elasticity levels; (b) an enclosure which is connected to the concave sides of the two symmetric plano-concave elastic portions of the attachment member; and (c) one or more biometric sensors which collect data concerning arm tissue which are part of (or attached to) the enclosure.

In an example, an attachment member can be a band, strap, bracelet, bangle, armlet, cuff, or sleeve. In an example, an elastic portion of an attachment member can be made from elastic and/or stretchable fabric. In an example, an enclosure can be arcuate. In an example, an enclosure can be circular. In an example, a device can further comprise a display screen on the outward-facing surface of an enclosure. In an example, a biometric sensor can be a spectroscopic sensor which is configured to measure the spectrum of light energy reflected from (and/or absorbed by) tissue of a person's arm. In an example, a biometric sensor can be an electromagnetic energy sensor which is configured to measure parameters and/or patterns of electromagnetic energy passing through (and/or emitted by) tissue of a person's arm. In an example, measured parameters and/or patterns of electromagnetic energy can be selected from the group consisting of: impedance, resistance, conductivity, and electromagnetic wave pattern.

With respect to specific components, the example shown in FIG. 46 includes: first elastic portion 4602 of an attachment member; second elastic portion 4603 of an attachment member; first inelastic portion 4601 of an attachment member; second inelastic portion 4604 of an attachment member; enclosure 4605 with a display screen on its outward-facing surface; and biometric sensors 4606 and 4607. In an example, this device can further comprise one or more components selected from the group consisting of: a data processor; a battery and/or energy harvesting unit; a display screen; a data transmitter; and a data receiver. In an example, relevant embodiment variations discussed elsewhere in this disclosure can also apply to this example.

FIG. 47 shows another example of a wearable device for the arm with one or more close-fitting biometric sensors.

This figure shows the device from a top-down perspective, as it would appear spanning the anterior (upper) surface of a person's wrist (or other portion of the person's arm) in a circumferential manner. The example shown in FIG. 47 is like the one shown in FIG. 46 except that in FIG. 47 the elastic portions are tapered (narrower in width) as they approach their connections with the enclosure.

With respect to specific components, the example shown in FIG. 47 includes: first tapered (width-varying) elastic portion 4702 of an attachment member; second tapered (width-varying) elastic portion 4703 of an attachment member; first inelastic portion 4701 of an attachment member; second inelastic portion 4704 of an attachment member; enclosure 4705 with a display screen on its outward-facing surface; and biometric sensors 4706 and 4707. In an example, this device can further comprise one or more components selected from the group consisting of: a data processor; a battery and/or energy harvesting unit; a display screen; a data transmitter; and a data receiver. In an example, relevant embodiment variations discussed elsewhere in this disclosure can also apply to this example.

FIG. 48 shows another example of a wearable device for the arm with one or more close-fitting biometric sensors. This figure shows the device from a top-down perspective, as it would appear spanning the anterior (upper) surface of a person's wrist (or other portion of the person's arm) in a circumferential manner. The example shown in FIG. 48 is like the one shown in FIG. 46 except that in FIG. 48 there are four elastic portions, two connected to each side of the enclosure. Further, each elastic portion has a shape which is triangular and/or pennant shaped.

The example shown in FIG. 48 is a wearable device for the arm with one or more close-fitting biometric sensors comprising: (a) an attachment member which is configured to span at least 60% of the circumference of a person's arm, wherein this attachment member further comprises—four tapered (width-varying) elastic portions, wherein these elastic portions have a first elasticity level, and wherein these elastic portions are configured to be worn on the anterior (upper) portion of a person's arm; and one or more inelastic portions which comprise the remainder of the attachment member, wherein these inelastic portions have a second elasticity level which is less than the first elasticity level; (b) an enclosure, wherein a first side of the enclosure is connected to tapered ends of two of the four elastic portions of the attachment member and wherein a second (opposite) side of the enclosure is connected to tapered ends of the other two of the four elastic portions of the attachment member; and (c) one or more biometric sensors which collect data concerning arm tissue, wherein these sensors are part of (or attached to) the enclosure.

With respect to specific components, the example shown in FIG. 48 includes: first, second, third, and fourth tapered elastic portions (4802, 4803, 4804, and 4805) of an attachment member; first and second inelastic portions (4801 and 4806) of an attachment member; enclosure 4807 with a display screen on its outward-facing surface; and biometric sensors 4808 and 4809. In an example, this device can further comprise one or more components selected from the group consisting of: a data processor; a battery and/or energy harvesting unit; a display screen; a data transmitter; and a data receiver. In an example, relevant embodiment variations discussed elsewhere in this disclosure can also apply to this example.

FIG. 49 shows another example of a wearable device for the arm with one or more close-fitting biometric sensors. This figure shows the device from a top-down perspective, as it would appear spanning the anterior (upper) surface of a person's wrist (or other portion of the person's arm) in a circumferential manner. The example shown in FIG. 49 is like the one shown in FIG. 46 except that in FIG. 49 there are two elastic portions on each side of the enclosure which criss-cross each other, forming an "X" on each side of the enclosure. This design can help to keep the enclosure and sensors close to the surface of the arm for more consistent collection of biometric data.

The example shown in FIG. 49 is a wearable device for the arm with one or more close-fitting biometric sensors comprising: (a) an enclosure which is configured to be worn on a person's arm; (b) one or more biometric sensors which collect data concerning arm tissue, wherein these sensors are part of (or attached to) the enclosure; and (c) an attachment member which is configured to attach the enclosure to the person's arm, wherein the attachment member is configured to span at least 60% of the circumference of the person's arm, wherein the portion of the attachment member that connects to the enclosure includes elastic bands (or straps) on each side of the enclosure which criss-cross each other. In an example, the criss-crossing bands (or straps) on each side of the enclosure form an "X" on each side of the enclosure.

With respect to specific components, the example shown in FIG. 49 includes: inelastic portion 4901 of the attachment member; inelastic portion 4902 of the attachment member; enclosure 4903 with an outward-facing display screen; biometric sensors 4904 and 4905; and elastic bands (or straps) 4906, 4907, 4908, 4909, 4910, and 4911. In an example, this device can further comprise one or more components selected from the group consisting of: a data processor; a battery and/or energy harvesting unit; a display screen; a data transmitter; and a data receiver. In an example, relevant embodiment variations discussed elsewhere in this disclosure can also apply to this example.

FIG. 50 shows another example of a wearable device for the arm with one or more close-fitting biometric sensors. This figure shows the device from a top-down perspective, as it would appear spanning the anterior (upper) surface of a person's wrist (or other portion of the person's arm) in a circumferential manner. The example shown in FIG. 50 is like the one shown in FIG. 46 except that in FIG. 50 there are two parallel elastic bands (or straps) connected to the enclosure. This design can help to keep the enclosure and sensors close to the surface of the arm for more consistent collection of biometric data.

The example shown in FIG. 50 is a wearable device for the arm with one or more close-fitting biometric sensors comprising: (a) an enclosure which is configured to be worn on a person's arm; (b) one or more biometric sensors which collect data concerning arm tissue, wherein these sensors are part of (or attached to) the enclosure; and (c) an attachment member which is configured to attach the enclosure to the person's arm, wherein the attachment member is configured to span at least 60% of the circumference of the person's arm, and wherein the portion of the attachment member that connects to the enclosure includes two parallel elastic bands (or straps) connected to the enclosure.

With respect to specific components, the example shown in FIG. 50 includes: inelastic portion 5001 of the attachment member; inelastic portion 5002 of the attachment member; enclosure 5003 with an outward-facing display screen; biometric sensors 5004 and 5005; and two parallel elastic bands (or straps) 5006 and 5007. In an example, this device can further comprise one or more components selected from the group consisting of: a data processor; a battery and/or energy harvesting unit; a display screen; a data transmitter; and a data receiver. In an example, relevant embodiment variations discussed elsewhere in this disclosure can also apply to this example.

FIG. 51 shows another example of a wearable device for the arm with one or more close-fitting biometric sensors. This figure shows the device from a top-down perspective, as it would appear spanning the anterior (upper) surface of a person's wrist (or other portion of the person's arm) in a circumferential manner. The example shown in FIG. 51 is like the one shown in FIG. 46 except that in FIG. 51 there are three parallel elastic bands (or straps) connected to the enclosure. This design can help to keep the enclosure and sensors close to the surface of the arm for more consistent collection of biometric data.

The example shown in FIG. 51 is a wearable device for the arm with one or more close-fitting biometric sensors comprising: (a) an enclosure which is configured to be worn on a person's arm; (b) one or more biometric sensors which collect data concerning arm tissue, wherein these sensors are part of (or attached to) the enclosure; and (c) an attachment member which is configured to attach the enclosure to the person's arm, wherein the attachment member is configured to span at least 60% of the circumference of the person's arm, and wherein the portion of the attachment member that connects to the enclosure includes three parallel elastic bands (or straps) connected to the enclosure.

With respect to specific components, the example shown in FIG. 51 includes: inelastic portion 5101 of the attachment member; inelastic portion 5102 of the attachment member; enclosure 5103 with an outward-facing display screen; biometric sensors 5104 and 5105; and three parallel elastic bands (or straps) 5106, 5107, and 5108. In an example, this device can further comprise one or more components selected from the group consisting of: a data processor; a battery and/or energy harvesting unit; a display screen; a data transmitter; and a data receiver. In an example, relevant embodiment variations discussed elsewhere in this disclosure can also apply to this example.

FIG. 52 shows another example of a wearable device for the arm with one or more close-fitting biometric sensors. This figure shows the device from a top-down perspective, as it would appear spanning the anterior (upper) surface of a person's wrist (or other portion of the person's arm) in a circumferential manner. The example shown in FIG. 52 is like the one shown in FIG. 51 except that the three elastic bands (or straps) are not parallel.

With respect to specific components, the example shown in FIG. 52 includes: inelastic portion 5201 of the attachment member; inelastic portion 5202 of the attachment member; enclosure 5203 with an outward-facing display screen; biometric sensors 5204 and 5205; and three elastic bands (or straps) 5206, 5207, and 5208. In an example, this device can further comprise one or more components selected from the group consisting of: a data processor; a battery and/or energy harvesting unit; a display screen; a data transmitter; and a data receiver. In an example, relevant embodiment variations discussed elsewhere in this disclosure can also apply to this example.

FIG. 53 shows another example of a wearable device for the arm with one or more close-fitting biometric sensors. This figure shows the device from a top-down perspective, as it would appear spanning the anterior (upper) surface of a person's wrist (or other portion of the person's arm) in a circumferential manner. The example shown in FIG. 53 can be generally described as an arm-worn device with biometric sensors in an enclosure, wherein the enclosure is suspended on the surface of the arm by four elastic bands, and wherein each elastic band is individually connected to one of four points which are equally-spaced around the circumference of the enclosure. This enclosure suspension design can help to keep the sensors close to the surface of the arm for more consistent collection of biometric data.

The example shown in FIG. 53 can be specified as a wearable device for the arm with one or more close-fitting biometric sensors comprising: (a) an arcuate enclosure which is configured to be worn on a person's arm; (b) one or more biometric sensors which collect data concerning arm tissue, wherein these sensors are part of (or attached to) the enclosure; and (c) four elastic bands (or straps), each of which is connected to one of four points which are equally spaced around the circumference of the enclosure. In an example, each of the four elastic bands (or straps) can have one end which is connected to the enclosure and one end which is connected to an inelastic band, strap, bracelet, or armlet which is configured to span at least 50% of the circumference of the arm.

In another example, a wearable device for the arm with one or more close-fitting biometric sensors can comprise: (a) a quadrilateral enclosure which is configured to be worn on a person's arm; (b) one or more biometric sensors which collect data concerning arm tissue, wherein these sensors are part of (or attached to) the enclosure; and (c) four elastic bands (or straps), each of which is connected to one side of the enclosure. In an example, each of the four elastic bands (or straps) can have one end which is connected to the enclosure and one end which is connected to an inelastic band, strap, bracelet, or armlet which is configured to span at least 50% of the circumference of the arm.

With respect to specific components, the example shown in FIG. 53 includes: inelastic portion 5301 of the attachment member; inelastic portion 5302 of the attachment member; enclosure 5303 with an outward-facing display screen; biometric sensors 5304 and 5305; and four elastic bands (or straps) 5306, 5307, 5308, and 5309. In an example, this device can further comprise one or more components selected from the group consisting of: a data processor; a battery and/or energy harvesting unit; a display screen; a data transmitter; and a data receiver. In an example, relevant embodiment variations discussed elsewhere in this disclosure can also apply to this example.

FIG. 54 shows another example of a wearable device for the arm with one or more close-fitting biometric sensors. This figure shows the device from a top-down perspective, as it would appear spanning the anterior (upper) surface of a person's wrist (or other portion of the person's arm) in a circumferential manner. The example shown in FIG. 54 can be generally described as an arm-worn device with biometric sensors in an enclosure, wherein the enclosure is suspended on the surface of the arm by four elastic suspension bands (or straps) connected to three parallel attachment bands or straps which encircle the arm. This enclosure suspension design can help to keep the sensors close to the surface of the arm for more consistent collection of biometric data.

The example shown in FIG. 54 can be specified as a wearable device for the arm with one or more close-fitting biometric sensors comprising: (a) an enclosure which is configured to be worn on a person's arm; (b) one or more biometric sensors which collect data concerning arm tissue, wherein these sensors are part of (or attached to) the enclosure; and (c) three parallel attachment bands, including proximal, middle, distal attachment bands; wherein each of the three parallel attachment bands is configured to span at least 60% of the circumference of the arm; and (d) four elastic suspension bands, wherein the four suspension bands are connected to the four sides of the enclosure, respectively; wherein two of the suspension bands are also connected to the proximal attachment band and the distal attachment band, respectively; and wherein the other two of the suspension bands are also connected to the middle attachment band. In an example, the word "strap" can be substituted for the word "band" in the above specification.

With respect to specific components, the example shown in FIG. 54 includes: a distal attachment band 5401, ends 5402 and 5403 of a middle attachment band, proximal attachment band 5404, enclosure 5405 with outward-facing display screen, biometric sensors 5406 and 5407, and four suspension bands 5408, 5409, 5410, and 5411. In an example, this device can further comprise one or more components selected from the group consisting of: a data processor; a battery and/or energy harvesting unit; a display screen; a data transmitter; and a data receiver. In an example, relevant embodiment variations discussed elsewhere in this disclosure can also apply to this example.

FIG. 55 shows another example of a wearable device for the arm with one or more close-fitting biometric sensors. This figure shows the device from a top-down perspective, as it would appear spanning the anterior (upper) surface of a person's wrist (or other portion of the person's arm) in a circumferential manner. The example shown in FIG. 55 can be described as a wrist-worn device with a gimbaled enclosure that contains one or more biometric sensors. The gimbal mechanism around the enclosure enables the enclosure and sensors to remain relatively flat against the surface of the arm, even if the device shifts, rotates, and/or twists on the person's arm. This can help to maintain consistent measurement of biometric data from the arm.

The example in FIG. 55 can be specified as a wearable device for the arm with one or more close-fitting biometric sensors comprising: (a) an attachment member which is configured to span at least 60% of the circumference of a person's arm; (b) a gimbal mechanism which is connected to the attachment member, wherein this gimbal mechanism further comprises two or more concentric rings which are axially connected so that they can move relative to each other; (c) an enclosure within the most central concentric ring of the gimbal mechanism; and (d) one or more biometric sensors which are part of (or attached to) the enclosure, wherein these biometric sensors are configured to collect data concerning arm tissue.

In an example, an attachment member can be a strap, band, bracelet, bangle, chain, ring, armlet, cuff, gauntlet, or sleeve. In an example, an attachment member can stretch to span the entire circumference of a person's arm. In an example, an attachment member can have two ends which connect to each other to hold the attachment member onto a person's arm. In an example, an attachment member can be sufficiently rigid and/or resilient in shape that it has ends which hold onto the person's arm even though the ends are not connected to each other.

In an example, a gimbal mechanism can comprise two concentric (inner and outer) rings which pivot relative to each other, wherein these rings are connected by one or more axles at opposite sides of the inner ring. In an example, a gimbal mechanism can comprise three concentric (inner, central, and outer) rings which pivot relative to each other, wherein the outer and central rings are connected by one or more axles at a first set of opposite sides of the central ring, wherein the central and inner rings are connected by one or more axles at a second set of opposite sides of the central ring, and wherein the second set is at locations which are rotated around the circumference of the center ring by 90-degrees relative to the locations of the first set.

In an example, a biometric sensor can be a spectroscopic sensor which is configured to measure the spectrum of light energy reflected from (and/or absorbed by) tissue of the person's arm. In an example, a biometric sensor can be an electromagnetic energy sensor which is configured to measure parameters and/or patterns of electromagnetic energy passing through (and/or emitted by) tissue of the person's arm. In an example, measured parameters and/or patterns of electromagnetic energy can be selected from the group consisting of: impedance, resistance, conductivity, and electromagnetic wave pattern.

In an example, an enclosure can further comprise a display screen which is seen on the outward-facing surface of the enclosure. In an example, the enclosure can be circular. In an example, this device can further comprise one or more components selected from the group consisting of: a data processor; a battery and/or energy harvesting unit; a display screen; a data transmitter; and a data receiver. In an example, relevant embodiment variations discussed elsewhere in this disclosure can also apply to this example.

With respect to specific components, the example shown in FIG. 55 includes: first portion 5501 of an attachment member; second portion 5502 of the attachment member; enclosure 5503 with an outward-facing display screen; biometric sensors 5504 and 5505 within the enclosure; inner ring 5506, central ring 5507, and outer ring 5508 of a gimbal mechanism; first set of axles 5509 and 5510 connecting the inner ring and the central ring; and second set of axles 5511 and 5512 connecting the central ring and the outer ring.

FIG. 56 shows another example of a wearable device for the arm with one or more close-fitting biometric sensors. This figure shows the device from a top-down perspective, as it would appear spanning the anterior (upper) surface of a person's wrist (or other portion of the person's arm) in a circumferential manner. The example shown in FIG. 56 is a wrist-worn device with an enclosure containing one or more biometric sensors, wherein this enclosure is suspended by a radial plurality of elastic (and/or stretchable or springy) suspension members which connect to locations on the circumference of the enclosure. In an example, this design can be called a "sunburst suspension system" because the elastic (and/or stretchable or springy) suspension members look like the radial sunrays in a traditional "sunburst" drawing. The "sunburst suspension" design enables the enclosure and sensors to remain relatively flat against the surface of the arm, even if the device shifts, rotates, and/or twists on the person's arm. This can help to maintain consistent measurement of biometric data from the arm.

The example in FIG. 56 can be specified as a wearable device for the arm with one or more close-fitting biometric sensors comprising: (a) an attachment member which is configured to span at least 60% of the circumference of a person's arm; (b) an enclosure; (c) one or more biometric sensors which are part of (or attached to) the enclosure, wherein these biometric sensors are configured to collect data concerning arm tissue; and (d) a plurality of elastic (and/or stretchable or springy) suspension members, wherein these suspension members flexibly connect the enclosure to the attachment member, wherein each of these suspension members is connected at one end to a location on the circumference of the enclosure and connected at its other end to the attachment member, and wherein the longitudinal axis of each of the suspension members is substantially parallel with a virtual radial spoke outward from the center of the enclosure.

In an example, an attachment member can be a strap, band, bracelet, bangle, chain, ring, armlet, cuff, gauntlet, or sleeve. In an example, an attachment member can stretch to span the entire circumference of a person's arm. In an example, an attachment member can have two ends which connect to each other to hold the attachment member onto a person's arm. In an example, an attachment member can be sufficiently rigid and/or resilient in shape that it has ends which hold onto the person's arm, even though the ends of the attachment member are not connected to each other.

In an example, an enclosure can be circular. In an example, an enclosure can further comprise a display screen which is seen on the outward-facing surface of the enclosure. In an example, a biometric sensor can be a spectroscopic sensor which is configured to measure the spectrum of light energy reflected from (and/or absorbed by) tissue of the person's arm. In an example, a biometric sensor can be an electromagnetic energy sensor which is configured to measure parameters and/or patterns of electromagnetic energy passing through (and/or emitted by) tissue of the person's arm. In an example, measured parameters and/or patterns of electromagnetic energy can be selected from the group consisting of: impedance, resistance, conductivity, and electromagnetic wave pattern.

In an example, a suspension member can be a spring. In an example, a suspension member can be an elastic band or strap. In an example, the locations on the circumference of the enclosure to which the suspension members are connected can be evenly distributed around the circumference of the enclosure. In an example, there can be four suspension members. In an example, there can be six suspension members. In an example, there can be eight suspension members. In an example, this device can further comprise one or more components selected from the group consisting of: a data processor; a battery and/or energy harvesting unit; a display screen; a data transmitter; and a data receiver. In an example, relevant embodiment variations discussed elsewhere in this disclosure can also apply to this example.

With respect to specific components, the example shown in FIG. 56 includes: first portion 5601 of an attachment member; second portion 5602 of the attachment member; enclosure 5603 with an outward-facing display screen; biometric sensors 5604 and 5605 within the enclosure; a plurality of spring suspension members, including 5606; and ring 5607.

FIG. 57 shows another example of a wearable device for the arm with one or more close-fitting biometric sensors. This figure shows the device from a top-down perspective, as it would appear spanning the anterior (upper) surface of a person's wrist (or other portion of the person's arm) in a circumferential manner. The example shown in FIG. 57 is a flexible arm-worn device with two arcuate enclosures which contain biometric sensors.

The example in FIG. 57 can be specified as a wearable device for the arm with one or more close-fitting biometric sensors comprising: (a) a flexible attachment member which is configured to span at least 60% of the circumference of a person's arm; (b) a first arcuate enclosure whose center is at a first location on the circumference of the flexible attachment member; (c) a first biometric sensor which is part of (or attached to) the first arcuate enclosure, wherein this first biometric sensor is configured to collect data concerning arm tissue; (d) a second arcuate enclosure whose center is at a second location on the circumference of the flexible attachment member, wherein the distance between the first and second locations is greater than one-half inch; and (e) a second biometric sensor which is part of (or attached to) the second arcuate enclosure, wherein this second biometric sensor is configured to collect data concerning arm tissue.

In an example, a flexible attachment member can be a strap, band, bracelet, bangle, chain, ring, armlet, cuff, gauntlet, or sleeve. In an example, a flexible attachment member can stretch to span the entire circumference of a person's arm. In an example, a flexible attachment member can have two ends which connect to each other to hold the attachment member onto a person's arm. In an example, a flexible attachment member can be sufficiently rigid and/or resilient in shape that it has ends which hold onto the person's arm, even though the ends of the attachment member are not connected to each other.

In an example, an arcuate enclosure containing a biometric sensor can be circular. In an example, this device can further comprise a display screen between the two arcuate enclosures. In an alternative example, each of the arcuate enclosures can have a display screen on its outward-facing side. In an example, a biometric sensor can be a spectroscopic sensor which is configured to measure the spectrum of light energy reflected from (and/or absorbed by) tissue of the person's arm. In an example, a biometric sensor can be an electromagnetic energy sensor which is configured to measure parameters and/or patterns of electromagnetic energy passing through (and/or emitted by) tissue of the person's arm. In an example, measured parameters and/or patterns of electromagnetic energy can be selected from the group consisting of: impedance, resistance, conductivity, and electromagnetic wave pattern.

With respect to specific components, the example shown in FIG. 57 includes: flexible attachment member 5701; central display screen 5702; first arcuate enclosure 5703; first biometric sensor 5704; second arcuate enclosure 5705; and second biometric sensor 5706. In an example, this device can further comprise one or more components selected from the group consisting of: a data processor; a battery and/or energy harvesting unit; a display screen; a data transmitter; and a data receiver. In an example, relevant embodiment variations discussed elsewhere in this disclosure can also apply to this example.

FIG. 58 shows another example of a wearable device for the arm with one or more close-fitting biometric sensors. The left side of this figure shows the device from a top-down perspective, as it would appear spanning the anterior (upper) surface of a person's wrist (or other portion of the person's arm) in a circumferential manner. The right side of this figure shows the device from a bottom-up perspective, as it would appear spanning the posterior (lower) surface of a person's wrist (or other portion of the person's arm) in a circumferential manner. The example shown in FIG. 58 can be described as an arm-worn device with an arcuate enclosure to which a strap or band is connected diagonally.

The example in FIG. 58 can be specified as a wearable device for the arm with one or more close-fitting biometric sensors comprising: (a) an arcuate enclosure which is configured to be worn on a person's arm; (b) one or more biometric sensors which are configured to collect data concerning arm tissue and which are part of (or attached to) the arcuate enclosure; and (c) an attachment member which is configured to span at least 60% of the circumference of a person's arm, wherein a first portion of this attachment member is connected to the arcuate enclosure between the 12 o'clock and 3 o'clock positions (or 0-degree and 90-degree positions using compass coordinates) of the circumference of the enclosure; and wherein a second portion of this attachment member is connected to the arcuate enclosure between the 6 o'clock and 9 o'clock positions (or 180-degree and 270-degree positions using compass coordinates) of the circumference of the enclosure.

With respect to specific components, the example shown in FIG. 58 includes: attachment member 5801; enclosure 5802 with an outward-facing display screen; and biometric sensors 5803 and 5804 within the enclosure. In an example, this device can further comprise one or more components selected from the group consisting of: a data processor; a battery and/or energy harvesting unit; a display screen; a data transmitter; and a data receiver. Relevant embodiment variations discussed with respect to FIG. 55 or elsewhere in this disclosure can also be applied to this example.

FIG. 59 shows another example of a wearable device for the arm with one or more close-fitting biometric sensors. This figure shows the device from a top-down perspective, as it would appear spanning the anterior (upper) surface of a person's wrist (or other portion of the person's arm) in a circumferential manner. The example shown in FIG. 59 can be colorfully described as a "two gummi worm" design—because it looks like two gummi worms crawling in a symmetric manner around portions of the circumference of an enclosure.

The example in FIG. 59 can be specified as a wearable device for the arm with one or more close-fitting biometric sensors comprising: (a) an arcuate enclosure which is configured to be worn on a person's arm; (b) one or more biometric sensors which are configured to collect data concerning arm tissue and which are part of (or attached to) the arcuate enclosure; and (c) an attachment member which is configured to span at least 60% of the circumference of a person's arm, wherein a first portion of this attachment member spans most of the circumference of the arcuate enclosure between the 10 o'clock and 2 o'clock positions (or 300-degree and 60-degree positions using compass coordinates); and wherein a second portion of this attachment member spans most of the circumference of the arcuate enclosure between the 4 o'clock and 8 o'clock positions (or 120-degree and 240-degree positions using compass coordinates).

With respect to specific components, the example shown in FIG. 59 includes: first portion 5901 of an attachment member; second portion 5902 of an attachment member; enclosure 5903 with an outward-facing display screen; and biometric sensors 5904 and 5905 within the enclosure. In an example, this device can further comprise one or more components selected from the group consisting of: a data processor; a battery and/or energy harvesting unit; a display screen; a data transmitter; and a data receiver. Relevant embodiment variations discussed with respect to FIG. 55 or elsewhere in this disclosure can also be applied to this example.

FIG. 60 shows another example of a wearable device for the arm with one or more close-fitting biometric sensors. This figure shows the device from a top-down perspective, as it would appear spanning the anterior (upper) surface of a person's wrist (or other portion of the person's arm) in a circumferential manner. The example shown in FIG. 60 can be generally described as an arm-worn device with a bifurcating band, wherein one branch of the band is connected to a display screen and the other branch of the band is connected to a circumferentially-sliding enclosure which contains one or more biometric sensors. Having biometric sensors on a separate circumferentially-sliding enclosure enables adjustment of the circumferential location from which biometric data is collected, without changing the location of a display screen.

The example in FIG. 60 can be specified as a wearable device for the arm with one or more close-fitting biometric sensors comprising: (a) an attachment member which is configured to span at least 60% of the circumference of a person's arm, wherein this attachment member has a first circumferential portion which bifurcates into a first branch and a second branch, and wherein this attachment member has a second circumferential portion in which the first branch and the second branch reconverge; (b) a display screen which is connected to the first branch of the attachment member; (c) a circumferentially-sliding enclosure which is connected to the second branch of the attachment member; and (d) one or more biometric sensors which are configured to collect data concerning arm tissue and which are part of (or attached to) the circumferentially-sliding enclosure.

With respect to specific components, the example shown in FIG. 60 includes: bifurcating attachment member 6001; display screen 6002 on a first branch of the attachment member; circumferentially-sliding enclosure 6003 on a second branch of the attachment member; and biometric sensor 6004 within the circumferentially-sliding enclosure. In an example, this device can further comprise one or more components selected from the group consisting of: a data processor; a battery and/or energy harvesting unit; a display screen; a data transmitter; and a data receiver. Relevant embodiment variations discussed with respect to FIG. 55 or elsewhere in this disclosure can also be applied to this example.

FIG. 61 shows another example of a wearable device for the arm with one or more close-fitting biometric sensors. This figure shows the device from a top-down perspective, as it would appear spanning the anterior (upper) surface of a person's wrist (or other portion of the person's arm) in a circumferential manner.

The example in FIG. 61 can be specified as a wearable device for the arm with one or more close-fitting biometric sensors comprising: (a) an attachment member which is configured to span at least 60% of the circumference of a person's arm, wherein this attachment member further comprises a plurality of various-shaped (rigid) polygons which are inter-connected by flexible strips and/or joints; (b) an enclosure which is connected to the attachment member; and (c) one or more biometric sensors which are configured to collect data concerning arm tissue and which are part of (or attached to) the enclosure. Such a design can help to keep the enclosure (and thus the sensors) flat against the surface of the person's arm, even if the attachment member shifts, twists, or rotates.

In an example, a majority of the various-shaped polygons can have five sides. In an example, a majority of the various-shaped polygons can have six sides. In an example, a majority of the various-shaped polygons can have unequal sides. In an example, a majority of the various-shaped polygons can have unequal angles between sides. In an example, sides of the various-shaped polygons can be inter-connected by strips of flexible fabric. In an example, sides of the various-shaped polygons can be inter-connected by hinge joints. In an example, the enclosure can have a display screen on its outward-facing surface.

With respect to specific components, the example shown in FIG. 61 includes: a plurality of various-shaped inter-connected polygons, including polygon 6101; a plurality of flexible joints, including joint 6102; an arcuate enclosure

6103 which further comprises a display screen on its outward-facing surface; and biometric sensors 6104 and 6105 within the enclosure. In an example, this device can further comprise one or more components selected from the group consisting of: a data processor; a battery and/or energy harvesting unit; a display screen; a data transmitter; and a data receiver. Relevant embodiment variations discussed with respect to FIG. 55 or elsewhere in this disclosure can also be applied to this example.

FIG. 62 shows another example of a wearable device for the arm with one or more close-fitting biometric sensors. This figure shows the device from a top-down perspective, as it would appear spanning the anterior (upper) surface of a person's wrist (or other portion of the person's arm) in a circumferential manner. In this example, an attachment member has a honeycomb configuration. This can help to keep the enclosure (and thus the sensors) flat against the surface of the person's arm, even if the attachment member shifts, twists, or rotates.

The example in FIG. 62 can be specified as a wearable device for the arm with one or more close-fitting biometric sensors comprising: (a) an attachment member which is configured to span at least 60% of the circumference of a person's arm, wherein this attachment member further comprises a plurality of flexibly-connected (rigid) hexagons; (b) an enclosure which is connected to the attachment member; and (c) one or more biometric sensors which are configured to collect data concerning arm tissue and which are part of (or attached to) the enclosure.

With respect to specific components, the example shown in FIG. 62 includes: a plurality of hexagons, including hexagon 6201; a plurality of flexible joints, including joint 6202; an arcuate enclosure 6203 which further comprises a display screen on its outward-facing surface; and biometric sensors 6204 and 6205 within the enclosure. In an example, this device can further comprise one or more components selected from the group consisting of: a data processor; a battery and/or energy harvesting unit; a display screen; a data transmitter; and a data receiver. Relevant embodiment variations discussed with respect to FIG. 55 or elsewhere in this disclosure can also be applied to this example.

FIG. 63 shows another example of a wearable device for the arm with one or more close-fitting biometric sensors. This figure shows the device from a side perspective, as it would appear encircling a lateral cross-section of a person's wrist (or other portion of the person's arm). In this example, one or more biometric sensors are located on a portion of the device which is diametrically-opposite (e.g. symmetric relative to the circumferential center of the device) from the portion of the device which includes a display screen. In an example, one or more biometric sensors can be configured to be worn on the posterior (lower) surface of an arm and a display screen can be configured to be worn on the anterior (upper) surface of the arm, or vice versa.

The specific example in FIG. 63 can be specified as a wearable device for the arm with one or more close-fitting biometric sensors comprising: (a) an attachment member which is configured to span at least 60% of the circumference of a person's arm, wherein this attachment member further comprises a first portion with a first elasticity level spanning completely or partially (clockwise) between the 9 o'clock and 3 o'clock (or 270-degree and 90-degree) positions around the device circumference and a second portion with a second elasticity level spanning completely or partially (clockwise) between the 3 o'clock and 9 o'clock (or 90-degree and 270-degree) positions around the device circumference, wherein the second elasticity level is greater than the first elasticity level; (b) a display screen which is part of (or connected to) the first portion of the attachment member; (c) an enclosure which is part of (or connected to) the second portion of the attachment member; and (d) one or more biometric sensors which are configured to collect data concerning arm tissue and which are part of (or attached to) the enclosure.

In an example, the display screen can be centrally located with respect to the first portion of the attachment member. In an example, the center of the display screen can be located at the 12 o'clock (or 0-degrees) position on the circumference of the device. In an example, the enclosure can be centrally located with respect to the second portion of the attachment member. In an example, the center of the display screen can be located at the 6 o'clock (or 180-degrees) position on the circumference of the device.

With respect to specific components, the example shown in FIG. 63 includes: elastic segments 6301 and 6304 of an attachment member; inelastic segments 6302 and 6303 of an attachment member; display screen 6305; enclosure 6306; and biometric sensor 6307. In an example, this device can further comprise one or more components selected from the group consisting of: a data processor; a battery and/or energy harvesting unit; a display screen; a data transmitter; and a data receiver. Relevant embodiment variations discussed with respect to FIG. 55 or elsewhere in this disclosure can also be applied to this example.

FIG. 64 shows another example of a wearable device for the arm with one or more close-fitting biometric sensors. This figure shows the device from a side perspective, as it would appear encircling a lateral cross-section of a person's wrist (or other portion of the person's arm). In this example, one or more biometric sensors are located on a portion of the device which is diametrically-opposite (e.g. symmetric relative to the circumferential center of the device) from the portion of the device which includes a display screen and there is a connector (such as a buckle, clip, clasp, pin, plug, or hook-and-eye mechanism) on the device between the sensors and the screen.

The example in FIG. 64 can be specified as a wearable device for the arm with one or more close-fitting biometric sensors comprising: (a) an attachment member which is configured to span at least 60% of the circumference of a person's arm; (b) a display screen which is part of (or connected to) the attachment member at a first location along the circumference of the device; (c) an enclosure which is part of (or connected to) the attachment member at a second location along the circumference of the device, wherein the second location is on the opposite side of the device (e.g. through the circumferential center of the device) from the first location; (d) one or more biometric sensors which are configured to collect data concerning arm tissue and which are part of (or attached to) the enclosure; and (e) a connector which connects two ends of the attachment member to each other, wherein this connector is at a location along the circumference of the device which is between the display screen and the enclosure.

The example in FIG. 64 can also be specified as a wearable device for the arm with one or more close-fitting biometric sensors comprising: (a) an attachment member which is configured to span at least 60% of the circumference of a person's arm; (b) a display screen which is located between the 10 o'clock and 2 o'clock (or 300-degree and 60-degree) positions on the circumference of the attachment member; (c) an enclosure which is located between the 4 o'clock and 8 o'clock (or 120-degree and 240-degree) positions on the circumference of the attachment member;

(d) one or more biometric sensors which are configured to collect data concerning arm tissue and which are part of (or attached to) the enclosure; and (e) a connector which connects two ends of the attachment member to each other, wherein this connector is at a location along the circumference of the device which is between the display screen and the enclosure.

In an example, the center of the display screen can be located at the 12 o'clock (or 0-degrees) position on the circumference of the device. In an example, the center of the display screen can be located at the 6 o'clock (or 180-degrees) position on the circumference of the device. In an example, a connector can be selected from the group consisting of: buckle, clip, clasp, hook, plug, pin, snap, and hook-and-eye mechanism.

With respect to specific components, the example shown in FIG. 64 includes: segments 6401, 6402, and 6403 of an attachment member; connector 6404; display screen 6405; enclosure 6406; and biometric sensor 6407. In an example, this device can further comprise one or more components selected from the group consisting of: a data processor; a battery and/or energy harvesting unit; a display screen; a data transmitter; and a data receiver. Relevant embodiment variations discussed with respect to FIG. 55 or elsewhere in this disclosure can also be applied to this example.

FIG. 65 shows another example of a wearable device for the arm with one or more close-fitting biometric sensors. This figure shows the device from a side perspective, as it would appear encircling a lateral cross-section of a person's wrist (or other portion of the person's arm). In this example, there are one or more biometric sensors which are opposite a display screen, a connector between the sensors and the screen, and a hinge which is opposite the connector. If portions of an attachment member connecting these components are relatively rigid, then this example can be called a "clam shell" design.

The example in FIG. 65 can be specified as a wearable device for the arm with one or more close-fitting biometric sensors comprising: (a) an attachment member which is configured to span at least 60% of the circumference of a person's arm; (b) a display screen which is part of (or connected to) the attachment member at a first location around the circumference of the device; (c) an enclosure which is part of (or connected to) the attachment member at a second location around the circumference of the device, wherein the second location is on the opposite (e.g. through the circumferential center) side of the device from the first location; (d) one or more biometric sensors which are configured to collect data concerning arm tissue and which are part of (or attached to) the enclosure; and (e) a connector which connects two ends of the attachment member to each other at a third location around the circumference of the device, wherein this third location is between the first and second locations; (f) a hinge (or joint) which connects two portions of the attachment member to each other at a fourth location around the circumference of the device, wherein this fourth location is on the opposite (e.g. through the circumferential center) side of the device from the third location.

The example in FIG. 65 can also be specified as a wearable device for the arm with one or more close-fitting biometric sensors comprising: (a) an attachment member which is configured to span at least 60% of the circumference of a person's arm; (b) a display screen which is located between the 10 o'clock and 2 o'clock (or 300-degree and 60-degree) positions on the circumference of the attachment member; (c) an enclosure which is located between the 4 o'clock and 8 o'clock (or 120-degree and 240-degree) positions on the circumference of the attachment member; (d) one or more biometric sensors which are configured to collect data concerning arm tissue and which are part of (or attached to) the enclosure; (e) a connector which connects two ends of the attachment member to each other, wherein this connector is located between the 7 o'clock and 11 o'clock (or 210-degree and 330-degree) positions on the circumference of the attachment member; and (f) a hinge which connects two portions of the attachment member to each other, wherein this hinge is located between the 1 o'clock and 5 o'clock (or 30-degree and 150-degree) positions on the circumference of the attachment member.

In an example, the center of the display screen can be located at the 12 o'clock (or 0-degrees) position on the circumference of the device. In an example, the center of the display screen can be located at the 6 o'clock (or 180-degrees) position on the circumference of the device. In an example, a connector can be selected from the group consisting of: buckle, clip, clasp, hook, plug, pin, snap, and hook-and-eye mechanism.

With respect to specific components, the example shown in FIG. 65 includes: segments 6501, 6502, and 6503 of an attachment member; connector 6504; hinge 6505; display screen 6506; enclosure 6507; and biometric sensor 6508. In an example, this device can further comprise one or more components selected from the group consisting of: a data processor; a battery and/or energy harvesting unit; a display screen; a data transmitter; and a data receiver. Relevant embodiment variations discussed with respect to FIG. 55 or elsewhere in this disclosure can also be applied to this example.

FIG. 66 shows another example of a wearable device for the arm with one or more close-fitting biometric sensors. This figure shows the device from a side perspective, as it would appear encircling a lateral cross-section of a person's wrist (or other portion of the person's arm). This example is similar to the one shown in FIG. 65 except a biometric sensor is on the center-facing surface of a compressible member.

With respect to specific components, the example shown in FIG. 66 includes: segments 6601, 6602, and 6603 of an attachment member; connector 6604; hinge 6605; display screen 6606; compressible member 6607; and biometric sensor 6608. In an example, this device can further comprise one or more components selected from the group consisting of: a data processor; a battery and/or energy harvesting unit; a display screen; a data transmitter; and a data receiver.

In an example, a compressible member can be an elastic member which is filled with a fluid, gel, or gas. In an example, a compressible member can be a pneumatic or hydraulic chamber which is filled with a fluid, gel, or gas. In an example, a compressible member can be a balloon. In an example, a compressible member can be made from compressible foam. Relevant embodiment variations discussed with respect to FIG. 65 or elsewhere in this disclosure can also be applied to this example.

FIG. 67 shows another example of a wearable device for the arm with one or more close-fitting biometric sensors. This figure shows the device from a top-down perspective, as it would appear spanning the anterior (upper) surface of a person's wrist (or other portion of the person's arm) in a circumferential manner. Described generally, the example shown in FIG. 67 is a biometric-sensing device with proximal and distal arcuate display screens which are attached to a person's arm by a band, wherein the band has one holes on each side of a virtual line connecting the centers of the two displays.

Described more specifically, the example shown in FIG. 67 is a wearable device for the arm with one or more close-fitting biometric sensors comprising: (a) a proximal arcuate display screen, wherein this proximal arcuate display screen is a first distance from a person's shoulder; (b) a distal arcuate display screen, wherein this distal arcuate display screen is a second distance from a person's shoulder, and wherein the second distance is greater than the first distance; (c) an attachment member which attaches the proximal arcuate display screen and the distal arcuate display screen to the person's arm, wherein this attachment member has one hole on each side of a virtual line connecting the center of the proximal arcuate display screen and the center of the distal arcuate display screen; and (d) one or more biometric sensors which are configured to collect data concerning arm tissue.

In an example, a display screen can be circular. In an example, a display screen can be activated by touch and/or gesture. In an example, a virtual line connecting the center of a proximal display screen and the center of a distal display screen can parallel to the longitudinal axis of the arm. In an example, holes on each side of this virtual line can be circular. In an example, the area of a hole in an attachment member can be half of the area of a display screen. In an example, the area of a hole in an attachment member can be the same as the area of a display screen. In an example, the area of a hole in an attachment member can be between 50% and 100% of the area of a display screen.

In an example, an attachment member can be a strap, band, bracelet, bangle, ring, armlet, gauntlet, cuff, or sleeve. In an example, an attachment member can be wider as it spans the anterior (upper) surface of a person's arm. In an example, an attachment member can be attached to a person's arm by connecting two ends of the attachment member with a clasp, clip, buckle, hook, pin, plug, or hook-and-eye mechanism. In an example, the attachment member can be attached to a person's arm by stretching and sliding it over the person's hand onto the arm. In an example, the attachment member can be attached to a person's arm by applying force to pull two ends apart to slip the member over the arm, wherein the two ends retract back towards each other when the force is removed.

In an example, a biometric sensor can be a spectroscopic sensor which is configured to measure the spectrum of light energy reflected from (and/or absorbed by) tissue of the person's arm. In an example, a biometric sensor can be an electromagnetic energy sensor which is configured to measure parameters and/or patterns of electromagnetic energy passing through (and/or emitted by) tissue of the person's arm. In an example, measured parameters and/or patterns of electromagnetic energy can be selected from the group consisting of: impedance, resistance, conductivity, and electromagnetic wave pattern.

Specific components in the example shown in FIG. 67 include: attachment member 6701 which has a hole on each side of a central longitudinal axis of the anterior (upper) surface of an arm; distal display screen 6702; proximal display screen 6704; and biometric sensors 6703 and 6705. In an example, this device can further comprise one or more components selected from the group consisting of: a data processor; a battery and/or energy harvesting unit; a data transmitter; and a data receiver. In an example, this device can function as a smart watch. Relevant embodiment variations discussed elsewhere in this disclosure can also be applied to this example.

FIG. 68 shows another example of a wearable device for the arm with one or more close-fitting biometric sensors. This figure shows the device from a top-down perspective, as it would appear spanning the anterior (upper) surface of a person's wrist (or other portion of the person's arm) in a circumferential manner. Described generally, the example shown in FIG. 68 is an arm-worn biometric-sensing device with: proximal and distal arcuate display screens; and right and left side enclosures with biometric sensors.

Described more specifically, the example shown in FIG. 68 is a wearable device for the arm with one or more close-fitting biometric sensors comprising: (a) a proximal arcuate display screen, wherein this proximal arcuate display screen is a first distance from a person's shoulder; (b) a distal arcuate display screen, wherein this distal arcuate display screen is a second distance from a person's shoulder, and wherein the second distance is greater than the first distance; (c) a right-side enclosure, wherein the center of this right-side enclosure is to the right of a virtual line connecting the center of the proximal arcuate display screen and the center of the distal arcuate display screen, and wherein this right-side enclosure further comprises a biometric sensor that is configured to collect data concerning arm tissue; (d) a left-side enclosure, wherein the center of this left-side enclosure is to the left of a virtual line connecting the center of the proximal arcuate display screen and the center of the distal arcuate display screen, and wherein this left-side enclosure further comprises a biometric sensor that is configured to collect data concerning arm tissue; and (e) an attachment member which attaches the proximal arcuate display screen, the distal arcuate display screen, the right-side enclosure, and the left-side enclosure to the person's arm.

In an example, a display screen can be circular. In an example, a display screen can be activated by touch and/or gesture. In an example, a virtual line connecting the center of a proximal display screen and the center of a distal display screen can parallel to the longitudinal axis of the arm. In an example, an attachment member can be a strap, band, bracelet, bangle, ring, armlet, gauntlet, cuff, or sleeve. In an example, an attachment member can be wider as it spans the anterior (upper) surface of a person's arm. In an example, an attachment member can be attached to a person's arm by connecting two ends of the attachment member with a clasp, clip, buckle, hook, pin, plug, or hook-and-eye mechanism. In an example, the attachment member can be attached to a person's arm by stretching and sliding it over the person's hand onto the arm. In an example, the attachment member can be attached to a person's arm by applying force to pull two ends apart to slip the member over the arm, wherein the two ends retract back towards each other when the force is removed.

In an example, a biometric sensor can be a spectroscopic sensor which is configured to measure the spectrum of light energy reflected from (and/or absorbed by) tissue of the person's arm. In an example, a biometric sensor can be an electromagnetic energy sensor which is configured to measure parameters and/or patterns of electromagnetic energy passing through (and/or emitted by) tissue of the person's arm. In an example, measured parameters and/or patterns of electromagnetic energy can be selected from the group consisting of: impedance, resistance, conductivity, and electromagnetic wave pattern.

Specific components in the example shown in FIG. 68 include: attachment member 6801; distal display screen 6802; proximal display screen 6803; right-side enclosure 6806 with biometric sensor 6807; and left-side enclosure 6804 with biometric sensor 6805. In an example, this device can further comprise one or more components selected from the group consisting of: a data processor; a battery and/or energy harvesting unit; a data transmitter; and a data receiver. In an example, this device can function as a smart watch. Relevant embodiment variations discussed elsewhere in this disclosure can also be applied to this example.

FIG. 69 shows another example of a wearable device for the arm with one or more close-fitting biometric sensors. This figure shows the device from a top-down perspective, as it would appear spanning the anterior (upper) surface of a person's wrist (or other portion of the person's arm) in a circumferential manner. Described generally, the example shown in FIG. 69 is an arm-worn biometric-sensing device with proximal and distal arcuate display screens which are circumferentially attached to an arm by a bifurcating band (or strap) and also connected to each other by a band (or strap) along the central longitudinal axis of the anterior (upper) surface of the arm.

Described more specifically, the example shown in FIG. 69 is a wearable device for the arm with one or more close-fitting biometric sensors comprising: (a) a proximal arcuate display screen, wherein this proximal arcuate display screen is configured to be worn a first distance from a person's shoulder; (b) a distal arcuate display screen, wherein this distal arcuate display screen is configured to be worn a second distance from a person's shoulder, and wherein the second distance is greater than the first distance; (c) one or more biometric sensors that are configured to collect data concerning arm tissue; (d) a bifurcated attachment member, wherein this bifurcated attachment member bifurcates into a proximal and distal branches as it spans the anterior (upper) surface of the person's arm, wherein these proximal and distal branches reconverge as the bifurcated attachment member further spans the anterior (upper) surface of the person's arm, wherein the proximal branch is configured to attach the proximal arcuate display screen to the person's arm, and wherein the distal branch is configured to attach the distal arcuate display screen to the person's arm; and (e) an inter-display connecting band (or strip) which connects the proximal arcuate display screen to the distal arcuate display screen.

In an example, a display screen can be circular. In an example, a display screen can be activated by touch and/or gesture. In an example, a virtual line connecting the center of a proximal display screen and the center of a distal display screen can parallel to the longitudinal axis of the arm. In an example, an inter-display connecting band (or strip) connecting the center of a proximal display screen and the center of a distal display screen can parallel to the longitudinal axis of the arm.

In an example, an attachment member can be a strap, band, bracelet, bangle, ring, armlet, gauntlet, cuff, or sleeve. In an example, an attachment member can be wider as it spans the anterior (upper) surface of a person's arm. In an example, an attachment member can be attached to a person's arm by connecting two ends of the attachment member with a clasp, clip, buckle, hook, pin, plug, or hook-and-eye mechanism. In an example, the attachment member can be attached to a person's arm by stretching and sliding it over the person's hand onto the arm. In an example, the attachment member can be attached to a person's arm by applying force to pull two ends apart to slip the member over the arm, wherein the two ends retract back towards each other when the force is removed.

In an example, a biometric sensor can be a spectroscopic sensor which is configured to measure the spectrum of light energy reflected from (and/or absorbed by) tissue of the person's arm. In an example, a biometric sensor can be an electromagnetic energy sensor which is configured to measure parameters and/or patterns of electromagnetic energy passing through (and/or emitted by) tissue of the person's arm. In an example, measured parameters and/or patterns of electromagnetic energy can be selected from the group consisting of: impedance, resistance, conductivity, and electromagnetic wave pattern.

Specific components in the example shown in FIG. 69 include: bifurcated attachment member 6901; distal display screen 6902; proximal display screen 6904; biometric sensors 6903 and 6905; and inter-display connecting band 6906. In an example, this device can further comprise one or more components selected from the group consisting of: a data processor; a battery and/or energy harvesting unit; a data transmitter; and a data receiver. In an example, this device can function as a smart watch. Relevant embodiment variations discussed elsewhere in this disclosure can also be applied to this example.

FIG. 70 shows another example of a wearable device for the arm with one or more close-fitting biometric sensors. The left side of this figure shows the device from a top-down perspective, as it would appear spanning the anterior (upper) surface of a person's wrist (or other portion of the person's arm) in a circumferential manner. The right side of this figure shows the device from a bottom-up perspective, as it would appear spanning the posterior (lower) surface of a person's wrist (or other portion of the person's arm) in a circumferential manner. Described generally, the example shown in FIG. 70 is an arm-worn biometric-sensing device with proximal and distal arcuate display screens which are attached to a person's arm by a band with an "S"-shaped portion spanning the anterior (upper) portion of the arm.

Described more specifically, the example shown in FIG. 70 is a wearable device for the arm with one or more close-fitting biometric sensors comprising: (a) a proximal arcuate display screen, wherein this proximal arcuate display screen is configured to be worn a first distance from a person's shoulder; (b) a distal arcuate display screen, wherein this distal arcuate display screen is configured to be worn a second distance from a person's shoulder, and wherein the second distance is greater than the first distance; (c) one or more biometric sensors that are configured to collect data concerning arm tissue; (d) a attachment member which is attached to the right side of the proximal arcuate display screen and to the left side of the distal arcuate display screen; (e) an inter-display connecting band which connects the distal portion of the proximal display screen to the proximal portion of the distal arcuate display screen.

Alternatively, a wearable device for the arm with one or more close-fitting biometric sensors can comprise: (a) a proximal arcuate display screen, wherein this proximal arcuate display screen is configured to be worn a first distance from a person's shoulder; (b) a distal arcuate display screen, wherein this distal arcuate display screen is configured to be worn a second distance from a person's shoulder, and wherein the second distance is greater than the first distance; (c) one or more biometric sensors that are configured to collect data concerning arm tissue; (d) a attachment member which is attached to the left side of the proximal arcuate display screen and to the right side of the distal arcuate display screen; (e) an inter-display band which connects the distal portion of the proximal display screen to the proximal portion of the distal arcuate display screen.

In an example, an attachment member can be a strap, band, bracelet, bangle, ring, armlet, gauntlet, cuff, or sleeve. In an example, an attachment member can be attached to a person's arm by connecting two ends of the attachment member with a clasp, clip, buckle, hook, pin, plug, or hook-and-eye mechanism. In an example, the attachment member can be attached to a person's arm by stretching and sliding it over the person's hand onto the arm. In an example, the attachment member can be attached to a person's arm by applying force to pull two ends apart to slip the member over the arm, wherein the two ends retract back towards each other when the force is removed.

In an example, a biometric sensor can be a spectroscopic sensor which is configured to measure the spectrum of light energy reflected from (and/or absorbed by) tissue of the person's arm. In an example, a biometric sensor can be an electromagnetic energy sensor which is configured to measure parameters and/or patterns of electromagnetic energy passing through (and/or emitted by) tissue of the person's arm. In an example, measured parameters and/or patterns of electromagnetic energy can be selected from the group consisting of: impedance, resistance, conductivity, and electromagnetic wave pattern.

Specific components in the example shown in FIG. 70 include: attachment member 7001; connector 7002; distal display screen 7003; proximal display screen 7005; biometric sensors 7004 and 7006; and inter-display band 7007. In an example, this device can further comprise one or more components selected from the group consisting of: a data processor; a battery and/or energy harvesting unit; a data transmitter; and a data receiver. In an example, this device can function as a smart watch. Relevant embodiment variations discussed elsewhere in this disclosure can also be applied to this example.

FIG. 71 shows another example of a wearable device for the arm with one or more close-fitting biometric sensors. This figure shows the device from a top-down perspective, as it would appear spanning the anterior (upper) surface of a person's wrist (or other portion of the person's arm) in a circumferential manner. The example shown in FIG. 71 can be described as a wearable device with two bands which encircle an arm, wherein these two bands are movably-attached to each other in a manner which allows a second band (with biometric sensors) to be rotated relative to a first band. Such rotation enables adjustment of the locations of one or more biometric sensors relative to the arm in order to improve collection of biometric data from arm tissue.

More specifically, the example shown in FIG. 71 is a wearable device for the arm with one or more close-fitting biometric sensors comprising: (a) a first band which is configured to span at least 60% of the circumference of a person's arm; (b) a second band which is configured to span at least 60% of the circumference of the person's arm, wherein the first band and the second band are attached to each other by a mechanism that enables the second band to be circumferentially-rotated relative to the first band; and (c) one or more biometric sensors which are configured to collect data concerning arm tissue, wherein these biometric sensors are part of (or attached to) the second band.

More generally, the example shown in FIG. 71 is a wearable device for the arm with one or more close-fitting biometric sensors comprising: (a) a first attachment member which is configured to span at least 60% of the circumference of a person's arm; (b) a second attachment member which is configured to span at least 60% of the circumference of the person's arm, wherein the first attachment member and the second attachment member are attached to each other by a mechanism that enables the second attachment member to be circumferentially-rotated relative to the first attachment member; and (c) one or more biometric sensors which are configured to collect data concerning arm tissue, wherein these biometric sensors are part of (or attached to) the second attachment member.

In an example, an attachment member can be a band, ring, strap, bracelet, bangle, or armlet. In an example, a band or other attachment member can be attached to a person's arm by connecting two ends of the attachment member with a clasp, clip, buckle, hook, pin, plug, or hook-and-eye mechanism. In an example, a band or other attachment member can be attached to a person's arm by stretching and sliding it over the person's hand onto the arm. In an example, a band or other attachment member can be attached to a person's arm by applying force to pull two ends apart to slip the member over the arm, wherein the two ends retract back towards each other when the force is removed.

In an example, a first attachment member can be attached to a person's arm in a relatively-fixed manner, so that it does not substantively rotate and/or shift around the circumference of the arm. In an example, a second attachment member can be attached to a person's arm in a relatively-loose manner, so that it can rotate around the circumference of the arm. In an example, a second attachment member can be attached (or connected) to the first attachment member by a connection mechanism which enables the second attachment member to be rotated around the circumference of the person's arm (relative to the first attachment member).

When the second attachment member contains one or more biometric sensors, rotation of the second attachment member also rotates these sensors relative to the circumference of the arm. This enables a user to find the optimal locations around the circumference of the arm from which to collect biometric data for a selected application. In an example, this device can further include a locking mechanism which locks the location of the second attachment member relative to the first attachment member when the optimal location for sensors is found. In an example, a connection mechanism between the two attachment members can be a ball-bearing mechanism. In an example, a connection mechanism can be a sliding tongue-and-groove (or tongue-and-slot) mechanism.

In an example, a biometric sensor can be a spectroscopic sensor which is configured to measure the spectrum of light energy reflected from (and/or absorbed by) tissue of the person's arm. In an example, a biometric sensor can be an electromagnetic energy sensor which is configured to measure parameters and/or patterns of electromagnetic energy passing through (and/or emitted by) tissue of the person's arm. In an example, measured parameters and/or patterns of electromagnetic energy can be selected from the group consisting of: impedance, resistance, conductivity, and electromagnetic wave pattern.

In an example, this device can further comprise one or more components selected from the group consisting of: a data processor; a battery and/or energy harvesting unit; a data transmitter; a data receiver; and a display screen. In an example, a first attachment member can include a display screen on its outward-facing surface. In an example, this device can function as a smart watch. Relevant embodiment variations discussed elsewhere in this disclosure can also be applied to this example. Specific components in the example shown in FIG. 71 include: first band 7101; second band 7102; display screen 7103; and biometric sensors including 7104.

FIG. 72 shows another example of a wearable device for the arm with one or more close-fitting biometric sensors. This figure shows the device from a top-down perspective, as it would appear spanning the anterior (upper) surface of a person's wrist (or other portion of the person's arm) in a circumferential manner. The example shown in FIG. 72 is like the one shown in FIG. 71, except that in FIG. 72 there are three bands instead of two and biometric sensors are on a central band which rotates relative to distal and proximal bands. Such rotation enables adjustment of the locations of one or more biometric sensors relative to the arm in order to improve collection of biometric data from arm tissue.

The example shown in FIG. 72 is a wearable device for the arm with one or more close-fitting biometric sensors comprising: (a) a distal attachment member which is configured to span at least 60% of the circumference of a person's arm; (b) a proximal attachment member which is configured to span at least 60% of the circumference of a person's arm; (c) a central attachment member which is configured to span at least 60% of the circumference of the person's arm, wherein this central attachment member is between the distal and proximal attachment members, and wherein this central attachment member is circumferentially-rotated relative to the distal and proximal attachment members; and (d) one or more biometric sensors which are configured to collect data concerning arm tissue, wherein these biometric sensors are part of (or attached to) the central attachment member.

In an example, an attachment member can be a band, ring, strap, bracelet, bangle, or armlet. In an example, a band or other attachment member can be attached to a person's arm by connecting two ends of the attachment member with a clasp, clip, buckle, hook, pin, plug, or hook-and-eye mechanism. In an example, a band or other attachment member can be attached to a person's arm by stretching and sliding it over the person's hand onto the arm. In an example, a band or other attachment member can be attached to a person's arm by applying force to pull two ends apart to slip the member over the arm, wherein the two ends retract back towards each other when the force is removed.

In an example, distal and proximal attachment members can be attached to a person's arm in a relatively-fixed manner, so that they do not substantively rotate and/or shift around the circumference of the arm. In an example, a central attachment member can be attached to a person's arm in a relatively-loose manner, so that it can rotate around the circumference of the arm. In an example, a central attachment member can be attached (or connected) to the distal and proximal attachment members by a connection mechanism which enables the second attachment member to be rotated around the circumference of the person's arm.

When a central attachment member contains one or more biometric sensors, rotation of the central attachment member also rotates these sensors relative to the circumference of the arm. This enables a user to find the optimal locations around the circumference of the arm from which to collect biometric data for a selected application. In an example, this device can further include a locking mechanism which locks the location of the central attachment member relative to the distal and proximal attachment members when the optimal location for sensors is found. In an example, a connection mechanism between the two attachment members can be a ball-bearing mechanism. In an example, a connection mechanism can be a sliding tongue-and-groove (or tongue-and-slot) mechanism.

In an example, a biometric sensor can be a spectroscopic sensor which is configured to measure the spectrum of light energy reflected from (and/or absorbed by) tissue of the person's arm. In an example, a biometric sensor can be an electromagnetic energy sensor which is configured to measure parameters and/or patterns of electromagnetic energy passing through (and/or emitted by) tissue of the person's arm. In an example, measured parameters and/or patterns of electromagnetic energy can be selected from the group consisting of: impedance, resistance, conductivity, and electromagnetic wave pattern.

In an example, this device can further comprise one or more components selected from the group consisting of: a data processor; a battery and/or energy harvesting unit; a data transmitter; a data receiver; and a display screen. In an example, a distal and/or proximal attachment member can include a display screen on an outward-facing surface. In an example, this device can function as a smart watch. Relevant embodiment variations discussed elsewhere in this disclosure can also be applied to this example. Specific components in the example shown in FIG. 72 include: distal band 7201; central band 7202; proximal band 7203; display screens 7204 and 7205; and biometric sensors including 7206.

FIG. 73 shows another example of a wearable device for the arm with one or more close-fitting biometric sensors. This figure shows the device from a top-down perspective, as it would appear spanning the anterior (upper) surface of a person's wrist (or other portion of the person's arm) in a circumferential manner. The example shown in FIG. 73 can be described as an arm-wearable device with a relatively-rigid band and a relatively-elastic band, wherein each of these bands spans at least 60% of the circumference of a person's arm, wherein these bands are connected to each other, and wherein there are biometric sensors on the relatively-elastic band.

More specifically, the example shown in FIG. 73 is a wearable device for the arm with one or more close-fitting biometric sensors comprising: (a) an inelastic attachment member which is configured to span at least 60% of the circumference of a person's arm, wherein this inelastic attachment member has a first elasticity level; (b) an elastic attachment member which is configured to span at least 60% of the circumference of a person's arm, wherein this elastic attachment member has a second elasticity level, wherein the second elasticity level is greater than the first elasticity level, and wherein the elastic attachment member is connected to the inelastic attachment member; and (c) one or more biometric sensors which are configured to collect data concerning arm tissue, wherein these biometric sensors are part of (or attached to) the elastic attachment member.

In an example, an attachment member can be a band, ring, strap, bracelet, bangle, armlet, sleeve, or cuff. In an example, a band or other attachment member can be attached to a person's arm by connecting two ends of the attachment member with a clasp, clip, buckle, hook, pin, plug, or hook-and-eye mechanism. In an example, a band or other attachment member can be attached to a person's arm by stretching and sliding it over the person's hand onto the arm. In an example, a band or other attachment member can be attached to a person's arm by applying force to pull two ends apart to slip the member over the arm, wherein the two ends retract back towards each other when the force is removed.

In an example, a biometric sensor can be a spectroscopic sensor which is configured to measure the spectrum of light energy reflected from (and/or absorbed by) tissue of the person's arm. In an example, a biometric sensor can be an electromagnetic energy sensor which is configured to measure parameters and/or patterns of electromagnetic energy passing through (and/or emitted by) tissue of the person's arm. In an example, measured parameters and/or patterns of electromagnetic energy can be selected from the group consisting of: impedance, resistance, conductivity, and electromagnetic wave pattern.

In an example, this device can further comprise one or more components selected from the group consisting of: a data processor; a battery and/or energy harvesting unit; a data transmitter; a data receiver; and a display screen. In an example, this device can function as a smart watch. Relevant embodiment variations discussed elsewhere in this disclosure can also be applied to this example. Specific components in the example shown in FIG. 73 include: inelastic band 7301; elastic band 7302; display screen 7303; and biometric sensors including 7304.

FIG. 74 shows another example of a wearable device for the arm with one or more close-fitting biometric sensors. This figure shows the device from a top-down perspective, as it would appear spanning the anterior (upper) surface of a person's wrist (or other portion of the person's arm) in a circumferential manner. The example shown in FIG. 74 can be described as an arm-wearable device with two or more modular and connectable bands, wherein each band spans at least 60% of the circumference of a person's arm, and wherein one or more of these bands house biometric sensors.

More specifically, the example shown in FIG. 74 is a wearable device for the arm with one or more close-fitting biometric sensors comprising: (a) a first modular band which is configured to span at least 60% of the circumference of a person's arm; (b) a second modular band which is configured to span at least 60% of the circumference of a person's arm, wherein the first modular band and the second modular band have a first configuration in which they are not connected to each other and are not worn by a person, wherein the first band and the second band have a second configuration wherein they are connected to each other and worn on a person's arm, and wherein the first band and the second band can be changed from the first configuration to the second configuration by the person who wears them, and wherein the first band and the second band can be changed back from the second configuration to the first configuration by the person who wears them; and (c) one or more biometric sensors which are configured to collect data concerning arm tissue, wherein these biometric sensors are part of (or attached to) one or both of the modular bands.

In an example, an attachment member can be a band, ring, strap, bracelet, bangle, armlet, sleeve, or cuff. In an example, a band or other attachment member can be attached to a person's arm by connecting two ends of the attachment member with a clasp, clip, buckle, hook, pin, plug, or hook-and-eye mechanism. In an example, a band or other attachment member can be attached to a person's arm by stretching and sliding it over the person's hand onto the arm. In an example, a band or other attachment member can be attached to a person's arm by applying force to pull two ends apart to slip the member over the arm, wherein the two ends retract back towards each other when the force is removed.

In an example, a biometric sensor can be a spectroscopic sensor which is configured to measure the spectrum of light energy reflected from (and/or absorbed by) tissue of the person's arm. In an example, a biometric sensor can be an electromagnetic energy sensor which is configured to measure parameters and/or patterns of electromagnetic energy passing through (and/or emitted by) tissue of the person's arm. In an example, measured parameters and/or patterns of electromagnetic energy can be selected from the group consisting of: impedance, resistance, conductivity, and electromagnetic wave pattern.

In an example, this device can further comprise one or more components selected from the group consisting of: a data processor; a battery and/or energy harvesting unit; a data transmitter; a data receiver; and a display screen. In an example, this device can function as a smart watch. Relevant embodiment variations discussed elsewhere in this disclosure can also be applied to this example. Specific components in the example shown in FIG. 74 include: first modular band 7401; second modular band 7402; temporary connectors 7403 and 7404; and display screens 7405 and 7406.

FIG. 75 shows another example of a wearable device for the arm with one or more close-fitting biometric sensors. This figure shows the device from a side perspective, as it would appear encircling a lateral cross-section of a person's arm.

The example in FIG. 75 can be described as an arm-wearable device with a partial-circumferential inner elastic band and biometric sensors. Such a device can have an outer inelastic band with a first elasticity level which spans a first percentage of the arm circumference and an inner elastic band with a second elasticity level which spans a second percentage of the arm circumference—wherein the second percentage is less than the first percentage and the second elasticity level is greater than the first elasticity level. In the example shown in FIG. 75, an outer inelastic band (and display screen) spans the entire arm circumference and a semi-circular inner elastic band (interior relative to the outer inelastic band) spans only half of the arm circumference. This design can provide an overall semi-rigid structure (for housing a display screen), but can also keep biometric sensors close against the surface of the arm for consistent collection of biometric data.

More specifically, the example shown in FIG. 75 is a wearable device for the arm with one or more close-fitting biometric sensors comprising: (a) an outer inelastic band which is configured to span a first percentage of a person's arm and which has a first elasticity level; (b) an inner elastic band which is configured to span a second percentage of a person's arm and which has a second elasticity level, wherein this inner elastic band is configured to be closer to the surface of the arm than the outer inelastic band, wherein the second percentage is less than the first percentage, and wherein the second elasticity level is greater than the first elasticity level; and (c) one or more biometric sensors which are configured to collect data concerning arm tissue, wherein these biometric sensors are part of (or attached to) the inner elastic band.

Alternatively, the example shown in FIG. 75 can be specified as a wearable device for the arm with one or more close-fitting biometric sensors comprising: (a) an outer inelastic band with a first arcuate length and a first elasticity level; (b) an inner elastic band with a second arcuate length and a second elasticity level, wherein this inner elastic band is located on the concave side of the outer elastic band, wherein the second percentage is less than the first percentage, and wherein the second elasticity level is greater than the first elasticity level; and (c) one or more biometric sensors which are configured to collect data concerning arm tissue, wherein these biometric sensors are part of (or attached to) the inner elastic band.

In an example, the word "ring", "strap", "bracelet", "bangle", "armlet", "sleeve", or "cuff" can be substituted for the word "band" in the above specifications. In an example, an outer inelastic band can span Y % of the circumference of a person's arm and an inner elastic band can span X % of the circumference of a person's arm, wherein Y % is at least 20 percentage points greater than X %. In an example, Y % can be 75% and X % can be 50%. In an example, the ends of the inner elastic band can be attached to the outer inelastic band. In an example, an inner elastic band can be configured to span the anterior (upper) surface of a person's arm. In an example, an inner elastic band can be configured to span the posterior (lower) surface of a person's arm.

In an example, an outer inelastic band can be attached to a person's arm by connecting two ends of an outer inelastic band with a clasp, clip, buckle, hook, pin, plug, or hook-and-eye mechanism. In an example, an outer inelastic band can be attached to a person's arm by stretching and sliding it over the person's hand onto the arm. In an example, an outer inelastic band can be attached to a person's arm by applying force to pull two ends apart to slip the member over the arm, wherein the two ends retract back towards each other when the force is removed.

In an example, a biometric sensor can be a spectroscopic sensor which is configured to measure the spectrum of light energy reflected from (and/or absorbed by) tissue of the person's arm. In an example, a biometric sensor can be an electromagnetic energy sensor which is configured to measure parameters and/or patterns of electromagnetic energy passing through (and/or emitted by) tissue of the person's arm. In an example, measured parameters and/or patterns of electromagnetic energy can be selected from the group consisting of: impedance, resistance, conductivity, and electromagnetic wave pattern.

In an example, this device can further comprise one or more components selected from the group consisting of: a data processor; a battery and/or energy harvesting unit; a data transmitter; a data receiver; and a display screen. In an example, this device can function as a smart watch. Relevant embodiment variations discussed elsewhere in this disclosure can also be applied to this example. Specific components in the example shown in FIG. 75 include: four segments (7501, 7502, 7504, and 7505) of an outer inelastic band; inner elastic band 7507; biometric sensors (7508, 7509, and 7510); outer elastic band clasp 7503; and display screen 7506.

FIG. 76 shows another example of a wearable device for the arm with one or more close-fitting biometric sensors. This figure shows the device from a side perspective, as it would appear encircling a lateral cross-section of a person's wrist (or other portion of their arm). The example in FIG. 76 is like the one shown in FIG. 75, except that in FIG. 76 the outer inelastic band is sufficiently resilient that its ends hold onto the person's arm without the need for a clasp. The outer inelastic band can be attached to a person's arm by applying force to pull two ends apart to slip the member over the arm, wherein the two ends retract back towards each other when the force is removed.

In an example, this device can further comprise one or more components selected from the group consisting of: a data processor; a battery and/or energy harvesting unit; a data transmitter; a data receiver; and a display screen. In an example, this device can function as a smart watch. Relevant embodiment variations discussed elsewhere in this disclosure can also be applied to this example. Specific components in the example shown in FIG. 76 include: four segments (7601, 7602, 7604, and 7605) of an outer inelastic band; inner elastic band 7607; biometric sensors (7608, 7609, and 7610); and display screen 7606.

FIG. 77 shows another example of a wearable device for the arm with one or more close-fitting biometric sensors. This figure shows the device from a side perspective, as it would appear encircling a lateral cross-section of a person's arm. The example in FIG. 77 can be described as an arm-wearable device with an outer arcuate inelastic band, an inner arcuate elastic band, and biometric sensors which are part of the inner band. This design can provide an overall semi-rigid structure (e.g. to hold a rigid display screen in place) and also keep biometric sensors close against the surface of the arm for consistent collection of biometric data.

The example shown in FIG. 77 can be specified as a wearable device for the arm with one or more close-fitting biometric sensors comprising: (a) an outer arcuate inelastic band which is configured to span at least 60% of the circumference of a person's arm and which has a first elasticity level; (b) an inner arcuate elastic band which is located on (and attached to) the concave side of the outer arcuate band and which has a second elasticity level, wherein the second elasticity level is greater than the first elasticity level; and (c) one or more biometric sensors which are configured to collect data concerning arm tissue, wherein these biometric sensors are part of (or attached to) the inner arcuate elastic band. In various examples, a ring, strap, bracelet, bangle, armlet, sleeve, or cuff can be substituted for a band.

Alternatively, the example shown in FIG. 77 can be specified as a wearable device for the arm with one or more close-fitting biometric sensors comprising: (a) an outer arcuate inelastic band, wherein this outer arcuate inelastic band is configured to span at least 60% of the circumference of a person's arm, wherein this outer arcuate inelastic band is configured to be a first average distance from the surface of the person's arm, and wherein this outer arcuate inelastic band has a first elasticity level; (b) an inner arcuate elastic band, wherein this inner arcuate elastic band is attached to the outer arcuate inelastic band, wherein this inner arcuate elastic band is configured to be an second average distance from the surface of the person's arm, wherein this inner arcuate elastic band has a second elasticity level, wherein the second average distance is less than the first average distance, and wherein the second elasticity level is greater than the first elasticity level; and (c) one or more biometric sensors which are configured to collect data concerning arm tissue, wherein these biometric sensors are part of (or attached to) the inner arcuate elastic band. In various examples, a ring, strap, bracelet, bangle, armlet, sleeve, or cuff can be substituted for a band.

In an example, an outer arcuate inelastic band can be attached to a person's arm by connecting two ends of the outer inelastic band with a clasp, clip, buckle, hook, pin, plug, or hook-and-eye mechanism. In an example, an outer arcuate inelastic band can be attached to a person's arm by stretching and sliding it over the person's hand onto the arm. In an example, an outer arcuate inelastic band can be attached to a person's arm by applying force to pull two ends apart to slip the member over the arm, wherein the two ends retract back towards each other when the force is removed. In an example, an inner arcuate elastic band can be made from a stretchable fabric. In an example, an inner arcuate elastic band can be attached to an outer arcuate inelastic band at the ends of the arcuate inelastic band. In an example, an inner arcuate elastic band can be attached to an outer arcuate inelastic band near mid-points of segments of the outer arcuate inelastic band.

In an example, a biometric sensor can be a spectroscopic sensor which is configured to measure the spectrum of light energy reflected from (and/or absorbed by) tissue of the person's arm. In an example, a biometric sensor can be an electromagnetic energy sensor which is configured to measure parameters and/or patterns of electromagnetic energy passing through (and/or emitted by) tissue of the person's arm. In an example, measured parameters and/or patterns of electromagnetic energy can be selected from the group consisting of: impedance, resistance, conductivity, and electromagnetic wave pattern.

In an example, this device can further comprise one or more components selected from the group consisting of: a data processor; a battery and/or energy harvesting unit; a data transmitter; a data receiver; and a display screen. In an example, this device can function as a smart watch. Relevant embodiment variations discussed elsewhere in this disclosure can also be applied to this example. Specific components in the example shown in FIG. 77 include: four segments (7701, 7702, 7704, and 7705) of an outer inelastic band; inner elastic band 7707; biometric sensors (7708, 7709, and 7710); and display screen 7706.

FIG. 78 shows another example of a wearable device for the arm with one or more close-fitting biometric sensors. This figure shows the device from a side perspective, as it would appear encircling a lateral cross-section of a person's wrist (or other portion of the person's arm). The example in FIG. 78 can be described as an arm-wearable device with an outer rigid "clam shell" structure to hold a display screen in place and an inner arcuate elastic band to keep biometric sensors close against the surface of the arm.

The example shown in FIG. 78 can be specified as a wearable device for the arm with one or more close-fitting biometric sensors comprising: (a) a clam shell structure which is configured to span the circumference of a person's arm, wherein this clam shell structure further comprises: an upper half-circumferential portion, a lower half-circumferential portion, a joint (and/or hinge) between these portions on a first side of these portions, and a connector which reversibly connects these portions on a second side of these portions; (b) an arcuate elastic band which is located within the concavity of the clam shell structure and is attached to the clam shell structure; and (c) one or more biometric sensors which are configured to collect data concerning arm tissue, wherein these biometric sensors are part of (or attached to) the arcuate elastic band.

In an example, an upper half-circumferential portion of a clam shell structure can span the anterior (upper) surface of a person's arm and a lower half-circumferential portion of a clam shell structure can span the posterior (lower) surface of the person's arm. In an example, there can be a display screen on the outer surface of one or both portions of a clam shell structure. In an example, a connector which reversibly connects the upper and lower portions of a clam shell structure can be selected from the group consisting of: clasp, clip, buckle, hook, pin, plug, and hook-and-eye mechanism. In an example, an inner arcuate elastic band can be made from a stretchable fabric. In an example, an inner arcuate elastic band can be attached to an upper half-circumferential portion of a clam shell structure.

In an example, a biometric sensor can be a spectroscopic sensor which is configured to measure the spectrum of light energy reflected from (and/or absorbed by) tissue of the person's arm. In an example, a biometric sensor can be an electromagnetic energy sensor which is configured to measure parameters and/or patterns of electromagnetic energy passing through (and/or emitted by) tissue of the person's arm. In an example, measured parameters and/or patterns of electromagnetic energy can be selected from the group consisting of: impedance, resistance, conductivity, and electromagnetic wave pattern.

In an example, this device can further comprise one or more components selected from the group consisting of: a data processor; a battery and/or energy harvesting unit; a data transmitter; a data receiver; and a display screen. In an example, this device can function as a smart watch. Relevant embodiment variations discussed elsewhere in this disclosure can also be applied to this example. Specific components in the example shown in FIG. 78 include: two segments 7802 and 7803 of an upper half-circumferential portion of a clam shell structure; a lower half-circumferential portion 7801 of the clam shell structure; a joint (or hinge) 7804 between the upper and lower portions of the clam shell structure; a reversible connector 7805 between the upper and lower portions of the clam shell structure; an inner elastic band 7807; biometric sensors 7808, 7809, and 7810; and display screen 7806.

FIG. 79 shows another example of a wearable device for the arm with one or more close-fitting biometric sensors. This figure shows the device from a side perspective, as it would appear encircling a lateral cross-section of a person's wrist (or other portion of the person's arm). The example in FIG. 79 is like the one shown in FIG. 78, except that in FIG. 79 an inner arcuate elastic band spans the posterior (lower) surface of a person's arm. Specific components in the example shown in FIG. 79 include: two segments 7902 and 7903 of an upper half-circumferential portion of a clam shell structure; a lower half-circumferential portion 7901 of the clam shell structure; a joint (or hinge) 7904 between the upper and lower portions of the clam shell structure; a reversible connector 7905 between the upper and lower portions of the clam shell structure; an inner elastic band 7907; biometric sensors 7908, 7909, and 7910; and display screen 7906.

FIG. 80 shows another example of a wearable device for the arm with one or more close-fitting biometric sensors. This figure shows the device from a side perspective, as it would appear encircling a lateral cross-section of a person's wrist (or other portion of the person's arm). The example in FIG. 80 can be described as an arm-wearable device with an outer rigid "clam shell" structure and inward-facing flexible undulations to keep biometric sensors close against the surface of the arm.

The example shown in FIG. 80 can be specified as a wearable device for the arm with one or more close-fitting biometric sensors comprising: (a) a clam shell structure which is configured to span the circumference of a person's arm, wherein this clam shell structure further comprises: an upper half-circumferential portion, a lower half-circumferential portion, a joint (and/or hinge) between these portions on a first side of these portions, and a connector which reversibly connects these portions on a second side of these portions; (b) an inward-facing undulating member which is part of (or attached to) the clam shell structure; and (c) one or more biometric sensors which are configured to collect data concerning arm tissue, wherein these biometric sensors are part of (or attached to) the undulating member.

In an example, an upper half-circumferential portion of a clam shell structure can span the anterior (upper) surface of a person's arm and a lower half-circumferential portion of a clam shell structure can span the posterior (lower) surface of the person's arm. In an example, there can be a display screen on the outer surface of one or both portions of a clam shell structure. In an example, a connector which reversibly connects the upper and lower portions of a clam shell structure can be selected from the group consisting of: clasp, clip, buckle, hook, pin, plug, and hook-and-eye mechanism. In an example, an inward-facing undulating member can have a sinusoidal shape. In an example, an inward-facing undulating member can be flexible and/or compressible. In an example, an inward-facing undulating member can be elastic and filled with a liquid, gel, or gas.

In an example, a biometric sensor can be a spectroscopic sensor which is configured to measure the spectrum of light energy reflected from (and/or absorbed by) tissue of the person's arm. In an example, a biometric sensor can be an electromagnetic energy sensor which is configured to measure parameters and/or patterns of electromagnetic energy passing through (and/or emitted by) tissue of the person's arm. In an example, measured parameters and/or patterns of electromagnetic energy can be selected from the group consisting of: impedance, resistance, conductivity, and electromagnetic wave pattern.

In an example, this device can further comprise one or more components selected from the group consisting of: a data processor; a battery and/or energy harvesting unit; a data transmitter; a data receiver; and a display screen. In an example, this device can function as a smart watch. Relevant embodiment variations discussed elsewhere in this disclosure can also be applied to this example. Specific components in the example shown in FIG. 80 include: two segments 8002 and 8003 of an upper half-circumferential portion of a clam shell structure; a lower half-circumferential portion 8001 of the clam shell structure; a joint (or hinge) 8004 between the upper and lower portions of the clam shell structure; a reversible connector 8005 between the upper and lower portions of the clam shell structure; inward-facing undulating members including 8007 and 8008; biometric sensors including 8009 and 8010; and display screen 8006.

FIG. 81 shows another example of a wearable device for the arm with one or more close-fitting biometric sensors. This figure shows the device from a top-down perspective, as it would appear spanning the anterior (upper) surface of a person's wrist (or other portion of the person's arm) in a circumferential manner. The example in FIG. 81 can be described as an arm-wearable device with two display screens suspended by an elastic material between two arcuate bands.

The example shown in FIG. 81 can be specified as a wearable device for the arm with one or more close-fitting biometric sensors comprising: (a) a distal arcuate band which is configured to span at least 60% of the circumference of a person's arm; (b) a proximal arcuate band which is configured to span at least 60% of the circumference of a person's arm, wherein distal is defined as further from a person's shoulder and proximal is defined as closer to the person's shoulder; (c) an elastic member that is between the distal arcuate band and the proximal arcuate band which connects the distal actuate band to the proximal arcuate band; and (d) two arcuate display screens between the distal arcuate band and the proximal arcuate band, wherein these display screens are attached to the elastic member; and (e) one or more biometric sensors which are configured to collect data concerning arm tissue. In various examples, a ring, strap, bracelet, or bangle can be substituted for a band.

In an example, an arcuate band can undulate laterally as it spans the circumference a person's arm. In an example, distal and proximal arcuate bands can curve away from each other as they span a central portion of the anterior (upper) surface of a person's arm and can curve back toward each other as they span a side surface of the person's arm. In an example, an arcuate band can be attached to a person's arm by connecting two ends of the arcuate band with a clasp, clip, buckle, hook, pin, plug, or hook-and-eye mechanism. In an example, an arcuate band can be attached to a person's arm by stretching and sliding it over the person's hand onto the arm. In an example, an arcuate band can be attached to a person's arm by applying force to pull two ends apart to slip the member over the arm, wherein the two ends retract back towards each other when the force is removed.

In an example, an elastic member can be made from elastic fabric. In an example, an elastic member can be an elastic mesh. In an example, an elastic member can have four arcuate sides: two convex sides and two concave sides. In an example, one concave side can connect to the distal arcuate band and the other concave side can connect to the proximal band. In an example, two convex sides can be between the two bands. In an example, an elastic member can completely surround the perimeters of two display screens. In an example, an elastic member can flexibly-suspend two display screens between two arcuate bands. In an example, a display screen can be circular. In an example, the centers of two display screens can be connected to form a virtual line which is parallel to the longitudinal axis of an arm. In an example, the centers of two display screens can be connected to form a virtual line which is parallel to a line which is perpendicular to the circumferences of distal and proximal arcuate bands.

In an example, biometric sensors can be part of (or attached to) display screens and/or enclosures which house display screens. In an example, a biometric sensor can be a spectroscopic sensor which is configured to measure the spectrum of light energy reflected from (and/or absorbed by) tissue of the person's arm. In an example, a biometric sensor can be an electromagnetic energy sensor which is configured to measure parameters and/or patterns of electromagnetic energy passing through (and/or emitted by) tissue of the person's arm. In an example, measured parameters and/or patterns of electromagnetic energy can be selected from the group consisting of: impedance, resistance, conductivity, and electromagnetic wave pattern.

In an example, this device can further comprise one or more components selected from the group consisting of: a data processor; a battery and/or energy harvesting unit; a data transmitter; a data receiver; and a display screen. In an example, this device can function as a smart watch. Relevant embodiment variations discussed elsewhere in this disclosure can also be applied to this example. Specific components in the example shown in FIG. 81 include: distal arcuate band 8101; proximal arcuate band 8102; elastic member 8103 between the two arcuate bands; display screens 8104 and 8105 suspended by the elastic member; and biometric sensors 8106 and 8107.

FIG. 82 shows another example of a wearable device for the arm with one or more close-fitting biometric sensors. This figure shows the device from a top-down perspective, as it would appear spanning the anterior (upper) surface of a person's wrist (or other portion of the person's arm) in a circumferential manner. The example in FIG. 82 can be described as an arm-wearable device with two display screens which are suspended by elastic straps between two arcuate bands.

The example shown in FIG. 82 can be specified as a wearable device for the arm with one or more close-fitting biometric sensors comprising: (a) a distal arcuate band which is configured to span at least 60% of the circumference of a person's arm; (b) a proximal arcuate band which is configured to span at least 60% of the circumference of a person's arm, wherein distal is further from a person's shoulder and proximal is closer to the person's shoulder; (c) a plurality of elastic straps between the distal arcuate band and the proximal arcuate band which connect the distal actuate band to the proximal arcuate band; and (d) two arcuate display screens between the distal arcuate band and the proximal arcuate band, wherein these display screens are attached to the plurality of elastic straps; and (e) one or more biometric sensors which are configured to collect data concerning arm tissue. In an example, a ring, bracelet, or bangle can be substituted for a band.

In an example, an arcuate band can undulate laterally as it spans the circumference a person's arm. In an example, distal and proximal arcuate bands can curve away from each other as they span a central portion of the anterior (upper) surface of a person's arm and can curve back toward each other as they span a side surface of the person's arm. In an example, an arcuate band can be attached to a person's arm by connecting two ends of the arcuate band with a clasp, clip, buckle, hook, pin, plug, or hook-and-eye mechanism. In an example, an arcuate band can be attached to a person's arm by stretching and sliding it over the person's hand onto the arm. In an example, an arcuate band can be attached to a person's arm by applying force to pull two ends apart to slip the member over the arm, wherein the two ends retract back towards each other when the force is removed.

In an example, an elastic strap can be made from elastic fabric. In an example, an elastic strap can be an elastic mesh. In an example, each display screen can be connected to three elastic straps. In an example, each display screen can be connected to three elastic straps with connection points which are substantially equidistant around the circumference of a display screen. In an example, each arcuate band can be connected to two elastic straps. In an example, two display screens can be connected by one elastic strap. In an example, there can be five elastic straps in total. In an example, a display screen can be circular. In an example, the centers of two display screens can be connected to form a virtual line which is parallel to the longitudinal axis of an arm. In an example, the centers of two display screens can be connected to form a virtual line which is parallel to a line which is perpendicular to the circumferences of distal and proximal arcuate bands.

In an example, biometric sensors can be part of (or attached to) display screens and/or enclosures which house display screens. In an example, a biometric sensor can be a spectroscopic sensor which is configured to measure the spectrum of light energy reflected from (and/or absorbed by) tissue of the person's arm. In an example, a biometric sensor can be an electromagnetic energy sensor which is configured to measure parameters and/or patterns of electromagnetic energy passing through (and/or emitted by) tissue of the person's arm. In an example, measured parameters and/or patterns of electromagnetic energy can be selected from the group consisting of: impedance, resistance, conductivity, and electromagnetic wave pattern.

In an example, this device can further comprise one or more components selected from the group consisting of: a data processor; a battery and/or energy harvesting unit; a data transmitter; a data receiver; and a display screen. In an example, this device can function as a smart watch. Relevant embodiment variations discussed elsewhere in this disclosure can also be applied to this example. Specific components in the example shown in FIG. 82 include: distal arcuate band 8201; proximal arcuate band 8202; a plurality of elastic straps including 8203, 8204, 8205, 8206, and 8207; display screens 8208 and 8210 suspended by the elastic straps; and biometric sensors 8209 and 8211.

FIG. 83 shows another example of a wearable device for the arm with one or more close-fitting biometric sensors. This figure shows the device from a top-down perspective, as it would appear spanning the anterior (upper) surface of a person's wrist (or other portion of the person's arm) in a circumferential manner. The example in FIG. 83 can be described as an arm-wearable device with two display screens whose centers are at 12 o'clock and 6 o'clock positions around a circular band on the anterior (upper) surface of an arm.

The example shown in FIG. 83 can be specified as a wearable device for the arm with one or more close-fitting biometric sensors comprising: (a) a distal arcuate band which is configured to span at least 60% of the circumference of a person's arm; (b) a proximal arcuate band which is configured to span at least 60% of the circumference of a person's arm, wherein distal is further from a person's shoulder and proximal is closer to the person's shoulder; (c) a distal display screen on the distal arcuate band; (d) a proximal display screen on the proximal arcuate band; (e) a right circle-segment band which connects the right side of the distal display screen to the right side of the proximal display screen; (f) a left circle-segment band which connects the left side of the distal display screen to the left side of the proximal display screen; and (g) one or more biometric sensors which are configured to collect data concerning arm tissue.

In an example, an arcuate band can be attached to a person's arm by connecting two ends of the arcuate band with a clasp, clip, buckle, hook, pin, plug, or hook-and-eye mechanism. In an example, an arcuate band can be attached to a person's arm by stretching and sliding it over the person's hand onto the arm. In an example, an arcuate band can be attached to a person's arm by applying force to pull two ends apart to slip the member over the arm, wherein the two ends retract back towards each other when the force is removed. In an example, a display screen can be circular. In an example, the centers of two display screens can be connected to form a virtual line which is parallel to the longitudinal axis of an arm. In an example, the centers of two display screens can be connected to form a virtual line which is parallel to a line which is perpendicular to the circumferences of distal and proximal arcuate bands.

In an example, biometric sensors can be part of (or attached to) display screens and/or enclosures which house display screens. In an example, a biometric sensor can be a spectroscopic sensor which is configured to measure the spectrum of light energy reflected from (and/or absorbed by) tissue of the person's arm. In an example, a biometric sensor can be an electromagnetic energy sensor which is configured to measure parameters and/or patterns of electromagnetic energy passing through (and/or emitted by) tissue of the person's arm. In an example, measured parameters and/or patterns of electromagnetic energy can be selected from the group consisting of: impedance, resistance, conductivity, and electromagnetic wave pattern.

In an example, this device can further comprise one or more components selected from the group consisting of: a data processor; a battery and/or energy harvesting unit; a data transmitter; a data receiver; and a display screen. In an example, this device can function as a smart watch. Relevant embodiment variations discussed elsewhere in this disclosure can also be applied to this example. Specific components in the example shown in FIG. 83 include: portions 8301 and 8302 of a distal arcuate band; portions 8303 and 8304 of a proximal arcuate band; display screens 8307 and 8309; right circle-segment band 8306; left circle-segment band 8305; and biometric sensors 8308 and 8310.

FIG. 84 shows another example of a wearable device for the arm with one or more close-fitting biometric sensors. This figure shows the device from a top-down perspective, as it would appear spanning the anterior (upper) surface of a person's wrist (or other portion of the person's arm) in a circumferential manner. The example in FIG. 84 can be described as an arm-wearable device with two display screens suspended by an oval (or elliptical or circular) elastic member between two arcuate bands.

The example shown in FIG. 84 can be specified as a wearable device for the arm with one or more close-fitting biometric sensors comprising: (a) a distal arcuate band which is configured to span at least 60% of the circumference of a person's arm; (s) a proximal arcuate band which is configured to span at least 60% of the circumference of a person's arm, wherein distal is defined as further from a person's shoulder and proximal is defined as closer to the person's shoulder; (t) an oval (or elliptical or circular) elastic member that is between the distal arcuate band and the proximal arcuate band which connects the distal actuate band to the proximal arcuate band; and (r) two arcuate display screens between the distal arcuate band and the proximal arcuate band, wherein these display screens are attached to the oval (or elliptical or circular) elastic member; and (o) one or more biometric sensors which are configured to collect data concerning arm tissue. In various examples, a ring, strap, bracelet, or bangle can be substituted for a band.

In an example, an arcuate band can undulate laterally as it spans the circumference a person's arm. In an example, distal and proximal arcuate bands can curve away from each other as they span a central portion of the anterior (upper) surface of a person's arm and can curve back toward each other as they span a side surface of the person's arm. In an example, an arcuate band can be attached to a person's arm by connecting two ends of the arcuate band with a clasp, clip, buckle, hook, pin, plug, or hook-and-eye mechanism. In an example, an arcuate band can be attached to a person's arm by stretching and sliding it over the person's hand onto the arm. In an example, an arcuate band can be attached to a person's arm by applying force to pull two ends apart to slip the member over the arm, wherein the two ends retract back towards each other when the force is removed.

In an example, an oval (or elliptical or circular) elastic member can be made from elastic fabric. In an example, an oval (or elliptical or circular) elastic member can be an elastic mesh. In an example, an oval (or elliptical or circular) elastic member can completely surround the perimeters of two display screens. In an example, an oval (or elliptical or circular) elastic member can flexibly-suspend two display screens between two arcuate bands. In an example, a display screen can be circular. In an example, the centers of two display screens can be connected to form a virtual line which is parallel to the longitudinal axis of an arm. In an example, the centers of two display screens can be connected to form a virtual line which is parallel to a line which is perpendicular to the circumferences of distal and proximal arcuate bands.

In an example, biometric sensors can be part of (or attached to) display screens and/or enclosures which house display screens. In an example, a biometric sensor can be a spectroscopic sensor which is configured to measure the spectrum of light energy reflected from (and/or absorbed by) tissue of the person's arm. In an example, a biometric sensor can be an electromagnetic energy sensor which is configured to measure parameters and/or patterns of electromagnetic energy passing through (and/or emitted by) tissue of the person's arm. In an example, measured parameters and/or patterns of electromagnetic energy can be selected from the group consisting of: impedance, resistance, conductivity, and electromagnetic wave pattern.

In an example, this device can further comprise one or more components selected from the group consisting of: a data processor; a battery and/or energy harvesting unit; a data transmitter; a data receiver; and a display screen. In an example, this device can function as a smart watch. Relevant embodiment variations discussed elsewhere in this disclosure can also be applied to this example. Specific components in the example shown in FIG. 84 include: distal arcuate band 8401; proximal arcuate band 8402; oval (or elliptical or circular) elastic member 8403 between the two arcuate bands; display screens 8404 and 8405 suspended by the oval (or elliptical or circular) elastic member; and biometric sensors 8406 and 8407.

Concluding Examples

In an example, a wearable spectroscopic sensor to measure food consumption based on the interaction between light and the human body can comprise a wearable food-consumption monitor that is configured to be worn on a person's wrist, arm, hand or finger. In an example, a wearable spectroscopic sensor to measure food consumption based on the interaction between light and the human body can monitor light energy that is reflected from a person's body tissue, absorbed by the person's body tissue, or has passed through the person's body tissue. In an example, a wearable spectroscopic sensor to measure food consumption based on the interaction between light and the human body can identify consumption of a selected type of food, ingredient, or nutrient using spectral analysis. In an example, a spectroscopic sensor can be a white light spectroscopic sensor, an infrared spectroscopic sensor, a near-infrared spectroscopic sensor, an ultraviolet spectroscopic sensor, an ion mobility spectroscopic sensor, a mass spectrometry sensor, a backscattering spectrometry sensor, or a spectrophotometer.

In an example, a wearable device to measure a person's food consumption based on the interaction between light energy and the person's body can comprise: (a) at least one wearable spectroscopic sensor that collects data concerning the spectrum of light energy reflected from a person's body tissue, absorbed by the person's body tissue, and/or having passed through the person's body tissue, wherein this data is used to measure the person's consumption of one or more selected types of food, ingredients, and/or nutrients; (b) a data processing unit; and (c) a power source.

In an example, a device can further comprise an attachment member selected from the group consisting of: finger ring, smart watch, wrist band, wrist bracelet, armlet, cuff, and sleeve. In an example, a device can be configured to be worn on a person's finger, hand, wrist, and/or arm. In an example, a spectroscopic sensor can be selected from the group consisting of: white light spectroscopic sensor, infrared light spectroscopic sensor, near-infrared light spectroscopic sensor, and ultraviolet light spectroscopic sensor. In an example, a spectroscopic sensor can be selected from the group consisting of spectrometer, spectrophotometer, ion mobility spectroscopic sensor, and backscattering spectrometry sensor.

In an example, this device can further comprise a first spectroscopic sensor at a first location on the device and a second spectroscopic sensor at a second location on the device, wherein the distance along a circumference of the device from the first location to the second location is at least a quarter inch. In an example, a spectroscopic sensor can be moved along the circumference of the device. In an example, moving the spectroscopic sensor along the circumference of the device changes the location of the spectroscopic sensor relative to the person's body.

In an example, a device can further comprise a first spectroscopic sensor which is configured to project a beam of light onto the surface of a person's body at a first angle and a second spectroscopic sensor which is configured to project a beam of light onto the surface of the person's body at a second angle, wherein the first angle differs from the second angle by at least 10 degrees. In an example, a spectroscopic sensor can be rotated relative to the rest of the device. In an example, rotating the spectroscopic sensor changes the angle at which the spectroscopic sensor projects a beam of light onto the surface of the person's body.

In an example, a device can further comprise an elastic member filled with a flowable substance (such as a gas or liquid) and this elastic member pushes a spectroscopic sensor toward the surface of the person's body. In an example, a device can further comprise an elastic strap (or band) spanning less than 60% of the circumference of the device and this elastic strap (or band) pushes or pulls a spectroscopic sensor toward the surface of the person's body. In an example, a device can further comprise a spring which pushes or pulls a spectroscopic sensor toward the surface of the person's body.

In an example, this device can further comprise: (a) an attachment member which is configured to span at least 60% of the circumference of a person's wrist and/or arm, wherein this attachment member further comprises one or more elastic portions which are configured to span the anterior surface of the person's wrist and/or arm and one or more inelastic portions which are configured to span the posterior surface of the person's wrist and/or arm; and (b) an enclosure which is connected to the elastic portions of the attachment member, wherein a spectroscopic sensor is part of the enclosure.

In an example, this device can further comprise: (a) an attachment member which is configured to span at least 60% of the circumference of a person's wrist and/or arm, wherein this attachment member further comprises one or more anterior inelastic portions which are configured to span the anterior surface of the person's wrist and/or arm, one or more posterior inelastic portions which are configured to span the posterior surface of the person's wrist and/or arm, and one or more elastic portions which connect the anterior and posterior inelastic portions; and (b) an enclosure which is configured to be worn on the anterior portion of the wrist and/or arm, wherein a spectroscopic sensor is part of the enclosure.

In an example, this device can further comprise: (a) an attachment member which is configured to span at least 60% of the circumference of a person's wrist and/or arm, wherein this attachment member further comprises a first elastic portion with a first elasticity level, a second elastic portion with a second elasticity level, and an inelastic portion with a third elasticity level, wherein the third elasticity level is less than each of the first and second elasticity levels; and (b) an enclosure which is connected between the first and second elastic portions, wherein a spectroscopic sensor is part of the enclosure.

In an example, this device can further comprise: (a) an outer inelastic band which is configured to span a first percentage of a person's wrist and/or arm and which has a first elasticity level; (b) an inner elastic band which is configured to span a second percentage of the person's wrist and/or arm and which has a second elasticity level, wherein the inner elastic band is configured to be closer to the surface of the wrist and/or arm than the outer inelastic band, wherein the second percentage is less than the first percentage, and wherein the second elasticity level is greater than the first elasticity level, and wherein a spectroscopic sensor is part of the inner elastic band.

In an example, this device can further comprise: (a) an outer arcuate inelastic band which is configured to span at least 60% of the circumference of a person's wrist and/or arm and which has a first elasticity level; (b) an inner arcuate elastic band which is located on the concave side of the outer arcuate band and which has a second elasticity level, wherein the second elasticity level is greater than the first elasticity level, and wherein a spectroscopic sensor is part of the inner arcuate elastic band.

In an example, this device can further comprise a clam shell structure which is configured to span the circumference of a person's wrist and/or arm, wherein this clam shell structure further comprises: (a) an upper half-circumferential portion, (b) a lower half-circumferential portion, (c) a joint between these portions on a first side of these portions, and (d) a connector which reversibly connects these portions on a second side of these portions; and (e) an inward-facing undulating member which is part of or attached to the clam shell structure, wherein a spectroscopic sensor is part of or attached to the undulating member.

In an example, this device can further comprise: (a) circumferentially-undulating attachment member which is configured to span at least a portion of the circumference of a person's wrist and/or arm; and (b) a plurality of spectroscopic sensors which collect data concerning wrist and/or arm tissue, wherein each sensor is located at the proximal portion of an undulation, and wherein the proximal portion of an undulation is the portion of an undulating wave which is closest to the circumferential center of the device.

In an example, this device can further comprise: (a) an attachment member which is configured to span at least 60% of the circumference of a person's wrist and/or arm; (b) an enclosure, wherein a spectroscopic sensor is part of the enclosure; and (c) a plurality of elastic, stretchable, and/or springy suspension members, wherein these suspension members flexibly connect the enclosure to the attachment member, wherein each of these suspension members is connected at one end to a location on the circumference of the enclosure and connected at its other end to the attachment member, and wherein the longitudinal axis of each of the suspension members is substantially parallel with a virtual radial spoke outward from the center of the enclosure.

I claim:

1. A wearable device to measure a person's consumption of one or more selected types of food, ingredients, and/or nutrients based on the interaction between light energy and the person's body comprising:

a smart watch or band, wherein the smart watch or band is configured to be worn on a person's wrist or arm, wherein the smart watch or band has six undulations around its circumference, wherein the six undulations are sinusoidal, wherein the six undulations engage sides of the person's wrist or arm with symmetrically-opposite waves in order to avoid rotational shifting and associated biometric measurement errors which can occur with a non-undulating circular or oval watch or band, wherein a proximal portion of an undulation is the portion of the undulation which is closest to the circumferential center of the smart watch or band;
a plurality of spectroscopic sensors on the proximal portions of some or all of the six undulations, wherein the plurality of spectroscopic sensors collect data concerning the spectrum of light energy reflected from a person's body tissue, absorbed by the person's body tissue, and/or having passed through the person's body tissue, and wherein the collected data is used to measure the person's consumption of one or more selected types of food, ingredients, and/or nutrients;
a data processing unit; and
a power source.

* * * * *